United States Patent
Desir et al.

(10) Patent No.: US 12,227,595 B2
(45) Date of Patent: Feb. 18, 2025

(54) ANTI-RENALASE ANTIBODIES FOR THE TREATMENT AND PREVENTION OF DISEASES AND DISORDERS

(71) Applicant: Yale University, New Haven, CT (US)

(72) Inventors: Gary Desir, Woodbridge, CT (US); Bryce Nelson, West Haven, CT (US)

(73) Assignee: Yale University, New Haven, CT (US)

( * ) Notice: Subject to any disclaimer, the term of this patent is extended or adjusted under 35 U.S.C. 154(b) by 1033 days.

(21) Appl. No.: 16/958,960

(22) PCT Filed: Dec. 27, 2018

(86) PCT No.: PCT/US2018/067611
§ 371 (c)(1),
(2) Date: Jun. 29, 2020

(87) PCT Pub. No.: WO2019/133667
PCT Pub. Date: Jul. 4, 2019

(65) Prior Publication Data
US 2022/0348684 A1    Nov. 3, 2022

Related U.S. Application Data

(60) Provisional application No. 62/611,609, filed on Dec. 29, 2017.

(51) Int. Cl.
*C07K 16/40* (2006.01)
*G01N 33/574* (2006.01)

(52) U.S. Cl.
CPC ......... *C07K 16/40* (2013.01); *G01N 33/5743* (2013.01); *C07K 2317/24* (2013.01); *C07K 2317/565* (2013.01); *C07K 2317/92* (2013.01)

(58) Field of Classification Search
CPC ............... C07K 16/40; C07K 2317/24; C07K 2317/565; C07K 2317/92; G01N 33/5743
See application file for complete search history.

(56) References Cited

U.S. PATENT DOCUMENTS

2017/0226228 A1    8/2017    Desir

FOREIGN PATENT DOCUMENTS

| CN | 106659772 | | 5/2017 | |
|---|---|---|---|---|
| JP | 2017521401 | | 8/2017 | |
| JP | 2017521401 | A | 8/2017 | |
| TW | 200738255 | | 10/2007 | |
| WO | 2013056352 | | 4/2013 | |
| WO | 2014014899 | A1 | 1/2014 | |
| WO | 2015058861 | | 4/2015 | |
| WO | WO-2015200790 | A2 * | 12/2015 | ....... A61K 39/39558 |
| WO | 2016015162 | | 2/2016 | |

OTHER PUBLICATIONS

Wang et al., Renalase-Specific Polyclonal Antibody and Its Application in the Detection of Renalase's Expression, 2012, Hybridoma, vol. 31, No. 5, pp. 378-381 (Year: 2012).*
Sela-Culang et al., The structural basis of antibody-antigen recognition, 2013, Frontiers in Immunology, vol. 4, Article 302, pp. 1-13 (Year: 2013).*
Kussie et al., A Single Engineered Amino Acid Substitution Changes Antibody Fine Specificity, 1994, Journal of Immunology, pp. 146-152 (Year: 1994).*
Baca et al., Journal of Biological Chemistry, American Society for Biochemistry and Molecular Biology, 272:10678-10684.
Beaupre et al., 2015, "Metabolic function for human renalase: oxidation of isomeric forms of β-NAD(P)H that are inhibitory to primary metabolism", Biochemistry., 54(3):795-806.
Chinese Office Action (including English translation) issued in App. No. CN20188084379, dated Oct. 28, 2022, 10 pages.
Dankort et al., 2009, "BRAF(V600E) cooperates with Pten silencing to elicit metastatic melanoma." Nature genetics. 41:544-52.
Desir et al., 2012 J Am Heart Assoc. 1(e002634; Desir et al., 2012 J Am Soc Hypertens.
Desir et al., 2012 J Am Soc Hypertens. 6(6):417-26.
European Patent Office Communication issued in Appln. No. 1 8897086.7 (Extended European Search Report dated Dec. 20, 2021).
European Patent Office Communication issued in Appln. No. 1 8897086.7 (Office Action dated Mar. 11, 2023).
European Patent Office Communication issued in Appln. No. 1 8897086.7 (Partial Supplementary European Search Report dated Sep. 17, 2021).
Farzaneh-Far et al., A Functional Polymorphism in Renalase (Glu37Asp) Is Associated with Cardiac Hypertrophy, Dysfunction, and Ischemia: Data from the Heart and Soul Study, 2010 PLoS One. 5(10):e13496.
Gray-Schopfer et al., 2007 Nature. 445:851-7.
Hidalgo et al., 2010 New England Journal of Medicine, 362(17):1605-17.
Hollander et al, 2016, Cancer Research, 76: 3884-3894.
Japanese Office Action (including English translation) issued in App. No. JP2020-536124, dated Jun. 6, 2023, 5 pages.
Japanese Office Action (including English translation) issued in App. No. JP2020-536124, dated Oct. 18, 2022, 16 pages.
Jones et al., 2008, "Core Signaling Pathways in Human Pancreatic Cancers Revealed by Global Genomic Analyses." Science. 321(5897):1801-6.
Lee et al., 'Renalase Protects against Ischemic AKI,' 2013, J Am Soc Nephrol, 24:445-455.
Lesinski et al., 2013, "The potential for targeting the STAT3 pathway as a novel therapy for melanoma." Future Oncology. 9:925-7.
Li et al., Catecholamines Regulate the Activity, Secretion, and Synthesis of Renalase, 2008 Circulation. 117(10):1277-82.
Lowe et al., 2014, "Increasing Incidence of Melanoma among Middle-Aged Adults: An Epidemiologic Study in Olmsted County, Minnesota" Mayo Clinic Proceedings., 89:52-9.

(Continued)

*Primary Examiner* — Jeffrey Stucker
*Assistant Examiner* — Brittney E Donoghue
(74) *Attorney, Agent, or Firm* — Riverside Law LLP

(57) ABSTRACT

The present invention relates to compositions and methods for binding and inhibiting renalase. In one embodiment, the renalase binding molecule inhibits renalase activity. Thus, in diseases and conditions where a reduction of renalase activity is beneficial, such inhibitory renalase binding molecules may act as therapeutics.

11 Claims, 47 Drawing Sheets
Specification includes a Sequence Listing.

(56) References Cited

OTHER PUBLICATIONS

Nolen et al., Prediagnostic Serum Biomarkers as Early Detection Tools for Pancreatic Cancer in a Large Prospective Cohort Study, 2014 PLoS One. 9(4):e94928.
Wang et al., 2008, "Identification, expression and tissue distribution of a renalase homologue from mouse." Mol Biol Rep. 35(4):613-20.
Wang et al., 2014 Journal of the American Society of Nephrology. DOI:10.1681/asn.2013060665.
Wang Feng et al., PLOS One, vol. 7, p. e46442, XP055826003.
World Cancer Report 2014. WHO Press; 2014.
Xiaojia Guo et el., Scientific Reports, vol. 6, XP055753854.
Xu et al., 2005, Renalase is a novel, soluble monoamine oxidase that regulates cardiac function and blood pressure, J Clin Invest. 115 (5):1275-80.
Yajima et al., 2012, RAS/RAF/MEK/ERK and PI3K/PTEN/AKT Signaling in Malignant Melanoma Progression and Therapy, Dermatology research and practice. 2012:354191.
Desir et al., 'Renalase Lowers Ambulatory Blood Pressure by Metabolizing Circulating Adrenaline,' 2012, J. of the Am. Heart Assn, 1(4):e002634. 11 pages.
Farzaneh-Far et al., 2010, "Telomere Length Trajectory and Its Determinants in Persons with Coronary Artery Disease: Longitudinal Findings from the Heart and Soul Study", PLoS One., 5(10):e13496.
Fedchenko et al., 2016, "Renalase Secreted by Human Kidney HEK293T Cells Lacks its N-Terminal Peptide: Implications for Putative Mechanisms of Renalase Action", Kidney Blood Press. Res., 41:593-603.
Gray-Schopfer et al., 2007, "Melanoma biology and new targeted therapy." Nature. 445:851-7.
Green, L. & Jakobovits, 1998, "Regulation of B Cell Development by Variable Gene Complexity in Mice Reconstituted with Human Immunoglobulin Yeast Artificial Chromosomes", Exp. Med., 188:483-95.
Green, L. et al., 1994, "Antigen-specific human monoclonal antibodies from mice engineered with human Ig heavy and light chain YACs", Nature Genet. ,7:13-21.
Hidalgo et al., 2012, "New insights into pancreatic cancer biology." Annals of Oncology. 23(suppl 10):x135-x8.
Kolodecik et al. 2017; The serum protein renalase reduces injury in experimental pancreatitis. J. Bio. Chem. 292(51):21047-21059.
Li et al., 2008, "Catecholamines Regulate the Activity, Secretion, and Synthesis of Renalase", Circulation., 117(10):1277-82.
Nolen et al., 2014, "Prediagnostic Serum Biomarkers as Early Detection Tools for Pancreatic Cancer in a Large Prospective Cohort Study." PLoS One. 9(4):e94928.
Xu et al., 'Renalase is a novel, soluble monoamine oxidase that regulates cardiac function and blood pressure,' 2005, J Clin Invest, 115: 1275-1280.

\* cited by examiner

| SEQ ID NO | Peptide antigens used to immunize rabbits | | | | | |
|---|---|---|---|---|---|---|
| | Antigen Code | Antigen Sequence | Specificity | Polyclonal | Monoclonal | Monoclonal Name |
| 1 | 1A | AVWDKADDSGGRMTTAC | R1, R2 | Yes | | |
| 2 | 1B | AVWDKAEDSGGRMTTAC | R1, R2 | Yes | | |
| 3 | 1C | CTPHYAKKHQRFYDEL | R1, R2 | Yes | Yes | 1C-22-1 |
| 4 | 1D | CIRFVSIDNKKRNIESSEIGP | R1, R2 | Yes | Yes | 1D-28-4<br>1D-37-10 |
| 5 | 1E | PGQMTLHHKPFLAC | R1, R2 | Yes | | |
| 6 | 1F | CVLEALKNYI | R1 | Yes | Yes | 1F-26-1<br>1F-42-7 |
| 7 | 3A | PSAGVILGC | R2 | Yes | Yes | 3A-5-2 |
| | Whole Protein | See FIG. 2 | R1, R2 | Yes (E2930) | | |

FIG. 1

SEQ ID NO: 8

Full-length renalase-1 protein sequence

```
1   --MAQVLIVGAGMTGSLCAALLRQTSGFLIYLAVNDKAEDSGGRMTTACSPHNPQCTADLGA
61  --QYITCTPHYAKKHQRFYDELLAYGTLRPLSSPIEGMVMKEGDCNFVAPQGISSIIKHYLK
121 --ESGAEVYFHRVTQINLRDDKMEVSKQTGSPEQFDLIVLTMPVPEILQLQGDITTLISEC
181 --QRQQLEAVSYSSSRYALGLFYEAGTKIDVPWAGQYITSNPCIRFVSIDNKKRNIESSEIGP
241 --SLVIHTTVPFGVTLEHSIEDVQELVFQQLENILEGLPQPIATKCQWRHSQVTNRRANC
301 --PGQMTLHHKPFLACGGDGFTQSNFDSCITSALCVLEAIKNYI
```

FIG. 2

| SEQ ID NO | Anti-1D epitope Monoclonal 1D-28-4 heavy chain coding sequence: |
|---|---|
| 52 | atggagactgggctgcgctggcttctcctggtcgctgtgctcaaaggtgtccagtgtcag |
| 9 | M E T G L R W L L L V A V L K G V Q C Q |
| 52 | tcggtggaggagtccggggggtcgcctggtcacgcctggggacaccctgacactcacctgc |
| 9 | S V E E S G G R L V P S T L T L T C |
| 52 | acagtctctggattctccctcagtagttttgcagtgggctgggtccgccaggctccaggg |
| 9 | T V S G F S <u>L S S F A V G</u> W V R Q A P G |
| 52 | aaggggctggaatacatcggaatcattagtagtgttggtattacacgctacgcgagctgg |
| 9 | K G L E Y I G <u>I I S S V G I T R Y A S W</u> |
| 52 | gcggcggccgattcaccatctccaaaacctcgacaacggtggatctgaaaatcaccagt |
| 9 | <u>A A G</u> R F T I S K T S T T V D L K I T S |
| 52 | ccgacaaccgaggacacggccacctattttgtgccagatatggttatagtggtgatgtt |
| 9 | P T T E D T A T Y F C A R <u>Y G Y S G D V</u> |
| 52 | aatcggttggatctctggggccagggcaccctggtcaccgtctcctcagggcaacctaag |
| 9 | <u>N R L D L</u> W G Q G T L V T V S S G Q P K |
| 52 | gctccatcagtcttcccactggcccctgctgcggggacaacccagctcacggtgacc |
| 9 | A P S V F P L A P C C G D T P S T V T |
| 52 | ctgggctgcctggtcaaagggtacctcccggagccagtgaccgtgacctggaactcgggc |
| 9 | L G C L V K G Y L P E P V T V T W N S G |
| 52 | accctcaccaatggggtacgcacctttccgtccgtccggcagtctcaggcctctactcg |
| 9 | T L T N G V R T F P S V R Q S S G L Y S |
| 52 | ctgagcagcgtggtgagcgtgacctcaagcagcagccgtcacctgcaacgtggcccag |
| 9 | L S S V V S V T S S S Q P V T C N V A H |
| 52 | ccagcaacaccaaagtggacaagaccgttgcgccctcgacatgcagcaagcccacg |
| 9 | P A T N T K V D K T V A P S T C S K P T |
| 52 | tgcccaccccctgaactcctggggggaccgtctgtcttcatcttccccccaaaacccaag |
| 9 | C P P P E L L G G P S V F I F P P K P K |
| 52 | gacacccctcatgatctcacgcaccccgaggtcacatgcgtggtggtggacgtgagccag |

FIG. 4

| SEQ ID NO | |
|---|---|
| 9 | D T L M I S R T P E V T C V V V D V S Q |
| 52 | gatgacccgaggtgcagttcacatggtacataaacaacgagcaggtgcgcaccgccgg |
| 9 | D P E V Q F T W Y I N N E Q V R T A R |
| 52 | ccgccgctacgggagcagcagttcaacagcacgatccgcgtggtcagcaccctcccatc |
| 9 | P P L R E Q Q F N S T I R V V S T L P I |
| 52 | gcgaccaggactggctgaggggcaaggagttcaagtgcaaagtccacaacaaggcactc |
| 9 | A H Q D W L R G K E F K C K V H N K A L |
| 52 | ccggccccatcgagaaaaccatctccaaagccagagggcagcccctggagccgaaggtc |
| 9 | P A P I E K T I S K A R G Q P L E P K V |
| 52 | tacaccatgggccctccccggggaggagctgagcagcaggtcggtcagcctgacctgcatg |
| 9 | Y T M G P P R E E L S S R V S L T C M |
| 52 | atcaacggcttctaccttccgacatctcggtggagtgggagaagaacgggaaggcagag |
| 9 | I N G F Y P S D I S V E W E K N G K A E |
| 52 | gacaactacaagaccacgccggccgtgctggacagcgacggctcctacttcctctacagc |
| 9 | D N Y K T T P A V L D S D G S Y F L Y S |
| 52 | aagctctcagtgcccacgagtgagtggcagcggggcgacgtcttcacctgctccgtgatg |
| 9 | K L S V P T S E W Q R G D V F T C S V M |
| 52 | cacgaggccttgcacaaccactacacgcagaagtccatctcccgctctccgggtaaatga |
| 9 | H E A L H N H Y T Q K S I S R S P G K - |

FIG. 4 (CONTINUED)

| SEQ ID NO | Anti-1D epitope Monoclonal 1D-28-4 Light chain coding sequence: |
|---|---|
| 53 | atggacacgagggcccccactcagctgctggggctcctgctgctctggctcccaggtgcc |
| 10 | M D T R A P T Q L L G L L L L W L P G A |
| 53 | acattgcccaagtgctgacccagactgcatcgccgtgtctgcagctgtgggaggcaca |
| 10 | T L A Q V L T Q T A S P V S A A V G G T |
| 53 | gtcaccatcaattgccaggccagtcagagtgtttatgataacaacaactagcctggtat |
| 10 | V T I N C Q A <u>S Q S V Y D N N N L A</u> W Y |
| 53 | cagcagaaaccagggcagcctcccaagcaactgatctatggtgcatccactctggcatct |
| 10 | Q Q K P G Q P P K Q L I Y <u>G A S T L A S</u> |
| 53 | ggggtctcatcgcggttcaaaggcagtggatctgggacacagttcactctcaccatcagc |

FIG. 5

| SEQ ID NO | |
|---|---|
| 10 | G V S S R F K G S G S G T Q F T L T I S |
| 53 | ggcgtgcagtgtgacgatgctgccacttactactgtctaggcgaatttagttgtagtagt |
| 10 | G V Q C D D A A T Y Y C <u>L G E F S C S S</u> |
| 53 | gctgattgtttgcttcggcggagggaccgaggtggtcgtcaaaggtgatccagttgca |
| 10 | <u>A D C F A</u> F G G G T E V V V K G D P V A |
| 53 | cctactgtcctcatcttcccaccatctgctgatcttgtggcaactggaacagtcaccatc |
| 10 | P T V L I F P P S A D L V A T G T V T I |
| 53 | gtgtgtgtggcgaataaatactttccggatgtcaccgtcacctgggaggtggatggcacc |
| 10 | V C V A N K Y F P D V T V T W E V D G T |
| 53 | acccaaacaactggcatcgagaacagtaaaacaccgcagaattctgcagattgtacctac |
| 10 | T Q T T G I E N S K T P Q N S A D C Y |
| 53 | aacctcagcagcactctgacactgaccagcacacagtacaacagccacaaagagtacacc |
| 10 | N L S S T L T L T S T Q Y N S H K E Y T |
| 53 | tgcaaggtgacccagggcacgacctcagtcgtccagagcttcaatagggggtgactgttag |
| 10 | C K V T Q G T T S V V Q S F N R G D C - |

FIG. 5 (CONTINUED)

| SEQ ID NO | Anti-1D epitope Monoclonal 1D-37-10 heavy chain coding sequence: |
|---|---|
| 60 | atggagactgggctgcgctggcttctcctggtcgctgtgctcaaaggtgtccagtgtcag |
| 17 | M E T G L R W L L L V A V L K G V Q C Q |
| 60 | tcggtggaggagtccgggggtcgcctggtcacgcctggaggatccctgacactcacctgc |
| 17 | S V E E S G G R L V T P G G S L T L T C |
| 60 | acagtctctggattctccctcagtgactatgcaataatctgggtccgccaggctccaggg |
| 17 | T V S G F S <u>L S D Y A I I</u> W V R Q A P G |
| 60 | aaggggctggaatacatcgcaattattggtagtagtggtgacacattctacgcgacctgg |
| 17 | K G L E Y I A <u>I I G S S G D T F Y A T W</u> |
| 60 | gcgaaaggccgattcaccatctccaaaacctcgaccacggtggatctgaaaatgaccagt |
| 17 | <u>A K G</u> R F T I S K T S T T V D L K M T S |
| 60 | ctgacagccgcggacacggccacctatttctgtgcccacgttatgctggtactactgat |
| 17 | L T A A D T A T Y F C A P <u>R Y A G T T D</u> |
| 60 | tatcatgatgctttgatccctggggccaggcaactggtcaccgtctcctcagggcaa |

FIG. 6

| SEQ ID NO | |
|---|---|
| 17 | Y H D A F D P  W G P G T L V T V S S G Q |
| 60 | cctaaggctccatcagtcttcccactggccccctgctgcggggacacacccagctccacg |
| 17 | P K A P S V F P L A P C C G D T P S S T |
| 60 | gtgaccctgggctgcctggtcaaagggtacctccggagccagtgaccgtgacctggaac |
| 17 | V T L G C L V K G Y L P E P V T V T W N |
| 60 | tcgggcaccctcaccaatggggtacgcacctttcccgtccgtccggcagtcctcaggcctc |
| 17 | S G T L T N G V R T F P S V R Q S S G L |
| 60 | tactcgctgagcagcgtggtgagcgtgacctcaagcagccagccgtcacctgcaacgtg |
| 17 | Y S L S S V V S V T S S Q P V T C N V |
| 60 | gccacccagccaccaacaccaaagtggacaagaccgttgcgccctcgacatgcagcaag |
| 17 | A H P A T N T K V D K T V A P S T C S K |
| 60 | cccacgtgcccacccctgaactcctggggggaccgtctgtcttcatcttccccccaaaa |
| 17 | P T C P P P E L L G G P S V F I F P P K |
| 60 | cccaaggacacccatgatctcacgcaccccgaggtcacatgcgtggtggtggacgtg |
| 17 | P K D T L M I S R T P E V T C V V V D V |
| 60 | agccaggatgaccccgaggtgcagttcacatggtacataaacaacgagcaggtgcgcacc |
| 17 | S Q D D P E V Q F T W Y I N N E Q V R T |
| 60 | gccggccgctacggagcagcagttcaacagcacgatccgcgtggtcagcacctc |
| 17 | A R P P L R E Q Q F N S T I R V V S T L |
| 60 | ccatcgcgcaccaggactggctgagggcaaggagttcaagtgcaaagtccacaacaag |

FIG. 6 (CONTINUED)

| SEQ ID NO | |
|---|---|
| 17 | P I A H Q D W L R G K E F K C K V H N K |
| 60 | gcactcccggccccatcgagaaaaccatctccaaagccagagggcagccctggagcc |
| 17 | A L P A P I E K T I S K A R G Q P L E P |
| 60 | aaggtctacaccatgggccctccccggggagctgagcagcaggtcggtcagcctgacc |
| 17 | K V Y T M G P P R E L S S R S V S L T |
| 60 | tgcatgatcaacggcttctacccttccgacatctcggtggagtgggagaagaacgggaag |
| 17 | C M I N G F Y P S D I S V E W E K N G K |
| 60 | gcagaggacaactacaagaccacgccggccgtgctggacagcgacggctcctacttcctc |
| 17 | A E D N Y K T T P A V L D S D G S Y F L |
| 60 | tacagcaagctctcagtgcccacgagtgagtggcagcggggcgacgtcttcacctgctcc |
| 17 | Y S K L S V P T S E W Q R G D V F T C S |
| 60 | gtgatgcacgaggccttgcacaaccactacacgcagaagtccatctcccgctctccgggt |
| 17 | V M H E A L H N H Y T Q K S I S R S P G |
| 60 | aaatga |
| 17 | K - |

FIG. 6 (CONTINUED)

| SEQ ID NO | Anti-ID epitope Monoclonal 1D-37-10 light-chain coding sequence: |
|---|---|
| 61 | atggacacgagggccccactcagctgctggggctcctgctgctctggctcccaggtgcc |
| 18 | M D T R A P T Q L L G L L L L W L P G A |
| 61 | agatgtgccgaagtagtgatgacccagactccagcctccatggaggcacctatgggaggc |
| 18 | R C A E V V M T Q T P A S M E A P M G G |
| 61 | acagtcaccatcaagtgccaggccagtcagaacatttacaactacttatcctggtatcag |
| 18 | T V T I K C Q A S Q N I Y N Y L S W Y Q |
| 61 | cagaaaccagggcagcctcccaagctcctagtctacaaggcctccactctgacttctggg |
| 18 | Q K P G Q P P K L L V Y K A S T L T S G |
| 61 | gtcccgtcgcgcttcaaaggcagtggatctgggacacagttcactctcaccatcagcgac |
| 18 | V P S R F K G S G S G T Q F T L T I S D |
| 61 | ctggagtgtgccgatgctgccacttactactgtcaaatcaattactctatttataatcat |
| 18 | L E C A D A A T Y Y C Q I N Y S I Y N H |
| 61 | tataatattattttggcggagggaccgaggtggtcgtcaagggtgatccagttgcacct |
| 18 | Y N I I F G G G T E V V V K G D P V A P |
| 61 | actgtcctcatcttcccaccatctgctgatcttgtggcaactggaacagtcaccatcgtg |
| 18 | T V L I F P P S A D L V A T G T V T I V |
| 61 | tgtgtggcgaataaatactttcccgatgtcaccgtcacctgggaggtggatggcaccacc |
| 18 | C V A N K Y F P D V T V T W E V D G T T |
| 61 | caaacaactggcatcgagaacagtaaaacaccgcagaattctgcagattgtacctacaac |
| 18 | Q T T G I E N S K T P Q N S A D C T Y N |
| 61 | ctcagcagcactctgacactgaccagcacacagtacaacagccacaaagagtacacctgc |
| 18 | L S S T L T L T S T Q Y N S H K E Y T C |
| 61 | aaggtgacccagggcacgacctcagtcgtccagagcttcaataggggtgactgttag |
| 18 | K V T Q G T T S V V Q S F N R G D C - |

FIG. 7

| SEQ ID NO | Anti-1F epitope Monoclonal 1F-26-1 heavy chain coding sequence: |
|---|---|
| 68 | atggagactgggctgcgctggcttctcctggtcgctgtgctcaaaggtgtccagtgtcag |
| 25 | M E T G L R W L L L V A V L K G V Q C Q |
| 68 | tcggtgaaggagtccgagggaggtctcttcaagccaacggatatcctgacactcacctgc |
| 25 | S V K E S E G G L F K P T D I L T L T C |
| 68 | acagtctctggattctccctcagtagctatggagtgacctggggtccgccaggctccaggg |
| 25 | T V S G F S <u>L S S Y G V T</u> W V R Q A P G |
| 68 | aacgggctggagtggatcggattgattggtgatcgtggtactacgttctacgcgagctgg |
| 25 | N G L E W I G <u>L I G D R G T T F Y A S W</u> |
| 68 | gcgaaaagccgatcaccatcaccagaaacaccaacctgaacacggtgactctgaaaatg |
| 25 | <u>A K S</u> R S I I T R N T N L N T V T L K M |
| 68 | accaggctgacagccgcggacacggccacctatttctgtgcgaggggggagtgggtatggt |
| 25 | T R L T A A D T A T Y F C A R <u>G S G Y G</u> |
| 68 | gctcgcatctggggcccaggcaccctggtcaccgtctcctcatggcaacctaaggctcca |
| 25 | <u>A R I</u> W G P G T L V T V S S W Q P K A P |
| 68 | tcagtcttcccactggcccctgctgcggggacacaccagctccacggtgaccctgggc |
| 25 | S V F P L A P C C G D T P S S T V T L G |
| 68 | tgcctggtcaagggctacctcccggagccagtgactgtgacctggaactcgggcaccctc |
| 25 | C L V K G Y L P E P V T V T W N S G T L |
| 68 | accaatggggtacgcaccttcccgtccgtccggcagtcctcaggcctctactcgctgagc |
| 25 | T N G V R T F P S V R Q S S G L Y S L S |
| 68 | agcgtggtgagcgtgaccctcaagcagcagccgtcacctgcaacgtggcccaccagcc |
| 25 | S V V S V T S S Q P V T C N V A H P A |

FIG. 8

| SEQ ID NO | |
|---|---|
| 68 | accaacaccaaagtggacaagaccgttgcgcctcgacatgcagcaagcccacgtgcca |
| 25 | T N T K V D K T V A P S T C S K P T C P |
| 68 | ccctgaactcctgggggaccgtctgtcttcatcttccccccaaaacccaaggacacc |
| 25 | P P E L L G P S V F I F P P K P K D T |
| 68 | ctcatgatctcacgcacccccgaggtcacatgcgtggtggtggacgtgagccaggatgac |
| 25 | L M I S R T P E V T C V V V D V S Q D D |
| 68 | cccgaggtgcagttcacatggtacataaacaacgagcaggtggcaccgccggccgcg |
| 25 | P E V Q F T W Y I N N E Q V R T A R P P |
| 68 | ctacggggagcagcagttcaacagcacgatccgcgtggtcagcaccctccccatcgcgcac |
| 25 | L R E Q Q F N S T I R V V S T L P I A H |
| 68 | caggactggctgaggggcaaggagttcaagtgcaaagtccacaacaaggcactcccggcc |
| 25 | Q D W L R G K E F K C K V H N K A L P A |
| 68 | cccatcgagaaaaccatctccaaagccagagggcagcccctggagccgaaggtctacacc |
| 25 | P I E K T I S K A R G Q P L E P K V Y T |
| 68 | atgggcccctcccgggaggagctgagcagcaggtcggtcagcctgacctgcatgatcaac |
| 25 | M G P P R E E L S S R S V S L T C M I N |
| 68 | ggcttctaccctccgacatctcggtggagtgggagaagaacgggaaggcagaggacaac |
| 25 | G F Y P S D I S V E W E K N G K A E D N |
| 68 | tacaagaccacgccggccgtgctggacagcgacggctcctacttcctctacagcaagctc |
| 25 | Y K T T P A V L D S D G S Y F L Y S K L |
| 68 | tcagtgcccacgagtgagtggcagcggggcgacgtcttcacctgctccgtgatgcacgag |
| 25 | S V P T S E W Q R G D V F T C S V M H E |
| 68 | gccttgcacaaccactacacgcagaagtccatctcccgctctccgggtaaatga |
| 25 | A L H N H Y T Q K S I S R S P G K - |

FIG. 8 (CONTINUED)

| SEQ ID NO | Anti-1F epitope Monoclonal 1F-26-1 light-chain coding sequence: |
|---|---|
| 69 | atggacacgagggcccccactcagctcctggggctcctgctgctctggctcccaggtgcc |
| 26 | M D T R A P T Q L L G L L L L W L P G A |
| 69 | acatttgcccaagtgctgacccagactccatcgcctgtgtctgcagctgtgggaggcaca |
| 26 | T F A Q V L T Q T P S P V S A A V G G T |
| 69 | gtcaccatcaattgccagtccagtcagagtgtttataagaacaactacttagcctggtat |
| 26 | V T I N C Q S <u>S Q S V Y K N N Y L A</u> W Y |
| 69 | cagcagaaaccagggcagcctcccaagctcctatctacgaaacatccaaactggcatct |
| 26 | Q Q K P G Q P P K L L I Y <u>E T S K L A S</u> |
| 69 | ggggtcccacgcggttcagcggcagtgggtctgggacacagttcactctcaccatcagc |
| 26 | G V P R F S G S G S G T Q F T L T I S |
| 69 | agcgtgcagtgtgacgatgctgccacttactactgtcaaggcggttatagtggtgttgat |
| 26 | S V Q C D D A A T Y Y C <u>Q G G Y S G V D</u> |
| 69 | tttatggcttttggcggagggaccgaggtggtcgtcaaaggtgatccagttgcacctact |
| 26 | <u>F M A</u> F G G G T E V V V K G D P V A P T |
| 69 | gtcctcatcttcccaccatctgctgatcttgtggcaactggaacagtcaccatcgtgtgt |
| 26 | V L I F P P S A D L V A T G T V T I V C |
| 69 | gtggcgaataaatactttcccgatgtcaccgtcacctgggaggtggatggcaccacccaa |
| 26 | V A N K Y F P D V T V T W E V D G T T Q |
| 69 | acaactggcatcgagaacagtaaaacaccgcagaattctgcagattgtacctacaacctc |
| 26 | T T G I E N S K T P Q N S A D C T Y N L |
| 69 | agcagcactctgacactgaccagcacacagtacaacagccacaaagagtacacctgcaag |
| 26 | S S T L T L T S T Q Y N S H K E Y T C K |
| 69 | gtgacccagggcacgaccctcagtcgtccagagcttcaataggggtgactgttag |
| 26 | V T Q G T T S V V Q S F N R G D - |

FIG. 9

| SEQ ID NO | Anti-1F epitope Monoclonal 1F-42-7 heavy-chain coding sequence: |
|---|---|
| 76 | atggagactgggctgcgctggcttctcctggtcgctgtgctcaaaggtgtccagtgtcag |
| 33 | M E T G L R W L L L V A V L K G V Q C Q |
| 76 | tcggtgaaggagtccgagggaggtctcttcaagccaacggataccctgacactcacctgc |
| 33 | S V K E S E G G L F K P T D T L T L T C |
| 76 | acagtctctggattctccctcactacctatggagtgacctgggtccgccaggctccaggg |
| 33 | T V S G F S <u>L T T Y G V T</u> W V R Q A P G |
| 76 | aatgggctggagtggatcggattgattggtgatcgcggtaccacttactacgcgagctgg |
| 33 | N G L E W I G <u>L I G D R G T T Y Y A S W</u> |
| 76 | gtgaatggccgatccaccatcaccagaaacaccaacctgaacacggtgactctgaaaatg |
| 33 | <u>V N G</u> R S T I T R N T N L N T V T L K M |
| 76 | accaggctgacagccgcggacacggccacctatttctgtgcgagggggagtggatatggt |
| 33 | T R L T A A D T A T Y F C A R <u>G S G Y G</u> |
| 76 | gctcgcatctggggcccaggcaccctggtcaccgtcgcctcatggcaacctaaggctcca |
| 33 | <u>A R I</u> W G P G T L V T V A S W Q P K A P |
| 76 | tcagtcttcccactggcccctgctgcggggacacccagctccacggtgaccctgggc |
| 33 | S V F P L A P C C G D T P S S T V T L G |
| 76 | tgcctggtcaaagggtacctcccggagccagtgaccgtgacctggaactcgggcaccctc |
| 33 | C L V K G Y L P E P V T V T W N S G T L |
| 76 | accaatggggtacgcaccttcccgtcgtcggcagtcctcaggctctactcgctgagc |
| 33 | T N G V R T F P S V R Q S S G L Y S L |
| 76 | agcgtggtgagcgtgacctcaagcagccagcccgtcacctgcaacgtggcccaccagcc |
| 33 | S V V S V T S S S Q P V T C N V A H P A |
| 76 | accaacaccaaagtggacaagaccgttgcgccctcgacatgcagcaagcccacgtgccca |
| 33 | T N T K V D K T V A P S T C S K P T C P |

FIG. 10

| SEQ ID NO | |
|---|---|
| 76 | ccccctgaactcctggggggaccgtctgtcttcatcttcccccaaaacccaaggacacc |
| 33 | P P E L L G G P S V F I F P P K P K D T |
| 76 | ctcatgatctcacgcaccccgaggtcacatgcgtggtggtggacgtgagccaggatgac |
| 33 | L M I S R T P E V T C V V V D V S Q D D |
| 76 | cccgaggtgcagttcacatggtacataaacaacgagcaggtgcgcaccgcccggccgcg |
| 33 | P E V Q F T W Y I N N E Q V R T A R P P |
| 76 | ctacgggagcagcagttcaacagcacgatccgcgtggtcagcacccTccccatcgcgcac |
| 33 | L R E Q Q F N S T I R V V S T L P I A H |
| 76 | caggactggctgaggggcaaggagttcaagtgcaaagtccacaacaaggcactcccggcc |
| 33 | Q D W L R G K E F K C K V H N K A L P A |
| 76 | cccatcgagaaaaccatctccaaagccagagggcagccctggagccgaaggtctacacc |
| 33 | P I E K T I S K A R G Q P L E P K V Y T |
| 76 | atgggccctccccggggaggagctgagcagcaggtcggtcagcctgacctgcatgatcaac |
| 33 | M G P P R E E L S S R S V S L T C M I N |
| 76 | ggcttctacccttccgacatctcggtggagtgggagaagaacgggaaggcagaggacaac |
| 33 | G F Y P S D I S V E W E K N G K A E D N |
| 76 | tacaagaccacgccggccgtgctggacagcgacggctcctacttcctctacagcaagctc |
| 33 | Y K T T P A V L D S D G S Y F L Y S K L |
| 76 | tcagtgcccacgagtgagtggcagcggggcgacgtcttcacctgctccgtgatgcacgag |
| 33 | S V P T S E W Q R G D V F T C S V M H E |
| 76 | gccttgcacaaccactacacgcagaagtccatctcccgctctccgggtaaatga |
| 33 | A L H N H Y T Q K S I S R S P G K - |

FIG. 10 (CONTINUED)

| SEQ ID NO | Anti-1F epitope Monoclonal 1F-42-7 light-chain coding sequence: |
|---|---|
| 77 | atggacacgagggcccccactcagctcctggggctcctgctgctctggctcccaggtgcc |
| 34 | M D T R A P T Q L L G L L L L W L P G A |
| 77 | acatttgcccaagtgctgacccagactccatcccccatgtctgcagctctgggaggcaca |
| 34 | T F A Q V L T Q T P S P M S A A L G G T |
| 77 | gtcaccatcaattgccagtccagtcagactgtttataacaataactacttatcctggtat |
| 34 | V T I N C Q S <u>S Q T V Y N N N Y L S</u> W Y |
| 77 | cagcagaaaccagggcagcctcccaagctcctttatctacgaaacatccaaactgtcatct |
| 34 | Q Q K P G Q P P K L L I Y <u>R T S K L S S</u> |
| 77 | ggggtcccacggcggttcagcggcagtgggtctgggacacagttcactctcaccatcagc |
| 34 | G V P R R F S G S G S G T Q F T L T I S |
| 77 | agcgtgcagtgtgacgatgctgccacttactactgtcaaggcggttatagtggtgttgat |
| 34 | S V Q C D D A A T Y Y C Q <u>G G Y S G V D</u> |
| 77 | tttatggctttcggcggagggaccgaggtggtcgtcaaaggtgatccagttgcacctact |
| 34 | <u>F M A</u> F G G G T E V V V K G D P V A P T |
| 77 | gtcctcatcttcccaccatctgctgatcttgtggcaactggaacagtcaccatcgtgtgt |
| 34 | V L I F P P S A D L V A T G T V T I V C |
| 77 | gtggcgaataaatactttccgatgtcaacgtcacctgggaggtggatggcaccacccaa |
| 34 | V A N K Y F P M S T S P G R W M A P P K |
| 77 | acaactggcatcgagaacagtaaaacaccgcagaattctgcagattgtacctacaacctc |
| 34 | T T G I E N S K T P Q N S A D C T Y N L |
| 77 | agcagcactctgacactgaccagcacaacagtacaacagccacaaagagtacacctgcaag |
| 34 | S S T L T L T S T T V Q Q P Q R V H L K |
| 77 | gtgacccagggcacgaccctcagtcgtccagagcttcaataggggtgactgttag |
| 34 | V T Q G T T L S R P E L Q * G * L * |

FIG. 11

| SEQ ID NO | Anti-renalase-2 epitope Monoclonal 3A-5-2 heavy-chain coding sequence: |
|---|---|
| 84 | atggagactgggctgcgctggcttctcctggtcgctgtgctcaaaggtgtccagtgtcag |
| 41 | M E T G L R W L L L V A V L K G V Q C Q |
| 84 | tcgctggaggagtccggggggtcgcctggtcacgcctgggacaccctgacactcacctgc |
| 41 | S L E E S G G R L V T P G T P L T L T C |
| 84 | acagtctctggattctccctcaataactaccacatatactgggtccgccaggctccagga |
| 41 | T V S G F S <u>L N N Y H I Y</u> W V R Q A P G |
| 84 | aaggggctggaatacatcggaatcatttcaatggtggcacatattacgcgagatggaca | 
| 41 | K G L E Y I G <u>I I F N G G T Y Y A R W T</u> |
| 84 | aaaggccgattcaccatctccaaaacctcgaccacggtggatctgaaaatgaccagtctg |
| 41 | <u>K G</u> R F T I S K T S T T V D L K M T S L |
| 84 | acaaccgaggacacggccacctatttctgtgccagaggggacggcatctgggggcccaggc |
| 41 | T T E D T A T Y F C A R <u>G D G I</u> W G P G |
| 84 | accctggtcaccgtctccttagggcaacctaaggctccatcagtcttcccactggcccc |
| 41 | T L V T V S L G Q P K A P S V F P L A P |
| 84 | tgctgcggggacacacccagctccacggtgaccctgggctgcctggtcaaagggtacctc |
| 41 | C C G D T P S S T V T L G C L V K G Y L |

FIG. 12

| SEQ ID NO | |
|---|---|
| 84 | ccgagccagtgaccgtgacctggaactcgggcacctcaccaatgggtacgcacctc |
| 41 | P E P V T V T W N S G T L T N G V R T F |
| 84 | ccgtccgtccggcagtcctcaggcctctactcgctgagcagcgtggtgagcgtgacctca |
| 41 | P S V R Q S S G L Y S L S S V V S V T S |
| 84 | agcagccagcccgtcacctgcaacgtggccacccagccaccaacaccaagtggacaag |
| 41 | S S Q P V T C N V A H P A T N T K V D K |
| 84 | accgttgagcccctcgacatgcagcaagccaacgtgccaccccctgaactcctggggga |
| 41 | T V E P S C S K P T C P P P E L L G G |
| 84 | ccgtcctgtcttcatcttccccccaaaacccaaggacaccctcatgatctcacggacccc |
| 41 | P S V F I F P P K P K D T L M I S R T P |
| 84 | gaggtcacatgcgtggtggtggacgtgagccaggatgaccccgaggtgcagttcacatgg |
| 41 | E V T C V V V D V S Q D D P E V Q F T W |
| 84 | tacataaacaacgagcaggtgcgcacgcccgcgccgtacgggagcagcagttcaac |
| 41 | Y I N N E Q V R T A R P P L R E Q Q F N |
| 84 | agcacgatccgcgtggtcagcaccctccccatcgcgcaccaggactggctgaggggcaag |
| 41 | S T I R V V S T L P I A H Q D W L R G K |

FIG. 12 (CONTINUED)

| SEQ ID NO | |
|---|---|
| 84 | gagttcaagtgcaaagtccacaacaaggcactcccggcccccatcgagaaaaccatctcc |
| 41 | E F K C K V H N K A L P A P I E K T I S |
| 84 | aaagccagagggcagcccctggagccgaaggtctacaccatgggccctcccggggaggag |
| 41 | K A R G Q P L E P K V Y T M G P P R E E |
| 84 | ctgagcagcaggtcggtcagcctgacctgcatgatcaacggcttctaccccttcgacatc |
| 41 | L S S R S V S L T C M I N G F Y P S D I |
| 84 | tcggtggagtggagaagaacgggaaggcagaggacaactacaagaccacgcctgccgtg |
| 41 | S V E W R K N G K A E D N Y K T T P A V |
| 84 | ctggacagcgacggctcctacttcctctacagcaagctctcagtgcccacgagtgagtgg |
| 41 | L D S D G S Y F L Y S K L S V P T S E W |
| 84 | cagcggggcgacgtcttcacctgctccgtgatgcacgaggccttgcacaaccactacacg |
| 41 | Q R G D V F T C S V M H E A L H N H Y T |
| 84 | cagaagtccatctcccgctctccgggtaaatga |
| 41 | Q K S I S R S P G K - |

FIG. 12 (CONTINUED)

| SEQ ID NO | Anti-renalase-2 epitope Monoclonal 3A-5-2 light-chain coding sequence: |
|---|---|
| 85 | atggacacgagggccccactcagctgctggggctcctgctgctctggctcccaggtgcc |
| 42 | M D T R A P T Q L L G L L L L W L P G A |
| 85 | acatttgcccaagtgctgacccagactccagcctccgtgtctgcagctgtgggaggcaca |
| 42 | T F A Q V L T Q T P A S V S A A V G G T |
| 85 | gtcaccatcaattgccaggcaagtcagagtgttttaataacaactatttagcctggtat |
| 42 | V T I N C Q A <u>S Q S V F N N Y L A</u> W Y |
| 85 | cagcagaaaccagggcagcctcccaagcgcctgatctattctgcatccactctggcgtct |
| 42 | Q Q K P G Q P P K R L I Y <u>S A S T L A S</u> |
| 85 | ggggtctcatcgcggttcaaaggcagtggatctgggacagaattcactctgaccatgagt |
| 42 | G V S S R F K G S G S G T E F T L T M S |
| 85 | ggcgtggagtgtgacgatgctgccacttactactgtgcaggcagttttgattgtaatagt |
| 42 | G V E C D D A A T Y Y C <u>A G S F D C N S</u> |
| 85 | ggtgattgtgttgcttcggcggagggaccgaggtggtggtcaagggtgatccagttgca |
| 42 | <u>G D C V A</u> F G S G T E V V V K G D P V A |
| 85 | cctactgtcctcatcttcccaccagctgctgatcaggtggcaactggaacagtcaccatc |
| 42 | P T V L I F P P A A D Q V A T G T V T I |
| 85 | gtgtgtgtggcgaataaatactttcccgatgtcaccgtcacctgggaggtggatggcacc |
| 42 | V C V A N K Y F P D V T V T W E V D G T |
| 85 | acccaaacaactggcatcgagaacagtaaaacaccgcagaattctgcagattgtacctac |
| 42 | T Q T T G I E N S K T P Q N S A D C T Y |
| 85 | aacctcagcagcactctgacactgaccagcacacagtacaacagccacaaagagtacacc |
| 42 | N L S S T L T L T S T Q Y N S H K E Y T |
| 85 | tgcaaggtgacccagggcacgacctcagtcgtccagagcttcaataggggtgactgttag |
| 42 | C K V T Q G T T S V V Q S F N R G D C - |

FIG. 13

Antibodies raised against a renalase-2 peptide are specific for renalase-2 in ELISA
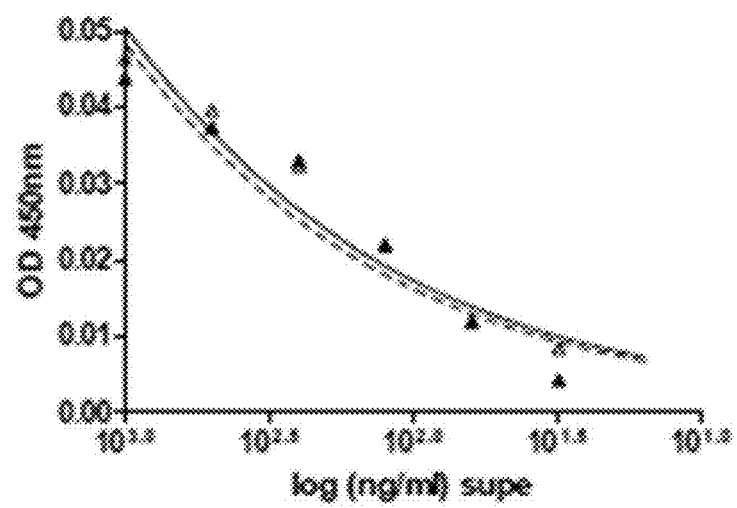
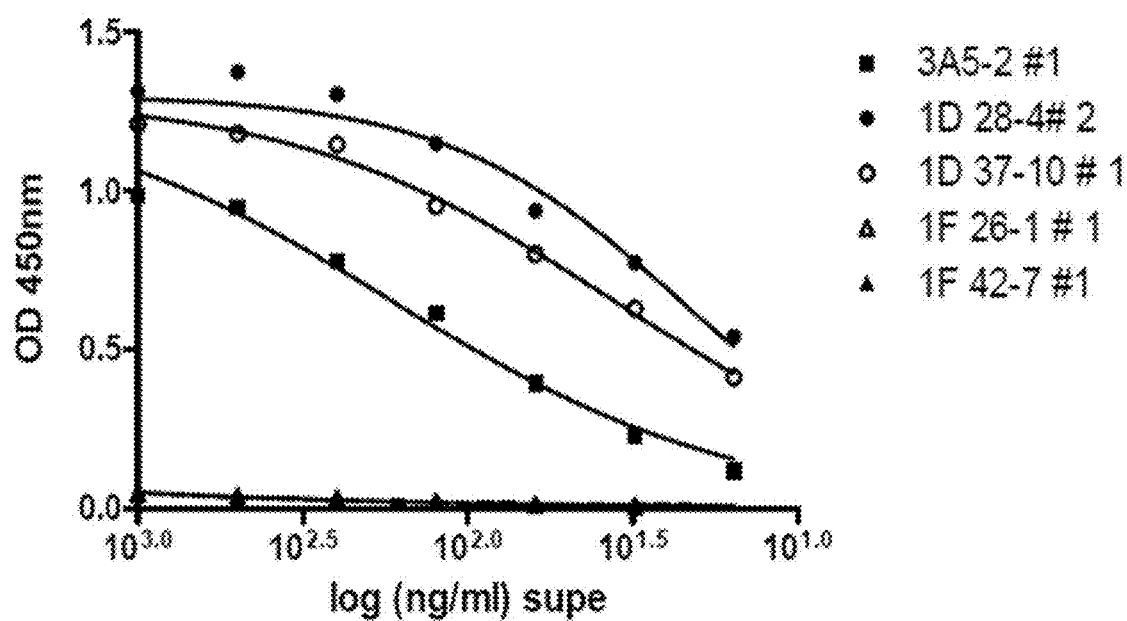
FIG. 17

Overlapping epitopes can be detected by competition ELISA.

Summary of Anti-renalase Antibody Binding affinity.

| IgG | ka (M-1s-1) | kd (s-1) | KD (nM) |
|---|---|---|---|
| Bio-1D 28-4 | 6.467(4)e4 | 2.04(3)e-5 | 0.316(5) |
| Bio-1F 42-7 | 3.928(5)e4 | 9.47(6)e-5 | 2.41(2) |
| Bio-1D 37-10 | 1.749(5)e4 | 4.67(4)e-5 | 2.67(3) |
| Bio-1F 26-1 | 4.526(8)e4 | 1.020(9)e-4 | 2.25(2) |

FIG. 22

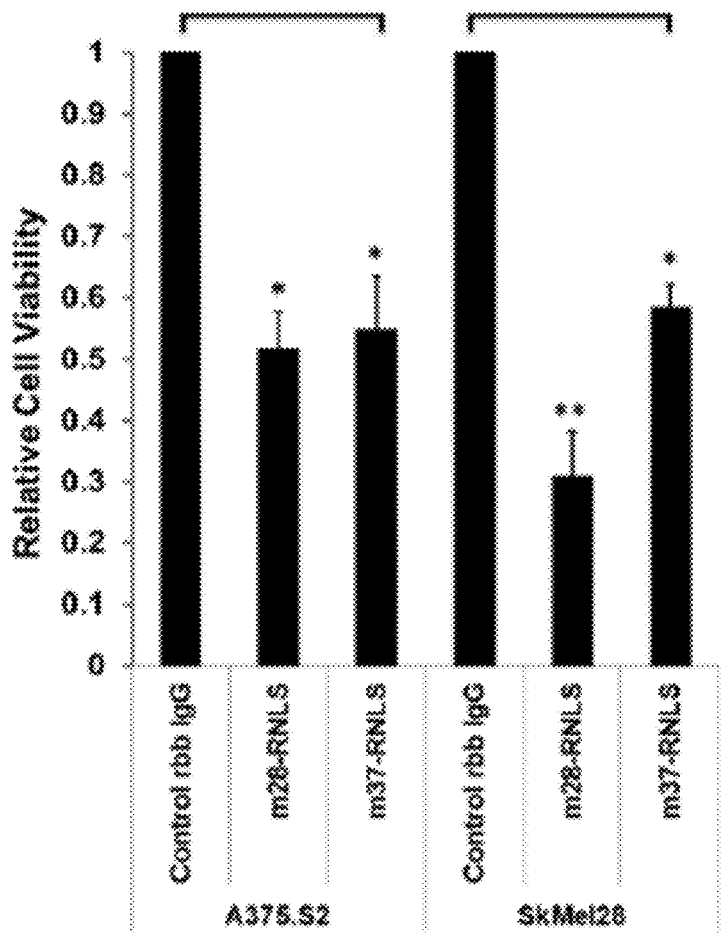
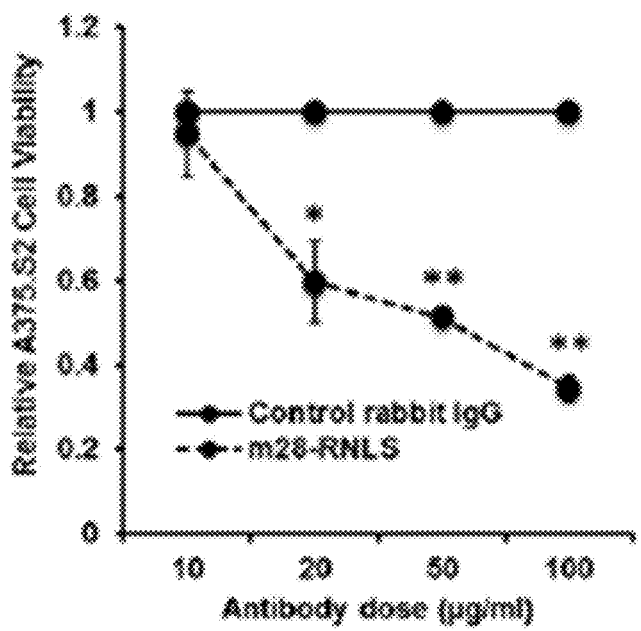
FIG. 24

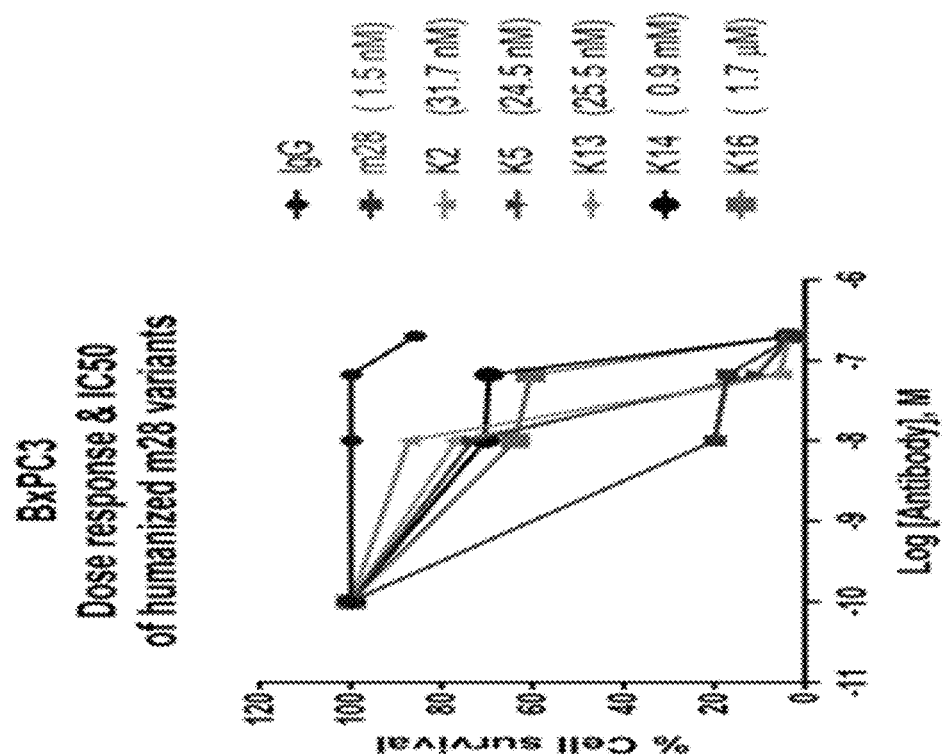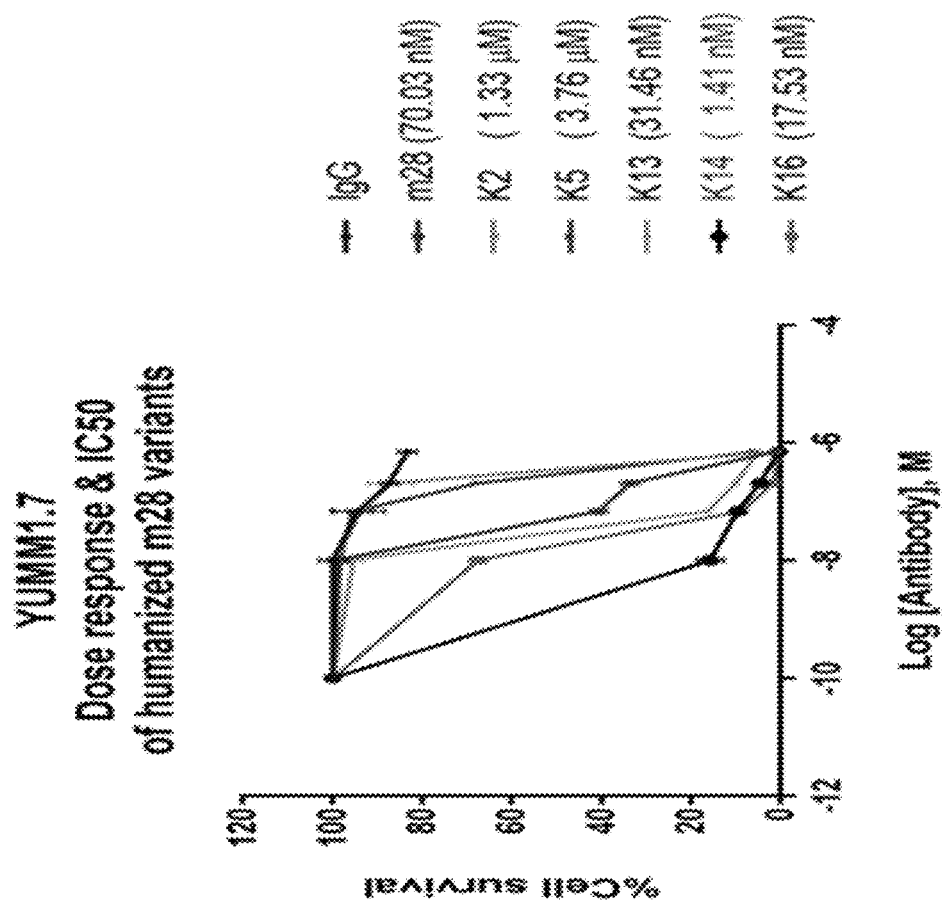
FIG. 36

SEQUENCE LISTING

```
<160> NUMBER OF SEQ ID NOS: 231

<210> SEQ ID NO 1
<211> LENGTH: 17
<212> TYPE: PRT
<213> ORGANISM: Artificial Sequence
<220> FEATURE:
<223> OTHER INFORMATION: Chemically Synthesized, antigen seq 1a

<400> SEQUENCE: 1

Ala Val Trp Asp Lys Ala Asp Asp Ser Gly Gly Arg Met Thr Thr Ala
1               5                   10                  15

Cys

<210> SEQ ID NO 2
<211> LENGTH: 17
<212> TYPE: PRT
<213> ORGANISM: Artificial Sequence
<220> FEATURE:
<223> OTHER INFORMATION: Chemically Synthesized, antigen seq 1b

<400> SEQUENCE: 2

Ala Val Trp Asp Lys Ala Glu Asp Ser Gly Gly Arg Met Thr Thr Ala
1               5                   10                  15

Cys
```

-continued

```
<210> SEQ ID NO 3
<211> LENGTH: 16
<212> TYPE: PRT
<213> ORGANISM: Artificial Sequence
<220> FEATURE:
<223> OTHER INFORMATION: Chemically Synthesized, antigen seq 1c

<400> SEQUENCE: 3

Cys Thr Pro His Tyr Ala Lys Lys His Gln Arg Phe Tyr Asp Glu Leu
1               5                   10                  15

<210> SEQ ID NO 4
<211> LENGTH: 21
<212> TYPE: PRT
<213> ORGANISM: Artificial Sequence
<220> FEATURE:
<223> OTHER INFORMATION: Chemically Synthesized, antigen seq 1d

<400> SEQUENCE: 4

Cys Ile Arg Phe Val Ser Ile Asp Asn Lys Lys Arg Asn Ile Glu Ser
1               5                   10                  15

Ser Glu Ile Gly Pro
            20

<210> SEQ ID NO 5
<211> LENGTH: 14
<212> TYPE: PRT
<213> ORGANISM: Artificial Sequence
<220> FEATURE:
<223> OTHER INFORMATION: Chemically Synthesized, antigen seq 1e

<400> SEQUENCE: 5

Pro Gly Gln Met Thr Leu His His Lys Pro Phe Leu Ala Cys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Chemically Synthesized, antigen seq 1f

<400> SEQUENCE: 6

Cys Val Leu Glu Ala Leu Lys Asn Tyr Ile
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Chemically Synthesized, antigen seq 3a

<400> SEQUENCE: 7

Pro Ser Ala Gly Val Ile Leu Gly Cys
1               5

<210> SEQ ID NO 8
<211> LENGTH: 342
<212> TYPE: PRT
<213> ORGANISM: Artificial Sequence
<220> FEATURE:
<223> OTHER INFORMATION: Hu Renalase-1 protein - polymorphism resulting
      in the highlighted glutamate amino acid at position 37

<400> SEQUENCE: 8

Met Ala Gln Val Leu Ile Val Gly Ala Gly Met Thr Gly Ser Leu Cys
```

```
                1               5                       10                      15
            Ala Ala Leu Leu Arg Arg Gln Thr Ser Gly Pro Leu Tyr Leu Ala Val
                        20                  25                  30

Trp Asp Lys Ala Glu Asp Ser Gly Gly Arg Met Thr Thr Ala Cys Ser
                        35                  40                  45

Pro His Asn Pro Gln Cys Thr Ala Asp Leu Gly Ala Gln Tyr Ile Thr
                        50                  55                  60

Cys Thr Pro His Tyr Ala Lys Lys His Gln Arg Phe Tyr Asp Glu Leu
             65                  70                  75                  80

Leu Ala Tyr Gly Val Leu Arg Pro Leu Ser Ser Pro Ile Glu Gly Met
                                85                  90                  95

Val Met Lys Glu Gly Asp Cys Asn Phe Val Ala Pro Gln Gly Ile Ser
                        100                 105                 110

Ser Ile Ile Lys His Tyr Leu Lys Glu Ser Gly Ala Glu Val Tyr Phe
                        115                 120                 125

Arg His Arg Val Thr Gln Ile Asn Leu Arg Asp Asp Lys Trp Glu Val
                        130                 135                 140

Ser Lys Gln Thr Gly Ser Pro Glu Gln Phe Asp Leu Ile Val Leu Thr
            145                 150                 155                 160

Met Pro Val Pro Glu Ile Leu Gln Leu Gln Gly Asp Ile Thr Thr Leu
                        165                 170                 175

Ile Ser Glu Cys Gln Arg Gln Gln Leu Glu Ala Val Ser Tyr Ser Ser
                        180                 185                 190

Arg Tyr Ala Leu Gly Leu Phe Tyr Glu Ala Gly Thr Lys Ile Asp Val
                        195                 200                 205

Pro Trp Ala Gly Gln Tyr Ile Thr Ser Asn Pro Cys Ile Arg Phe Val
                        210                 215                 220

Ser Ile Asp Asn Lys Lys Arg Asn Ile Glu Ser Ser Glu Ile Gly Pro
            225                 230                 235                 240

Ser Leu Val Ile His Thr Thr Val Pro Phe Gly Val Thr Tyr Leu Glu
                        245                 250                 255

His Ser Ile Glu Asp Val Gln Glu Leu Val Phe Gln Gln Leu Glu Asn
                        260                 265                 270

Ile Leu Pro Gly Leu Pro Gln Pro Ile Ala Thr Lys Cys Gln Lys Trp
                        275                 280                 285

Arg His Ser Gln Val Thr Asn Ala Ala Ala Asn Cys Pro Gly Gln Met
                        290                 295                 300

Thr Leu His His Lys Pro Phe Leu Ala Cys Gly Gly Asp Gly Phe Thr
            305                 310                 315                 320

Gln Ser Asn Phe Asp Gly Cys Ile Thr Ser Ala Leu Cys Val Leu Glu
                        325                 330                 335

Ala Leu Lys Asn Tyr Ile
                        340

<210> SEQ ID NO 9
<211> LENGTH: 459
<212> TYPE: PRT
<213> ORGANISM: Artificial Sequence
<220> FEATURE:
<223> OTHER INFORMATION: Chemically Synthesized, mAb 1D-28-4 full length
      heavy chain amino acid

<400> SEQUENCE: 9

Met Glu Thr Gly Leu Arg Trp Leu Leu Leu Val Ala Val Leu Lys Gly
 1               5                  10                  15
```

-continued

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Phe Ala Val Gly Trp Val Arg Gln Ala Pro Gly Lys Gly Leu Glu
    50                  55                  60

Tyr Ile Gly Ile Ile Ser Ser Val Gly Ile Thr Arg Tyr Ala Ser Trp
65                  70                  75                  80

Ala Ala Gly Arg Phe Thr Ile Ser Lys Thr Ser Thr Val Asp Leu
                85                  90                  95

Lys Ile Thr Ser Pro Thr Thr Glu Asp Thr Ala Thr Tyr Phe Cys Ala
            100                 105                 110

Arg Tyr Gly Tyr Ser Gly Asp Val Asn Arg Leu Asp Leu Trp Gly Gln
        115                 120                 125

Gly Thr Leu Val Thr Val Ser Ser Gly Gln Pro Lys Ala Pro Ser Val
    130                 135                 140

Phe Pro Leu Ala Pro Cys Cys Gly Asp Thr Pro Ser Ser Thr Val Thr
145                 150                 155                 160

Leu Gly Cys Leu Val Lys Gly Tyr Leu Pro Glu Pro Val Thr Val Thr
                165                 170                 175

Trp Asn Ser Gly Thr Leu Thr Asn Gly Val Arg Thr Phe Pro Ser Val
            180                 185                 190

Arg Gln Ser Ser Gly Leu Tyr Ser Leu Ser Ser Val Val Ser Val Thr
        195                 200                 205

Ser Ser Ser Gln Pro Val Thr Cys Asn Val Ala His Pro Ala Thr Asn
210                 215                 220

Thr Lys Val Asp Lys Thr Val Ala Pro Ser Thr Cys Ser Lys Pro Thr
225                 230                 235                 240

Cys Pro Pro Pro Glu Leu Leu Gly Gly Pro Ser Val Phe Ile Phe Pro
                245                 250                 255

Pro Lys Pro Lys Asp Thr Leu Met Ile Ser Arg Thr Pro Glu Val Thr
        260                 265                 270

Cys Val Val Val Asp Val Ser Gln Asp Asp Pro Glu Val Gln Phe Thr
    275                 280                 285

Trp Tyr Ile Asn Asn Glu Gln Val Arg Thr Ala Arg Pro Pro Leu Arg
290                 295                 300

Glu Gln Gln Phe Asn Ser Thr Ile Arg Val Val Ser Thr Leu Pro Ile
305                 310                 315                 320

Ala His Gln Asp Trp Leu Arg Gly Lys Glu Phe Lys Cys Lys Val His
                325                 330                 335

Asn Lys Ala Leu Pro Ala Pro Ile Glu Lys Thr Ile Ser Lys Ala Arg
        340                 345                 350

Gly Gln Pro Leu Glu Pro Lys Val Tyr Thr Met Gly Pro Pro Arg Glu
    355                 360                 365

Glu Leu Ser Ser Arg Ser Val Ser Leu Thr Cys Met Ile Asn Gly Phe
370                 375                 380

Tyr Pro Ser Asp Ile Ser Val Glu Trp Glu Lys Asn Gly Lys Ala Glu
385                 390                 395                 400

Asp Asn Tyr Lys Thr Thr Pro Ala Val Leu Asp Ser Asp Gly Ser Tyr
                405                 410                 415

Phe Leu Tyr Ser Lys Leu Ser Val Pro Thr Ser Glu Trp Gln Arg Gly
        420                 425                 430

Asp Val Phe Thr Cys Ser Val Met His Glu Ala Leu His Asn His Tyr

```
                    435                 440                 445
Thr Gln Lys Ser Ile Ser Arg Ser Pro Gly Lys
    450                 455

<210> SEQ ID NO 10
<211> LENGTH: 239
<212> TYPE: PRT
<213> ORGANISM: Artificial Sequence
<220> FEATURE:
<223> OTHER INFORMATION: Chemically Synthesized, mAb 1D-28-4 full length
      light chain amino acid

<400> SEQUENCE: 10

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Pro
            20                  25                  30

Val Ser Ala Ala Val Gly Gly Thr Val Thr Ile Asn Cys Gln Ala Ser
        35                  40                  45

Gln Ser Val Tyr Asp Asn Asn Asn Leu Ala Trp Tyr Gln Gln Lys Pro
    50                  55                  60

Gly Gln Pro Pro Lys Gln Leu Ile Tyr Gly Ala Ser Thr Leu Ala Ser
65                  70                  75                  80

Gly Val Ser Ser Arg Phe Lys Gly Ser Gly Ser Gly Thr Gln Phe Thr
                85                  90                  95

Leu Thr Ile Ser Gly Val Gln Cys Asp Asp Ala Ala Thr Tyr Tyr Cys
            100                 105                 110

Leu Gly Glu Phe Ser Cys Ser Ser Ala Asp Cys Phe Ala Phe Gly Gly
        115                 120                 125

Gly Thr Glu Val Val Val Lys Gly Asp Pro Val Ala Pro Thr Val Leu
    130                 135                 140

Ile Phe Pro Pro Ser Ala Asp Leu Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235

<210> SEQ ID NO 11
<211> LENGTH: 7
<212> TYPE: PRT
<213> ORGANISM: Artificial Sequence
<220> FEATURE:
<223> OTHER INFORMATION: Chemically Synthesized, 1D-28-4 heavy chain
      CDR1 amino acid

<400> SEQUENCE: 11

Leu Ser Ser Phe Ala Val Gly
1               5

<210> SEQ ID NO 12
<211> LENGTH: 16
<212> TYPE: PRT
```

```
<213> ORGANISM: Artificial Sequence
<220> FEATURE:
<223> OTHER INFORMATION: Chemically Synthesized, 1D-28-4 heavy chain
      CDR2 amino acid

<400> SEQUENCE: 12

Ile Ile Ser Ser Val Gly Ile Thr Arg Tyr Ala Ser Trp Ala Ala Gly
1               5                   10                  15

<210> SEQ ID NO 13
<211> LENGTH: 12
<212> TYPE: PRT
<213> ORGANISM: Artificial Sequence
<220> FEATURE:
<223> OTHER INFORMATION: Chemically Synthesized, 1D-28-4 heavy chain
      CDR3 amino acid

<400> SEQUENCE: 13

Tyr Gly Tyr Ser Gly Asp Val Asn Arg Leu Asp Leu
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Chemically Synthesized, 1D-28-4 light chain
      CDR1 amino acid

<400> SEQUENCE: 14

Ser Gln Ser Val Tyr Asp Asn Asn Asn Leu Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Chemically Synthesized, 1D-28-4 light chain
      CDR2 amino acid

<400> SEQUENCE: 15

Gly Ala Ser Thr Leu Ala Ser
1               5

<210> SEQ ID NO 16
<211> LENGTH: 13
<212> TYPE: PRT
<213> ORGANISM: Artificial Sequence
<220> FEATURE:
<223> OTHER INFORMATION: Chemically Synthesized, 1D-28-4 light chain
      CDR3 amino acid

<400> SEQUENCE: 16

Leu Gly Glu Phe Ser Cys Ser Ser Ala Asp Cys Phe Ala
1               5                   10

<210> SEQ ID NO 17
<211> LENGTH: 461
<212> TYPE: PRT
<213> ORGANISM: Artificial Sequence
<220> FEATURE:
<223> OTHER INFORMATION: Chemically Synthesized, mAb 1D-37-10 full
      length heavy chain amino acid

<400> SEQUENCE: 17

Met Glu Thr Gly Leu Arg Trp Leu Leu Leu Val Ala Val Leu Lys Gly
1               5                   10                  15
```

-continued

Val Gln Cys Gln Ser Val Glu Glu Ser Gly Gly Arg Leu Val Thr Pro
              20                  25                  30
Gly Gly Ser Leu Thr Leu Thr Cys Thr Val Ser Gly Phe Ser Leu Ser
         35                  40                  45
Asp Tyr Ala Ile Ile Trp Val Arg Gln Ala Pro Gly Lys Gly Leu Glu
 50                  55                  60
Tyr Ile Ala Ile Ile Gly Ser Ser Gly Asp Thr Phe Tyr Ala Thr Trp
 65                  70                  75                  80
Ala Lys Gly Arg Phe Thr Ile Ser Lys Thr Ser Thr Thr Val Asp Leu
                 85                  90                  95
Lys Met Thr Ser Leu Thr Ala Ala Asp Thr Ala Thr Tyr Phe Cys Ala
             100                 105                 110
Pro Arg Tyr Ala Gly Thr Thr Asp Tyr His Asp Ala Phe Asp Pro Trp
             115                 120                 125
Gly Pro Gly Thr Leu Val Thr Val Ser Ser Gly Gln Pro Lys Ala Pro
 130                 135                 140
Ser Val Phe Pro Leu Ala Pro Cys Cys Gly Asp Thr Pro Ser Ser Thr
145                 150                 155                 160
Val Thr Leu Gly Cys Leu Val Lys Gly Tyr Leu Pro Glu Pro Val Thr
                 165                 170                 175
Val Thr Trp Asn Ser Gly Thr Leu Thr Asn Gly Val Arg Thr Phe Pro
             180                 185                 190
Ser Val Arg Gln Ser Ser Gly Leu Tyr Ser Leu Ser Ser Val Val Ser
             195                 200                 205
Val Thr Ser Ser Ser Gln Pro Val Thr Cys Asn Val Ala His Pro Ala
             210                 215                 220
Thr Asn Thr Lys Val Asp Lys Thr Val Ala Pro Ser Thr Cys Ser Lys
225                 230                 235                 240
Pro Thr Cys Pro Pro Pro Glu Leu Leu Gly Gly Pro Ser Val Phe Ile
                 245                 250                 255
Phe Pro Pro Lys Pro Lys Asp Thr Leu Met Ile Ser Arg Thr Pro Glu
             260                 265                 270
Val Thr Cys Val Val Val Asp Val Ser Gln Asp Asp Pro Glu Val Gln
             275                 280                 285
Phe Thr Trp Tyr Ile Asn Asn Glu Gln Val Arg Thr Ala Arg Pro Pro
             290                 295                 300
Leu Arg Glu Gln Gln Phe Asn Ser Thr Ile Arg Val Val Ser Thr Leu
305                 310                 315                 320
Pro Ile Ala His Gln Asp Trp Leu Arg Gly Lys Glu Phe Lys Cys Lys
                 325                 330                 335
Val His Asn Lys Ala Leu Pro Ala Pro Ile Glu Lys Thr Ile Ser Lys
             340                 345                 350
Ala Arg Gly Gln Pro Leu Glu Pro Lys Val Tyr Thr Met Gly Pro Pro
             355                 360                 365
Arg Glu Glu Leu Ser Ser Arg Ser Val Ser Leu Thr Cys Met Ile Asn
             370                 375                 380
Gly Phe Tyr Pro Ser Asp Ile Ser Val Glu Trp Glu Lys Asn Gly Lys
385                 390                 395                 400
Ala Glu Asp Asn Tyr Lys Thr Thr Pro Ala Val Leu Asp Ser Asp Gly
                 405                 410                 415
Ser Tyr Phe Leu Tyr Ser Lys Leu Ser Val Pro Thr Ser Glu Trp Gln
             420                 425                 430

Arg Gly Asp Val Phe Thr Cys Ser Val Met His Glu Ala Leu His Asn
            435                 440                 445

His Tyr Thr Gln Lys Ser Ile Ser Arg Ser Pro Gly Lys
    450                 455                 460

<210> SEQ ID NO 18
<211> LENGTH: 238
<212> TYPE: PRT
<213> ORGANISM: Artificial Sequence
<220> FEATURE:
<223> OTHER INFORMATION: Chemically Synthesized, mAb 1D-37-10 full
      length light chain amino acid

<400> SEQUENCE: 18

Met Asp Thr Arg Ala Pro Thr Gln Leu Leu Gly Leu Leu Leu Leu Trp
1               5                   10                  15

Leu Pro Gly Ala Arg Cys Ala Glu Val Val Met Thr Gln Thr Pro Ala
            20                  25                  30

Ser Met Glu Ala Pro Met Gly Gly Thr Val Thr Ile Lys Cys Gln Ala
        35                  40                  45

Ser Gln Asn Ile Tyr Asn Tyr Leu Ser Trp Tyr Gln Gln Lys Pro Gly
    50                  55                  60

Gln Pro Pro Lys Leu Leu Val Tyr Lys Ala Ser Thr Leu Thr Ser Gly
65                  70                  75                  80

Val Pro Ser Arg Phe Lys Gly Ser Gly Ser Gly Thr Gln Phe Thr Leu
                85                  90                  95

Thr Ile Ser Asp Leu Glu Cys Ala Asp Ala Ala Thr Tyr Tyr Cys Gln
            100                 105                 110

Ile Asn Tyr Ser Ile Tyr Asn His Tyr Asn Ile Ile Phe Gly Gly Gly
        115                 120                 125

Thr Glu Val Val Val Lys Gly Asp Pro Val Ala Pro Thr Val Leu Ile
    130                 135                 140

Phe Pro Pro Ser Ala Asp Leu Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Cys Lys Val Thr Gln
    210                 215                 220

Gly Thr Thr Ser Val Val Gln Ser Phe Asn Arg Gly Asp Cys
225                 230                 235

<210> SEQ ID NO 19
<211> LENGTH: 7
<212> TYPE: PRT
<213> ORGANISM: Artificial Sequence
<220> FEATURE:
<223> OTHER INFORMATION: Chemically Synthesized, 1D-37-10 heavy chain
      CDR1 amino acid

<400> SEQUENCE: 19

Leu Ser Asp Tyr Ala Ile Ile
1               5

<210> SEQ ID NO 20
<211> LENGTH: 16

```
<212> TYPE: PRT
<213> ORGANISM: Artificial Sequence
<220> FEATURE:
<223> OTHER INFORMATION: Chemically Synthesized, 1D-37-10 heavy chain
      CDR2 amino acid

<400> SEQUENCE: 20

Ile Ile Gly Ser Ser Gly Asp Thr Phe Tyr Ala Thr Trp Ala Lys Gly
1               5                   10                  15

<210> SEQ ID NO 21
<211> LENGTH: 14
<212> TYPE: PRT
<213> ORGANISM: Artificial Sequence
<220> FEATURE:
<223> OTHER INFORMATION: Chemically Synthesized, 1D-37-10 heavy chain
      CDR3 amino acid

<400> SEQUENCE: 21

Arg Tyr Ala Gly Thr Thr Asp Tyr His Asp Ala Phe Asp Pro
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Chemically Synthesized, 1D-37-10 light chain
      CDR1 amino acid

<400> SEQUENCE: 22

Ser Gln Asn Ile Tyr Asn Tyr Leu Ser
1               5

<210> SEQ ID NO 23
<211> LENGTH: 7
<212> TYPE: PRT
<213> ORGANISM: Artificial Sequence
<220> FEATURE:
<223> OTHER INFORMATION: Chemically Synthesized, 1D-37-10 light chain
      CDR2 amino acid

<400> SEQUENCE: 23

Lys Ala Ser Thr Leu Thr Ser
1               5

<210> SEQ ID NO 24
<211> LENGTH: 13
<212> TYPE: PRT
<213> ORGANISM: Artificial Sequence
<220> FEATURE:
<223> OTHER INFORMATION: Chemically Synthesized, 1D-37-10 light chain
      CDR3 amino acid

<400> SEQUENCE: 24

Gln Ile Asn Tyr Ser Ile Tyr Asn His Tyr Asn Ile Ile
1               5                   10

<210> SEQ ID NO 25
<211> LENGTH: 457
<212> TYPE: PRT
<213> ORGANISM: Artificial Sequence
<220> FEATURE:
<223> OTHER INFORMATION: Chemically Synthesized, mAb 1F-26-1 full length
      heavy chain amino acid

<400> SEQUENCE: 25

Met Glu Thr Gly Leu Arg Trp Leu Leu Leu Val Ala Val Leu Lys Gly
```

```
1               5                   10                  15
Val Gln Cys Gln Ser Val Lys Glu Ser Glu Gly Gly Leu Phe Lys Pro
                20                  25                  30
Thr Asp Thr Leu Thr Leu Thr Cys Thr Val Ser Gly Phe Ser Leu Ser
                35                  40                  45
Ser Tyr Gly Val Thr Trp Val Arg Gln Ala Pro Gly Asn Gly Leu Glu
                50                  55                  60
Trp Ile Gly Leu Ile Gly Asp Arg Gly Thr Thr Phe Tyr Ala Ser Trp
65                  70                  75                  80
Ala Lys Ser Arg Ser Thr Ile Thr Arg Asn Thr Asn Leu Asn Thr Val
                85                  90                  95
Thr Leu Lys Met Thr Arg Leu Thr Ala Ala Asp Thr Ala Thr Tyr Phe
                100                 105                 110
Cys Ala Arg Gly Ser Gly Tyr Gly Ala Arg Ile Trp Gly Pro Gly Thr
                115                 120                 125
Leu Val Thr Val Ser Ser Trp Gln Pro Lys Ala Pro Ser Val Phe Pro
                130                 135                 140
Leu Ala Pro Cys Cys Gly Asp Thr Pro Ser Ser Thr Val Thr Leu Gly
145                 150                 155                 160
Cys Leu Val Lys Gly Tyr Leu Pro Glu Pro Val Thr Val Thr Trp Asn
                165                 170                 175
Ser Gly Thr Leu Thr Asn Gly Val Arg Thr Phe Pro Ser Val Arg Gln
                180                 185                 190
Ser Ser Gly Leu Tyr Ser Leu Ser Val Val Ser Val Thr Ser Ser
                195                 200                 205
Ser Gln Pro Val Thr Cys Asn Val Ala His Pro Ala Thr Asn Thr Lys
                210                 215                 220
Val Asp Lys Thr Val Ala Pro Ser Thr Cys Ser Lys Pro Thr Cys Pro
225                 230                 235                 240
Pro Pro Glu Leu Leu Gly Gly Pro Ser Val Phe Ile Phe Pro Pro Lys
                245                 250                 255
Pro Lys Asp Thr Leu Met Ile Ser Arg Thr Pro Glu Val Thr Cys Val
                260                 265                 270
Val Val Asp Val Ser Gln Asp Asp Pro Glu Val Gln Phe Thr Trp Tyr
                275                 280                 285
Ile Asn Asn Glu Gln Val Arg Thr Ala Arg Pro Pro Leu Arg Glu Gln
                290                 295                 300
Gln Phe Asn Ser Thr Ile Arg Val Val Ser Thr Leu Pro Ile Ala His
305                 310                 315                 320
Gln Asp Trp Leu Arg Gly Lys Glu Phe Lys Cys Lys Val His Asn Lys
                325                 330                 335
Ala Leu Pro Ala Pro Ile Glu Lys Thr Ile Ser Lys Ala Arg Gly Gln
                340                 345                 350
Pro Leu Glu Pro Lys Val Tyr Thr Met Gly Pro Pro Arg Glu Glu Leu
                355                 360                 365
Ser Ser Arg Ser Val Ser Leu Thr Cys Met Ile Asn Gly Phe Tyr Pro
                370                 375                 380
Ser Asp Ile Ser Val Glu Trp Glu Lys Asn Gly Lys Ala Glu Asp Asn
385                 390                 395                 400
Tyr Lys Thr Thr Pro Ala Val Leu Asp Ser Asp Gly Ser Tyr Phe Leu
                405                 410                 415
Tyr Ser Lys Leu Ser Val Pro Thr Ser Glu Trp Gln Arg Gly Asp Val
                420                 425                 430
```

```
Phe Thr Cys Ser Val Met His Glu Ala Leu His Asn His Tyr Thr Gln
            435                 440                 445

Lys Ser Ile Ser Arg Ser Pro Gly Lys
        450                 455

<210> SEQ ID NO 26
<211> LENGTH: 237
<212> TYPE: PRT
<213> ORGANISM: Artificial Sequence
<220> FEATURE:
<223> OTHER INFORMATION: Chemically Synthesized, mAb 1F-26-1 full length
      light chain amino acid

<400> SEQUENCE: 26

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Gly Thr Val Thr Ile Asn Cys Gln Ser Ser
        35                  40                  45

Gln Ser Val Tyr Lys Asn Asn Tyr Leu Ala Trp Tyr Gln Gln Lys Pro
    50                  55                  60

Gly Gln Pro Pro Lys Leu Leu Ile Tyr Glu Thr Ser Lys Leu Ala Ser
65                  70                  75                  80

Gly Val Pro Pro Arg Phe Ser Gly Ser Gly Ser Gly Thr Gln Phe Thr
                85                  90                  95

Leu Thr Ile Ser Ser Val Gln Cys Asp Asp Ala Ala Thr Tyr Tyr Cys
            100                 105                 110

Gln Gly Gly Tyr Ser Gly Val Asp Phe Met Ala Phe Gly Gly Gly Thr
        115                 120                 125

Glu Val Val Val Lys Gly Asp Pro Val Ala Pro Thr Val Leu Ile Phe
130                 135                 140

Pro Pro Ser Ala Asp Leu Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235

<210> SEQ ID NO 27
<211> LENGTH: 7
<212> TYPE: PRT
<213> ORGANISM: Artificial Sequence
<220> FEATURE:
<223> OTHER INFORMATION: Chemically Synthesized, 1F-26-1 heavy chain
      CDR1 amino acid

<400> SEQUENCE: 27

Leu Ser Ser Tyr Gly Val Thr
1               5

<210> SEQ ID NO 28
```

```
<211> LENGTH: 16
<212> TYPE: PRT
<213> ORGANISM: Artificial Sequence
<220> FEATURE:
<223> OTHER INFORMATION: Chemically Synthesized, 1F-26-1 heavy chain
      CDR2 amino acid

<400> SEQUENCE: 28

Leu Ile Gly Asp Arg Gly Thr Thr Phe Tyr Ala Ser Trp Ala Lys Ser
1               5                   10                  15

<210> SEQ ID NO 29
<211> LENGTH: 8
<212> TYPE: PRT
<213> ORGANISM: Artificial Sequence
<220> FEATURE:
<223> OTHER INFORMATION: Chemically Synthesized, 1F-26-1 heavy chain
      CDR3 amino acid

<400> SEQUENCE: 29

Gly Ser Gly Tyr Gly Ala Arg Ile
1               5

<210> SEQ ID NO 30
<211> LENGTH: 11
<212> TYPE: PRT
<213> ORGANISM: Artificial Sequence
<220> FEATURE:
<223> OTHER INFORMATION: Chemically Synthesized, 1F-26-1 light chain
      CDR1 amino acid

<400> SEQUENCE: 30

Ser Gln Ser Val Tyr Lys Asn Asn Tyr Leu Ala
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Chemically Synthesized, 1F-26-1 light chain
      CDR2 amino acid

<400> SEQUENCE: 31

Glu Thr Ser Lys Leu Ala Ser
1               5

<210> SEQ ID NO 32
<211> LENGTH: 11
<212> TYPE: PRT
<213> ORGANISM: Artificial Sequence
<220> FEATURE:
<223> OTHER INFORMATION: Chemically Synthesized, 1F-26-1 light chain
      CDR3 amino acid

<400> SEQUENCE: 32

Gln Gly Gly Tyr Ser Gly Val Asp Phe Met Ala
1               5                   10

<210> SEQ ID NO 33
<211> LENGTH: 457
<212> TYPE: PRT
<213> ORGANISM: Artificial Sequence
<220> FEATURE:
<223> OTHER INFORMATION: Chemically Synthesized, mAb 1F-42-7 full length
      heavy chain amino acid

<400> SEQUENCE: 33
```

```
Met Glu Thr Gly Leu Arg Trp Leu Leu Leu Val Ala Val Leu Lys Gly
1               5                   10                  15

Val Gln Cys Gln Ser Val Lys Glu Ser Glu Gly Gly Leu Phe Lys Pro
            20                  25                  30

Thr Asp Thr Leu Thr Leu Thr Cys Thr Val Ser Gly Phe Ser Leu Thr
                35                  40                  45

Thr Tyr Gly Val Thr Trp Val Arg Gln Ala Pro Gly Asn Gly Leu Glu
            50                  55                  60

Trp Ile Gly Leu Ile Gly Asp Arg Gly Thr Thr Tyr Tyr Ala Ser Trp
65                  70                  75                  80

Val Asn Gly Arg Ser Thr Ile Thr Arg Asn Thr Asn Leu Asn Thr Val
                85                  90                  95

Thr Leu Lys Met Thr Arg Leu Thr Ala Ala Asp Thr Ala Thr Tyr Phe
                100                 105                 110

Cys Ala Arg Gly Ser Gly Tyr Gly Ala Arg Ile Trp Gly Pro Gly Thr
            115                 120                 125

Leu Val Thr Val Ala Ser Trp Gln Pro Lys Ala Pro Ser Val Phe Pro
        130                 135                 140

Leu Ala Pro Cys Cys Gly Asp Thr Pro Ser Ser Thr Val Thr Leu Gly
145                 150                 155                 160

Cys Leu Val Lys Gly Tyr Leu Pro Glu Pro Val Thr Val Thr Trp Asn
                165                 170                 175

Ser Gly Thr Leu Thr Asn Gly Val Arg Thr Phe Pro Ser Val Arg Gln
            180                 185                 190

Ser Ser Gly Leu Tyr Ser Leu Ser Ser Val Val Ser Val Thr Ser Ser
            195                 200                 205

Ser Gln Pro Val Thr Cys Asn Val Ala His Pro Ala Thr Asn Thr Lys
        210                 215                 220

Val Asp Lys Thr Val Ala Pro Ser Thr Cys Ser Lys Pro Thr Cys Pro
225                 230                 235                 240

Pro Pro Glu Leu Leu Gly Gly Pro Ser Val Phe Ile Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Asp Asp Pro Glu Val Gln Phe Thr Trp Tyr
        275                 280                 285

Ile Asn Asn Glu Gln Val Arg Thr Ala Arg Pro Pro Leu Arg Glu Gln
290                 295                 300

Gln Phe Asn Ser Thr Ile Arg Val Val Ser Thr Leu Pro Ile Ala His
305                 310                 315                 320

Gln Asp Trp Leu Arg Gly Lys Glu Phe Lys Cys Lys Val His Asn Lys
                325                 330                 335

Ala Leu Pro Ala Pro Ile Glu Lys Thr Ile Ser Lys Ala Arg Gly Gln
            340                 345                 350

Pro Leu Glu Pro Lys Val Tyr Thr Met Gly Pro Pro Arg Glu Glu Leu
        355                 360                 365

Ser Ser Arg Ser Val Ser Leu Thr Cys Met Ile Asn Gly Phe Tyr Pro
370                 375                 380

Ser Asp Ile Ser Val Glu Trp Glu Lys Asn Gly Lys Ala Glu Asp Asn
385                 390                 395                 400

Tyr Lys Thr Thr Pro Ala Val Leu Asp Ser Asp Gly Ser Tyr Phe Leu
                405                 410                 415

Tyr Ser Lys Leu Ser Val Pro Thr Ser Glu Trp Gln Arg Gly Asp Val
```

```
                    420                 425                 430
Phe Thr Cys Ser Val Met His Glu Ala Leu His Asn His Tyr Thr Gln
            435                 440                 445

Lys Ser Ile Ser Arg Ser Pro Gly Lys
        450                 455

<210> SEQ ID NO 34
<211> LENGTH: 237
<212> TYPE: PRT
<213> ORGANISM: Artificial Sequence
<220> FEATURE:
<223> OTHER INFORMATION: Chemically Synthesized, mAb 1F-42-7 full length
      light chain amino acid

<400> SEQUENCE: 34

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Met Ser Ala Ala Leu Gly Gly Thr Val Thr Ile Asn Cys Gln Ser Ser
        35                  40                  45

Gln Thr Val Tyr Asn Asn Asn Tyr Leu Ser Trp Tyr Gln Gln Lys Pro
    50                  55                  60

Gly Gln Pro Pro Lys Leu Leu Ile Tyr Glu Thr Ser Lys Leu Ser Ser
65                  70                  75                  80

Gly Val Pro Pro Arg Phe Ser Gly Ser Gly Ser Gly Thr Gln Phe Thr
                85                  90                  95

Leu Thr Ile Ser Ser Val Gln Cys Asp Asp Ala Ala Thr Tyr Tyr Cys
            100                 105                 110

Gln Gly Gly Tyr Ser Gly Val Asp Phe Met Ala Phe Gly Gly Gly Thr
        115                 120                 125

Glu Val Val Val Lys Gly Asp Pro Val Ala Pro Thr Val Leu Ile Phe
    130                 135                 140

Pro Pro Ser Ala Asp Leu Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235

<210> SEQ ID NO 35
<211> LENGTH: 7
<212> TYPE: PRT
<213> ORGANISM: Artificial Sequence
<220> FEATURE:
<223> OTHER INFORMATION: Chemically Synthesized, 1F-42-7 heavy chain
      CDR1 amino acid

<400> SEQUENCE: 35

Leu Thr Thr Tyr Gly Val Thr
1               5
```

```
<210> SEQ ID NO 36
<211> LENGTH: 16
<212> TYPE: PRT
<213> ORGANISM: Artificial Sequence
<220> FEATURE:
<223> OTHER INFORMATION: Chemically Synthesized, 1F-42-7 heavy chain
      CDR2 amino acid

<400> SEQUENCE: 36

Leu Ile Gly Asp Arg Gly Thr Thr Tyr Tyr Ala Ser Trp Val Asn Gly
1               5                   10                  15

<210> SEQ ID NO 37
<211> LENGTH: 8
<212> TYPE: PRT
<213> ORGANISM: Artificial Sequence
<220> FEATURE:
<223> OTHER INFORMATION: Chemically Synthesized, 1F-42-7 heavy chain
      CDR3 amino acid

<400> SEQUENCE: 37

Gly Ser Gly Tyr Gly Ala Arg Ile
1               5

<210> SEQ ID NO 38
<211> LENGTH: 11
<212> TYPE: PRT
<213> ORGANISM: Artificial Sequence
<220> FEATURE:
<223> OTHER INFORMATION: Chemically Synthesized, 1F-42-7 light chain
      CDR1 amino acid

<400> SEQUENCE: 38

Ser Gln Thr Val Tyr Asn Asn Asn Tyr Leu Ser
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Chemically Synthesized, 1F-42-7 light chain
      CDR2 amino acid

<400> SEQUENCE: 39

Glu Thr Ser Lys Leu Ser Ser
1               5

<210> SEQ ID NO 40
<211> LENGTH: 10
<212> TYPE: PRT
<213> ORGANISM: Artificial Sequence
<220> FEATURE:
<223> OTHER INFORMATION: Chemically Synthesized, 1F-42-7 light chain
      CDR3 amino acid

<400> SEQUENCE: 40

Gln Gly Gly Tyr Ser Gly Val Asp Phe Met
1               5                   10

<210> SEQ ID NO 41
<211> LENGTH: 450
<212> TYPE: PRT
<213> ORGANISM: Artificial Sequence
<220> FEATURE:
<223> OTHER INFORMATION: Chemically Synthesized, mAb 3A-5-2 full length
      heavy chain amino acid

<400> SEQUENCE: 41
```

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Phe Ser Leu Asn
            35                  40                  45

Asn Tyr His Ile Tyr Trp Val Arg Gln Ala Pro Gly Lys Gly Leu Glu
        50                  55                  60

Tyr Ile Gly Ile Ile Phe Asn Gly Gly Thr Tyr Tyr Ala Arg Trp Thr
65                      70                  75                  80

Lys Gly Arg Phe Thr Ile Ser Lys Thr Ser Thr Thr Val Asp Leu Lys
                85                  90                  95

Met Thr Ser Leu Thr Thr Glu Asp Thr Ala Thr Tyr Phe Cys Ala Arg
                100                 105                 110

Gly Asp Gly Ile Trp Gly Pro Gly Thr Leu Val Thr Val Ser Leu Gly
            115                 120                 125

Gln Pro Lys Ala Pro Ser Val Phe Pro Leu Ala Pro Cys Cys Gly Asp
130                 135                 140

Thr Pro Ser Ser Thr Val Thr Leu Gly Cys Leu Val Lys Gly Tyr Leu
145                 150                 155                 160

Pro Glu Pro Val Thr Val Thr Trp Asn Ser Gly Thr Leu Thr Asn Gly
                165                 170                 175

Val Arg Thr Phe Pro Ser Val Arg Gln Ser Ser Gly Leu Tyr Ser Leu
                180                 185                 190

Ser Ser Val Val Ser Val Thr Ser Ser Gln Pro Val Thr Cys Asn
            195                 200                 205

Val Ala His Pro Ala Thr Asn Thr Lys Val Asp Lys Thr Val Ala Pro
        210                 215                 220

Ser Thr Cys Ser Lys Pro Thr Cys Pro Pro Glu Leu Leu Gly Gly
225                 230                 235                 240

Pro Ser Val Phe Ile Phe Pro Pro Lys Pro Lys Asp Thr Leu Met Ile
                245                 250                 255

Ser Arg Thr Pro Glu Val Thr Cys Val Val Asp Val Ser Gln Asp
            260                 265                 270

Asp Pro Glu Val Gln Phe Thr Trp Tyr Ile Asn Asn Glu Gln Val Arg
        275                 280                 285

Thr Ala Arg Pro Pro Leu Arg Glu Gln Gln Phe Asn Ser Thr Ile Arg
        290                 295                 300

Val Val Ser Thr Leu Pro Ile Ala His Gln Asp Trp Leu Arg Gly Lys
305                 310                 315                 320

Glu Phe Lys Cys Lys Val His Asn Lys Ala Leu Pro Ala Pro Ile Glu
                325                 330                 335

Lys Thr Ile Ser Lys Ala Arg Gly Gln Pro Leu Glu Pro Lys Val Tyr
            340                 345                 350

Thr Met Gly Pro Pro Arg Glu Glu Leu Ser Ser Arg Ser Val Ser Leu
            355                 360                 365

Thr Cys Met Ile Asn Gly Phe Tyr Pro Ser Asp Ile Ser Val Glu Trp
370                 375                 380

Glu Lys Asn Gly Lys Ala Glu Asp Asn Tyr Lys Thr Pro Ala Val
385                 390                 395                 400

Leu Asp Ser Asp Gly Ser Tyr Phe Leu Tyr Ser Lys Leu Ser Val Pro
                405                 410                 415
```

```
Thr Ser Glu Trp Gln Arg Gly Asp Val Phe Thr Cys Ser Val Met His
            420                 425                 430

Glu Ala Leu His Asn His Tyr Thr Gln Lys Ser Ile Ser Arg Ser Pro
        435                 440                 445

Gly Lys
    450

<210> SEQ ID NO 42
<211> LENGTH: 239
<212> TYPE: PRT
<213> ORGANISM: Artificial Sequence
<220> FEATURE:
<223> OTHER INFORMATION: Chemically Synthesized, mAb 3A-5-2 full length
      light chain amino acid

<400> SEQUENCE: 42

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ala Ser
            20                  25                  30

Val Ser Ala Ala Val Gly Gly Thr Val Thr Ile Asn Cys Gln Ala Ser
        35                  40                  45

Gln Ser Val Phe Asn Asn Tyr Leu Ala Trp Tyr Gln Gln Lys Pro
    50                  55                  60

Gly Gln Pro Pro Lys Arg Leu Ile Tyr Ser Ala Ser Thr Leu Ala Ser
65                  70                  75                  80

Gly Val Ser Ser Arg Phe Lys Gly Ser Gly Ser Gly Thr Glu Phe Thr
                85                  90                  95

Leu Thr Met Ser Gly Val Glu Cys Asp Asp Ala Ala Thr Tyr Tyr Cys
            100                 105                 110

Ala Gly Ser Phe Asp Cys Asn Ser Gly Asp Cys Val Ala Phe Gly Gly
            115                 120                 125

Gly Thr Glu Val Val Lys Gly Asp Pro Val Ala Pro Thr Val Leu
        130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235

<210> SEQ ID NO 43
<211> LENGTH: 7
<212> TYPE: PRT
<213> ORGANISM: Artificial Sequence
<220> FEATURE:
<223> OTHER INFORMATION: Chemically Synthesized, 3A-5-2 heavy chain CDR1
      amino acid

<400> SEQUENCE: 43

Leu Asn Asn Tyr His Ile Tyr
1               5
```

<210> SEQ ID NO 44
<211> LENGTH: 15
<212> TYPE: PRT
<213> ORGANISM: Artificial Sequence
<220> FEATURE:
<223> OTHER INFORMATION: Chemically Synthesized, 3A-5-2 heavy chain CDR2
      amino acid

<400> SEQUENCE: 44

Ile Ile Phe Asn Gly Gly Thr Tyr Tyr Ala Arg Trp Thr Lys Gly
1               5                   10                  15

<210> SEQ ID NO 45
<211> LENGTH: 4
<212> TYPE: PRT
<213> ORGANISM: Artificial Sequence
<220> FEATURE:
<223> OTHER INFORMATION: Chemically Synthesized, 3A-5-2 heavy chain CDR3
      amino acid

<400> SEQUENCE: 45

Gly Asp Gly Ile
1

<210> SEQ ID NO 46
<211> LENGTH: 11
<212> TYPE: PRT
<213> ORGANISM: Artificial Sequence
<220> FEATURE:
<223> OTHER INFORMATION: Chemically Synthesized, 3A-5-2 light chain CDR1
      amino acid

<400> SEQUENCE: 46

Ser Gln Ser Val Phe Asn Asn Asn Tyr Leu Ala
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Chemically Synthesized, 3A-5-2 light chain CDR2
      amino acid

<400> SEQUENCE: 47

Ser Ala Ser Thr Leu Ala Ser
1               5

<210> SEQ ID NO 48
<211> LENGTH: 13
<212> TYPE: PRT
<213> ORGANISM: Artificial Sequence
<220> FEATURE:
<223> OTHER INFORMATION: Chemically Synthesized, 3A-5-2 light chain CDR3
      amino acid

<400> SEQUENCE: 48

Ala Gly Ser Phe Asp Cys Asn Ser Gly Asp Cys Val Ala
1               5                   10

<210> SEQ ID NO 49
<211> LENGTH: 1029
<212> TYPE: DNA
<213> ORGANISM: Artificial Sequence
<220> FEATURE:
<223> OTHER INFORMATION: Chemically Synthesized, Human Renalase-1
      nucleic acid sequence - Note potential polymorphism at nucleotide
      position 111

<400> SEQUENCE: 49

```
atggcgcagg tgctgatcgt gggcgccggg atgacaggaa gcttgtgcgc tgcgctgctg      60
aggaggcaga cgtccggtcc cttgtacctt gctgtgtggg acaaggctga ggactcaggg     120
ggaagaatga ctacagcctg cagtcctcat aatcctcagt gcacagctga cttgggtgct     180
cagtacatca cctgcactcc tcattatgcc aaaaaacacc aacgttttta tgatgaactg     240
ttagcctatg gcgttttgag gcctctaagc tcgcctattg aaggaatggt gatgaaagaa     300
ggagactgta actttgtggc acctcaagga atttcttcaa ttattaagca ttacttgaaa     360
gaatcaggtg cagaagtcta cttcagacat cgtgtgacac agatcaacct aagagatgac     420
aaatgggaag tatccaaaca aacaggctcc cctgagcagt ttgatcttat tgttctcaca     480
atgccagttc ctgagattct gcagcttcaa ggtgacatca ccaccttaat tagtgaatgc     540
caaaggcagc aactggaggc tgtgagctac tcctctcgat atgctctggg cctcttttat     600
gaagctggta cgaagattga tgtcccttgg gctgggcagt acatcaccag taatccctgc     660
atacgcttcg tctccattga taataagaag cgcaatatag agtcatcaga aattgggcct     720
tccctcgtga ttcacaccac tgtcccattt ggagttacat acttggaaca cagcattgag     780
gatgtgcaag agttagtctt ccagcagctg gaaaacattt tgccgggttt gcctcagcca     840
attgctacca atgccaaaa atggagacat tcacaggtta caaatgctgc tgccaactgt     900
cctggccaaa tgactctgca tcacaaacct ttccttgcat gtggagggga tggatttact     960
cagtccaact tgatggctg catcacttct gccctatgtg ttctggaagc tttaaagaat    1020
tatatttaa                                                           1029
```

<210> SEQ ID NO 50
<211> LENGTH: 315
<212> TYPE: PRT
<213> ORGANISM: Artificial Sequence
<220> FEATURE:
<223> OTHER INFORMATION: Chemically Synthesized, Human Renalase-2 amino
      acid sequence - polymorphism resulting in the highlighted
      glutamate amino acid at position 37

<400> SEQUENCE: 50

```
Met Ala Gln Val Leu Ile Val Gly Ala Gly Met Thr Gly Ser Leu Cys
1               5                   10                  15

Ala Ala Leu Leu Arg Arg Gln Thr Ser Gly Pro Leu Tyr Leu Ala Val
            20                  25                  30

Trp Asp Lys Ala Glu Asp Ser Gly Gly Arg Met Thr Thr Ala Cys Ser
        35                  40                  45

Pro His Asn Pro Gln Cys Thr Ala Asp Leu Gly Ala Gln Tyr Ile Thr
    50                  55                  60

Cys Thr Pro His Tyr Ala Lys Lys His Gln Arg Phe Tyr Asp Glu Leu
65                  70                  75                  80

Leu Ala Tyr Gly Val Leu Arg Pro Leu Ser Ser Pro Ile Glu Gly Met
                85                  90                  95

Val Met Lys Glu Gly Asp Cys Asn Phe Val Ala Pro Gln Gly Ile Ser
            100                 105                 110

Ser Ile Ile Lys His Tyr Leu Lys Glu Ser Gly Ala Glu Val Tyr Phe
        115                 120                 125

Arg His Arg Val Thr Gln Ile Asn Leu Arg Asp Asp Lys Trp Glu Val
    130                 135                 140

Ser Lys Gln Thr Gly Ser Pro Glu Gln Phe Asp Leu Ile Val Leu Thr
```

```
                145                 150                 155                 160
Met Pro Val Pro Glu Ile Leu Gln Leu Gln Gly Asp Ile Thr Thr Leu
                165                 170                 175

Ile Ser Glu Cys Gln Arg Gln Leu Glu Ala Val Ser Tyr Ser Ser
            180                 185                 190

Arg Tyr Ala Leu Gly Leu Phe Tyr Glu Ala Gly Thr Lys Ile Asp Val
        195                 200                 205

Pro Trp Ala Gly Gln Tyr Ile Thr Ser Asn Pro Cys Ile Arg Phe Val
    210                 215                 220

Ser Ile Asp Asn Lys Lys Arg Asn Ile Glu Ser Ser Glu Ile Gly Pro
225                 230                 235                 240

Ser Leu Val Ile His Thr Thr Val Pro Phe Gly Val Thr Tyr Leu Glu
                245                 250                 255

His Ser Ile Glu Asp Val Gln Glu Leu Val Phe Gln Gln Leu Glu Asn
            260                 265                 270

Ile Leu Pro Gly Leu Pro Gln Pro Ile Ala Thr Lys Cys Gln Lys Trp
        275                 280                 285

Arg His Ser Gln Val Pro Ser Ala Gly Val Ile Leu Gly Cys Ala Lys
    290                 295                 300

Ser Pro Trp Met Met Ala Ile Gly Phe Pro Ile
305                 310                 315
```

<210> SEQ ID NO 51
<211> LENGTH: 945
<212> TYPE: DNA
<213> ORGANISM: Artificial Sequence
<220> FEATURE:
<223> OTHER INFORMATION: Chemically Synthesized, Human Ren 2 nucleic
      acid sequence - Note potential polymorphism at nucleotide position
      111

<400> SEQUENCE: 51

```
atggcgcagg tgctgatcgt gggcgccggg atgacaggaa gcttgtgcgc tgcgctgctg      60
aggaggcaga cgtccggtcc cttgtacctt gctgtgtggg acaaggctga ggactcaggg     120
ggaagaatga ctacagcctg cagtcctcat aatcctcagt gcacagctga cttgggtgct     180
cagtacatca cctgcactcc tcattatgcc aaaaaacacc aacgttttta tgatgaactg     240
ttagcctatg gcgttttgag gcctctaagc tcgcctattg aaggaatggt gatgaaagaa     300
ggagactgta actttgtggc acctcaagga atttcttcaa ttattaagca ttacttgaaa     360
gaatcaggtg cagaagtcta cttcagacat cgtgtgacac agatcaacct aagagatgac     420
aaatgggaag tatccaaaca aacaggctcc cctgagcagt ttgatcttat tgttctcaca     480
atgccagttc ctgagattct gcagcttcaa ggtgacatca ccaccttaat tagtgaatgc     540
caaaggcagc aactggaggc tgtgagctac tcctctcgat atgctctggg cctcttttat     600
gaagctggta cgaagattga tgtcccttgg gctgggcagt acatcaccag taatccctgc     660
atacgcttcg tctccattga taataagaag cgcaatatag agtcatcaga aattgggcct     720
tccctcgtga ttcacaccac tgtcccattt ggagttacat acttggaaca cagcattgag     780
gatgtgcaag agttagtctt ccagcagctg gaaaacattt tgccgggttt gcctcagcca     840
attgctacca atgccaaaaa atggagacat tcacaggtac caagtgctgg tgtgattcta     900
ggatgtgcga agagcccctg gatgatggcg attggatttc ccatc                    945
```

<210> SEQ ID NO 52
<211> LENGTH: 1380

<212> TYPE: DNA
<213> ORGANISM: Artificial Sequence
<220> FEATURE:
<223> OTHER INFORMATION: Chemically Synthesized, mAb 1D-28-4 full length
heavy chain nucleic acid

<400> SEQUENCE: 52

| | | | | | |
|---|---|---|---|---|---|
| atggagactg | ggctgcgctg | gcttctcctg | gtcgctgtgc | tcaaaggtgt | ccagtgtcag | 60 |
| tcggtggagg | agtccggggg | tcgcctggtc | acgcctggga | cacccctgac | actcacctgc | 120 |
| acagtctctg | gattctccct | cagtagtttt | gcagtgggct | gggtccgcca | ggctccaggg | 180 |
| aaggggctgg | aatacatcgg | aatcattagt | agtgttggta | ttacacgcta | cgcgagctgg | 240 |
| gcggccggcc | gattcaccat | ctccaaaacc | tcgaccacgg | tggatctgaa | aatcaccagt | 300 |
| ccgacaaccg | aggacacggc | cacctatttt | tgtgccagat | atggttatag | tggtgatgtt | 360 |
| aatcggttgg | atctctgggg | ccagggcacc | ctggtcaccg | tctcctcagg | gcaacctaag | 420 |
| gctccatcag | tcttcccact | ggccccctgc | tgcgggaca | cacccagctc | cacggtgacc | 480 |
| ctgggctgcc | tggtcaaagg | gtacctcccg | gagccagtga | ccgtgacctg | gaactcgggc | 540 |
| accctcacca | tggggtacg | caccttcccg | tccgtccggc | agtcctcagg | cctctactcg | 600 |
| ctgagcagcg | tggtgagcgt | gacctcaagc | agccagcccg | tcacctgcaa | cgtggcccac | 660 |
| ccagccacca | acaccaaagt | ggacaagacc | gttgcgccct | cgacatgcag | caagcccacg | 720 |
| tgcccacccc | ctgaactcct | gggggaccg | tctgtcttca | tcttccccc | aaacccaag | 780 |
| gacaccctca | tgatctcacg | caccccccgag | gtcacatgcg | tggtggtgga | cgtgagccag | 840 |
| gatgaccccg | aggtgcagtt | cacatggtac | ataaacaacg | agcaggtgcg | caccgcccgg | 900 |
| ccgccgctac | gggagcagca | gttcaacagc | acgatccgcg | tggtcagcac | cctccccatc | 960 |
| gcgcaccagg | actggctgag | gggcaaggag | ttcaagtgca | aagtccacaa | caaggcactc | 1020 |
| ccggcccca | tcgagaaaac | catctccaaa | gccagagggc | agccctgga | gccgaaggtc | 1080 |
| tacaccatgg | gccctccccg | ggaggagctg | agcagcaggt | cggtcagcct | gacctgcatg | 1140 |
| atcaacggct | tctaccctc | cgacatctcg | gtggagtggg | agaagaacgg | gaaggcagag | 1200 |
| gacaactaca | agaccacgcc | ggccgtgctg | gacagcgacg | gctcctactt | cctctacagc | 1260 |
| aagctctcag | tgcccacgag | tgagtggcag | cggggcgacg | tcttcacctg | ctccgtgatg | 1320 |
| cacgaggcct | tgcacaacca | ctacacgcag | aagtccatct | cccgctctcc | gggtaaatga | 1380 |

<210> SEQ ID NO 53
<211> LENGTH: 720
<212> TYPE: DNA
<213> ORGANISM: Artificial Sequence
<220> FEATURE:
<223> OTHER INFORMATION: Chemically Synthesized, mAb 1D-28-4 full length
light chain nucleic acid

<400> SEQUENCE: 53

| | | | | | |
|---|---|---|---|---|---|
| atggacacga | gggcccccac | tcagctgctg | gggctcctgc | tgctctggct | cccaggtgcc | 60 |
| acatttgccc | aagtgctgac | ccagactgca | tcgcccgtgt | ctgcagctgt | gggaggcaca | 120 |
| gtcaccatca | attgccaggc | cagtcagagt | gtttatgata | acaacaactt | agcctggtat | 180 |
| cagcagaaac | cagggcagcc | tcccaagcaa | ctgatctatg | gtgcatccac | tctggcatct | 240 |
| ggggtctcat | cgcggttcaa | aggcagtgga | tctgggacac | agttcactct | caccatcagc | 300 |
| ggcgtgcagt | gtgacgatgc | tgccacttac | tactgtctag | cgaatttag | ttgtagtagt | 360 |
| gctgattgtt | ttgctttcgg | cggagggacc | gaggtggtcg | tcaaaggtga | tccagttgca | 420 |

```
cctactgtcc tcatcttccc accatctgct gatcttgtgg caactggaac agtcaccatc    480
gtgtgtgtgg cgaataaata ctttcccgat gtcaccgtca cctgggaggt ggatggcacc    540
acccaaacaa ctggcatcga gaacagtaaa acaccgcaga attctgcaga ttgtacctac    600
aacctcagca gcactctgac actgaccagc acacagtaca acagccacaa agagtacacc    660
tgcaaggtga cccagggcac gacctcagtc gtccagagct caatagggg tgactgttag     720
```

<210> SEQ ID NO 54
<211> LENGTH: 21
<212> TYPE: DNA
<213> ORGANISM: Artificial Sequence
<220> FEATURE:
<223> OTHER INFORMATION: Chemically Synthesized, 1D-28-4 heavy chain
      CDR1 nucleic acid

<400> SEQUENCE: 54
ctcagtagtt ttgcagtggg c                                              21

<210> SEQ ID NO 55
<211> LENGTH: 48
<212> TYPE: DNA
<213> ORGANISM: Artificial Sequence
<220> FEATURE:
<223> OTHER INFORMATION: Chemically Synthesized, 1D-28-4 heavy chain
      CDR2 nucleic acid

<400> SEQUENCE: 55
atcattagta gtgttggtat tacacgctac gcgagctggg cggccggc                 48

<210> SEQ ID NO 56
<211> LENGTH: 36
<212> TYPE: DNA
<213> ORGANISM: Artificial Sequence
<220> FEATURE:
<223> OTHER INFORMATION: Chemically Synthesized, 1D-28-4 heavy chain
      CDR3 nucleic acid

<400> SEQUENCE: 56
tatggttata gtggtgatgt taatcggttg gatctc                              36

<210> SEQ ID NO 57
<211> LENGTH: 33
<212> TYPE: DNA
<213> ORGANISM: Artificial Sequence
<220> FEATURE:
<223> OTHER INFORMATION: Chemically Synthesized, 1D-28-4 light chain
      CDR1 nucleic acid

<400> SEQUENCE: 57
agtcagagtg tttatgataa caacaactta gcc                                 33

<210> SEQ ID NO 58
<211> LENGTH: 21
<212> TYPE: DNA
<213> ORGANISM: Artificial Sequence
<220> FEATURE:
<223> OTHER INFORMATION: Chemically Synthesized, 1D-28-4 light chain
      CDR2 nucleic acid

<400> SEQUENCE: 58
ggtgcatcca ctctggcatc t                                              21

<210> SEQ ID NO 59
<211> LENGTH: 39
<212> TYPE: DNA

<213> ORGANISM: Artificial Sequence
<220> FEATURE:
<223> OTHER INFORMATION: Chemically Synthesized, 1D-28-4 light chain
      CDR3 nucleic acid

<400> SEQUENCE: 59
ctaggcgaat ttagttgtag tagtgctgat tgttttgct                              39

<210> SEQ ID NO 60
<211> LENGTH: 1386
<212> TYPE: DNA
<213> ORGANISM: Artificial Sequence
<220> FEATURE:
<223> OTHER INFORMATION: Chemically Synthesized, mAb 1D-37-10 full
      length heavy chain nucleic acid

<400> SEQUENCE: 60
atggagactg ggctgcgctg gcttctcctg gtcgctgtgc tcaaaggtgt ccagtgtcag        60
tcggtggagg agtccggggg tcgcctggtc acgcctggag gatccctgac actcacctgc       120
acagtctctg gattctccct cagtgactat gcaataatct gggtccgcca ggctccaggg       180
aaggggctgg aatacatcgc aattattggt agtagtggtg acacattcta cgcgacctgg       240
gcgaaaggcc gattcaccat ctccaaaacc tcgaccacgg tggatctgaa aatgaccagt       300
ctgacagccg cggacacggc cacctatttc tgtgccccac gttatgctgg tactactgat       360
tatcatgatg cttttgatcc ctggggccca ggcactttgg tcaccgtctc ctcagggcaa       420
cctaaggctc catcagtctt cccactggcc cctgctgcg ggacacacc cagctccacg        480 gtgaccctgg ctgcctggt caaagggtac ctcccggagc cagtgaccgt gacctggaac       540
tcgggcaccc tcaccaatgg ggtacgcacc ttcccgtccg tcggcagtc ctcaggcctc        600 tactcgctga gcagcgtggt gagcgtgacc tcaagcagcc agcccgtcac ctgcaacgtg       660
gcccacccag ccaccaacac caaagtggac aagaccgttg cgcctcgac atgcagcaag       720 cccacgtgcc cacccctga actcctgggg ggaccgtctg tcttcatctt ccccccaaaa       780
cccaaggaca ccctcatgat ctcacgcacc cccgaggtca catgcgtggt ggtggacgtg       840
agccaggatg accccgaggt gcagttcaca tggtacataa caacgagca ggtgcgcacc        900 gcccggccgc cgctacggga gcagcagttc aacagcacga tccgcgtggt cagcaccctc       960
cccatcgcgc accaggactg gctgaggggc aaggagttca gtgcaaagt ccacaacaag       1020 gcactcccgg ccccatcga gaaaccatc tccaaagcca gagggcagcc cctggagccg       1080
aaggtctaca ccatgggccc tccccggag agctgagca gcaggtcggt cagcctgacc       1140
tgcatgatca acggcttcta cccttccgac atctcggtgg agtgggagaa gaacggaag       1200 gcagaggaca actacaagac cacgccggcc gtgctggaca cgacggctc ctacttcctc       1260 tacagcaagc tctcagtgcc cacgagtgag tggcagcggg gcgacgtctt cacctgctcc       1320
gtgatgcacg aggccttgca caaccactac acgcagaagt ccatctcccg ctctccgggt       1380
aaatga                                                                1386

<210> SEQ ID NO 61
<211> LENGTH: 717
<212> TYPE: DNA
<213> ORGANISM: Artificial Sequence
<220> FEATURE:
<223> OTHER INFORMATION: Chemically Synthesized, mAb 1D-37-10 full
      length light chain nucleic acid

<400> SEQUENCE: 61

```
atggacacga gggcccccac tcagctgctg gggctcctgc tgctctggct cccaggtgcc    60
agatgtgccg aagtagtgat gacccagact ccagcctcca tggaggcacc tatgggaggc   120
acagtcacca tcaagtgcca ggccagtcag aacatttaca actacttatc ctggtatcag   180
cagaaaccag gcagcctcc caagctccta gtctacaagg cctccactct gacttctggg   240
gtcccgtcgc gcttcaaagg cagtggatct gggacacagt tcactctcac catcagcgac   300
ctggagtgtg ccgatgctgc cacttactac tgtcaaatca attactctat ttataatcat   360
tataatatta ttttggcgg agggaccgag gtggtcgtca agggtgatcc agttgcacct   420
actgtcctca tcttcccacc atctgctgat cttgtggcaa ctggaacagt caccatcgtg   480
tgtgtggcga ataaatactt tcccgatgtc accgtcacct gggaggtgga tggcaccacc   540
caaacaactg gcatcgagaa cagtaaaaca ccgcagaatt ctgcagattg tacctacaac   600
ctcagcagca ctctgacact gaccagcaca cagtacaaca gccacaaaga gtacacctgc   660
aaggtgaccc agggcacgac ctcagtcgtc cagagcttca atagggtga ctgttag      717
```

```
<210> SEQ ID NO 62
<211> LENGTH: 21
<212> TYPE: DNA
<213> ORGANISM: Artificial Sequence
<220> FEATURE:
<223> OTHER INFORMATION: Chemically Synthesized, 1D-37-10 heavy chain
      CDR1 nucleic acid

<400> SEQUENCE: 62
ctcagtgact atgcaataat c                                              21
```

```
<210> SEQ ID NO 63
<211> LENGTH: 48
<212> TYPE: DNA
<213> ORGANISM: Artificial Sequence
<220> FEATURE:
<223> OTHER INFORMATION: Chemically Synthesized, 1D-37-10 heavy chain
      CDR2 nucleic acid

<400> SEQUENCE: 63
attattggta gtagtggtga cacattctac gcgacctggg cgaaaggc                 48
```

```
<210> SEQ ID NO 64
<211> LENGTH: 42
<212> TYPE: DNA
<213> ORGANISM: Artificial Sequence
<220> FEATURE:
<223> OTHER INFORMATION: Chemically Synthesized, 1D-37-10 heavy chain
      CDR3 nucleic acid

<400> SEQUENCE: 64
cgttatgctg gtactactga ttatcatgat gcttttgatc cc                       42
```

```
<210> SEQ ID NO 65
<211> LENGTH: 27
<212> TYPE: DNA
<213> ORGANISM: Artificial Sequence
<220> FEATURE:
<223> OTHER INFORMATION: Chemically Synthesized, 1D-37-10 light chain
      CDR1 nucleic acid

<400> SEQUENCE: 65
agtcagaaca tttacaacta cttatcc                                        27
```

```
<210> SEQ ID NO 66
<211> LENGTH: 21
```

```
<212> TYPE: DNA
<213> ORGANISM: Artificial Sequence
<220> FEATURE:
<223> OTHER INFORMATION: Chemically Synthesized, 1D-37-10 light chain
      CDR2 nucleic acid

<400> SEQUENCE: 66
aaggcctcca ctctgacttc t                                                21

<210> SEQ ID NO 67
<211> LENGTH: 39
<212> TYPE: DNA
<213> ORGANISM: Artificial Sequence
<220> FEATURE:
<223> OTHER INFORMATION: Chemically Synthesized, 1D-37-10 light chain
      CDR3 nucleic acid

<400> SEQUENCE: 67
caaatcaatt actctattta taatcattat aatattatt                             39

<210> SEQ ID NO 68
<211> LENGTH: 1374
<212> TYPE: DNA
<213> ORGANISM: Artificial Sequence
<220> FEATURE:
<223> OTHER INFORMATION: Chemically Synthesized, mAb 1F-26-1 full length
      heavy chain nucleic acid

<400> SEQUENCE: 68
atggagactg ggctgcgctg gcttctcctg gtcgctgtgc tcaaaggtgt ccagtgtcag     60
tcggtgaagg agtccgaggg aggtctcttc aagccaacgg ataccctgac actcacctgc    120
acagtctctg gattctccct cagtagctat ggagtgacct gggtccgcca ggctccaggg    180
aacgggctgg agtggatcgg attgattggt gatcgtggta ctacgttcta cgcgagctgg    240
gcgaaaagcc gatccaccat caccagaaac accaacctga cacggtgac tctgaaaatg     300 accaggctga cagccgcgga cacggccacc tatttctgtg cgaggggggag tgggtatggt   360 gctcgcatct ggggcccagg caccctggtc accgtctcct catggcaacc taaggctcca    420
tcagtcttcc cactggcccc ctgctgcggg gacacaccca gctccacggt gaccctgggc    480
tgcctggtca agggtacct cccggagcca gtgaccgtga cctggaactc gggcacccctc   540 accaatgggg tacgcacctt cccgtccgtc cggcagtcct caggcctcta ctcgctgagc    600
agcgtggtga gcgtgaccctc aagcagccag cccgtcacct gcaacgtggc ccacccagcc   660
accaacacca aagtggacaa gaccgttgcg ccctcgacat gcagcaagcc cacgtgccca    720 cccccctgaac tcctgggggg accgtctgtc ttcatcttcc ccccaaaacc caaggacacc   780
ctcatgatct cacgcacccc cgaggtcaca tgcgtggtgg tggacgtgag ccaggatgac    840
cccgaggtgc agttcacatg gtacataaac aacgagcagg tgcgcaccgc ccggccgccg    900
ctacgggagc agcagttcaa cagcacgatc cgcgtggtca gcaccctccc catcgcgcac    960
caggactggc tgagggggcaa ggagttcaag tgcaaagtcc acaacaaggc actcccggcc  1020
cccatcgaga aaaccatctc caaagccaga gggcagcccc tggagccgaa ggtctacacc   1080
atgggccctc cccggagga gctgagcagc aggtcggtca gcctgacctg catgatcaac   1140
ggcttctacc cttccgacat ctcggtggag tgggagaaga cgggaaggc agaggacaac    1200 tacaagacca cgccgccgcgt gctggacagc gacggctcct acttcctcta cagcaagctc   1260
tcagtgccca cgagtgagtg gcagcggggc gacgtcttca cctgctccgt gatgcacgag   1320
gccttgcaca accactacac gcagaagtcc atctcccgct ctccgggtaa atga        1374
```

<210> SEQ ID NO 69
<211> LENGTH: 714
<212> TYPE: DNA
<213> ORGANISM: Artificial Sequence
<220> FEATURE:
<223> OTHER INFORMATION: Chemically Synthesized, mAb 1F-26-1 full length
      light chain nucleic acid

<400> SEQUENCE: 69

```
atggacacga gggcccccac tcagctcctg gggctcctgc tgctctggct cccaggtgcc    60
acatttgccc aagtgctgac ccagactcca tcgcctgtgt ctgcagctgt gggaggcaca   120
gtcaccatca attgccagtc cagtcagagt gtttataaga caactacttt agcctggtat   180
cagcagaaac cagggcagcc tcccaagctc cttatctacg aaacatccaa actggcatct   240
ggggtcccac cgcggttcag cggcagtggg tctgggacac agttcactct caccatcagc   300
agcgtgcagt gtgacgatgc tgccacttac tactgtcaag gcggttatag tggtgttgat   360
tttatggctt tcggcggagg gaccgaggtg gtcgtcaaag gtgatccagt tgcacctact   420
gtcctcatct tcccaccatc tgctgatctt gtggcaactg gaacagtcac catcgtgtgt   480
gtggcgaata aatactttcc cgatgtcacc gtcacctggg aggtggatgg caccaccaa   540 acaactggca tcgagaacag taaaacaccg cagaattctg cagattgtac ctacaacctc   600
agcagcactc tgacactgac cagcacacag tacaacagcc acaaagagta cacctgcaag   660
gtgacccagg gcacgacctc agtcgtccag agcttcaata ggggtgactg ttag        714
```

<210> SEQ ID NO 70
<211> LENGTH: 21
<212> TYPE: DNA
<213> ORGANISM: Artificial Sequence
<220> FEATURE:
<223> OTHER INFORMATION: Chemically Synthesized, 1F-26-1 heavy chain
      CDR1 nucleic acid

<400> SEQUENCE: 70

```
ctcagtagct atggagtgac c                                              21
```

<210> SEQ ID NO 71
<211> LENGTH: 48
<212> TYPE: DNA
<213> ORGANISM: Artificial Sequence
<220> FEATURE:
<223> OTHER INFORMATION: Chemically Synthesized, 1F-26-1 heavy chain
      CDR2 nucleic acid

<400> SEQUENCE: 71

```
ttgattggtg atcgtggtac tacgttctac gcgagctggg cgaaaagc                 48
```

<210> SEQ ID NO 72
<211> LENGTH: 24
<212> TYPE: DNA
<213> ORGANISM: Artificial Sequence
<220> FEATURE:
<223> OTHER INFORMATION: Chemically Synthesized, 1F-26-1 heavy chain
      CDR3 nucleic acid

<400> SEQUENCE: 72

```
gggagtgggt atggtgctcg catc                                           24
```

<210> SEQ ID NO 73
<211> LENGTH: 33
<212> TYPE: DNA

```
<213> ORGANISM: Artificial Sequence
<220> FEATURE:
<223> OTHER INFORMATION: Chemically Synthesized, 1F-26-1 light chain
      CDR1 nucleic acid

<400> SEQUENCE: 73
agtcagagtg tttataagaa caactactta gcc                                   33

<210> SEQ ID NO 74
<211> LENGTH: 21
<212> TYPE: DNA
<213> ORGANISM: Artificial Sequence
<220> FEATURE:
<223> OTHER INFORMATION: Chemically Synthesized, 1F-26-1 light chain
      CDR2 nucleic acid

<400> SEQUENCE: 74
gaaacatcca aactggcatc t                                                21

<210> SEQ ID NO 75
<211> LENGTH: 33
<212> TYPE: DNA
<213> ORGANISM: Artificial Sequence
<220> FEATURE:
<223> OTHER INFORMATION: Chemically Synthesized, 1F-26-1 light chain
      CDR3 nucleic acid

<400> SEQUENCE: 75
caaggcggtt atagtggtgt tgattttatg gct                                   33

<210> SEQ ID NO 76
<211> LENGTH: 1374
<212> TYPE: DNA
<213> ORGANISM: Artificial Sequence
<220> FEATURE:
<223> OTHER INFORMATION: Chemically Synthesized, mAb 1F-42-7 full length
      heavy chain nucleic acid

<400> SEQUENCE: 76
atggagactg ggctgcgctg cttctcctg gtcgctgtgc tcaaaggtgt ccagtgtcag        60
tcggtgaagg agtccgaggg aggtctcttc aagccaacgg ataccctgac actcacctgc     120
acagtctctg gattctcccct cactacctat ggagtgacct gggtccgcca ggctccaggg    180
aatgggctgg agtggatcgg attgattggt gatcgcggta ccacttacta cgcgagctgg     240
gtgaatggcc gatccaccat caccagaaac accaacctga cacggtgac tctgaaaatg      300 accaggctga cagccgcgga cacggccacc tatttctgtg cgaggggag tggatatggt      360 gctcgcatct ggggcccagg caccctggtc accgtcgcct catggcaacc taaggctcca    420
tcagtcttcc cactggcccc ctgctgcggg gacacaccca gctccacggt gaccctgggc    480
tgcctggtca agggtacct cccggagcca gtgaccgtga cctggaactc gggcaccctc     540
accaatgggg tacgcacctt cccgtccgtc cggcagtcct caggcctcta ctcgctgagc    600
agcgtggtga gcgtgacctc aagcagccag cccgtcacct gcaacgtggc ccacccagcc    660
accaacacca agtggacaa gaccgttgcg ccctcgacat gcagcaagcc cacgtgccca    720 cccctgaac tctggggggg accgtctgtc ttcatcttcc cccaaaaacc caaggacacc     780
ctcatgatct cacgcacccc cgaggtcaca tgcgtggtgg tggacgtgag ccaggatgac   840
cccgaggtgc agttcacatg gtacataaac aacgagcagg tgcgcaccgc ccggccgccg   900
ctacgggagc agcagttcaa cagcacgatc cgcgtggtca gcaccctccc catcgcgcac   960
caggactggc tgagggcaa ggagttcaag tgcaaagtcc acaacaaggc actcccggcc   1020
```

```
cccatcgaga aaaccatctc caaagccaga gggcagcccc tggagccgaa ggtctacacc    1080
atgggccctc cccggggagga gctgagcagc aggtcggtca gcctgacctg catgatcaac    1140
ggcttctacc cttccgacat ctcggtggag tgggagaaga acgggaaggc agaggacaac    1200
tacaagacca cgccggccgt gctggacagc gacggctcct acttcctcta cagcaagctc    1260
tcagtgccca cgagtgagtg gcagcggggc gacgtcttca cctgctccgt gatgcacgag    1320
gccttgcaca accactacac gcagaagtcc atctcccgct ctccgggtaa atga          1374
```

<210> SEQ ID NO 77
<211> LENGTH: 714
<212> TYPE: DNA
<213> ORGANISM: Artificial Sequence
<220> FEATURE:
<223> OTHER INFORMATION: Chemically Synthesized, mAb 1F-42-7 full length
      light chain nucleic acid

<400> SEQUENCE: 77

```
atggacacga gggcccccac tcagctcctg gggctcctgc tgctctggct cccaggtgcc     60
acatttgccc aagtgctgac ccagactcca tcccccatgt ctgcagctct gggaggcaca    120
gtcaccatca attgccagtc cagtcagact gtttataaca ataactactt atcctggtat    180
cagcagaaac cagggcagcc tcccaagctc cttatctacg aaacatccaa actgtcatct    240
ggggtcccac cgcggttcag cggcagtggg tctgggacac agttcactct caccatcagc    300
agcgtgcagt gtgacgatgc tgccacttac tactgtcaag gcggttatag tggtgttgat    360
tttatggctt tcggcggagg gaccgaggtg gtcgtcaaag gtgatccagt tgcacctact    420
gtcctcatct tcccaccatc tgctgatctt gtggcaactg gaacagtcac catcgtgtgt    480
gtggcgaata aatactttcc cgatgtcacc gtcacctggg aggtggatgg caccacccaa    540
acaactggca tcgagaacag taaaacaccg cagaattctg cagattgtac ctacaacctc    600
agcagcactc tgacactgac cagcacacag tacaacagcc acaaagagta cacctgcaag    660
gtgacccagg gcacgacctc agtcgtccag agcttcaata ggggtgactg ttag          714
```

<210> SEQ ID NO 78
<211> LENGTH: 21
<212> TYPE: DNA
<213> ORGANISM: Artificial Sequence
<220> FEATURE:
<223> OTHER INFORMATION: Chemically Synthesized, 1F-42-7 heavy chain
      CDR1 nucleic acid

<400> SEQUENCE: 78

```
ctcactacct atggagtgac c                                               21
```

<210> SEQ ID NO 79
<211> LENGTH: 48
<212> TYPE: DNA
<213> ORGANISM: Artificial Sequence
<220> FEATURE:
<223> OTHER INFORMATION: Chemically Synthesized, 1F-42-7 heavy chain
      CDR2 nucleic acid

<400> SEQUENCE: 79

```
ttgattggtg atcgcggtac cacttactac gcgagctggg tgaatggc                  48
```

<210> SEQ ID NO 80
<211> LENGTH: 24
<212> TYPE: DNA
<213> ORGANISM: Artificial Sequence

```
<220> FEATURE:
<223> OTHER INFORMATION: Chemically Synthesized, 1F-42-7 heavy chain
      CDR3 nucleic acid

<400> SEQUENCE: 80
gggagtggat atggtgctcg catc                                          24

<210> SEQ ID NO 81
<211> LENGTH: 33
<212> TYPE: DNA
<213> ORGANISM: Artificial Sequence
<220> FEATURE:
<223> OTHER INFORMATION: Chemically Synthesized, 1F-42-7 light chain
      CDR1 nucleic acid

<400> SEQUENCE: 81
agtcagactg tttataacaa taactactta tcc                                33

<210> SEQ ID NO 82
<211> LENGTH: 21
<212> TYPE: DNA
<213> ORGANISM: Artificial Sequence
<220> FEATURE:
<223> OTHER INFORMATION: Chemically Synthesized, 1F-42-7 light chain
      CDR2 nucleic acid

<400> SEQUENCE: 82
gaaacatcca aactgtcatc t                                             21

<210> SEQ ID NO 83
<211> LENGTH: 30
<212> TYPE: DNA
<213> ORGANISM: Artificial Sequence
<220> FEATURE:
<223> OTHER INFORMATION: Chemically Synthesized, 1F-42-7 light chain
      CDR3 nucleic acid

<400> SEQUENCE: 83
ggcggttata gtggtgttga ttttatggct                                    30

<210> SEQ ID NO 84
<211> LENGTH: 1353
<212> TYPE: DNA
<213> ORGANISM: Artificial Sequence
<220> FEATURE:
<223> OTHER INFORMATION: Chemically Synthesized, mAb 3A-5-2 full length
      heavy chain nucleic acid

<400> SEQUENCE: 84
atggagactg ggctgcgctg gcttctcctg gtcgctgtgc tcaaaggtgt ccagtgtcag    60
tcgctggagg agtccggggg tcgcctggtc acgcctggga caccctgac actcacctgc    120 acagtctctg gattctccct caataactac cacatatact gggtccgcca ggctccagga    180
aaggggctgg aatacatcgg aatcattttc aatggtggca catattacgc gagatggaca    240
aaaggccgat tcaccatctc caaaacctcg accacggtgg atctgaaaat gaccagtctg    300
acaaccgagg acacggccac ctatttctgt gccagagggg acggcatctg ggcccaggc    360 accctggtca ccgtctcctt agggcaacct aaggctccat cagtcttccc actggccccc    420
tgctgcgggg acacacccag ctccacggtg accctgggct gcctggtcaa agggtacctc    480
ccggagccag tgaccgtgac ctggaactcg ggcaccctca ccaatggggt acgcaccttc    540
ccgtccgtcc ggcagtcctc aggcctctac tcgctgagca gcgtggtgag cgtgacctca    600
agcagccagc ccgtcacctg caacgtggcc cacccagcca ccaacaccaa agtggacaag    660
```

```
accgttgcgc cctcgacatg cagcaagccc acgtgcccac ccctgaact cctgggggga    720 ccgtctgtct tcatcttccc cccaaaaccc aaggacaccc tcatgatctc acgcaccccc    780
gaggtcacat gcgtggtggt ggacgtgagc caggatgacc ccgaggtgca gttcacatgg    840
tacataaaca acgagcaggt gcgcaccgcc cggccgccgc tacggagca gcagttcaac     900 agcacgatcc gcgtggtcag caccctcccc atcgcgcacc aggactggct gaggggcaag    960
gagttcaagt gcaaagtcca acaaggca ctcccggccc catcgagaa aaccatctcc      1020 aaagccagag gcagcccct ggagccgaag gtctacacca tgggccctcc ccgggaggag   1080
ctgagcagca ggtcggtcag cctgacctgc atgatcaacg gcttctaccc ttccgacatc    1140
tcggtggagt gggagaagaa cgggaaggca gaggacaact acaagaccac gccggccgtg   1200
ctggacagcg acggctccta cttcctctac agcaagctct cagtgcccac gagtgagtgg    1260
cagcggggcg acgtcttcac ctgctccgtg atgcacgagg ccttgcacaa ccactacacg    1320
cagaagtcca tctcccgctc tccgggtaaa tga                                 1353

<210> SEQ ID NO 85
<211> LENGTH: 720
<212> TYPE: DNA
<213> ORGANISM: Artificial Sequence
<220> FEATURE:
<223> OTHER INFORMATION: Chemically Synthesized, mAb 3A-5-2 full length
      light chain nucleic acid

<400> SEQUENCE: 85
atggacacga gggcccccac tcagctgctg gggctcctgc tgctctggct cccaggtgcc     60
acatttgccc aagtgctgac ccagactcca gcctccgtgt ctgcagctgt gggaggcaca   120
gtcaccatca attgccaggc cagtcagagt gttttttaata caactatttt agcctggtat   180
cagcagaaac cagggcagcc tcccaagcgc ctgatctatt ctgcatccac tctggcgtct   240
ggggtctcat cgcggttcaa aggcagtgga tctgggacag aattcactct gaccatgagt   300
ggcgtggagt gtgacgatgc tgccacttac tactgtgcag gcagttttga ttgtaatagt   360
ggtgattgtg ttgctttcgg cggagggacc gaggtggtgg tcaagggtga tccagttgca   420
cctactgtcc tcatcttccc accagctgct gatcaggtgg caactggaac agtcaccatc   480
gtgtgtgtgg cgaataaata ctttcccgat gtcaccgtca cctgggaggt ggatggcacc   540
acccaaacaa ctggcatcga aacagtaaaa acaccgcaga attctgcaga ttgtacctac   600
aacctcagca gcactctgac actgaccagc acacagtaca acagccacaa agagtacacc   660
tgcaaggtga cccagggcac gacctcagtc gtccagagct tcaatagggg tgactgttag   720

<210> SEQ ID NO 86
<211> LENGTH: 21
<212> TYPE: DNA
<213> ORGANISM: Artificial Sequence
<220> FEATURE:
<223> OTHER INFORMATION: Chemically Synthesized, 3A-5-2 heavy chain CDR1
      nucleic acid

<400> SEQUENCE: 86
ctcaataact accacatata c                                               21

<210> SEQ ID NO 87
<211> LENGTH: 45
<212> TYPE: DNA
<213> ORGANISM: Artificial Sequence
<220> FEATURE:
```

<223> OTHER INFORMATION: Chemically Synthesized, 3A-5-2 heavy chain CDR2
nucleic acid

<400> SEQUENCE: 87
atcattttca atggtggcac atattacgcg agatggacaa aaggc                45

<210> SEQ ID NO 88
<211> LENGTH: 12
<212> TYPE: DNA
<213> ORGANISM: Artificial Sequence
<220> FEATURE:
<223> OTHER INFORMATION: Chemically Synthesized, 3A-5-2 heavy chain CDR3
nucleic acid

<400> SEQUENCE: 88
ggggacggca tc                                                    12

<210> SEQ ID NO 89
<211> LENGTH: 33
<212> TYPE: DNA
<213> ORGANISM: Artificial Sequence
<220> FEATURE:
<223> OTHER INFORMATION: Chemically Synthesized, 3A-5-2 light chain CDR1
nucleic acid

<400> SEQUENCE: 89
agtcagagtg tttttaataa caactattta gcc                             33

<210> SEQ ID NO 90
<211> LENGTH: 21
<212> TYPE: DNA
<213> ORGANISM: Artificial Sequence
<220> FEATURE:
<223> OTHER INFORMATION: Chemically Synthesized, 3A-5-2 light chain CDR2
nucleic acid

<400> SEQUENCE: 90
tctgcatcca ctctggcgtc t                                          21

<210> SEQ ID NO 91
<211> LENGTH: 39
<212> TYPE: DNA
<213> ORGANISM: Artificial Sequence
<220> FEATURE:
<223> OTHER INFORMATION: Chemically Synthesized, 3A-5-2 light chain CDR3
nucleic acid

<400> SEQUENCE: 91
gcaggcagtt ttgattgtaa tagtggtgat tgtgttgct                       39

<210> SEQ ID NO 92
<211> LENGTH: 342
<212> TYPE: PRT
<213> ORGANISM: Artificial Sequence
<220> FEATURE:
<223> OTHER INFORMATION: Chemically Synthesized, Alternative Human
Renalase-1 protein - polymorphism resulting in the highlighted
aspartate amino acid at position 37

<400> SEQUENCE: 92

Met Ala Gln Val Leu Ile Val Gly Ala Gly Met Thr Gly Ser Leu Cys
1               5                   10                  15

Ala Ala Leu Leu Arg Arg Gln Thr Ser Gly Pro Leu Tyr Leu Ala Val
            20                  25                  30

Trp Asp Lys Ala Asp Asp Ser Gly Gly Arg Met Thr Thr Ala Cys Ser
        35                  40                  45

Pro His Asn Pro Gln Cys Thr Ala Asp Leu Gly Ala Gln Tyr Ile Thr
    50                  55                  60

Cys Thr Pro His Tyr Ala Lys Lys His Gln Arg Phe Tyr Asp Glu Leu
 65                  70                  75                  80

Leu Ala Tyr Gly Val Leu Arg Pro Leu Ser Ser Pro Ile Glu Gly Met
                 85                  90                  95

Val Met Lys Glu Gly Asp Cys Asn Phe Val Ala Pro Gln Gly Ile Ser
            100                 105                 110

Ser Ile Ile Lys His Tyr Leu Lys Glu Ser Gly Ala Glu Val Tyr Phe
            115                 120                 125

Arg His Arg Val Thr Gln Ile Asn Leu Arg Asp Asp Lys Trp Glu Val
130                 135                 140

Ser Lys Gln Thr Gly Ser Pro Glu Gln Phe Asp Leu Ile Val Leu Thr
145                 150                 155                 160

Met Pro Val Pro Glu Ile Leu Gln Leu Gln Gly Asp Ile Thr Thr Leu
                165                 170                 175

Ile Ser Glu Cys Gln Arg Gln Gln Leu Glu Ala Val Ser Tyr Ser Ser
            180                 185                 190

Arg Tyr Ala Leu Gly Leu Phe Tyr Glu Ala Gly Thr Lys Ile Asp Val
            195                 200                 205

Pro Trp Ala Gly Gln Tyr Ile Thr Ser Asn Pro Cys Ile Arg Phe Val
210                 215                 220

Ser Ile Asp Asn Lys Lys Arg Asn Ile Glu Ser Ser Glu Ile Gly Pro
225                 230                 235                 240

Ser Leu Val Ile His Thr Thr Val Pro Phe Gly Val Thr Tyr Leu Glu
                245                 250                 255

His Ser Ile Glu Asp Val Gln Glu Leu Val Phe Gln Gln Leu Glu Asn
            260                 265                 270

Ile Leu Pro Gly Leu Pro Gln Pro Ile Ala Thr Lys Cys Gln Lys Trp
            275                 280                 285

Arg His Ser Gln Val Thr Asn Ala Ala Ala Asn Cys Pro Gly Gln Met
290                 295                 300

Thr Leu His His Lys Pro Phe Leu Ala Cys Gly Gly Asp Gly Phe Thr
305                 310                 315                 320

Gln Ser Asn Phe Asp Gly Cys Ile Thr Ser Ala Leu Cys Val Leu Glu
                325                 330                 335

Ala Leu Lys Asn Tyr Ile
            340

<210> SEQ ID NO 93
<211> LENGTH: 1029
<212> TYPE: DNA
<213> ORGANISM: Artificial Sequence
<220> FEATURE:
<223> OTHER INFORMATION: Chemically Synthesized, Alternative Human
      Renalase-1 nucleic acid sequence - Note potential polymorphism at
      nucleotide position 111

<400> SEQUENCE: 93
atggcgcagg tgctgatcgt gggcgccggg atgacaggaa gcttgtgcgc tgcgctgctg      60
acgaggcaga cgtccggtcc cttgtacctt gctgtgtggg acaaggctga ggactcaggg     120
ggaagaatga ctacagcctg cagtcctcat aatcctcagt gcacagctga cttgggtgct     180
cagtacatca cctgcactcc tcattatgcc aaaaaacacc aacgttttta tgatgaactg     240
ttagcctatg gcgttttgag gcctctaagc tcgcctattg aaggaatggt gatgaaagaa     300

-continued

```
ggagactgta actttgtggc acctcaagga atttcttcaa ttattaagca ttacttgaaa    360
gaatcaggtg cagaagtcta cttcagacat cgtgtgacac agatcaacct aagagatgac    420
aaatgggaag tatccaaaca aacaggctcc cctgagcagt ttgatcttat tgttctcaca    480
atgccagttc ctgagattct gcagcttcaa ggtgacatca ccaccttaat tagtgaatgc    540
caaaggcagc aactggaggc tgtgagctac tcctctcgat atgctctggg cctcttttat    600
gaagctggta cgaagattga tgtcccttgg gctgggcagt acatcaccag taatccctgc    660
atacgcttcg tctccattga taataagaag cgcaatatag agtcatcaga aattgggcct    720
tccctcgtga ttcacaccac tgtcccattt ggagttacac acttggaaca cagcattgag    780
gatgtgcaag agttagtctt ccagcagctg gaaaacattt tgccgggttt gcctcagcca    840
attgctacca aatgccaaaa atggagacat tcacaggtta caaatgctgc tgccaactgt    900
cctggccaaa tgactctgca tcacaaacct ttccttgcat gtggagggga tggatttact    960
cagtccaact ttgatggctg catcacttct gccctatgtg ttctggaagc tttaaagaat   1020
tatatttaa                                                            1029
```

<210> SEQ ID NO 94
<211> LENGTH: 315
<212> TYPE: PRT
<213> ORGANISM: Artificial Sequence
<220> FEATURE:
<223> OTHER INFORMATION: Chemically Synthesized, Alternative Human
      Renalase-2 amino acid sequence - polymorphism resulting in the
      highlighted aspartate amino acid at position 37

<400> SEQUENCE: 94

```
Met Ala Gln Val Leu Ile Val Gly Ala Gly Met Thr Gly Ser Leu Cys
1               5                   10                  15

Ala Ala Leu Leu Arg Arg Gln Thr Ser Gly Pro Leu Tyr Leu Ala Val
            20                  25                  30

Trp Asp Lys Ala Asp Asp Ser Gly Gly Arg Met Thr Thr Ala Cys Ser
        35                  40                  45

Pro His Asn Pro Gln Cys Thr Ala Asp Leu Gly Ala Gln Tyr Ile Thr
    50                  55                  60

Cys Thr Pro His Tyr Ala Lys Lys His Gln Arg Phe Tyr Asp Glu Leu
65                  70                  75                  80

Leu Ala Tyr Gly Val Leu Arg Pro Leu Ser Ser Pro Ile Glu Gly Met
                85                  90                  95

Val Met Lys Glu Gly Asp Cys Asn Phe Val Ala Pro Gln Gly Ile Ser
            100                 105                 110

Ser Ile Ile Lys His Tyr Leu Lys Glu Ser Gly Ala Glu Val Tyr Phe
        115                 120                 125

Arg His Arg Val Thr Gln Ile Asn Leu Arg Asp Asp Lys Trp Glu Val
    130                 135                 140

Ser Lys Gln Thr Gly Ser Pro Glu Gln Phe Asp Leu Ile Val Leu Thr
145                 150                 155                 160

Met Pro Val Pro Glu Ile Leu Gln Leu Gln Gly Asp Ile Thr Thr Leu
                165                 170                 175

Ile Ser Glu Cys Gln Arg Gln Gln Leu Glu Ala Val Ser Tyr Ser Ser
            180                 185                 190

Arg Tyr Ala Leu Gly Leu Phe Tyr Glu Ala Gly Thr Lys Ile Asp Val
        195                 200                 205

Pro Trp Ala Gly Gln Tyr Ile Thr Ser Asn Pro Cys Ile Arg Phe Val
```

```
            210                 215                 220
Ser Ile Asp Asn Lys Lys Arg Asn Ile Glu Ser Ser Glu Ile Gly Pro
225                 230                 235                 240

Ser Leu Val Ile His Thr Thr Val Pro Phe Gly Val Thr Tyr Leu Glu
            245                 250                 255

His Ser Ile Glu Asp Val Gln Glu Leu Val Phe Gln Gln Leu Glu Asn
            260                 265                 270

Ile Leu Pro Gly Leu Pro Gln Pro Ile Ala Thr Lys Cys Gln Lys Trp
            275                 280                 285

Arg His Ser Gln Val Pro Ser Ala Gly Val Ile Leu Gly Cys Ala Lys
            290                 295                 300

Ser Pro Trp Met Met Ala Ile Gly Phe Pro Ile
305                 310                 315
```

<210> SEQ ID NO 95
<211> LENGTH: 945
<212> TYPE: DNA
<213> ORGANISM: Artificial Sequence
<220> FEATURE:
<223> OTHER INFORMATION: Chemically Synthesized, Alternative Human
      Renalase-2 nucleic acid sequence - Note potential polymorphism at
      nucleotide position 111

<400> SEQUENCE: 95

```
atggcgcagg tgctgatcgt gggcgccggg atgacaggaa gcttgtgcgc tgcgctgctg      60
acgaggcaga cgtccggtcc cttgtacctt gctgtgtggg acaaggctga ggactcaggg     120
ggaagaatga ctacagcctg cagtcctcat aatcctcagt gcacagctga cttgggtgct     180
cagtacatca cctgcactcc tcattatgcc aaaaaacacc aacgttttta tgatgaactg     240
ttagcctatg gcgttttgag gcctctaagc tcgcctattg aaggaatggt gatgaaagaa     300
ggagactgta actttgtggc acctcaagga atttcttcaa ttattaagca ttacttgaaa     360
gaatcaggtg cagaagtcta cttcagacat cgtgtgacac agatcaacct aagagatgac     420
aaatgggaag tatccaaaca aacaggctcc cctgagcagt ttgatcttat tgttctcaca     480
atgccagttc ctgagattct gcagcttcaa ggtgacatca ccaccttaat tagtgaatgc     540
caaaggcagc aactggaggc tgtgagctac tcctctcgat atgctctggg cctcttttat     600
gaagctggta cgaagattga tgtcccttgg gctgggcagt acatcaccag taatccctgc     660
atacgcttcg tctccattga taataagaag cgcaatatag agtcatcaga aattgggcct     720
tccctcgtga ttcacaccac tgtcccattt ggagttacat acttggaaca cagcattgag     780
gatgtgcaag agttagtctt ccagcagctg gaaaacattt tgccgggttt gcctcagcca     840
attgctacca atgccaaaaa atggagacat tcacaggtac caagtgctgg tgtgattcta     900
ggatgtgcga agagcccctg gatgatggcg attggatttc ccatc                      945
```

<210> SEQ ID NO 96
<211> LENGTH: 51
<212> TYPE: DNA
<213> ORGANISM: Artificial Sequence
<220> FEATURE:
<223> OTHER INFORMATION: Chemically Synthesized, BN452 M28 L1

<400> SEQUENCE: 96

```
tgccgtgcca gtcagagcgt gtatgacaac aacaacgtag cctggtatca a                51
```

<210> SEQ ID NO 97
<211> LENGTH: 17

```
<212> TYPE: PRT
<213> ORGANISM: Artificial Sequence
<220> FEATURE:
<223> OTHER INFORMATION: Chemically Synthesized, BN452 M28 L1

<400> SEQUENCE: 97

Cys Arg Ala Ser Gln Ser Val Tyr Asp Asn Asn Val Ala Trp Tyr
1               5                   10                  15

Gln

<210> SEQ ID NO 98
<211> LENGTH: 51
<212> TYPE: DNA
<213> ORGANISM: Artificial Sequence
<220> FEATURE:
<223> OTHER INFORMATION: Chemically Synthesized, BN453 M42 L1

<400> SEQUENCE: 98
tgccgtgcca gtcagaccgt gtataacaac aactacgtag cctggtatca a         51

<210> SEQ ID NO 99
<211> LENGTH: 17
<212> TYPE: PRT
<213> ORGANISM: Artificial Sequence
<220> FEATURE:
<223> OTHER INFORMATION: Chemically Synthesized, BN453 M42 L1

<400> SEQUENCE: 99

Cys Arg Ala Ser Gln Thr Val Tyr Asn Asn Asn Tyr Val Ala Trp Tyr
1               5                   10                  15

Gln

<210> SEQ ID NO 100
<211> LENGTH: 42
<212> TYPE: DNA
<213> ORGANISM: Artificial Sequence
<220> FEATURE:
<223> OTHER INFORMATION: Chemically Synthesized, BN454 M28 L2

<400> SEQUENCE: 100
aagcttctga tttacggcgc cagcaccctc tactctggag tc                    42

<210> SEQ ID NO 101
<211> LENGTH: 14
<212> TYPE: PRT
<213> ORGANISM: Artificial Sequence
<220> FEATURE:
<223> OTHER INFORMATION: Chemically Synthesized, BN454 M28 L2

<400> SEQUENCE: 101

Lys Leu Leu Ile Tyr Gly Ala Ser Thr Leu Tyr Ser Gly Val
1               5                   10

<210> SEQ ID NO 102
<211> LENGTH: 42
<212> TYPE: DNA
<213> ORGANISM: Artificial Sequence
<220> FEATURE:
<223> OTHER INFORMATION: Chemically Synthesized, BN455 M42 L2

<400> SEQUENCE: 102
aagcttctga tttacgaaac cagcaaactc tactctggag tc                    42

<210> SEQ ID NO 103
<211> LENGTH: 14
```

```
<212> TYPE: PRT
<213> ORGANISM: Artificial Sequence
<220> FEATURE:
<223> OTHER INFORMATION: Chemically Synthesized, BN455 M42 L2

<400> SEQUENCE: 103

Lys Leu Leu Ile Tyr Glu Thr Ser Lys Leu Tyr Ser Gly Val
1               5                   10

<210> SEQ ID NO 104
<211> LENGTH: 69
<212> TYPE: DNA
<213> ORGANISM: Artificial Sequence
<220> FEATURE:
<223> OTHER INFORMATION: Chemically Synthesized, BN456 M28 L3

<400> SEQUENCE: 104
gcaacttatt actgtctggg cgaattcagc tgcagcagcg ctgactgctt cgccttcgga     60
cagggtacc                                                             69

<210> SEQ ID NO 105
<211> LENGTH: 23
<212> TYPE: PRT
<213> ORGANISM: Artificial Sequence
<220> FEATURE:
<223> OTHER INFORMATION: Chemically Synthesized, BN456 M28 L3

<400> SEQUENCE: 105

Ala Thr Tyr Tyr Cys Leu Gly Glu Phe Ser Cys Ser Ser Ala Asp Cys
1               5                   10                  15

Phe Ala Phe Gly Gln Gly Thr
            20

<210> SEQ ID NO 106
<211> LENGTH: 63
<212> TYPE: DNA
<213> ORGANISM: Artificial Sequence
<220> FEATURE:
<223> OTHER INFORMATION: Chemically Synthesized, BN457 M42 L3

<400> SEQUENCE: 106
gcaacttatt actgtcaggg cggctacagc ggcgtggact tcatggcttt cggacagggt     60
acc                                                                   63

<210> SEQ ID NO 107
<211> LENGTH: 21
<212> TYPE: PRT
<213> ORGANISM: Artificial Sequence
<220> FEATURE:
<223> OTHER INFORMATION: Chemically Synthesized, BN457 M42 L3

<400> SEQUENCE: 107

Ala Thr Tyr Tyr Cys Gln Gly Gly Tyr Ser Gly Val Asp Phe Met Ala
1               5                   10                  15

Phe Gly Gln Gly Thr
            20

<210> SEQ ID NO 108
<211> LENGTH: 48
<212> TYPE: DNA
<213> ORGANISM: Artificial Sequence
<220> FEATURE:
<223> OTHER INFORMATION: Chemically Synthesized, BN458 M28 H1

<400> SEQUENCE: 108
```

-continued

```
gcttctggct tcaacctgag cagcttcgcc gttcactggg tgcgtcag        48
```

<210> SEQ ID NO 109
<211> LENGTH: 16
<212> TYPE: PRT
<213> ORGANISM: Artificial Sequence
<220> FEATURE:
<223> OTHER INFORMATION: Chemically Synthesized, BN458 M28 H1

<400> SEQUENCE: 109

Ala Ser Gly Phe Asn Leu Ser Ser Phe Ala Val His Trp Val Arg Gln
1               5                   10                  15

<210> SEQ ID NO 110
<211> LENGTH: 48
<212> TYPE: DNA
<213> ORGANISM: Artificial Sequence
<220> FEATURE:
<223> OTHER INFORMATION: Chemically Synthesized, BN459 M42 H1

<400> SEQUENCE: 110

```
gcttctggct tcaacctgac cacctacggc gttcactggg tgcgtcag        48
```

<210> SEQ ID NO 111
<211> LENGTH: 16
<212> TYPE: PRT
<213> ORGANISM: Artificial Sequence
<220> FEATURE:
<223> OTHER INFORMATION: Chemically Synthesized, BN459 M42 H1

<400> SEQUENCE: 111

Ala Ser Gly Phe Asn Leu Thr Thr Tyr Gly Val His Trp Val Arg Gln
1               5                   10                  15

<210> SEQ ID NO 112
<211> LENGTH: 57
<212> TYPE: DNA
<213> ORGANISM: Artificial Sequence
<220> FEATURE:
<223> OTHER INFORMATION: Chemically Synthesized, BN460 M28 H2

<400> SEQUENCE: 112

```
ctggaatggg ttgcaatcat cagcagcgtt ggcatcaccc gctatgccga tagcgtc    57
```

<210> SEQ ID NO 113
<211> LENGTH: 19
<212> TYPE: PRT
<213> ORGANISM: Artificial Sequence
<220> FEATURE:
<223> OTHER INFORMATION: Chemically Synthesized, BN460 M28 H2

<400> SEQUENCE: 113

Leu Glu Trp Val Ala Ile Ile Ser Ser Val Gly Ile Thr Arg Tyr Ala
1               5                   10                  15

Asp Ser Val

<210> SEQ ID NO 114
<211> LENGTH: 57
<212> TYPE: DNA
<213> ORGANISM: Artificial Sequence
<220> FEATURE:
<223> OTHER INFORMATION: Chemically Synthesized, BN461 M42 H2

<400> SEQUENCE: 114

```
ctggaatggg ttgcactgat cggcgatcgc ggcaccacct attatgccga tagcgtc    57
```

<210> SEQ ID NO 115
<211> LENGTH: 19
<212> TYPE: PRT
<213> ORGANISM: Artificial Sequence
<220> FEATURE:
<223> OTHER INFORMATION: Chemically Synthesized, BN461 M42 H2

<400> SEQUENCE: 115

Leu Glu Trp Val Ala Leu Ile Gly Asp Arg Gly Thr Thr Tyr Tyr Ala
1               5                   10                  15

Asp Ser Val

<210> SEQ ID NO 116
<211> LENGTH: 66
<212> TYPE: DNA
<213> ORGANISM: Artificial Sequence
<220> FEATURE:
<223> OTHER INFORMATION: Chemically Synthesized, BN462 M28 H3

<400> SEQUENCE: 116
tattattgtg ctcgctatgg ctatagcggc gacgtgaacc gcctggacct gtggggtcaa       60
ggaacc                                                                  66

<210> SEQ ID NO 117
<211> LENGTH: 22
<212> TYPE: PRT
<213> ORGANISM: Artificial Sequence
<220> FEATURE:
<223> OTHER INFORMATION: Chemically Synthesized, BN462 M28 H3

<400> SEQUENCE: 117

Tyr Tyr Cys Ala Arg Tyr Gly Tyr Ser Gly Asp Val Asn Arg Leu Asp
1               5                   10                  15

Leu Trp Gly Gln Gly Thr
            20

<210> SEQ ID NO 118
<211> LENGTH: 54
<212> TYPE: DNA
<213> ORGANISM: Artificial Sequence
<220> FEATURE:
<223> OTHER INFORMATION: Chemically Synthesized, BN463 M42 H3

<400> SEQUENCE: 118
tattattgtg ctcgcggcag cggctatggc gctcgcatct ggggtcaagg aacc             54

<210> SEQ ID NO 119
<211> LENGTH: 18
<212> TYPE: PRT
<213> ORGANISM: Artificial Sequence
<220> FEATURE:
<223> OTHER INFORMATION: Chemically Synthesized, BN463 M42 H3

<400> SEQUENCE: 119

Tyr Tyr Cys Ala Arg Gly Ser Gly Tyr Gly Ala Arg Ile Trp Gly Gln
1               5                   10                  15

Gly Thr

<210> SEQ ID NO 120
<211> LENGTH: 33
<212> TYPE: DNA
<213> ORGANISM: Artificial Sequence
<220> FEATURE:

<223> OTHER INFORMATION: Chemically Synthesized, BN464 M28 HC71

<400> SEQUENCE: 120
cgtttcacta taagcaaaga cacatccaaa aac                           33

<210> SEQ ID NO 121
<211> LENGTH: 11
<212> TYPE: PRT
<213> ORGANISM: Artificial Sequence
<220> FEATURE:
<223> OTHER INFORMATION: Chemically Synthesized, BN464 M28 HC71

<400> SEQUENCE: 121

Arg Phe Thr Ile Ser Lys Asp Thr Ser Lys Asn
1               5                   10

<210> SEQ ID NO 122
<211> LENGTH: 33
<212> TYPE: DNA
<213> ORGANISM: Artificial Sequence
<220> FEATURE:
<223> OTHER INFORMATION: Chemically Synthesized, BN465 M42 HC71

<400> SEQUENCE: 122
cgtttcacta taagccgcga cacatccaaa aac                           33

<210> SEQ ID NO 123
<211> LENGTH: 11
<212> TYPE: PRT
<213> ORGANISM: Artificial Sequence
<220> FEATURE:
<223> OTHER INFORMATION: Chemically Synthesized, BN465 M42 HC71

<400> SEQUENCE: 123

Arg Phe Thr Ile Ser Arg Asp Thr Ser Lys Asn
1               5                   10

<210> SEQ ID NO 124
<211> LENGTH: 39
<212> TYPE: DNA
<213> ORGANISM: Artificial Sequence
<220> FEATURE:
<223> OTHER INFORMATION: Chemically Synthesized, BN498 M28 L3 STOP

<400> SEQUENCE: 124
gcaacttatt actgttaatg ataattcgga cagggtacc                     39

<210> SEQ ID NO 125
<211> LENGTH: 5
<212> TYPE: PRT
<213> ORGANISM: Artificial Sequence
<220> FEATURE:
<223> OTHER INFORMATION: Chemically Synthesized, BN498 M28 L3 STOP,
      sequence prior to triple stop codons

<400> SEQUENCE: 125

Ala Thr Tyr Tyr Cys
1               5

<210> SEQ ID NO 126
<211> LENGTH: 39
<212> TYPE: DNA
<213> ORGANISM: Artificial Sequence
<220> FEATURE:
<223> OTHER INFORMATION: Chemically Synthesized, BN484 M28 H1 STOP

<400> SEQUENCE: 126

```
gcttctggct tcaattaatg ataacactgg gtgcgtcag                                    39
```

<210> SEQ ID NO 127
<211> LENGTH: 5
<212> TYPE: PRT
<213> ORGANISM: Artificial Sequence
<220> FEATURE:
<223> OTHER INFORMATION: Chemically Synthesized, BN484 M28 H1 STOP,
      sequence prior to triple stop codons

<400> SEQUENCE: 127

Ala Ser Gly Phe Asn
1               5

<210> SEQ ID NO 128
<211> LENGTH: 39
<212> TYPE: DNA
<213> ORGANISM: Artificial Sequence
<220> FEATURE:
<223> OTHER INFORMATION: Chemically Synthesized, BN467 M28 and M42 H2
      STOP

<400> SEQUENCE: 128

```
ctggaatggg ttgcatgata atgatatgcc gatagcgtc                                    39
```

<210> SEQ ID NO 129
<211> LENGTH: 5
<212> TYPE: PRT
<213> ORGANISM: Artificial Sequence
<220> FEATURE:
<223> OTHER INFORMATION: Chemically Synthesized, BN467 M28 and M42 H2
      STOP, sequence prior to triple stop codons

<400> SEQUENCE: 129

Leu Glu Trp Val Ala
1               5

<210> SEQ ID NO 130
<211> LENGTH: 39
<212> TYPE: DNA
<213> ORGANISM: Artificial Sequence
<220> FEATURE:
<223> OTHER INFORMATION: Chemically Synthesized, BN485 M28 and M42 H3
      STOP

<400> SEQUENCE: 130

```
tattattgtg ctcgctaatg ataatggggt caaggaacc                                    39
```

<210> SEQ ID NO 131
<211> LENGTH: 5
<212> TYPE: PRT
<213> ORGANISM: Artificial Sequence
<220> FEATURE:
<223> OTHER INFORMATION: Chemically Synthesized, BN485 M28 and M42 H3
      STOP, sequence prior to triple stop codons

<400> SEQUENCE: 131

Tyr Tyr Cys Ala Arg
1               5

<210> SEQ ID NO 132
<211> LENGTH: 39
<212> TYPE: DNA
<213> ORGANISM: Artificial Sequence
<220> FEATURE:
<223> OTHER INFORMATION: Chemically Synthesized, BN469 M42 L1 STOP -continued

<400> SEQUENCE: 132
tgccgtgcca gtcagtgata atgagtagcc tggtatcaa        39

<210> SEQ ID NO 133
<211> LENGTH: 5
<212> TYPE: PRT
<213> ORGANISM: Artificial Sequence
<220> FEATURE:
<223> OTHER INFORMATION: Chemically Synthesized, BN469 M42 L1 STOP,
      sequence prior to triple stop codons

<400> SEQUENCE: 133

Cys Arg Ala Ser Gln
1               5

<210> SEQ ID NO 134
<211> LENGTH: 39
<212> TYPE: DNA
<213> ORGANISM: Artificial Sequence
<220> FEATURE:
<223> OTHER INFORMATION: Chemically Synthesized, BN466 M42 H1 STOP

<400> SEQUENCE: 134
gcttctggct tcaactgata atgacactgg gtgcgtcag        39

<210> SEQ ID NO 135
<211> LENGTH: 5
<212> TYPE: PRT
<213> ORGANISM: Artificial Sequence
<220> FEATURE:
<223> OTHER INFORMATION: Chemically Synthesized, BN466 M42 H1 STOP,
      sequence prior to triple stop codons

<400> SEQUENCE: 135

Ala Ser Gly Phe Asn
1               5

<210> SEQ ID NO 136
<211> LENGTH: 69
<212> TYPE: DNA
<213> ORGANISM: Artificial Sequence
<220> FEATURE:
<223> OTHER INFORMATION: Chemically Synthesized, BN492 M28 L3
      randomization

<400> SEQUENCE: 136
gcaacttatt actgtctggg cgaattcagc tgcagcagcg ctgactgctt cgccttcgga    60
cagggtacc                                                          69

<210> SEQ ID NO 137
<211> LENGTH: 23
<212> TYPE: PRT
<213> ORGANISM: Artificial Sequence
<220> FEATURE:
<223> OTHER INFORMATION: Chemically Synthesized, BN492 M28 L3
      randomization

<400> SEQUENCE: 137

Ala Thr Tyr Tyr Cys Leu Gly Glu Phe Ser Cys Ser Ser Ala Asp Cys
1               5                   10                  15

Phe Ala Phe Gly Gln Gly Thr
            20

<210> SEQ ID NO 138
<211> LENGTH: 48

```
<210> SEQ ID NO 138
<211> LENGTH: 48
<212> TYPE: DNA
<213> ORGANISM: Artificial Sequence
<220> FEATURE:
<223> OTHER INFORMATION: Chemically Synthesized, BN488 M28 H1
      randomization

<400> SEQUENCE: 138
gcttctggct tcaacctgag cagcttcgcc gttcactggg tgcgtcag                    48

<210> SEQ ID NO 139
<211> LENGTH: 16
<212> TYPE: PRT
<213> ORGANISM: Artificial Sequence
<220> FEATURE:
<223> OTHER INFORMATION: Chemically Synthesized, BN488 M28 H1
      randomization

<400> SEQUENCE: 139

Ala Ser Gly Phe Asn Leu Ser Ser Phe Ala Val His Trp Val Arg Gln
1               5                   10                  15

<210> SEQ ID NO 140
<211> LENGTH: 57
<212> TYPE: DNA
<213> ORGANISM: Artificial Sequence
<220> FEATURE:
<223> OTHER INFORMATION: Chemically Synthesized, BN489 M28 H2
      randomization

<400> SEQUENCE: 140
ctggaatggg ttgcaatcat cagcagcgtt ggcatcaccc gctatgccga tagcgtc         57

<210> SEQ ID NO 141
<211> LENGTH: 19
<212> TYPE: PRT
<213> ORGANISM: Artificial Sequence
<220> FEATURE:
<223> OTHER INFORMATION: Chemically Synthesized, BN489 M28 H2
      randomization

<400> SEQUENCE: 141

Leu Glu Trp Val Ala Ile Ile Ser Ser Val Gly Ile Thr Arg Tyr Ala
1               5                   10                  15

Asp Ser Val

<210> SEQ ID NO 142
<211> LENGTH: 66
<212> TYPE: DNA
<213> ORGANISM: Artificial Sequence
<220> FEATURE:
<223> OTHER INFORMATION: Chemically Synthesized, BN490 M28 H3
      randomization

<400> SEQUENCE: 142
tattattgtg ctcgctatgg ctatagcggc gacgtgaacc gcctggacct gtggggtcaa      60
ggaacc                                                                 66

<210> SEQ ID NO 143
<211> LENGTH: 22
<212> TYPE: PRT
<213> ORGANISM: Artificial Sequence
<220> FEATURE:
<223> OTHER INFORMATION: Chemically Synthesized, BN490 M28 H3
      randomization

<400> SEQUENCE: 143
```

Tyr Tyr Cys Ala Arg Tyr Gly Tyr Ser Gly Asp Val Asn Arg Leu Asp
1               5                   10                  15

Leu Trp Gly Gln Gly Thr
                20

<210> SEQ ID NO 144
<211> LENGTH: 51
<212> TYPE: DNA
<213> ORGANISM: Artificial Sequence
<220> FEATURE:
<223> OTHER INFORMATION: Chemically Synthesized, BN496 M42 L1
      randomization

<400> SEQUENCE: 144
tgccgtgcca gtcagaccgt gtataacaac aactacgtag cctggtatca a          51

<210> SEQ ID NO 145
<211> LENGTH: 17
<212> TYPE: PRT
<213> ORGANISM: Artificial Sequence
<220> FEATURE:
<223> OTHER INFORMATION: Chemically Synthesized, BN496 M42 L1
      randomization

<400> SEQUENCE: 145

Cys Arg Ala Ser Gln Thr Val Tyr Asn Asn Asn Tyr Val Ala Trp Tyr
1               5                   10                  15

Gln

<210> SEQ ID NO 146
<211> LENGTH: 48
<212> TYPE: DNA
<213> ORGANISM: Artificial Sequence
<220> FEATURE:
<223> OTHER INFORMATION: Chemically Synthesized, BN493 M42 H1
      randomization

<400> SEQUENCE: 146
gcttctggct tcaacctgac cacctacggc gttcactggg tgcgtcag               48

<210> SEQ ID NO 147
<211> LENGTH: 16
<212> TYPE: PRT
<213> ORGANISM: Artificial Sequence
<220> FEATURE:
<223> OTHER INFORMATION: Chemically Synthesized, BN493 M42 H1
      randomization

<400> SEQUENCE: 147

Ala Ser Gly Phe Asn Leu Thr Thr Tyr Gly Val His Trp Val Arg Gln
1               5                   10                  15

<210> SEQ ID NO 148
<211> LENGTH: 57
<212> TYPE: DNA
<213> ORGANISM: Artificial Sequence
<220> FEATURE:
<223> OTHER INFORMATION: Chemically Synthesized, BN494 M42 H2
      randomization

<400> SEQUENCE: 148
ctggaatggg ttgcactgat cggcgatcgc ggcaccacct attatgccga tagcgtc     57

<210> SEQ ID NO 149
<211> LENGTH: 19
<212> TYPE: PRT

```
<213> ORGANISM: Artificial Sequence
<220> FEATURE:
<223> OTHER INFORMATION: Chemically Synthesized, BN494 M42 H2
      randomization

<400> SEQUENCE: 149

Leu Glu Trp Val Ala Leu Ile Gly Asp Arg Gly Thr Thr Tyr Tyr Ala
1               5                   10                  15

Asp Ser Val

<210> SEQ ID NO 150
<211> LENGTH: 54
<212> TYPE: DNA
<213> ORGANISM: Artificial Sequence
<220> FEATURE:
<223> OTHER INFORMATION: Chemically Synthesized, BN495 M42 H3
      randomization

<400> SEQUENCE: 150
tattattgtg ctcgcggcag cggctatggc gctcgcatct ggggtcaagg aacc           54

<210> SEQ ID NO 151
<211> LENGTH: 18
<212> TYPE: PRT
<213> ORGANISM: Artificial Sequence
<220> FEATURE:
<223> OTHER INFORMATION: Chemically Synthesized, BN495 M42 H3
      randomization

<400> SEQUENCE: 151

Tyr Tyr Cys Ala Arg Gly Ser Gly Tyr Gly Ala Arg Ile Trp Gly Gln
1               5                   10                  15

Gly Thr

<210> SEQ ID NO 152
<211> LENGTH: 7
<212> TYPE: PRT
<213> ORGANISM: Artificial Sequence
<220> FEATURE:
<223> OTHER INFORMATION: Chemically Synthesized, M28 Parental CDR-L1

<400> SEQUENCE: 152

Ser Val Tyr Asp Asn Asn Asn
1               5

<210> SEQ ID NO 153
<211> LENGTH: 4
<212> TYPE: PRT
<213> ORGANISM: Artificial Sequence
<220> FEATURE:
<223> OTHER INFORMATION: Chemically Synthesized, M28 Parental CDR-L2

<400> SEQUENCE: 153

Gly Ala Ser Thr
1

<210> SEQ ID NO 154
<211> LENGTH: 13
<212> TYPE: PRT
<213> ORGANISM: Artificial Sequence
<220> FEATURE:
<223> OTHER INFORMATION: Chemically Synthesized, M28 Parental CDR-L3

<400> SEQUENCE: 154

Leu Gly Glu Phe Ser Cys Ser Ser Ala Asp Cys Phe Ala
1               5                   10
```

```
<210> SEQ ID NO 155
<211> LENGTH: 6
<212> TYPE: PRT
<213> ORGANISM: Artificial Sequence
<220> FEATURE:
<223> OTHER INFORMATION: Chemically Synthesized, M28 Parental CDR-H1

<400> SEQUENCE: 155

Leu Ser Ser Phe Ala Val
1               5

<210> SEQ ID NO 156
<211> LENGTH: 9
<212> TYPE: PRT
<213> ORGANISM: Artificial Sequence
<220> FEATURE:
<223> OTHER INFORMATION: Chemically Synthesized, M28 Parental CDR-H2

<400> SEQUENCE: 156

Ile Ile Ser Ser Val Gly Ile Thr Arg
1               5

<210> SEQ ID NO 157
<211> LENGTH: 12
<212> TYPE: PRT
<213> ORGANISM: Artificial Sequence
<220> FEATURE:
<223> OTHER INFORMATION: Chemically Synthesized, M28 Parental CDR-H3

<400> SEQUENCE: 157

Tyr Gly Tyr Ser Gly Asp Val Asn Arg Leu Asp Leu
1               5                   10

<210> SEQ ID NO 158
<211> LENGTH: 7
<212> TYPE: PRT
<213> ORGANISM: Artificial Sequence
<220> FEATURE:
<223> OTHER INFORMATION: Chemically Synthesized, M28-K2 CDR-L1

<400> SEQUENCE: 158

Ser Val Tyr Asp Asn Asn Asn
1               5

<210> SEQ ID NO 159
<211> LENGTH: 4
<212> TYPE: PRT
<213> ORGANISM: Artificial Sequence
<220> FEATURE:
<223> OTHER INFORMATION: Chemically Synthesized, M28-K2 CDR-L2

<400> SEQUENCE: 159

Gly Ala Ser Thr
1

<210> SEQ ID NO 160
<211> LENGTH: 13
<212> TYPE: PRT
<213> ORGANISM: Artificial Sequence
<220> FEATURE:
<223> OTHER INFORMATION: Chemically Synthesized, M28-K2 CDR-L3

<400> SEQUENCE: 160

Leu Gly Glu Gly Pro Cys Ser Val Thr Asp Cys Leu Ile
1               5                   10
```

```
<210> SEQ ID NO 161
<211> LENGTH: 6
<212> TYPE: PRT
<213> ORGANISM: Artificial Sequence
<220> FEATURE:
<223> OTHER INFORMATION: Chemically Synthesized, M28-K2 CDR-H1

<400> SEQUENCE: 161

Leu Ser Ser Phe Ala Val
1               5

<210> SEQ ID NO 162
<211> LENGTH: 9
<212> TYPE: PRT
<213> ORGANISM: Artificial Sequence
<220> FEATURE:
<223> OTHER INFORMATION: Chemically Synthesized, M28-K2 CDR-H2

<400> SEQUENCE: 162

Leu Ile Gly Val Arg Gly Ser Leu Tyr
1               5

<210> SEQ ID NO 163
<211> LENGTH: 12
<212> TYPE: PRT
<213> ORGANISM: Artificial Sequence
<220> FEATURE:
<223> OTHER INFORMATION: Chemically Synthesized, M28-K2 CDR-H3

<400> SEQUENCE: 163

His Trp Tyr Ser Gly Gly Val Val Arg Leu Asp Ala
1               5                   10

<210> SEQ ID NO 164
<211> LENGTH: 7
<212> TYPE: PRT
<213> ORGANISM: Artificial Sequence
<220> FEATURE:
<223> OTHER INFORMATION: Chemically Synthesized, M28-K5 CDR-L1

<400> SEQUENCE: 164

Ser Val Tyr Asp Asn Asn Asn
1               5

<210> SEQ ID NO 165
<211> LENGTH: 4
<212> TYPE: PRT
<213> ORGANISM: Artificial Sequence
<220> FEATURE:
<223> OTHER INFORMATION: Chemically Synthesized, M28-K5 CDR-L2

<400> SEQUENCE: 165

Gly Ala Ser Thr
1

<210> SEQ ID NO 166
<211> LENGTH: 13
<212> TYPE: PRT
<213> ORGANISM: Artificial Sequence
<220> FEATURE:
<223> OTHER INFORMATION: Chemically Synthesized, M28-K5 CDR-L3

<400> SEQUENCE: 166

Leu Gly Glu Gly Pro Cys Ser Val Thr Asp Cys Leu Ile
1               5                   10
```

```
<210> SEQ ID NO 167
<211> LENGTH: 6
<212> TYPE: PRT
<213> ORGANISM: Artificial Sequence
<220> FEATURE:
<223> OTHER INFORMATION: Chemically Synthesized, M28-K5 CDR-H1

<400> SEQUENCE: 167

Leu Ser Ser Phe Ala Val
1               5

<210> SEQ ID NO 168
<211> LENGTH: 9
<212> TYPE: PRT
<213> ORGANISM: Artificial Sequence
<220> FEATURE:
<223> OTHER INFORMATION: Chemically Synthesized, M28-K5 CDR-H2

<400> SEQUENCE: 168

Leu Ile Ser Gly Arg Gly Thr Arg Phe
1               5

<210> SEQ ID NO 169
<211> LENGTH: 12
<212> TYPE: PRT
<213> ORGANISM: Artificial Sequence
<220> FEATURE:
<223> OTHER INFORMATION: Chemically Synthesized, M28-K5 CDR-H3

<400> SEQUENCE: 169

His Trp Tyr Ser Gly Val Val Arg Leu Asp Ala
1               5                   10

<210> SEQ ID NO 170
<211> LENGTH: 7
<212> TYPE: PRT
<213> ORGANISM: Artificial Sequence
<220> FEATURE:
<223> OTHER INFORMATION: Chemically Synthesized, M28-K9 CDR-L1

<400> SEQUENCE: 170

Ser Val Tyr Asp Asn Asn Asn
1               5

<210> SEQ ID NO 171
<211> LENGTH: 4
<212> TYPE: PRT
<213> ORGANISM: Artificial Sequence
<220> FEATURE:
<223> OTHER INFORMATION: Chemically Synthesized, M28-K9 CDR-L2

<400> SEQUENCE: 171

Gly Ala Ser Thr
1

<210> SEQ ID NO 172
<211> LENGTH: 13
<212> TYPE: PRT
<213> ORGANISM: Artificial Sequence
<220> FEATURE:
<223> OTHER INFORMATION: Chemically Synthesized, M28-K9 CDR-L3

<400> SEQUENCE: 172

Leu Gly Glu Gly Pro Cys Ser Val Thr Asp Cys Leu Ile
1               5                   10

<210> SEQ ID NO 173
```

```
<211> LENGTH: 6
<212> TYPE: PRT
<213> ORGANISM: Artificial Sequence
<220> FEATURE:
<223> OTHER INFORMATION: Chemically Synthesized, M28-K9 CDR-H1

<400> SEQUENCE: 173

Leu Ser Ser Phe Ala Val
1               5

<210> SEQ ID NO 174
<211> LENGTH: 9
<212> TYPE: PRT
<213> ORGANISM: Artificial Sequence
<220> FEATURE:
<223> OTHER INFORMATION: Chemically Synthesized, M28-K9 CDR-H2

<400> SEQUENCE: 174

Ile Ile Ser Ser Val Gly Ile Thr Arg
1               5

<210> SEQ ID NO 175
<211> LENGTH: 12
<212> TYPE: PRT
<213> ORGANISM: Artificial Sequence
<220> FEATURE:
<223> OTHER INFORMATION: Chemically Synthesized, M28-K9 CDR-H3

<400> SEQUENCE: 175

His Trp Tyr Ser Gly Gly Val Val Arg Leu Asp Ala
1               5                   10

<210> SEQ ID NO 176
<211> LENGTH: 7
<212> TYPE: PRT
<213> ORGANISM: Artificial Sequence
<220> FEATURE:
<223> OTHER INFORMATION: Chemically Synthesized, M28-K13 CDR-L1

<400> SEQUENCE: 176

Ser Val Tyr Asp Asn Asn Asn
1               5

<210> SEQ ID NO 177
<211> LENGTH: 4
<212> TYPE: PRT
<213> ORGANISM: Artificial Sequence
<220> FEATURE:
<223> OTHER INFORMATION: Chemically Synthesized, M28-K13 CDR-L2

<400> SEQUENCE: 177

Gly Ala Ser Thr
1

<210> SEQ ID NO 178
<211> LENGTH: 13
<212> TYPE: PRT
<213> ORGANISM: Artificial Sequence
<220> FEATURE:
<223> OTHER INFORMATION: Chemically Synthesized, M28-K13 CDR-L3

<400> SEQUENCE: 178

Leu Gly Glu Phe Ser Cys Ser Ser Ala Asp Cys Phe Ala
1               5                   10

<210> SEQ ID NO 179
<211> LENGTH: 6
```

```
<212> TYPE: PRT
<213> ORGANISM: Artificial Sequence
<220> FEATURE:
<223> OTHER INFORMATION: Chemically Synthesized, M28-K13 CDR-H1

<400> SEQUENCE: 179

Leu Ser Ser Phe Ala Val
1               5

<210> SEQ ID NO 180
<211> LENGTH: 9
<212> TYPE: PRT
<213> ORGANISM: Artificial Sequence
<220> FEATURE:
<223> OTHER INFORMATION: Chemically Synthesized, M28-K13 CDR-H2

<400> SEQUENCE: 180

Leu Ile Gly Val Arg Gly Ser Leu Tyr
1               5

<210> SEQ ID NO 181
<211> LENGTH: 12
<212> TYPE: PRT
<213> ORGANISM: Artificial Sequence
<220> FEATURE:
<223> OTHER INFORMATION: Chemically Synthesized, M28-K13 CDR-H3

<400> SEQUENCE: 181

His Trp Tyr Ser Gly Gly Val Val Arg Leu Asp Ala
1               5                   10

<210> SEQ ID NO 182
<211> LENGTH: 7
<212> TYPE: PRT
<213> ORGANISM: Artificial Sequence
<220> FEATURE:
<223> OTHER INFORMATION: Chemically Synthesized, M28-K14 CDR-L1

<400> SEQUENCE: 182

Ser Val Tyr Asp Asn Asn Asn
1               5

<210> SEQ ID NO 183
<211> LENGTH: 4
<212> TYPE: PRT
<213> ORGANISM: Artificial Sequence
<220> FEATURE:
<223> OTHER INFORMATION: Chemically Synthesized, M28-K14 CDR-L2

<400> SEQUENCE: 183

Gly Ala Ser Thr
1

<210> SEQ ID NO 184
<211> LENGTH: 13
<212> TYPE: PRT
<213> ORGANISM: Artificial Sequence
<220> FEATURE:
<223> OTHER INFORMATION: Chemically Synthesized, M28-K14 CDR-L3

<400> SEQUENCE: 184

Leu Gly Glu Gly Pro Cys Ser Val Thr Asp Cys Leu Ile
1               5                   10

<210> SEQ ID NO 185
<211> LENGTH: 6
<212> TYPE: PRT
```

```
<213> ORGANISM: Artificial Sequence
<220> FEATURE:
<223> OTHER INFORMATION: Chemically Synthesized, M28-K14 CDR-H1

<400> SEQUENCE: 185

Leu Ser Ser Phe Ala Val
1               5

<210> SEQ ID NO 186
<211> LENGTH: 9
<212> TYPE: PRT
<213> ORGANISM: Artificial Sequence
<220> FEATURE:
<223> OTHER INFORMATION: Chemically Synthesized, M28-K14 CDR-H2

<400> SEQUENCE: 186

Leu Ile Ser Gly Arg Gly Thr Arg Phe
1               5

<210> SEQ ID NO 187
<211> LENGTH: 12
<212> TYPE: PRT
<213> ORGANISM: Artificial Sequence
<220> FEATURE:
<223> OTHER INFORMATION: Chemically Synthesized, M28-K14 CDR-H3

<400> SEQUENCE: 187

Tyr Gly Tyr Ser Gly Asp Val Asn Arg Leu Asp Leu
1               5                   10

<210> SEQ ID NO 188
<211> LENGTH: 7
<212> TYPE: PRT
<213> ORGANISM: Artificial Sequence
<220> FEATURE:
<223> OTHER INFORMATION: Chemically Synthesized, M28-K16 CDR-L1

<400> SEQUENCE: 188

Ser Val Tyr Asp Asn Asn Asn
1               5

<210> SEQ ID NO 189
<211> LENGTH: 4
<212> TYPE: PRT
<213> ORGANISM: Artificial Sequence
<220> FEATURE:
<223> OTHER INFORMATION: Chemically Synthesized, M28-K16 CDR-L2

<400> SEQUENCE: 189

Gly Ala Ser Thr
1

<210> SEQ ID NO 190
<211> LENGTH: 13
<212> TYPE: PRT
<213> ORGANISM: Artificial Sequence
<220> FEATURE:
<223> OTHER INFORMATION: Chemically Synthesized, M28-K16 CDR-L3

<400> SEQUENCE: 190

Leu Gly Glu Phe Ser Cys Ser Ser Ala Asp Cys Phe Ala
1               5                   10

<210> SEQ ID NO 191
<211> LENGTH: 6
<212> TYPE: PRT
<213> ORGANISM: Artificial Sequence
```

```
<220> FEATURE:
<223> OTHER INFORMATION: Chemically Synthesized, M28-K16 CDR-H1

<400> SEQUENCE: 191

Leu Ser Ser Phe Ala Val
1               5

<210> SEQ ID NO 192
<211> LENGTH: 9
<212> TYPE: PRT
<213> ORGANISM: Artificial Sequence
<220> FEATURE:
<223> OTHER INFORMATION: Chemically Synthesized, M28-K16 CDR-H2

<400> SEQUENCE: 192

Leu Ile Ser Gly Arg Gly Thr Arg Phe
1               5

<210> SEQ ID NO 193
<211> LENGTH: 12
<212> TYPE: PRT
<213> ORGANISM: Artificial Sequence
<220> FEATURE:
<223> OTHER INFORMATION: Chemically Synthesized, M28-K16 CDR-H3

<400> SEQUENCE: 193

His Trp Tyr Ser Gly Gly Val Val Arg Leu Asp Ala
1               5                   10

<210> SEQ ID NO 194
<211> LENGTH: 7
<212> TYPE: PRT
<213> ORGANISM: Artificial Sequence
<220> FEATURE:
<223> OTHER INFORMATION: Chemically Synthesized, M42 Parental CDR-L1

<400> SEQUENCE: 194

Thr Val Tyr Asn Asn Asn Tyr
1               5

<210> SEQ ID NO 195
<211> LENGTH: 4
<212> TYPE: PRT
<213> ORGANISM: Artificial Sequence
<220> FEATURE:
<223> OTHER INFORMATION: Chemically Synthesized, M42 Parental CDR-L2

<400> SEQUENCE: 195

Glu Thr Ser Lys
1

<210> SEQ ID NO 196
<211> LENGTH: 11
<212> TYPE: PRT
<213> ORGANISM: Artificial Sequence
<220> FEATURE:
<223> OTHER INFORMATION: Chemically Synthesized, M42 Parental CDR-L3

<400> SEQUENCE: 196

Gln Gly Gly Tyr Ser Gly Val Asp Phe Met Ala
1               5                   10

<210> SEQ ID NO 197
<211> LENGTH: 6
<212> TYPE: PRT
<213> ORGANISM: Artificial Sequence
<220> FEATURE:
```

<223> OTHER INFORMATION: Chemically Synthesized, M42 Parental CDR-H1

<400> SEQUENCE: 197

Leu Thr Thr Tyr Gly Val
1               5

<210> SEQ ID NO 198
<211> LENGTH: 9
<212> TYPE: PRT
<213> ORGANISM: Artificial Sequence
<220> FEATURE:
<223> OTHER INFORMATION: Chemically Synthesized, M42 Parental CDR-H2

<400> SEQUENCE: 198

Leu Ile Gly Asp Arg Gly Thr Thr Tyr
1               5

<210> SEQ ID NO 199
<211> LENGTH: 8
<212> TYPE: PRT
<213> ORGANISM: Artificial Sequence
<220> FEATURE:
<223> OTHER INFORMATION: Chemically Synthesized, M42 Parental CDR-H3

<400> SEQUENCE: 199

Gly Ser Gly Tyr Gly Ala Arg Ile
1               5

<210> SEQ ID NO 200
<211> LENGTH: 7
<212> TYPE: PRT
<213> ORGANISM: Artificial Sequence
<220> FEATURE:
<223> OTHER INFORMATION: Chemically Synthesized, M42-K31 CDR-L1

<400> SEQUENCE: 200

Ser Val Tyr Arg Asn Asn Tyr
1               5

<210> SEQ ID NO 201
<211> LENGTH: 4
<212> TYPE: PRT
<213> ORGANISM: Artificial Sequence
<220> FEATURE:
<223> OTHER INFORMATION: Chemically Synthesized, M42-K31 CDR-L2

<400> SEQUENCE: 201

Glu Thr Ser Lys
1

<210> SEQ ID NO 202
<211> LENGTH: 11
<212> TYPE: PRT
<213> ORGANISM: Artificial Sequence
<220> FEATURE:
<223> OTHER INFORMATION: Chemically Synthesized, M42-K31 CDR-L3

<400> SEQUENCE: 202

Gln Gly Gly Tyr Ser Gly Val Asp Phe Met Ala
1               5                   10

<210> SEQ ID NO 203
<211> LENGTH: 6
<212> TYPE: PRT
<213> ORGANISM: Artificial Sequence
<220> FEATURE:
<223> OTHER INFORMATION: Chemically Synthesized, M42-K31 CDR-H1

```
<400> SEQUENCE: 203

Met Ser Ser Glu Arg Arg
1               5

<210> SEQ ID NO 204
<211> LENGTH: 9
<212> TYPE: PRT
<213> ORGANISM: Artificial Sequence
<220> FEATURE:
<223> OTHER INFORMATION: Chemically Synthesized, M42-K31 CDR-H2

<400> SEQUENCE: 204

Leu Ile Arg Asp Arg Gly Trp Asn Tyr
1               5

<210> SEQ ID NO 205
<211> LENGTH: 8
<212> TYPE: PRT
<213> ORGANISM: Artificial Sequence
<220> FEATURE:
<223> OTHER INFORMATION: Chemically Synthesized, M42-K31 CDR-H3

<400> SEQUENCE: 205

Gly Ile Cys Tyr Cys Ala Arg Ser
1               5

<210> SEQ ID NO 206
<211> LENGTH: 7
<212> TYPE: PRT
<213> ORGANISM: Artificial Sequence
<220> FEATURE:
<223> OTHER INFORMATION: Chemically Synthesized, M42-K34 CDR-L1

<400> SEQUENCE: 206

Ser Val Tyr Arg Asn Asn Tyr
1               5

<210> SEQ ID NO 207
<211> LENGTH: 4
<212> TYPE: PRT
<213> ORGANISM: Artificial Sequence
<220> FEATURE:
<223> OTHER INFORMATION: Chemically Synthesized, M42-K34 CDR-L2

<400> SEQUENCE: 207

Glu Thr Ser Lys
1

<210> SEQ ID NO 208
<211> LENGTH: 11
<212> TYPE: PRT
<213> ORGANISM: Artificial Sequence
<220> FEATURE:
<223> OTHER INFORMATION: Chemically Synthesized, M42-K34 CDR-L3

<400> SEQUENCE: 208

Gln Gly Gly Tyr Ser Gly Val Asp Phe Met Ala
1               5                   10

<210> SEQ ID NO 209
<211> LENGTH: 6
<212> TYPE: PRT
<213> ORGANISM: Artificial Sequence
<220> FEATURE:
<223> OTHER INFORMATION: Chemically Synthesized, M42-K34 CDR-H1
```

```
<400> SEQUENCE: 209

Leu Thr Thr Tyr Gly Val
1               5

<210> SEQ ID NO 210
<211> LENGTH: 9
<212> TYPE: PRT
<213> ORGANISM: Artificial Sequence
<220> FEATURE:
<223> OTHER INFORMATION: Chemically Synthesized, M42-K34 CDR-H2

<400> SEQUENCE: 210

Leu Ile Arg Asp Arg Gly Trp Asn Tyr
1               5

<210> SEQ ID NO 211
<211> LENGTH: 8
<212> TYPE: PRT
<213> ORGANISM: Artificial Sequence
<220> FEATURE:
<223> OTHER INFORMATION: Chemically Synthesized, M42-K34 CDR-H3

<400> SEQUENCE: 211

Gly Ile Cys Tyr Cys Ala Arg Ser
1               5

<210> SEQ ID NO 212
<211> LENGTH: 7
<212> TYPE: PRT
<213> ORGANISM: Artificial Sequence
<220> FEATURE:
<223> OTHER INFORMATION: Chemically Synthesized, M42-K35 CDR-L1

<400> SEQUENCE: 212

Thr Val Tyr Asn Asn Asn Tyr
1               5

<210> SEQ ID NO 213
<211> LENGTH: 4
<212> TYPE: PRT
<213> ORGANISM: Artificial Sequence
<220> FEATURE:
<223> OTHER INFORMATION: Chemically Synthesized, M42-K35 L2

<400> SEQUENCE: 213

Glu Thr Ser Lys
1

<210> SEQ ID NO 214
<211> LENGTH: 11
<212> TYPE: PRT
<213> ORGANISM: Artificial Sequence
<220> FEATURE:
<223> OTHER INFORMATION: Chemically Synthesized, M42-K35 L3

<400> SEQUENCE: 214

Gln Gly Gly Tyr Ser Gly Val Asp Phe Met Ala
1               5                   10

<210> SEQ ID NO 215
<211> LENGTH: 6
<212> TYPE: PRT
<213> ORGANISM: Artificial Sequence
<220> FEATURE:
<223> OTHER INFORMATION: Chemically Synthesized, M42-K35 H1

<400> SEQUENCE: 215
```

```
Met Ser Ser Glu Arg Arg
1               5
```

<210> SEQ ID NO 216
<211> LENGTH: 9
<212> TYPE: PRT
<213> ORGANISM: Artificial Sequence
<220> FEATURE:
<223> OTHER INFORMATION: Chemically Synthesized, M42-K35 H2

<400> SEQUENCE: 216

```
Leu Ile Arg Asp Arg Gly Trp Asn Tyr
1               5
```

<210> SEQ ID NO 217
<211> LENGTH: 8
<212> TYPE: PRT
<213> ORGANISM: Artificial Sequence
<220> FEATURE:
<223> OTHER INFORMATION: Chemically Synthesized, M42-K35 H3

<400> SEQUENCE: 217

```
Gly Ile Cys Tyr Cys Ala Arg Ser
1               5
```

<210> SEQ ID NO 218
<211> LENGTH: 360
<212> TYPE: DNA
<213> ORGANISM: Artificial Sequence
<220> FEATURE:
<223> OTHER INFORMATION: Chemically Synthesized, M28-humanized Fv
      sequence Heavy chain

<400> SEQUENCE: 218

```
gaggttcagc tggtggagtc tggcggtggc ctggtgcagc caggggggctc actccgtttg    60 tcctgtgcag cttctggctt caatctgagc agcttcgccg ttcactgggt gcgtcaggcc   120
ccgggtaagg gcctggaatg ggttgcaatc atcagcagcg ttggcatcac ccgctatgcc   180
gatagcgtca agggccgttt cactataagc aaagacacat ccaaaaacac agcctaccta   240
caaatgaaca gcttaagagc tgaggacact gccgtctatt attgtgctcg ctatggctat   300
agcggcgacg tgaaccgcct ggacctgtgg ggtcaaggaa ccctggtcac cgtctcctcg   360
```

<210> SEQ ID NO 219
<211> LENGTH: 120
<212> TYPE: PRT
<213> ORGANISM: Artificial Sequence
<220> FEATURE:
<223> OTHER INFORMATION: Chemically Synthesized, M28-humanized Fv
      sequence Heavy chain

<400> SEQUENCE: 219

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Ser Phe
            20                  25                  30

Ala Val His Trp Val Arg Gln Ala Pro Gly Lys Gly Leu Glu Trp Val
        35                  40                  45

Ala Ile Ile Ser Ser Val Gly Ile Thr Arg Tyr Ala Asp Ser Val Lys
    50                  55                  60

Gly Arg Phe Thr Ile Ser Lys Asp Thr Ser Lys Asn Thr Ala Tyr Leu
65                  70                  75                  80
```

```
Gln Met Asn Ser Leu Arg Ala Glu Asp Thr Ala Val Tyr Tyr Cys Ala
            85                  90                  95

Arg Tyr Gly Tyr Ser Gly Asp Val Asn Arg Leu Asp Leu Trp Gly Gln
        100                 105                 110

Gly Thr Leu Val Thr Val Ser Ser
        115                 120
```

```
<210> SEQ ID NO 220
<211> LENGTH: 342
<212> TYPE: DNA
<213> ORGANISM: Artificial Sequence
<220> FEATURE:
<223> OTHER INFORMATION: Chemically Synthesized, M28-humanized Fv
      sequence Light chain

<400> SEQUENCE: 220
gatatccaga tgacccagtc cccgagctcc ctgtccgcct ctgtgggcga tagggtcacc      60
atcacctgcc gtgccagtca gagcgtgtat gacaacaaca acgtagcctg gtatcaacag     120
aaaccaggaa aagctccgaa gcttctgatt tacggcgcca gcaccctcta ctctggagtc     180
ccttctcgct ctctggtag ccgttccggg acggatttca ctctgaccat cagcagtctg      240
cagccggaag acttcgcaac ttattactgt ctgggcgaat cagctgcag cagcgctgac     300 tgcttcgcct tcggacaggg taccaaggtg gagatcaaac ga                        342
```

```
<210> SEQ ID NO 221
<211> LENGTH: 114
<212> TYPE: PRT
<213> ORGANISM: Artificial Sequence
<220> FEATURE:
<223> OTHER INFORMATION: Chemically Synthesized, M28-humanized Fv
      sequence Light chain

<400> SEQUENCE: 221

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Tyr Asp Asn
            20                  25                  30

Asn Asn Val Ala Trp Tyr Gln Gln Lys Pro Gly Lys Ala Pro Lys Leu
        35                  40                  45

Leu Ile Tyr Gly Ala Ser Thr Leu Tyr Ser Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Leu Gly Glu Phe Ser Cys
                85                  90                  95

Ser Ser Ala Asp Cys Phe Ala Phe Gly Gln Gly Thr Lys Val Glu Ile
            100                 105                 110

Lys Arg
```

```
<210> SEQ ID NO 222
<211> LENGTH: 348
<212> TYPE: DNA
<213> ORGANISM: Artificial Sequence
<220> FEATURE:
<223> OTHER INFORMATION: Chemically Synthesized, M42 humanized Fv
      sequence Heavy chain

<400> SEQUENCE: 222
gaggttcagc tggtggagtc tggcggtggc ctggtgcagc cagggggctc actccgtttg      60
```

```
tcctgtgcag cttctggctt caacctgacc acctacggcg ttcactgggt gcgtcaggcc    120
ccgggtaagg gcctggaatg ggttgcactg atcggcgatc gcggcaccac ctattatgcc    180
gatagcgtca agggccgttt cactataagc cgcgacacat ccaaaaacac agcctaccta    240
caaatgaaca gcttaagagc tgaggacact gccgtctatt attgtgctcg cggcagcggc    300
tatggcgctc gcatctgggg tcaaggaacc ctggtcaccg tctcctcg               348
```

```
<210> SEQ ID NO 223
<211> LENGTH: 116
<212> TYPE: PRT
<213> ORGANISM: Artificial Sequence
<220> FEATURE:
<223> OTHER INFORMATION: Chemically Synthesized, M42 humanized Fv
      sequence Heavy chain

<400> SEQUENCE: 223
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Thr Thr Tyr
            20                  25                  30

Gly Val His Trp Val Arg Gln Ala Pro Gly Lys Gly Leu Glu Trp Val
        35                  40                  45

Ala Leu Ile Gly Asp Arg Gly Thr Thr Tyr Tyr Ala Asp Ser Val Lys
    50                  55                  60

Gly Arg Phe Thr Ile Ser Arg Asp Thr Ser Lys Asn Thr Ala Tyr Leu
65                  70                  75                  80

Gln Met Asn Ser Leu Arg Ala Glu Asp Thr Ala Val Tyr Tyr Cys Ala
                85                  90                  95

Arg Gly Ser Gly Tyr Gly Ala Arg Ile Trp Gly Gln Gly Thr Leu Val
            100                 105                 110

Thr Val Ser Ser
        115

```
<210> SEQ ID NO 224
<211> LENGTH: 336
<212> TYPE: DNA
<213> ORGANISM: Artificial Sequence
<220> FEATURE:
<223> OTHER INFORMATION: Chemically Synthesized, M42 humanized Fv
      sequence Light chain

<400> SEQUENCE: 224
gatatccaga tgacccagtc cccgagctcc ctgtccgcct ctgtgggcga tagggtcacc    60
atcacctgcc gtgccagtca gaccgtgtat aacaacaact acgtagcctg gtatcaacag    120
aaaccaggaa aagctccgaa gcttctgatt tacgaaacca gcaaactcta ctctggagtc    180
ccttctcgct ctctggtag ccgttccggg acggatttca ctctgaccat cagcagtctg    240
cagccggaag acttcgcaac ttattactgt cagggcggct acagcggcgt ggacttcatg    300
gctttcggac agggtaccaa ggtggagatc aaacga                              336
```

```
<210> SEQ ID NO 225
<211> LENGTH: 112
<212> TYPE: PRT
<213> ORGANISM: Artificial Sequence
<220> FEATURE:
<223> OTHER INFORMATION: Chemically Synthesized, M42 humanized Fv
      sequence Light chain

<400> SEQUENCE: 225
```

-continued

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Val Tyr Asn Asn
            20                  25                  30

Asn Tyr Val Ala Trp Tyr Gln Gln Lys Pro Gly Lys Ala Pro Lys Leu
        35                  40                  45

Leu Ile Tyr Glu Thr Ser Lys Leu Tyr Ser Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Gln Gly Gly Tyr Ser Gly
                85                  90                  95

Val Asp Phe Met Ala Phe Gly Gln Gly Thr Lys Val Glu Ile Lys Arg
            100                 105                 110
```

<210> SEQ ID NO 226
<211> LENGTH: 5
<212> TYPE: PRT
<213> ORGANISM: Artificial Sequence
<220> FEATURE:
<223> OTHER INFORMATION: Chemically Synthesized, BN498 M28 L3 STOP,
      sequence following triple stop codons of SEQ ID NO:125

<400> SEQUENCE: 226

```
Phe Gly Gln Gly Thr
1               5
```

<210> SEQ ID NO 227
<211> LENGTH: 5
<212> TYPE: PRT
<213> ORGANISM: Artificial Sequence
<220> FEATURE:
<223> OTHER INFORMATION: Chemically Synthesized, BN484 M28 H1 STOP,
      sequence following triple stop codons of SEQ ID NO:127

<400> SEQUENCE: 227

```
His Trp Val Arg Gln
1               5
```

<210> SEQ ID NO 228
<211> LENGTH: 5
<212> TYPE: PRT
<213> ORGANISM: Artificial Sequence
<220> FEATURE:
<223> OTHER INFORMATION: Chemically Synthesized, BN467 M28 and M42 H2
      STOP, sequence following triple stop codons of SEQ ID NO:129

<400> SEQUENCE: 228

```
Tyr Ala Asp Ser Val
1               5
```

<210> SEQ ID NO 229
<211> LENGTH: 5
<212> TYPE: PRT
<213> ORGANISM: Artificial Sequence
<220> FEATURE:
<223> OTHER INFORMATION: Chemically Synthesized, BN485 M28 and M42 H3
      STOP, sequence following triple stop codons of SEQ ID NO:131

<400> SEQUENCE: 229

```
Trp Gly Gln Gly Thr
1               5
```

<210> SEQ ID NO 230

```
<211> LENGTH: 5
<212> TYPE: PRT
<213> ORGANISM: Artificial Sequence
<220> FEATURE:
<223> OTHER INFORMATION: Chemically Synthesized, BN469 M42 L1 STOP,
      sequence following triple stop codons of SEQ ID NO:133

<400> SEQUENCE: 230

Val Ala Trp Tyr Gln
1               5

<210> SEQ ID NO 231
<211> LENGTH: 5
<212> TYPE: PRT
<213> ORGANISM: Artificial Sequence
<220> FEATURE:
<223> OTHER INFORMATION: Chemically Synthesized, BN466 M42 H1 STOP,
      sequence following triple stop codons of SEQ ID NO:135

<400> SEQUENCE: 231

His Trp Val Arg Gln
1               5
```

ANTI-RENALASE ANTIBODIES FOR THE TREATMENT AND PREVENTION OF DISEASES AND DISORDERS

CROSS REFERENCE TO RELATED APPLICATIONS

This application is a U.S. national phase application filed under 35 U.S.C. § 371 claiming benefit to International Patent Application No. PCT/US2018/067611, filed Dec. 27, 2018, which is entitled to priority under 35 U.S.C. § 119(e) to U.S. Provisional Patent Application No. 62/611,609, filed Dec. 29, 2017, each of which applications is hereby incorporated herein by reference in its entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file 047162-5248-00US Sequence Listing Revised_ST25.TXT, created on Sep. 21, 2020, 118,319 bytes, is hereby incorporated by reference.

BACKGROUND OF THE INVENTION

Renalase (RNLS) is a protein produced predominantly in the kidney, heart, skeletal muscle, testes and to a lesser extent in other tissues (Xu et al., 2005 J Clin Invest. 115 (5):1275-80 and Wang et al., 2008 Mol Biol Rep. 35(4): 613-20). Two isoform variants of renalase have been described, Renalase-1 and Renalase-2. These two forms of renalase differ due to differential splicing of the final exon. Renalase has been described as a novel flavin adenine dinucleotide-containing monoamine oxidase with an activity that selectively deaminates the catecholamines epinephrine, norepinephrine and dopamine. A deficiency of renalase in the plasma of patients with end-stage renal disease, in comparasion to healthy individuals, has been described. Catecholamines play a major role in the maintenance and modulation of blood pressure, including in disease, through effects on cardiac output and vascular resistance. The infusion of a recombinant form of renalase into rats caused a decrease in cardiac contractility, heart rate, and blood pressure. Patients with renal failure have been characterized with heightened levels of circulating catecholamines which correlate with hypertension and greater mortality through cardiovascular complications. Thus the protein renalase may play a role in the control and maintenance of catecholamine-induced changes in blood pressure and the deficiency of renalase observed in renal disease patients may be detrimental to outcomes.

A deficiency of renalase in the plasma of patients with end-stage renal disease, in comparasion to healthy individuals, has been described. Patients with renal failure have been characterized with heightened levels of circulating catecholamines which correlate with hypertension and greater mortality through cardiovascular complications. Thus the protein renalase may play a role in the control and maintenance of catecholamine-induced changes in blood pressure and the deficiency of renalase observed in renal disease patients may be detrimental to outcomes. However, little is known about the role of renalase in cancer.

An essential feature of cancer is dysregulation of cell senescence and death. Renalase (RNLS) is a secreted flavoprotein that protects against ischemic and toxic cellular injury by signaling through the plasma membrane calcium ATPase PMCA4b to activate the PI3K/AKT, and MAPK pathways.

Skin cancer is a common human malignancy, and its incidence has been increasing in developed countries (Gray-Schopfer et al., 2007 Nature. 445:851-7; Lowe et al., 2014 Mayo Clinic Proceedings. 89:52-9; Lesinski et al., 2013 Future oncology. 9:925-7). Melanoma is the deadliest form of skin cancer, with low survival rates once it becomes unresectable (Lowe et al., 2014 Mayo Clinic Proceedings. 89:52-9). It is a molecularly heterogeneous disease and some of the key alterations in signaling pathways that participate in disease development and progression have been identified. The Ras/Raf/MEK/ERK and the PI3K/AKT signaling pathways play key roles in the pathogenesis of melanoma (Gray-Schopfer et al., 2007 Nature. 445:851-7; Lesinski et al., 2013 Future oncology. 9:925-7; Yajima et al., 2012 Dermatology research and practice. 2012:354191). Mutations in Ras, Raf, PI3K or PTEN (PI3K inhibitor) can lead to the sustained activation of ERK and AKT, which in turn promote cell survival and proliferation. Dankort et al. demonstrated this well with conditional melanocyte-specific expression of $BRaf^{v600E}$ in mice, none of whom developed melanoma, however, revealed 100% penetrance of melanoma development when combined with silencing of the Pten tumor suppressor gene (Dankort et al., 2009 Nature genetics. 41:544-52). The elucidation of these pathogenic pathways has facilitated the development of specific inhibitors that target hyper-activated kinases. While these agents have proven effective in the treatment of selective groups of patients with metastatic melanoma, their beneficial actions are often short lived, hence the pressing need for the identification of additional therapeutic targets.

RNLS expression is markedly increased in melanoma tumors, and specifically in CD163+ tumor associated macrophages (TAMs). In a cohort of patients with primary melanoma, disease-specific survival was inversely correlated with RNLS expression in the tumor mass, suggesting a pathogenic role for RNLS. Inhibition of RNLS signaling using siRNA, anti-RNLS antibodies, or a RNLS derived inhibitory peptide significantly decreases melanoma cells survival in vitro. Anti-RNLS therapy with a monoclonal antibody markedly inhibits melanoma tumor growth in a xenograft mouse model. Treatment with m28-RNLS (also previously known as 1D-28-4), caused a marked reduction in endogenous RNLS expression, and in total and phosphorylated STAT3 in $CD163^+TAMs$. Increased apoptosis in tumor cells was temporally related to p38 MAPK mediated activation of the B-cell lymphoma 2 related protein Bax. Expression of the cell cycle inhibitor p21 increased and cell cycle arrest was documented. These results indicate that increased RNLS production by $CD163^+TAMs$ facilitates melanoma growth by activating STAT3, and that inhibition of RNLS signaling has potential therapeutic application in the management of melanoma.

Improved methods for the detection of renalase in bodily fluids and tissues may aid in the diagnosis and prognosis of renal disease, cardiovascular disease and/or cancer. However, the validation of renalase as a relevant biomarker requires highly selective reagents for its detection. Antibody-based technologies are widely used for the detection of biomarkers. To date there have been only a small number of reagent antibodies raised against renalase with no to minimal characterization.

Pancreatic cancer is one of the most lethal neoplasms, causing approximately 330,000 death globally and 40,000 in the US (World Cancer Report 2014. WHO Press; 2014).

Pancreas cancer is difficult to detect, and most cases are diagnosed at a late stage (Nolen et al., 2014 PLoS ONE. 9(4):e94928). Although there has been some progress in the use of chemotherapy of this cancer, the disease remains extremely resistant to all drug therapies (Hidalgo et al., 2010 New England Journal of Medicine. 362(17):1605-17). The overall 5-year survival for individuals with pancreatic cancer is <5% (Hidalgo et al., 2010 New England Journal of Medicine. 362(17):1605-17), and additional therapeutic targets are needed.

The development of pancreatic cancer relies on the stepwise accumulation of gene mutations (Jones et al., 2008 Science. 321(5897):1801-6), some of which cause abnormal MAPK, PI3K and JAK-STAT signaling. Progression from minimally dysplastic epithelium to dysplasia to invasive carcinoma reflects the stepwise accumulation of gene mutations that either activate oncogenes (e.g. KRAS2), or inactivate tumor suppressor genes 9e.g. CDKN2a/INK4a, TP53 and DPC4/SMaD4) (Hidalgo et al., 2012 Annals of Oncology. 23(suppl 10):x135-x8). Ninety-five, 90 and 75% of pancreatic tumors carry mutations in KRAS2, CDKN2a, and TP53, respectively. These mutations result in sustained and dysregulated proliferation that characterizes cancer growth. The mutational landscape and core signaling pathways in pancreatic ductal adenocarcinoma (PDAC) have been defined through a comprehensive genetic analysis of 24 advanced PDACs (Jones et al., 2008 Science. 321(5897): 1801-6). These data indicate that most PDACs contain a large number of genetic changes that are primarily point mutations, and which affect approximately 12 cell signaling pathways.

That study also identified five hundred and forty-one genes overexpressed in PDAC by at least 10-fold in 90% of the tumors. This included a 2 to 4-fold increase in the recently characterized protein, renalase (RNLS), in tumors or in tumor derived cell lines. RNLS, a novel secreted flavo-protein (Xu et al., 2005 J Clin Invest. 115(5):1275-80; Desir et al., 2012 J Am Heart Assoc. 1(e002634; Desir et al., 2012 J Am Soc Hypertens. 6(6):417-26; Li et al., 2008 Circulation. 117(10):1277-82) with NADH oxidase activity, (Farzaneh-Far et al., 2010 PLoS One. 5(10):e13496; Beaupre et al., 2015 Biochemistry. 54(3):795-806) promotes cell and organ survival (Lee et al., 2013 J Am Soc Nephrol. 24(3):445-55) through a receptor-mediated process that is independent of its intrinsic enzymatic activities (Wang et al., 2014 Journal of the American Society of Nephrology. DOI: 10.1681/asn.2013060665). RNLS rapidly activates protein kinase B (AKT), the extracellular signal-regulated kinase (ERK), and the mitogen activated protein kinase (p38). Chemical inhibition of either ERK or AKT abrogated the protective effect of RNLS (Wang et al., 2014 Journal of the American Society of Nephrology. DOI:10.1681/asn.2013060665).

Accordingly, there exists a need for improved methods and compositions that bind renalase, such as antibodies, for the detection, diagnosis, prevention and treatment of diseases or disorders including renal disease, cardiovascular disease, and cancer. The present invention addresses this need.

SUMMARY OF THE INVENTION

In one embodiment, the invention relates to a composition comprising an antibody or binding portion thereof that specifically binds to renalase.

In one embodiment, the antibody or binding portion thereof specifically binds to renalase with an affinity of at least $10^{-6}$ M.

In one embodiment, the antibody or binding portion thereof specifically binds a peptide comprising an amino acid sequence selected from SEQ ID NO: 1-8.

In one embodiment, the renalase is human renalase.

In one embodiment, the antibody or binding portion thereof is a monoclonal antibody, a polyclonal antibody, a single chain antibody, an immunoconjugate, a defucosylated antibody, or a bispecific antibody.

In one embodiment, the immunoconjugate comprises a therapeutic agent or a detection moiety.

In one embodiment, the antibody or binding portion thereof is selected from a humanized antibody, a chimeric antibody, a fully human antibody, and an antibody mimetic.

In one embodiment, the antibody or binding portion thereof comprises at least one of: a) a heavy chain (HC) CDR1 comprising an amino acid sequence of SEQ ID NO: 155, b) a HC CDR2 comprising an amino acid sequence selected from SEQ ID NO: 156, SEQ ID NO: 162, and SEQ ID NO: 168, c) a HC CDR3 comprising an amino acid sequence selected from SEQ ID NO: 157, and SEQ ID NO: 163, d) a light chain (LC) CDR1 comprising the amino acid sequence of SEQ ID NO: 152, e) a LC CDR2 comprising the amino acid sequence of SEQ ID NO: 153, and f) a LC CDR3 comprising an amino acid sequence selected from SEQ ID NO: 154, and SEQ ID NO: 160.

In one embodiment, the antibody or binding portion thereof comprises a HC CDR1 comprising the amino acid sequence of SEQ ID NO: 155, a HC CDR2 comprising the amino acid sequence of SEQ ID NO: 156, a HC CDR3 comprising the amino acid sequence of SEQ ID NO: 157, a LC CDR1 comprising the amino acid sequence of SEQ ID NO: 152, a LC CDR2 comprising the amino acid sequence of SEQ ID NO: 153, and a LC CDR3 comprising the amino acid sequence of SEQ ID NO: 154.

In one embodiment, the antibody or binding portion thereof comprises a $V_h$ comprising the amino acid sequence of SEQ ID NO: 219 and a $V_L$ comprising the amino acid sequence of SEQ ID NO: 221.

In one embodiment, the antibody or binding portion thereof comprises at least one of: a) a HC CDR1 comprising an amino acid sequence selected from SEQ ID NO: 197 and SEQ ID NO: 203, b) a HC CDR2 comprising an amino acid sequence selected from SEQ ID NO: 198 and SEQ ID NO: 204, c) a HC CDR3 comprising an amino acid sequence selected from SEQ ID NO: 199 and SEQ ID NO: 205, d) a LC CDR1 comprising an amino acid sequence selected from SEQ ID NO: 194 and SEQ ID NO: 200, e) a LC CDR2 comprising the amino acid sequence of SEQ ID NO: 195, f) and a LC CDR3 comprising the amino acid sequence of SEQ ID NO: 196.

In one embodiment, the antibody or binding portion thereof comprises a HC CDR1 comprising the amino acid sequence of SEQ ID NO: 197, a HC CDR2 comprising the amino acid sequence of SEQ ID NO: 198, a HC CDR3 comprising the amino acid sequence of SEQ ID NO: 199, a LC CDR1 comprising the amino acid sequence of SEQ ID NO: 194, a LC CDR2 comprising the amino acid sequence of SEQ ID NO: 195, and a LC CDR3 comprising the amino acid sequence of SEQ ID NO: 196.

In one embodiment, the antibody or binding portion thereof comprises a $V_h$ comprising the amino acid sequence of SEQ ID NO: 223 and $V_L$ comprising the amino acid sequence of SEQ ID NO: 225.

In one embodiment, the invention relates to an isolated nucleic acid molecule comprising a sequence encoding at least one antibody or binding portion thereof that specifically binds to renalase.

In one embodiment, the molecule comprises at least one nucleic acid sequence that is at least 80% identical to at least one nucleic acid sequence selected from SEQ ID NO: 218, SEQ ID NO: 220, SEQ ID NO: 222, and SEQ ID NO: 224.

In one embodiment, the invention relates to an expression vector comprising at least one nucleic acid sequence selected from SEQ ID NO: 218, SEQ ID NO: 220, SEQ ID NO: 222, and SEQ ID NO: 224.

In one embodiment, the invention relates to a cell comprising at least one nucleic acid sequence selected from SEQ ID NO: 218, SEQ ID NO: 220, SEQ ID NO: 222, and SEQ ID NO: 224.

In one embodiment, the invention relates to a method of treating a disease or disorder in a subject in need thereof, the method comprising administering to the subject a composition comprising an antibody or binding portion thereof that specifically binds to renalase.

In one embodiment, the method further comprises the step of administering to the subject at least one additional agent.

In one embodiment, the disease or disorder is at least one selected from renal disease, cardiovascular disease, pancreatitis, hepatitis, inflammatory disorders of the kidney, and cancer.

In one embodiment, the disease or disorder is cancer, and the cancer is pancreatic cancer or melanoma.

In one embodiment, the subject is human.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 1 depicts peptide antigens used to immunize rabbits (SEQ ID NOs: 1-7).

FIG. 2 depicts full-length renalase-1 protein sequence (SEQ ID NO: 8).

FIG. 4 depicts anti-1D epitope monoclonal 1D-28-4 heavy chain coding sequence (SEQ ID NO: 52) and amino acid sequence (SEQ ID NO: 9).

FIG. 5 depicts anti-1D epitope monoclonal 1D-28-4 light chain coding sequence (SEQ ID NO: 53) and amino acid sequence (SEQ ID NO: 10).

FIG. 6 depicts anti-1D epitope monoclonal 1D-37-10 heavy chain coding sequence (SEQ ID NO: 60) and amino acid sequence (SEQ ID NO: 17).

FIG. 7 depicts anti-1D epitope monoclonal 1D-37-10 light chain coding sequence (SEQ ID NO: 61) and amino acid sequence (SEQ ID NO: 18).

FIG. 8 depicts anti-1F epitope monoclonal 1F-26-1 heavy chain coding sequence (SEQ ID NO: 68) and amino acid sequence (SEQ ID NO: 25).

FIG. 9 depicts anti-1F epitope monoclonal 1F-26-1 light chain coding sequence (SEQ ID NO: 69) and amino acid sequence (SEQ ID NO: 26).

FIG. 10 depicts anti-1F epitope monoclonal 1F-42-7 heavy chain coding sequence (SEQ ID NO: 76) and amino acid sequence (SEQ ID NO: 33).

FIG. 11 depicts anti-1F epitope monoclonal 1F-42-7 light chain coding sequence (SEQ ID NO: 77) and amino acid sequence (SEQ ID NO: 34).

FIG. 12 depicts anti-renalase-2 epitope monoclonal 3A-5-2 heavy chain coding sequence (SEQ ID NO: 84) and amino acid sequence (SEQ ID NO: 41).

FIG. 13 depicts anti-renalase-2 epitope monoclonal 3A-5-2 light chain coding sequence (SEQ ID NO: 85) and amino acid sequence (SEQ ID NO: 42).

FIG. 17 depicts that antibodies 1D-28-4, 1D-37-10, 1F-42-7 and 1F-26-1 bound renalase-1 protein in a concentration-dependent manner by ELISA assay (FIG. 15). However, when the same antibodies were used to detect recombinant renalase-2 on an ELISA plate assay, only 1D-28-4 and 1D-37-10 showed robust, concentration-dependent binding. Antibody 3A5-2 was seen to bind to renalase-2 isoform in ELISA assay. Thus it can be seen that antibodies raised to peptides corresponding to one or other renalase isoform show specificity for the relevant full-length proteins.

FIG. 20, comprising (FIG. 20A) Biotinylated 1D 37-10 was competed by unconjugated 1D 28-4 (solid circle); analogously, the antibodies raised against the IF peptide also competed with one another: biotinylated IF 26-1 was competed by unconjugated IF 42-7 (solid triangle); the signal from the biotinylated monoclonal antibodies did not decrease when it was incubated with an unconjugated antibody from an unimmunized rabbit (clear circle and triangle). (FIG. 20B) In a further example, the polyclonal antibody E2930, raised against full-length renalase-1, was shown to compete with each of the biotinylated monoclonal antibodies 1D 37-10, IF 26-1, as well a mixture of the two biotinylated mAbs (solid circle, solid square, and clear diamond); again, a mixture of the two biotinylated antibodies was not competed by unconjugated antibody from an unimmunized rabbit (solid triangle); the competition seen with the polyclonal antibody E2930 against the two biotinylated monoclonal antibodies suggests that this polyclonal antibody binds to multiple epitopes on the renalase polypeptide.

FIG. 22 depicts a summary of anti-renalase antibody binding affinities.

FIG. 24 depicts that m28-RNLS demonstrated increasing levels of cytotoxicity in correlation with increasing treatment concentrations ($p<0.05$).

FIG. 36 depicts exemplary experiments assessing dose response and IC50 of humanized m28 variants.

DETAILED DESCRIPTION

Figure 3:
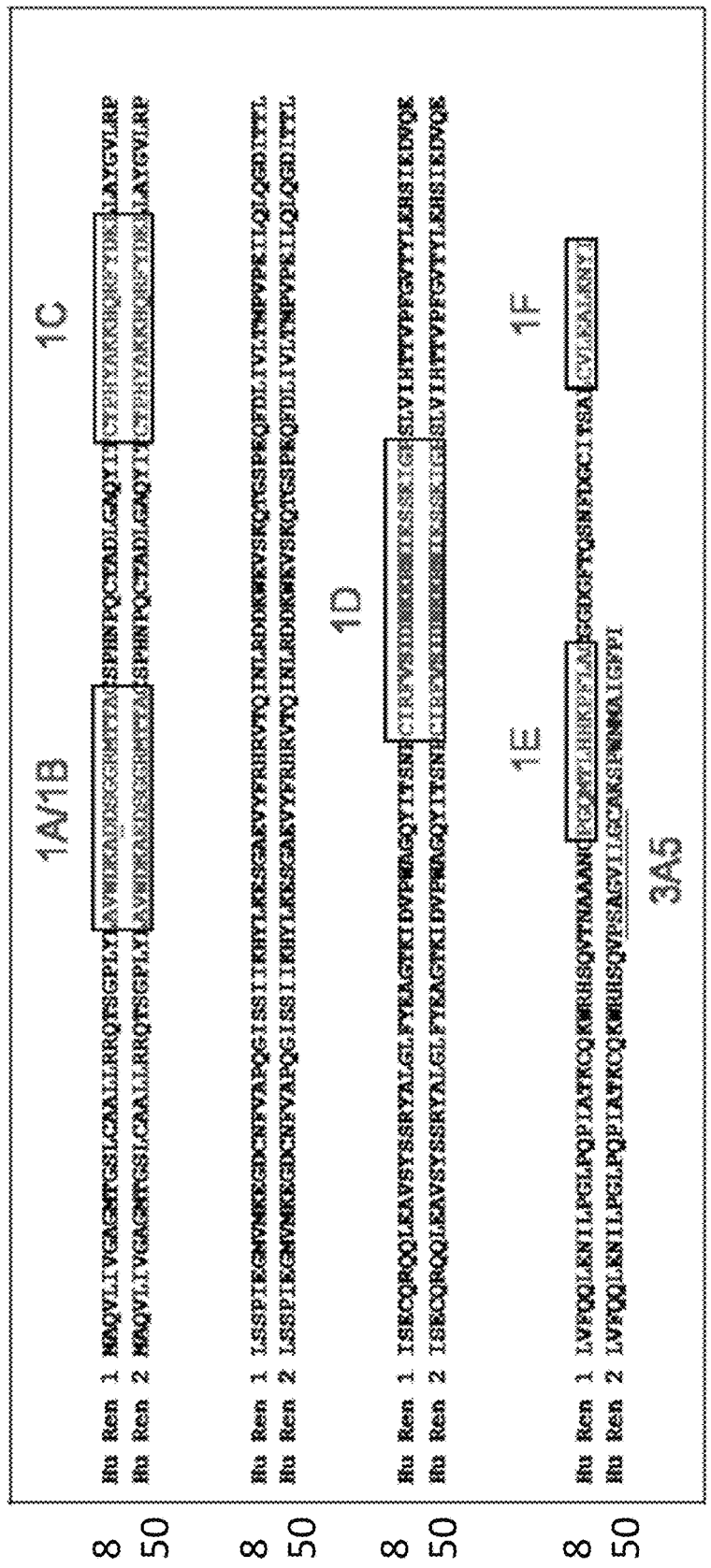
FIG. 3 depicts antigen positions within the renalase proteins (SEQ ID NO: 8 and SEQ ID NO: 50). Antigens 1A/1B, 1C, 1D, 1E, 1F, and 3A5 are depicted.

This invention relates to the inhibition of at least one biological activity of renalase using an agent that binds to renalase. In various embodiments, the invention is directed to compositions and methods for treating a renalase-associated pathology or renalase-associated condition in an individual by administering to a subject in need thereof an inhibitor of renalase. In various embodiments, the diseases and disorders diagnosable, preventable and treatable using the compositions and methods of the invention include acute renal failure (i.e., acute tubular necrosis, or ATN, an ischemic condition in the kidney), cardiovascular disease, pancreatitis, hepatitis, inflammatory disorders of the kidney, and cancer.

In one embodiment, the invention broadly relates to the treatment, prevention, and diagnosis of a renalase-associated condition, such as cancer. In one embodiment, the present invention is directed to methods and compositions for diagnosis, treatment, inhibition, prevention, or reduction of cancer. In one embodiment, the invention provides compositions and methods for modulating one or more of the level, production, and activity of renalase. In the context of cancer and related diseases and disorders, the invention provides compositions and methods for decreasing one or more of the level, production, and activity of renalase. Some aspects of the invention provide methods and compositions for the treatment, prevention, diagnosis or prognosis of cancer metastasis.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Generally, the nomenclature used herein and the laboratory procedures in cell culture, molecular genetics, organic chemistry, and nucleic acid chemistry and hybridization are those well-known and commonly employed in the art.

Standard techniques are used for nucleic acid and peptide synthesis. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, NY, and Ausubel et al., 2012, Current Protocols in Molecular Biology, John Wiley & Sons, NY), which are provided throughout this document.

The nomenclature used herein and the laboratory procedures used in analytical chemistry and organic syntheses described below are those well-known and commonly employed in the art. Standard techniques or modifications thereof are used for chemical syntheses and chemical analyses.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected/homeostatic) respective characteristic. Characteristics which are normal or expected for one cell, tissue type, or subject, might be abnormal for a different cell or tissue type.

The term "analog" as used herein generally refers to compounds that are generally structurally similar to the compound of which they are an analog, or "parent" compound. Generally analogs will retain certain characteristics of the parent compound, e.g., a biological or pharmacological activity. An analog may lack other, less desirable characteristics, e.g., antigenicity, proteolytic instability, toxicity, and the like. An analog includes compounds in which a particular biological activity of the parent is reduced, while one or more distinct biological activities of the parent are unaffected in the "analog." As applied to polypeptides, the term "analog" may have varying ranges of amino acid sequence identity to the parent compound, for example at least about 70%, more preferably at least about 80%-85% or about 86%-89%, and still more preferably at least about 90%, about 92%, about 94%, about 96%, about 98% or about 99% of the amino acids in a given amino acid sequence the parent or a selected portion or domain of the parent. As applied to polypeptides, the term "analog" generally refers to polypeptides which are comprised of a segment of about at least 3 amino acids that has substantial identity to at least a portion of a binding domain fusion protein. Analogs typically are at least 5 amino acids long, at least 20 amino acids long or longer, at least 50 amino acids long or longer, at least 100 amino acids long or longer, at least 150 amino acids long or longer, at least 200 amino acids long or longer, and more typically at least 250 amino acids long or longer. Some analogs may lack substantial biological activity but may still be employed for various uses, such as for raising antibodies to predetermined epitopes, as an immunological reagent to detect and/or purify reactive antibodies by affinity chromatography, or as a competitive or noncompetitive agonist, antagonist, or partial agonist of a binding domain fusion protein function.

The term "antibody," as used herein, refers to an immunoglobulin molecule which is able to specifically bind to a specific epitope of a binding partner molecule. Antibodies can be intact immunoglobulins derived from natural sources, or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab, Fab', F(ab)2 and F(ab')2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to at least one portion of an intact antibody and refers to the antigenic determining variable regions of an intact antibody. Examples of antibody fragments include, but are not limited to, Fab, Fab', F(ab')2, and Fv fragments, linear antibodies, sdAb (either $V_L$ or $V_H$), camelid $V_{HH}$ domains, scFv antibodies, and multi-specific antibodies formed from antibody fragments. The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it was derived. Unless specified, as used herein an scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

An "antibody heavy chain," as used herein, refers to the larger of the two types of polypeptide chains present in antibody molecules in their naturally occurring conformations, and which normally determines the class to which the antibody belongs.

An "antibody light chain," as used herein, refers to the smaller of the two types of polypeptide chains present in antibody molecules in their naturally occurring conformations. Kappa (κ) and lambda (λ) light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., 1989, Queen et al., Proc. Natl. Acad Sci USA, 86:10029-10035; 1991, Hodgson et al., Bio/Technology, 9:421). A suitable human acceptor antibody may be one selected from a conventional database, e.g., the KABAT database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies (see for example EP-A-0239400 and EP-A-054951).

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the binding specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the binding region and would be understood to be so by a skilled person. See for example Chothia et al., (1989) Conformations of immunoglobulin hypervariable regions; Nature 342, p 877-883.

The term "framework" or "framework sequence" refers to the remaining sequences of a variable region minus the CDRs. Because the exact definition of a CDR sequence may be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. An FR represents one of the four sub-regions, and FRs represents two or more of the four sub-regions constituting a framework region.

As used herein, an "immunoassay" refers to any binding assay that uses an antibody capable of binding specifically to a target molecule to detect and quantify the target molecule.

By the term "specifically binds," as used herein with respect to an antibody, is meant an antibody which recognizes a specific binding partner molecule, but does not substantially recognize or bind other molecules in a sample. For example, an antibody that specifically binds to a binding partner molecule from one species may also bind to that binding partner molecule from one or more species. But, such cross-species reactivity does not itself alter the classification of an antibody as specific. In another example, an antibody that specifically binds to binding partner molecule may also bind to different allelic forms of the binding partner molecule. However, such cross reactivity does not itself alter the classification of an antibody as specific.

In some instances, the terms "specific binding" or "specifically binding", can be used in reference to the interaction of an antibody, a protein, or a peptide with a second binding partner molecule, to mean that the interaction is dependent upon the presence of a particular structure (e.g., an antigenic determinant or epitope) on the binding partner molecule; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody. In some instances, the terms "specific binding" and "specifically binding" refers to selective binding, wherein the antibody recognizes a sequence or conformational epitope important for the enhanced affinity of binding to the binding partner molecule.

As used herein, the term "neutralizing" refers to neutralization of biological activity of a renalase when a binding protein specifically binds the renalase. Preferably a neutralizing binding protein is a neutralizing antibody, the binding of which to renalase results in inhibition of a biological activity of renalase. Preferably the neutralizing binding protein binds renalase and reduces a biologically activity of renalase by at least about 20%, 40%, 60%, 80%, 85% or more. In some embodiments, the renalase is human renalase.

The term "epitope" has its ordinary meaning of a site on binding partner molecule recognized by an antibody or a binding portion thereof or other binding molecule, such as, for example, an scFv. Epitopes may be molecules or segments of amino acids, including segments that represent a small portion of a whole protein or polypeptide. Epitopes may be conformational (i.e., discontinuous). That is, they may be formed from amino acids encoded by noncontiguous parts of a primary sequence that have been juxtaposed by protein folding.

The phrase "biological sample" as used herein, is intended to include any sample comprising a cell, a tissue, or a bodily fluid in which expression of a nucleic acid or polypeptide can be detected. Examples of such biological samples include but are not limited to blood, lymph, bone marrow, biopsies and smears. Samples that are liquid in nature are referred to herein as "bodily fluids." Biological samples may be obtained from a patient by a variety of techniques including, for example, by scraping or swabbing an area or by using a needle to obtain bodily fluids. Methods for collecting various body samples are well known in the art.

The term "cancer" as used herein is defined as disease characterized by the abnormal growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer (e.g., melanoma), pancreatic cancer, colorectal cancer, renal cancer, liver cancer, brain cancer, lymphoma, leukemia, lung cancer, sarcoma and the like.

As used herein, "conjugated" refers to covalent attachment of one molecule to a second molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As used herein, the term "derivative" includes a chemical modification of a polypeptide, polynucleotide, or other molecule. In the context of this invention, a "derivative polypeptide," for example, one modified by glycosylation, pegylation, or any similar process, retains binding activity. For example, the term "derivative" of binding domain includes binding domain fusion proteins, variants, or fragments that have been chemically modified, as, for example, by addition of one or more polyethylene glycol molecules, sugars, phosphates, and/or other such molecules, where the molecule or molecules are not naturally attached to wild-type binding domain fusion proteins. A "derivative" of a polypeptide further includes those polypeptides that are "derived" from a reference polypeptide by having, for example, amino acid substitutions, deletions, or insertions relative to a reference polypeptide. Thus, a polypeptide may be "derived" from a wild-type polypeptide or from any other polypeptide. As used herein, a compound, including polypeptides, may also be "derived" from a particular source, for example from a particular organism, tissue type, or from a particular polypeptide, nucleic acid, or other compound that is present in a particular organism or a particular tissue type.

The term "DNA" as used herein is defined as deoxyribonucleic acid.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of compound which is sufficient to provide a beneficial effect to the subject to which the compound is administered.

The term "high affinity" for binding domain polypeptides described herein refers to a dissociation constant (Kd) of at least about $10^{-6}$M, preferably at least about $10^{-7}$M, more preferably at least about $10^{-8}$M or stronger, more preferably at least about $10^{-9}$M or stronger, more preferably at least about $10^{-10}$M or stronger, for example, up to $10^{-12}$M or stronger. However, "high affinity" binding can vary for other binding domain polypeptides.

The term "inhibit," as used herein, means to suppress or block an activity or function, for example, about ten percent relative to a control value. Preferably, the activity is suppressed or blocked by 50% compared to a control value, more preferably by 75%, and even more preferably by 95%. "Inhibit," as used herein, also means to reduce the level of a molecule, a reaction, an interaction, a gene, an mRNA, and/or a protein's expression, stability, function or activity by a measurable amount or to prevent entirely. Inhibitors are compounds that, e.g., bind to, partially or totally block activity, decrease, prevent, delay activation, inactivate, desensitize, or down regulate a protein, a gene, and an mRNA stability, expression, function and activity, e.g., antagonists.

The terms "modulator" and "modulation" of a molecule of interest, as used herein in its various forms, is intended to encompass antagonism, agonism, partial antagonism and/or partial agonism of an activity associated the protease of interest. In various embodiments, "modulators" may inhibit or stimulate protease expression or activity. Such modulators include small molecules agonists and antagonists of a protease molecule, antisense molecules, ribozymes, triplex molecules, and RNAi polynucleotides, and others.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

"Isolated" means altered or removed from the natural state. For example, a nucleic acid or a peptide naturally present in its normal context in a living animal is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine. The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "conservative substitution," when describing a polypeptide, refers to a change in the amino acid composition of the polypeptide that does not substantially alter the activity of the polypeptide, i.e., substitution of amino acids with other amino acids having similar properties. Conservative substitution tables providing functionally similar amino acids are well known in the art. The following six groups each contain amino acids that are generally understood to represent conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W) (see also, Creighton, 1984, Proteins, W.H. Freeman and Company). In addition to the above-defined conservative substitutions, other modifications of amino acid residues can also result in "conservatively modified variants." For example, one may regard all charged amino acids as substitutions for each other whether they are positive or negative. In addition, conservatively modified variants can also result from individual substitutions, deletions or additions which alter, add or delete a single amino acid or a small percentage of amino acids, for example, often less than 5%, in an encoded sequence. Further, a conservatively modified variant can be made from a recombinant polypeptide by substituting a codon for an amino acid employed by the native or wild-type gene with a different codon for the same amino acid.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

By "pharmaceutically acceptable" it is meant, for example, a carrier, diluent or excipient that is compatible with the other ingredients of the formulation and generally safe for administration to a recipient thereof. As used herein, "carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well-known conventional methods.

The terms "patient," "subject," "individual," and the like are used interchangeably herein, and refer to any animal, preferably a mammal, and most preferably a human, having a complement system, including a human in need of therapy for, or susceptible to, a condition or its sequelae. Thus, the individual may include, for example, dogs, cats, pigs, cows, sheep, goats, horses, rats, monkeys, and mice and humans.

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

The phrase "percent (%) identity" or "percent identical" refers to the percentage of sequence similarity found in a comparison of two or more amino acid sequences. Percent identity can be determined electronically using any suitable software. Likewise, "similarity" between two polypeptides (or one or more portions of either or both of them) is determined by comparing the amino acid sequence of one polypeptide to the amino acid sequence of a second polypeptide. Any suitable algorithm useful for such comparisons can be adapted for application in the context of the invention.

A "therapeutic" treatment is a treatment administered to a subject who exhibits signs of pathology, for the purpose of diminishing or eliminating those signs.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The terms "treat," "treating," and "treatment," refer to therapeutic or preventative measures described herein. The methods of "treatment" employ administration to a subject, in need of such treatment, a composition of the present invention, for example, a subject afflicted a disease or disorder, or a subject who ultimately may acquire such a disease or disorder, in order to prevent, cure, delay, reduce the severity of, or ameliorate one or more symptoms of the disorder or recurring disorder, or in order to prolong the survival of a subject beyond that expected in the absence of such treatment.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

This invention relates to the binding and inhibition of renalase using an agent that specifically binds renalase. In various embodiments, the invention is directed to compositions and methods for treating a renalase-associated disease or disorder in an individual by administering to a subject in need thereof an inhibitor of renalase. In some embodiments, the renalase inhibitor is a renalase binding molecule. In some embodiments, the renalase binding molecule is an antibody. In various embodiments, the diseases and disorders diagnosable, preventable and treatable using the compositions and methods of the invention include acute renal failure (i.e., acute tubular necrosis, or ATN, an ischemic condition in the kidney), cardiovascular disease, pancreatitis, hepatitis, inflammatory disorders of the kidney, and cancer.

In one embodiment, the invention broadly relates to the treatment, prevention, and diagnosis of cancer. In one embodiment, the present invention is directed to methods and compositions for diagnosis, staging, treatment, inhibition, prevention, or reduction of cancer. In one embodiment, the invention provides compositions and methods for modulating one or more of the level, production, and activity of renalase. In the context of cancer and related diseases and disorders, the invention provides compositions and methods for decreasing one or more of the level, production, and activity of renalase. Some aspects of the invention provide methods and compositions for the treatment, prevention, diagnosis or prognosis of cancer metastasis.

Renalase Inhibitor Compositions and Methods of Use

In various embodiments, the present invention includes renalase inhibitor compositions and methods of treating or preventing a disease or disorder where a diminished level or activity of renalase is desired. One non-limiting example of a disease or disorder where a diminished level or activity of renalase is desired which can be treated or prevented with the compositions and methods of the invention includes cancer. In various embodiments, the renalase inhibitor compositions and methods of treatment or prevention of the invention diminish the amount of active renalase polypeptide, the amount of active renalase peptide fragment, the amount of renalase enzymatic activity, the amount of renalase substrate binding activity, the amount of renalase receptor binding activity, or a combination thereof.

It will be understood by one skilled in the art, based upon the disclosure provided herein, that a decrease in the level of active renalase encompasses a decrease in renalase expression, including transcription, translation, or both, and also encompasses promoting the degradation of renalase, including at the RNA level (e.g., RNAi, shRNA, etc.) and at the protein level (e.g., Ubiquitination, etc.) The skilled artisan will also appreciate, once armed with the teachings of the present invention, that a decrease in the level of active renalase includes a decrease in a renalase activity (e.g., enzymatic activity, substrate binding activity, receptor binding activity, etc.). Thus, decreasing the level or activity of renalase includes, but is not limited to, decreasing transcription, translation, or both, of a nucleic acid encoding renalase; and it also includes decreasing any activity of a renalase polypeptide, or peptide fragment thereof, as well. The renalase inhibitor compositions and methods of the invention can selectively inhibit renalase, or can inhibit both renalase and another molecule.

Inhibition of renalase can be assessed using a wide variety of methods, including those disclosed herein, as well as methods known in the art or to be developed in the future. That is, the routineer would appreciate, based upon the disclosure provided herein, that decreasing the level or activity of renalase can be readily assessed using methods that assess the level of a nucleic acid encoding renalase (e.g., mRNA), the level of a renalase polypeptide, or peptide fragment thereof, present in a biological sample, the level of renalase activity (e.g., enzymatic activity, substrate binding activity, receptor binding activity, etc.), or combinations thereof.

One skilled in the art, based upon the disclosure provided herein, would understand that the invention is useful in treating or preventing in a subject in need thereof, whether or not the subject is also being treated with other medication or therapy. Further, the skilled artisan would further appreciate, based upon the teachings provided herein, that the disease or disorders treatable by the compositions and methods described herein encompass any disease or disorder where renalase plays a role and where diminished renalase level or activity will promote a positive therapeutic outcome. In various embodiments, the disease or disorder treatable or preventable using the compounds and methods of the invention include acute renal failure (i.e., acute tubular necrosis, or ATN, an ischemic condition in the kidney), a cardiovascular disease or disorder (e.g., hypertension, pulmonary hypertension, systolic hypertension, diabetic hypertension, asymptomatic left ventricular dysfunction, chronic congestive heart failure, myocardial infarction, cardiac rhythm disturbance, atherosclerosis, etc.), cancer, heart disease or disorder, a kidney disease or disorder, a gastrointestinal disease or disorder, a liver disease or disorder, a lung disease or disorder, a pancreas disease or disorder (e.g., pancreatitis), mental disease or disorder (e.g., depression, anxiety, etc.), or a neurological disease or disorder.

In another embodiment, the renalase inhibitor of the invention can be administered to a patient who is being treated with exogenous renalase, recombinant renalase, renalase fragment, and/or renalase activator, in order to control, titrate, diminish, or stabilize the level or activity of endogenous and/or exogenous renalase in the patient.

The renalase inhibitor compositions and methods of the invention that decrease the level or activity (e.g., enzymatic activity, substrate binding activity, receptor binding activity, etc.) of renalase, or a renalase fragment, include, but should not be construed as being limited to, a chemical compound, a protein, a peptide, a peptidomemetic, an antibody, an antibody fragment, an antibody mimetic, a ribozyme, a small molecule chemical compound, an short hairpin RNA, RNAi, an antisense nucleic acid molecule (e.g., siRNA, miRNA, etc.), a nucleic acid encoding an antisense nucleic acid molecule, a nucleic acid sequence encoding a protein, a renalase receptor, a renalase receptor fragment, or combinations thereof. In some embodiments, the inhibitor is an allosteric inhibitor. One of skill in the art would readily appreciate, based on the disclosure provided herein, that a renalase inhibitor composition encompasses any chemical compound that decreases the level or activity of renalase, or a fragment thereof. Additionally, a renalase inhibitor composition encompasses a chemically modified compound, and derivatives, as is well known to one of skill in the chemical arts.

The renalase inhibitor compositions and methods of the invention that decrease the level or activity (e.g., enzymatic activity, substrate binding activity, receptor binding activity, etc.) of renalase, or a renalase fragment, include antibodies, and fragments thereof. The antibodies of the invention include a variety of forms of antibodies including, for example, polyclonal antibodies, monoclonal antibodies, intracellular antibodies ("intrabodies"), Fv, Fab and F(ab)2, single chain antibodies (scFv), heavy chain antibodies (such as camelid antibodies), synthetic antibodies, chimeric antibodies, and humanized antibodies. In one embodiment, the antibody of the invention is an antibody that specifically binds to renalase. In some embodiments, the antibodies of the invention are bispecific antibodies, where the first specificity is to renalase and the second specificity is to a targeting molecule on a cell or tissue to guide the bispecific antibody to an anatomic location where the targeting molecule is present and where the renalase binding is desired. In some embodiments, the antibodies of the invention are bispecific antibodies, where the first specificity is to renalase and the second specificity is to a second binding partner molecule (i.e., payload) that is carried by the antibodies second specificity and deployed to an anatomic location where renalase binding is desired.

In some embodiments, the administration to the subject of the renalase inhibitor (e.g., renalase binding molecule) of the invention for the treatment of cancer, serves to initiate and/or supplement an immune response by the subject's immune system against the cancer. The subject's immune response against the cancer can be any host defense or response, including an innate immune response, a humoral immune response, a cell-mediated immune response, or a combination thereof.

Further, one of skill in the art, when equipped with this disclosure and the methods exemplified herein, would appreciate that a renalase inhibitor composition includes such inhibitors as discovered in the future, as can be identified by well-known criteria in the art of pharmacology, such as the physiological results of inhibition of renalase as described in detail herein and/or as known in the art.

Therefore, the present invention is not limited in any way to any particular renalase inhibitor composition as exemplified or disclosed herein; rather, the invention encompasses those inhibitor compositions that would be understood by the routineer to be useful as are known in the art and as are discovered in the future.

Further methods of identifying and producing renalase inhibitor compositions are well known to those of ordinary skill in the art, including, but not limited, obtaining an inhibitor from a naturally occurring source (e.g., Streptomyces sp., Pseudomonas sp., Stylotella aurantium, etc.). Alternatively, a renalase inhibitor can be synthesized chemically. Further, the routineer would appreciate, based upon the teachings provided herein, that a renalase inhibitor composition can be obtained from a recombinant organism. Compositions and methods for chemically synthesizing renalase inhibitors and for obtaining them from natural sources are well known in the art and are described in the art.

One of skill in the art will appreciate that an inhibitor can be administered as a chemical compound, a protein, a peptide, a peptidomemetic, an antibody, an antibody fragment, an antibody mimetic, a ribozyme, a small molecule chemical compound, an short hairpin RNA, RNAi, an antisense nucleic acid molecule (e.g., siRNA, miRNA, etc.), a nucleic acid encoding an antisense nucleic acid molecule, a nucleic acid sequence encoding a protein, a renalase receptor, a renalase receptor fragment, or combinations thereof. Numerous vectors and other compositions and methods are well known for administering a protein or a nucleic acid construct encoding a protein to cells or tissues. Therefore, the invention includes a method of administering a protein or a nucleic acid encoding a protein that is an inhibitor of renalase. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will realize that diminishing the amount or activity of a molecule that itself increases the level or activity of renalase can serve in the compositions and methods of the present invention to decrease the level or activity of renalase.

Antisense oligonucleotides are DNA or RNA molecules that are complementary to some portion of an RNA molecule. When present in a cell, antisense oligonucleotides hybridize to an existing RNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of an antisense oligonucleotide to diminish the amount of renalase, or to diminish the amount of a molecule that causes an increase in the amount or activity of renalase, thereby decreasing the amount or activity of renalase.

Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing renalase, or of a gene expressing a protein that increases the level or activity of renalase, can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

Alternatively, inhibition of a gene expressing renalase, or of a gene expressing a protein that increases the level or activity of renalase, can be accomplished through the use of a short hairpin RNA or antisense RNA, including siRNA, miRNA, and RNAi. Given the nucleotide sequence of the molecule, one of ordinary skill in the art could synthesize such an short hairpin RNA or antisense RNA without undue experimentation, provided with the disclosure and references incorporated herein.

One of skill in the art will appreciate that inhibitors of renalase, or a renalase fragment, can be administered acutely (e.g., over a short period of time, such as a day, a week or a month) or chronically (e.g., over a long period of time, such as several months or a year or more). One of skill in the art will appreciate that inhibitors of renalase can be administered singly or in any combination with other agents. Further, renalase inhibitors can be administered singly or in any combination in a temporal sense, in that they may be administered concurrently, or before, and/or after each other. One of ordinary skill in the art will appreciate, based on the disclosure provided herein, that renalase inhibitor compositions can be used to treat or prevent a disease or disorder in a subject in need thereof, and that an inhibitor composition can be used alone or in any combination with another inhibitor to effect a therapeutic result.

In various embodiments, any of the inhibitors of renalase, or renalase fragment, of the invention described herein can be administered alone or in combination with other inhibitors of other molecules associated with cancer.

It will be appreciated by one of skill in the art, when armed with the present disclosure including the methods detailed herein, that the invention is not limited to treatment of a disease or disorder, such as cancer, that is already established. Particularly, the disease or disorder need not have manifested to the point of detriment to the subject; indeed, the disease or disorder need not be detected in a subject before treatment is administered. That is, significant disease or disorder does not have to occur before the present invention may provide benefit. Therefore, the present invention includes a method for preventing a disease or disorder in a subject, in that a renalase inhibitor composition, as discussed previously elsewhere herein, can be administered to a subject prior to the onset of the disease or disorder, thereby preventing the disease or disorder from developing. The preventive methods described herein also include the treatment of a subject that is in remission for the prevention of a recurrence of a disease or disorder.

One of skill in the art, when armed with the disclosure herein, would appreciate that the prevention of a disease or disorder encompasses administering to a subject a renalase inhibitor composition as a preventative measure against the disease or disorder, including cancer. As more fully discussed elsewhere herein, methods of decreasing the level or activity of renalase encompass a wide plethora of techniques for decreasing not only renalase activity, but also for decreasing expression of a nucleic acid encoding renalase, including either a decrease in transcription, a decrease in translation, or both.

Additionally, as disclosed elsewhere herein, one skilled in the art would understand, once armed with the teaching provided herein, that the present invention encompasses a method of preventing a wide variety of diseases, disorders and pathologies where a decrease in expression and/or activity of renalase mediates, treats or prevents the disease, disorder or pathology. Methods for assessing whether a disease relates to the levels or activity of renalase are known in the art. Further, the invention encompasses treatment or prevention of such diseases discovered in the future.

The invention encompasses administration of an inhibitor of renalase to practice the methods of the invention; the skilled artisan would understand, based on the disclosure provided herein, how to formulate and administer the appropriate renalase inhibitor to a subject. However, the present invention is not limited to any particular method of administration or treatment regimen.

The invention provides compositions that bind to renalase. In one embodiment, the renalase binding agent inhibits renalase levels or activity. Thus, in diseases and conditions where a reduction of renalase activity would be beneficial, such inhibitory renalase binding agents can potentially act as therapeutics.

In some instances, in addition to its potential therapeutic role, renalase can be used as a diagnostic marker for diseases or disorders including, but not limited, to acute renal failure (i.e., acute tubular necrosis, or ATN, an ischemic condition in the kidney), cardiovascular disease, pancreatitis, hepatitis, inflammatory disorders of the kidney, and cancer. Patients without a properly functioning kidney possess lower levels of renalase. Accordingly, also included in the invention are methods of diagnosing susceptibility to cardiovascular, heart, kidney, gastrointestinal, liver, lung, pancreas and mental and neurological related conditions, disorders and diseases, including cancer, based on the detection and/or quantitation of renalase using the renalase binding agents of the present invention. For example, cardiovascular conditions, disorders and diseases such as hypertension, asymptomatic left ventricular dysfunction, chronic congestive heart failure, myocardial infarction, cardiac rhythm disturbance, and atherosclerosis; mental conditions, disorders and diseases such as depression and anxiety; and heart conditions, disorders and diseases, such as pulmonary hypertension, can all be diagnosed, evaluated and monitored by determining renalase levels, such as renalase protein levels. For example, reduced levels of the renalase protein would be a diagnostic marker for a disorder associated with an increased sympathetic output. The compositions and methods of the present invention can be used to treat, prevent, reduce or ameliorate hypertension, including systolic hypertension, isolated systolic hypertension and diabetic hypertension. Moreover, the same benefit is anticipated for the more rare hypertensive disorder, pulmonary hypertension, as well as pancreatitis. Pulmonary hypertension is a rare blood vessel disorder of the lung in which the pressure in the pulmonary artery (the blood vessel that leads from the heart to the lungs) rises above normal levels and may become life threatening. The similarity in development of elevated blood pressure in the pulmonary bed with the increase in systemic blood pressure in diabetic hypertension and in isolated systolic hypertension suggests similar mechanisms are involved.

The renalase inhibitor compositions of the invention that decrease the level or activity (e.g., enzymatic activity, substrate binding activity, receptor binding activity, etc.) of renalase include, but should not be construed as being limited to, a chemical compound, a protein, a peptide, a peptidomemetic, an antibody, an antibody fragment, an antibody mimetic, a ribozyme, a small molecule chemical compound, an short hairpin RNA, RNAi, an antisense nucleic acid molecule (e.g., siRNA, miRNA, etc.), a nucleic acid encoding an antisense nucleic acid molecule, a nucleic acid sequence encoding a protein, a renalase receptor, a renalase receptor fragment, or combinations thereof. In some embodiments, the inhibitor is an allosteric inhibitor. One of skill in the art would readily appreciate, based on the disclosure provided herein, that a renalase inhibitor composition encompasses a chemical compound that decreases the level or activity of renalase. Additionally, a renalase inhibitor composition encompasses a chemically modified compound, and derivatives, as is well known to one of skill in the chemical arts.

The renalase inhibitor compositions of the invention that decrease the level or activity (e.g., enzymatic activity, substrate binding activity, receptor binding activity, etc.) of renalase include antibodies, and fragments thereof. The antibodies of the invention include a variety of forms of antibodies including, for example, polyclonal antibodies, monoclonal antibodies, intracellular antibodies ("intrabodies"), Fv, Fab and F(ab)2, single chain antibodies (scFv), heavy chain antibodies (such as camelid antibodies), synthetic antibodies, chimeric antibodies, and humanized antibodies. In one embodiment, the antibody of the invention is an antibody that specifically binds to renalase. In some embodiments, the antibodies of the invention are bispecific antibodies, where the first specificity is to renalase and the second specificity is to a targeting molecule to guide the bispecific antibody to an anatomic location where the renalase binding is desired. In some embodiments, the antibodies of the invention are bispecific antibodies, where the first specificity is to renalase and the second specificity is to a second binding partner molecule that is carried and deployed to an anatomic location where renalase binding is desired.

Antibodies, including a renalase binding fragments thereof, of the present invention include, in certain embodiments, antibody amino acid sequences disclosed herein encoded by any suitable polynucleotide, or any isolated or formulated antibody. Further, antibodies of the present disclosure comprise antibodies having the structural and/or functional features of anti-renalase antibodies described herein. In one embodiment, the anti-renalase antibody binds renalase and, thereby partially or substantially alters at least one biological activity of renalase (e.g., enzymatic activity, substrate binding activity, receptor binding activity, etc.). In some embodiments, the renalase is human renalase.

In one embodiment, anti-renalase antibodies of the invention immunospecifically bind at least one specified epitope specific to the renalase protein, peptide, subunit, fragment, portion or any combination thereof and do not specifically bind to other polypeptides, other than renalase from other species. The at least one epitope can comprise at least one antibody binding region that comprises at least one portion of the renalase protein. The term "epitope" as used herein refers to a protein determinant capable of binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

In some embodiments, the invention includes compositions comprising an antibody that specifically binds to renalase (e.g., binding portion of an antibody). In one embodiment, the anti-renalase antibody is a polyclonal antibody. In another embodiment, the anti-renalase antibody is a monoclonal antibody. In some embodiments, the anti-renalase antibody is a chimeric antibody. In further embodiments, the anti-renalase antibody is a humanized antibody. In some embodiments, the renalase is human renalase. In some embodiments, the antibodies of the invention specifically bind to at least one of SEQ ID NOs: 1-7, 8, 50, 92, 94, and fragments thereof.

The binding portion of an antibody comprises one or more fragments of an antibody that retain the ability to specifically bind to binding partner molecule (e.g., renalase). It has been shown that the binding function of an antibody can be performed by fragments of a full-length antibody. Examples of binding fragments encompassed within the term "binding portion" of an antibody include (i) a Fab fragment, a monovalent fragment consisting of the $V_L$, $V_H$, $C_L$ and $C_H1$ domains; (ii) a F(ab')2 fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "binding portion" of an antibody. These antibody fragments are obtained using conventional techniques known to those with skill in the art, and the fragments are screened for utility in the same manner as are intact antibodies. Binding portions can be produced by recombinant DNA techniques, or by enzymatic or chemical cleavage of intact immunoglobulins.

An antibody that binds to renalase of the invention is an antibody that inhibits, blocks, or interferes with at least one renalase activity (e.g., enzymatic activity, substrate binding activity, receptor binding activity, etc.), in vitro, in situ and/or in vivo. A suitable anti-renalase antibody, specified portion, or variant can also optionally affect at least one renalase activity or function, such as but not limited to, RNA, DNA or protein synthesis, protein release, renalase signaling, renalase cleavage, renalase activity, renalase receptor binding, renalase production and/or synthesis.

In one embodiment, antibodies of the invention bind renalase. In one embodiment, the antibodies specifically bind to renalase-1. In another embodiment, the antibodies specifically bind to renalase-2. In yet another embodiment, the antibodies specifically bind to both renalase-1 and renalase-2. In addition, epitope specific antibodies have been generated. Preferred antibodies of the invention include monoclonal antibodies 1C-22-1, 1D-28-4, 1D-37-10, 1F-26-1, 1F-42-7 and 3A-5-2. Examples of dual specificity antibodies, e.g. antibodies that recognize renalase-1 and renalase-2 include antibodies 1C-22-1, 1D-28-4, 1D-37-10, and polyclonal antibodies as described herein. Examples of renalase-type specific antibodies include 1F-26-1, 1F-42-7, which are specific for renalase-1. 3A-5-2 is specific for renalase-2. Antibody fragments of the invention include humanized heavy chain and light chain Fv regions, as set forth in SEQ ID NOs: 219, 221, 223, and 225. In various embodiments of the invention, an anti-renalase antibody or antibody fragment comprises humanized heavy chain and light chain Fv regions, as set forth in SEQ ID NOs: 219, 221, 223, and 225, or a fragment or portion thereof. Sequences encoding anti-renalase monoclonal antibodies are set forth in FIG. 4 through FIG. 13, and in Example 2.

The nucleic acid (SEQ ID NO: 52) and amino acid sequence (SEQ ID NO: 9) of the heavy chain coding sequence of monoclonal antibody 1D-28-4 are found in FIG. 4. The nucleic acid (SEQ ID NO: 53) and amino acid sequence (SEQ ID NO: 10) of the light chain coding sequence of monoclonal antibody 1D-28-4 are found in FIG. 5.

The nucleic acid (SEQ ID NO: 60) and amino acid sequence (SEQ ID NO: 17) of the heavy chain coding sequence of monoclonal antibody 1D-37-10 are found in FIG. 6. The nucleic acid (SEQ ID NO: 61) and amino acid sequence (SEQ ID NO: 18) of the light chain coding sequence of monoclonal antibody 1D-37-10 are found in FIG. 7.

The nucleic acid (SEQ ID NO: 68) and amino acid sequence (SEQ ID NO: 25) of the heavy chain coding sequence of monoclonal antibody 1F-26-1 are found in FIG. 8. The nucleic acid (SEQ ID NO: 69) and amino acid sequence (SEQ ID NO: 26) of the light chain coding sequence of monoclonal antibody 1F-26-1 are found in FIG. 9.

The nucleic acid (SEQ ID NO: 76) and amino acid sequence (SEQ ID NO: 33) of the heavy chain coding sequence of monoclonal antibody 1F-42-7 are found in FIG. 10. The nucleic acid (SEQ ID NO: 77) and amino acid sequence (SEQ ID NO: 34) of the light chain coding sequence of monoclonal antibody 1F-42-7 are found in FIG. 11.

The nucleic acid (SEQ ID NO: 84) and amino acid sequence (SEQ ID NO: 41) of the heavy chain coding sequence of monoclonal antibody 3A-5-2 are found in FIG. 12. The nucleic acid (SEQ ID NO: 85) and amino acid sequence (SEQ ID NO: 42) of the light chain coding sequence of monoclonal antibody 3A-5-2 are found in FIG. 13.

Given that certain of the monoclonal antibodies can bind to the renalase protein, the $V_H$ and $V_L$ sequences can be "mixed and matched" to create other anti-renalase binding molecules of this disclosure. Renalase binding of such "mixed and matched" antibodies can be tested using the binding assays described above and in the Examples (e.g., immunoblot, Bia-Core, etc.). Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Thus, in some embodiments, the inventio is an antibody or antibody fragment, wherein the antibody or antibody fragment comprises at least one polypeptide sequence encoding a novel heavy chain variable sequence. In other embodiments, the invention is an antibody or antibody fragment, wherein the antibody or antibody fragment comprises at least one polypeptide sequence encoding a novel light chain variable sequence.

In one embodiment, the first $V_H$ complementarity determining region (HC CDR1) comprises the amino acid sequence as set forth in SEQ ID NO: 155; the second $V_H$ complementarity determining region (HC CDR2) comprises the amino acid sequence selected from the group: SEQ ID NO: 156, SEQ ID NO: 162, and SEQ ID NO: 168; the third $V_H$ complementarity determining region (HC CDR3) comprises the amino acid sequence selected from the group: SEQ ID NO: 157, and SEQ ID NO: 163; the first $V_L$ complementarity determining region (LC CDR1) comprises the amino acid sequence as set forth in SEQ ID NO: 152; the second $V_L$ complementarity determining region (LC CDR2) comprises the amino acid sequence as set forth in SEQ ID NO: 153; the third $V_L$ complementarity determining region (LC CDR3) comprises the amino acid sequence selected from the group: SEQ ID NO: 154, and SEQ ID NO: 160. In one embodiment, the HC CDR1 comprises SEQ ID NO: 155; the HC CDR2 comprises SEQ ID NO: 156; the HC CDR3 comprises SEQ ID NO: 157; the LC CDR1 comprises SEQ ID NO: 152; the LC CDR2 comprises SEQ ID NO: 153; the LC CDR3 comprises SEQ ID NO: 154. In one embodiment, $V_H$ comprises SEQ ID NO: 219; $V_L$ comprises SEQ ID NO: 221. In one embodiment, the two polypeptides are linked by a linker to form a single chain variable fragment (scFv), wherein the arrangement of the polypeptides relative to the linker is selected from the group: $V_H$-linker-$V_L$, and $V_L$-linker-$V_H$.

In one embodiment, the first $V_H$ complementarity determining region (HC CDR1) comprises the amino acid sequence selected from the group: SEQ ID NO: 197, and SEQ ID NO: 203; the second $V_H$ complementarity determining region (HC CDR2) comprises the amino acid sequence selected from the group: SEQ ID NO: 198, and SEQ ID NO: 204; the third $V_H$ complementarity determining region (HC CDR3) comprises the amino acid sequence selected from the group: SEQ ID NO: 199, and SEQ ID NO: 205; the first $V_L$ complementarity determining region (LC CDR1) comprises the amino acid sequence selected from the group: SEQ ID NO: 194, and SEQ ID NO: 200; the second $V_L$ complementarity determining region (LC CDR2) comprises the amino acid sequence as set forth in SEQ ID NO: 195; the third $V_L$ complementarity determining region (LC CDR3) comprises the amino acid sequence as set forth in SEQ ID NO: 196. In one embodiment, the HC CDR1 comprises SEQ ID NO: 197; wherein the HC CDR2 comprises SEQ ID NO: 198; wherein the HC CDR3 comprises SEQ ID NO: 199; wherein the LC CDR1 comprises SEQ ID NO: 194; wherein the LC CDR2 comprises SEQ ID NO: 195; wherein the LC CDR3 comprises SEQ ID NO: 196. In one embodiment, $V_H$ comprises SEQ ID NO: 223; $V_L$ comprises SEQ ID NO: 225. In one embodiment, the two polypeptides are linked by a linker to form a single chain variable fragment (scFv), wherein the arrangement of the polypeptides relative to the linker is selected from the group: $V_H$-linker-$V_L$, and $V_L$-linker-$V_H$.

In various embodiments, the novel heavy chain variable sequence further comprises at least one additional polypeptide sequence. In various embodiments, the novel light chain variable sequence further comprises at least one additional polypeptide sequence. In one embodiment, the $V_H$ polypeptide further comprises a heavy chain $C_H1$ domain; the $V_L$ polypeptide further comprises a light chain $C_L$ domain. In one embodiment, the $V_H$ polypeptide further comprises a heavy chain $C_H1$ domain, a heavy chain $C_H2$ domain, and a heavy chain $C_H3$ domain to form an antibody heavy chain; the $V_L$ polypeptide further comprises a light chain $C_L$ domain to form an antibody light chain. In one embodiment, the antibody heavy chain and the antibody light chain are linked to form a half antibody. In one embodiment, the half antibody is linked to another half antibody to form an antibody. In various embodiments, the linking of the heavy chain to the light chain to form the half antibody, and the linking of the two half antibodies, is achieved using a disulfide bond. In other embodiments, the linking of the heavy chain to the light chain to form the half antibody, and the linking of the two half antibodies, is achieved using a bond or linkage that is not a disulfide bond.

In another aspect, this disclosure provides an isolated monoclonal antibody, or binding portion thereof comprising: (a) a heavy chain variable region comprising an amino acid sequence selected from the group consisting of SEQ ID NOs: 9, 17, 25, 33 and 41; and (b) a light chain variable region comprising an amino acid sequence selected from the group consisting of SEQ ID NOs: 10, 18, 26, 34 and 42, wherein the antibody specifically binds a renalase protein.

Preferred heavy and light chain combinations include: (a) a heavy chain variable region comprising the amino acid sequence of SEQ ID NO: 9 and a light chain variable region comprising the amino acid sequence of SEQ ID NO: 10; or (b) a heavy chain variable region comprising the amino acid sequence of SEQ ID NO: 17 and a light chain variable region comprising the amino acid sequence of SEQ ID NO: 18; or (c) a heavy chain variable region comprising the amino acid sequence of SEQ ID NO: 25 and a light chain variable region comprising the amino acid sequence of SEQ ID NO: 26; or (d) a heavy chain variable region comprising the amino acid sequence of SEQ ID NO: 33 and a light chain variable region comprising the amino acid sequence of SEQ ID NO: 34; or (e) a heavy chain variable region comprising the amino acid sequence of SEQ ID NO: 41 and a light chain variable region comprising the amino acid sequence of SEQ ID NO: 42.

In another aspect, this disclosure provides antibodies that comprise the heavy chain and light chain CDR1s, CDR2s and CDR3s of 1D-28-4, 1D-37-10, 1F-26-1, 1F-42-7 or 3A-5-2, or combinations thereof. The amino acid sequences of the $V_h$ CDR1s of 1D-28-4, 1D-37-10, 1F-26-1, 1F-42-7 and 3A-5-2 incorporate the sequences shown in SEQ ID NOs: 11, 19, 27, 35, and 43, respectively. The amino acid sequences of the $V_h$ CDR2s 1D-28-4, 1D-37-10, 1F-26-1, 1F-42-7 and 3A-5-2 incorporate the sequences shown in SEQ ID NOs: 12, 20, 28, 36, and 44, respectively. The amino acid sequences of the $V_h$ CDR3s of 1D-28-4, 1D-37-10, 1F-26-1, 1F-42-7 and 3A-5-2 incorporate the sequences shown in SEQ ID NOs: 13, 21, 29, 37, and 45, respectively. The amino acid sequences of the VK CDR1s of 1D-28-4, 1D-37-10, 1F-26-1, 1F-42-7 and 3A-5-2 incorporate the sequences shown in SEQ ID NOs: 14, 22, 30, 38, and 46, respectively. The amino acid sequences of the VK CDR2s of 1D-28-4, 1D-37-10, 1F-26-1, 1F-42-7 and 3A-5-2 incorporate the sequences shown in SEQ ID NOs: 15, 23, 31, 39 and 47. The amino acid sequences of the VK CDR3s of 1D-28-4, 1D-37-10, 1F-26-1, 1F-42-7 and 3A-5-2 incorporate the sequences shown in SEQ ID NOs: 16, 24, 32, 40 and 48, respectively. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to renalase family members and that binding specificity is provided primarily by the CDR1, CDR2, and CDR3 regions, the $V_h$ CDR1, CDR2, and CDR3 sequences and $V_l$ CDR1, CDR2, and CDR3 sequences can be "mixed and matched" (i.e., CDRs from different antibodies can be mixed and match, although each antibody must contain a $V_H$ CDR1, CDR2, and CDR3 and a $V_l$ CDR1, CDR2, and CDR3) to create other anti-renalase binding molecules of this disclosure. renalase binding of such "mixed and matched" antibodies can be tested using the binding assays described above and in the Examples (e.g., immunoblot, Biacore® analysis, etc). Preferably, when $V_h$ CDR sequences are mixed and matched, the CDR1, CDR2 and/or CDR3 sequence from a particular $V_h$ sequence is replaced with a structurally similar CDR sequence(s). Likewise, when $V_l$ CDR sequences are mixed and matched, the CDR1, CDR2 and/or CDR3 sequence from a particular $V_l$ sequence preferably is replaced with a structurally similar CDR sequence(s). It will be readily apparent to the ordinarily skilled artisan that novel $V_H$ and $V_l$ sequences can be created by substituting one or more $V_H$ and/or $V_l$ CDR region sequences with structurally similar sequences from the CDR sequences disclosed herein for monoclonal antibodies 1D-28-4, 1D-37-10, 1F-26-1, 1F42-7 or 3A-5-2.

Accordingly, in another aspect, the invention provides an isolated monoclonal antibody, or binding portion thereof comprising at least one selected from: (a) a heavy chain variable region CDR1 comprising an amino acid sequence selected from the group consisting of SEQ ID NOs: 11, 19, 27, 35, and 43; (b) a heavy chain variable region CDR2 comprising an amino acid sequence selected from the group consisting of SEQ ID NOs: 12, 20, 28, 36, and 44; (c) a heavy chain variable region CDR3 comprising an amino acid sequence selected from the group consisting of SEQ ID NOs: 13, 21, 29, 37, and 45; (d) a light chain variable region CDR1 comprising an amino acid sequence selected from the group consisting of SEQ ID NOs: 14, 22, 30, 38, and 46; (e) a light chain variable region CDR2 comprising an amino acid sequence selected from the group consisting of SEQ ID NOs: 15, 23, 31, 39 and 47; and (f) a light chain variable region CDR3 comprising an amino acid sequence selected from the group consisting of SEQ ID NOs: 16, 24, 32, 40 and 48; wherein the antibody specifically binds an renalase.

In another embodiment, the antibody comprises at least one of the CDRs selected from: (a) a heavy chain variable region CDR1 comprising SEQ ID NO: 11; (b) a heavy chain variable region CDR2 comprising SEQ ID NO: 12; (c) a heavy chain variable region CDR3 comprising SEQ ID NO: 13; (d) a light chain variable region CDR1 comprising SEQ ID NO: 14; (e) a light chain variable region CDR2 comprising SEQ ID NO: 15; and (f) a light chain variable region CDR3 comprising SEQ ID NO: 16.

In another embodiment, the antibody comprises at least one of the CDRs selected from: (a) a heavy chain variable region CDR1 comprising SEQ ID NO: 19; (b) a heavy chain variable region CDR2 comprising SEQ ID NO: 20; (c) a heavy chain variable region CDR3 comprising SEQ ID NO: 21; (d) a light chain variable region CDR1 comprising SEQ ID NO: 22; (e) a light chain variable region CDR2 comprising SEQ ID NO: 23; and (f) a light chain variable region CDR3 comprising SEQ ID NO: 24.

In another embodiment, the antibody comprises at least one of the CDRs selected from: (a) a heavy chain variable region CDR1 comprising SEQ ID NO: 27; (b) a heavy chain variable region CDR2 comprising SEQ ID NO: 28; (c) a heavy chain variable region CDR3 comprising SEQ ID NO: 29; (d) a light chain variable region CDR1 comprising SEQ ID NO: 30; (e) a light chain variable region CDR2 comprising SEQ ID NO:31; and (f) a light chain variable region CDR3 comprising SEQ ID NO: 32.

In another other embodiment, the antibody comprises at least one of the CDRs selected from: (a) a heavy chain variable region CDR1 comprising SEQ ID NO: 35; (b) a heavy chain variable region CDR2 comprising SEQ ID NO: 36; (c) a heavy chain variable region CDR3 comprising SEQ ID NO: 37; (d) a light chain variable region CDR1 comprising SEQ ID NO: 38; (e) a light chain variable region CDR2 comprising SEQ ID NO: 39; and (f) a light chain variable region CDR3 comprising SEQ ID NO: 40.

In another embodiment, the antibody comprises at least one of the CDRs selected from: (a) a heavy chain variable region CDR1 comprising SEQ ID NO: 43; (b) a heavy chain variable region CDR2 comprising SEQ ID NO: 44; (c) a heavy chain variable region CDR3 comprising SEQ ID NO: 45; (d) a light chain variable region CDR1 comprising SEQ ID NO: 46; (e) a light chain variable region CDR2 comprising SEQ ID NO: 47; and (f) a light chain variable region CDR3 comprising SEQ ID NO: 48.

The foregoing isolated anti-renalase antibody CDR sequences establish a novel family of renalase binding proteins, isolated in accordance with this invention, and comprising polypeptides that include the CDR sequences listed. To generate and to select CDR's of the invention having renalase binding and/or renalase detection and/or renalase neutralization activity, standard methods known in the art for generating binding proteins of the present invention and assessing the renalase and/or renalase binding and/or detection and/or neutralizing characteristics of those binding protein may be used, including but not limited to those specifically described herein.

Preferably, renalase binding molecules (e.g., antibodies, etc.) of the present invention, exhibit a high capacity to detect and bind renalase in a complex mixture of salts, compounds and other polypeptides, e.g., as assessed by any one of several in vitro and in vivo assays known in the art. The skilled artisan will understand that the renalase binding molecules (e.g., antibodies, etc.) described herein as useful in the methods of diagnosis and treatment and prevention of disease, are also useful in procedures and methods of the invention that include, but are not limited to, an immunochromatography assay, an immunodot assay, a Luminex assay, an ELISA assay, an ELISPOT assay, a protein microarray assay, a Western blot assay, a mass spectrophotometry assay, a radioimmunoassay (RIA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, FACS, a protein chip assay, separation and purification processes, and affinity chromatography (see also, 2007, Van Emon, Immunoassay and Other Bioanalytical Techniques, CRC Press; 2005, Wild, Immunoassay Handbook, Gulf Professional Publishing; 1996, Diamandis and Christopoulos, Immunoassay, Academic Press; 2005, Joos, Microarrays in Clinical Diagnosis, Humana Press; 2005, Hamdan and Righetti, Proteomics Today, John Wiley and Sons; 2007).

More preferably, the renalase binding molecules (e.g., antibodies, etc.) of the present invention, exhibit a high capacity to reduce or to neutralize renalase activity (e.g., enzymatic activity, substrate binding activity, receptor binding activity, etc.) as assessed by any one of several in vitro and in vivo assays known in the art. For example, these renalase binding molecules (e.g., antibodies, etc.) neutralize renalase-associated or renalase-mediated disease or disorder. Preferably, renalase binding molecules (e.g., antibodies, etc.) of the present invention, also exhibit a high capacity to reduce or to neutralize renalase activity. In some embodiments, the renalase is human renalase.

As used herein, a renalase binding molecule (e.g., antibody, etc.) that "specifically binds to a renalase protein" is intended to refer to a renalase binding molecule (e.g., antibody, etc.) that binds to a renalase protein of any animal. In some embodiments, that antibody binds to human renalase. Preferably, the a renalase binding molecule (e.g., antibody, etc.) binds to a renalase protein with a KD of $1\times10^{-6}$ M or less, more preferably $1\times10^{-7}$ M or less, more preferably $1\times10^{-8}$ M or less, more preferably $5\times10^{-9}$ M or less, more preferably $1\times10^{-9}$ M or less or even more preferably $3\times10^{-10}$ M or less. The term "does not substantially bind" to a protein or cells, as used herein, means does not bind or does not bind with a high affinity to the protein or cells, i.e., binds to the protein or cells with a KD of greater than $1\times10^{6}$ M or more, more preferably $1\times10^{5}$ M or more, more preferably $1\times10^{4}$ M or more, more preferably $1\times10^{3}$ M or more, even more preferably $1\times10^{2}$ M or more. The term "KD", as used herein, is intended to refer to the dissociation constant, which is obtained from the ratio of Kd to Ka (i.e., Kd/Ka) and is expressed as a molar concentration (M). KD values for a renalase binding molecule (e.g., antibody, etc.) can be determined using methods well established in the art. A preferred method for determining the KD of a binding molecule (e.g., antibody, etc.) is by using surface plasmon resonance, preferably using a biosensor system such as a Biacore® system.

As used herein, the term "high affinity" for an IgG antibody refers to an antibody having a KD of $1\times10^{-7}$ M or less, more preferably $5\times10^{-8}$ M or less, even more preferably $1\times10^{-8}$ M or less, even more preferably $5\times10^{-9}$ M or less and even more preferably $1\times10^{-9}$ M or less for a target binding partner molecule. However, "high affinity" binding can vary for other antibody isotypes. For example, "high affinity" binding for an IgM isotype refers to an antibody having a KD of $10^{-6}$ M or less, more preferably $10^{-7}$ M or less, even more preferably $10^{-8}$ M or less.

In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

Generation Of Anti-Renalase Antibodies

The invention provides compositions that bind to renalase. The renalase molecules disclosed herein are a class of molecules that include those having high and/or significant sequence identity with other polypeptides disclosed herein. More specifically, the putative renalase will share at least about 40% sequence identity with a nucleic acid having the sequence SEQ ID NO: 49 or 51. More preferably, a nucleic acid encoding renalase has at least about 45% identity, or at least about 50% identity, or at least about 55% identity, or at least about 60% identity, or at least about 65% identity, or at least about 70% identity, or at least about 75% identity, or at least about 80% identity, or at least about 85% identity, or at least about 90% identity, or at least about 95% identity, or at least about 98%, or at least about 99% sequence identity with SEQ ID NO: 49 or 51 disclosed herein. Even more preferably, the nucleic acid is SEQ ID NO: 49 or 51 or 93 or 95. The term "renalase" also includes renalase isoforms. The renalase gene contains 9 exons spanning 310188 bp in chromosome 10 of human genome. The renalase clone (SEQ ID NO: 49, GenBank accession number: BC005364) disclosed herein is the gene containing exons 1, 2, 3, 4, 5, 6, 8. There are at least two additional alternatively-spliced forms of renalase protein as shown in the human genome database. One alternatively spliced form contains exons 1, 2, 3, 4, 5, 6, 9, identified by clones in the human genome database as GenBank accession number AK002080 and NMJ18363, the sequences of which are expressly incorporated herein by reference. The other alternatively spliced form contains exons 5, 6, 7, 8, identified by clones in the human genome database as GenBank accession number BX648154, the sequence of which is expressly incorpoated herein by reference. Unless otherwise indicated, "renalase" encompasses all known renalases (e.g., rat renalase, and human renalase), and renalases to be discovered, including but not limited to, human renalase and chimpanzee renalase, having the characteristics and/or physical features of the renalase disclosed herein.

In addition, the putative renalase shares at least about 60% sequence identity with a polypeptide having the sequence SEQ ID NO: 8 or 50. More preferably, renalase has at least about 45% identity, or at least about 50% identity, or at least about 55% identity, or at least about 60% identity, or at least about 65% identity, or at least about 70% identity, or at least about 75% identity, or at least about 80% identity, or at least about 85% identity, or at least about 90% identity, or at least about 95% identity, or at least about 98%, or at least about 99% sequence identity with SEQ ID NO: 8 or 50 disclosed herein. Even more preferably, the renalase polypeptide has the amino acid sequence of SEQ ID NO: 8 or 50 or 92 or 94.

In one embodiment, the antibodies of the invention can be generated by using a peptide derived from the sequence of renalase to immunize an animal whereby the animal produces antibodies directed against the immunogen. Exemplary immunogens include peptide derived from renalase. That is, peptides having fragments of the renalase sequence can be used in the inventions. Peptides can be produced in a variety of ways, including expression as recombinant peptides, expression as larger polypeptides and cleaved enzymatically or chemically. Alternatively, they may be produced synthetically as is known in the art. Preferred peptides as used to generate affinity reagents of the present invention are found in FIG. 1 (SEQ ID NOs: 1-7).

Anti-renalase antibodies of the present invention can be optionally produced by a variety of techniques, including the standard somatic cell hybridization technique (hybridoma method) of Kohler and Milstein (1975) Nature 256:495. In the hybridoma method, a mouse or other appropriate host animal, such as a hamster or macaque monkey, is immunized as described herein to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

Methods for producing and screening for specific antibodies using hybridoma technology are routine and well known in the art. In one embodiment, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse or rabbit or other species immunized with polypeptide or peptide of the invention with myeloma cells and then screening the hybridomas resulting from the fusion for hybridoma clones that secrete an antibody able to bind a polypeptide of the invention. Briefly, mice can be immunized with a renalase polypeptide or peptide thereof. In a preferred embodiment, the renalase polypeptide or peptide thereof is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

Alternatively, rabbits can be immunized with a renalase polypeptide or peptide thereof. In this embodiment, either full length renalase proteins or peptides derived from renalase can be used as immunogens.

Renalase used in the invention can take a variety of forms. For example, they can include purified renalase proteins or fragments thereof, recombinantly produced renalase or fragments thereof. In some embodiments, the renalase is human renalase. When recombinant renalase is used, it can be produced in eukaryotic or prokaryotic cells as is known in the art. Additional immunogens include peptides derived from renalase. That is, peptides having fragments of the renalase sequence can be used in the inventions. Peptides can be produced in a variety of ways, including expression as recombinant peptides, expression as larger polypeptides and cleaved enzymatically or chemically. Alternatively, they may be produced synthetically as is known in the art. Preferred peptides as used to generate affinity reagents of the present invention are found in FIG. 1 (SEQ ID NOs:1-7). The full-length amino acid sequence of human renalase is depicted in SEQ ID NO:8, where a known polymorphism is possible as indicated (compare to SEQ ID NO. 92). The amino acid sequence of renalase-2 is found in SEQ ID NO:50, again where a known polymorphism is possible as indicated (compare to SEQ ID NO. 94). It is appreciated that other polymorphisms exist. These also are included in the definition of renalase. In some embodiments, the renalase binding molecules of the invention specifically bind to at least one of SEQ ID NOS:1-7, 8, 50, 92, 94, and fragments thereof.

The anti-renalase antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-renalase antibody can be isolated from such animals and immortalized using suitable methods, such as the methods described herein. Alternatively, the antibody coding sequences may be cloned, introduced into a suitable vector, and used to transfect a host cell for expression and isolation of the antibody by methods taught herein and those known in the art.

The use of transgenic mice carrying human immunoglobulin (Ig) loci in their germline configuration provide for the isolation of high affinity fully human monoclonal antibodies directed against a variety of targets including human self antigens for which the normal human immune system is tolerant (Lonberg, N. et al., U.S. Pat. Nos. 5,569,825, 6,300,129 and 1994, Nature 368:856-9; Green, L. et al., 1994, Nature Genet. 7:13-21; Green, L. & Jakobovits, 1998, Exp. Med. 188:483-95; Lonberg, N. and Huszar, D., 1995, Int. Rev. Immunol. 13:65-93; Kucherlapati, et al. U.S. Pat. No. 6,713,610; Bruggemann, M. et al., 1991, Eur. J. Immunol. 21:1323-1326; Fishwild, D. et al., 1996, Nat. Biotechnol. 14:845-851; Mendez, M. et al., 1997, Nat. Genet. 15:146-156; Green, L., 1999, J. Immunol. Methods 231:11-23; Yang, X. et al., 1999, Cancer Res. 59:1236-1243; Bruggemann, M. and Taussig, M J., Curr. Opin. Biotechnol. 8:455-458, 1997; Tomizuka et al. W002043478). The endogenous immunoglobulin loci in such mice can be disrupted or deleted to eliminate the capacity of the animal to produce antibodies encoded by endogenous genes. In addition, companies such as Abgenix, Inc. (Freemont, Calif.) and Medarex (San Jose, Calif) can be engaged to provide human antibodies directed against a selected target binding partner molecule (e.g., antigen, etc.) using technology as described elsewhere herein.

In another embodiment, the human antibody is selected from a phage library, where that phage comprises human immunoglobulin genes and the library expresses human antibody binding domains as, for example, single chain antibodies (scFv), as Fab, or some other construct exhibiting paired or unpaired antibody variable regions (Vaughan et lo al. Nature Biotechnology 14:309-314 (1996): Sheets et al. PITAS (USA) 95:6157-6162 (1998)); Hoogenboom and Winter, J. Mol. Biol., 227:381 (1991); Marks et al. J. Mol. Biol., 222:581 (1991)). Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Preparation of immunogenic antigens, and monoclonal antibody production can be performed using any suitable technique such as recombinant protein production. The immunogenic antigens can be administered to an animal in the form of purified protein, or protein mixtures including whole cells or cell or tissue extracts, or the antigen can be formed de novo in the animal's body from nucleic acids encoding said antigen or a portion thereof.

The isolated nucleic acids of the present invention can be made using (a) recombinant methods, (b) synthetic techniques, (c) purification techniques, or combinations thereof, as well-known in the art. DNA encoding the monoclonal antibodies is readily isolated and sequenced using methods known in the art (e.g., by using oligonucleotide probes that are capable of binding specifically to genes encoding the heavy and light chains of murine antibodies). Where a hybridoma is produced, such cells can serve as a source of such DNA. Alternatively, using display techniques wherein the coding sequence and the translation product are linked, such as phage or ribosomal display libraries, the selection of the binder and the nucleic acid is simplified. After phage selection, the antibody coding regions from the phage can be isolated and used to generate whole antibodies, including human antibodies, or any other desired binding fragment, and expressed in any desired host, including mammalian cells, insect cells, plant cells, yeast, and bacteria.

Humanized Antibodies

The invention further provides humanized immunoglobulins (or antibodies) which bind human renalase. The humanized forms of immunoglobulins have variable framework region(s) substantially from a human immunoglobulin (termed an acceptor immunoglobulin) and CDRs substantially from a non-human mAbs which specifically binds renalase. The constant region(s), if present, are also substantially from a human immunoglobulin. The humanized antibodies exhibit KD for renalase of at least about $10^{-6}$ M (1 μM), about $10^{-7}$ M (100 nM), or less. The binding affinity of the humanized antibodies may be greater or less than that of the mouse antibody from which they were derived. To affect a change in affinity, improve affinity, of the humanized antibody for renalase substitutions in either the CDR residues or the human residues may be made.

The source for production of humanized antibody which binds to renalase is preferably the 1D-28-4, 1D-37-10, 1F-26-1, 1F-42-7 or 3A-5-2 rabbit monoclonal antibodies whose generation, isolation and characterization are described in the Examples provided herein, although other antibodies, which compete with the 1D-28-4, 1D-37-10, 1F-26-1, 1F42-7 or 3A-5-2 antibodies for binding to renalase can also be used. The identified CDRs set forth in the sequence listing can be a starting point of the humanization process. For example, any one or more of the following amino acid sequences (and corresponding nucleic acid sequences thereof) can be a starting point of the humanization process: (a) a heavy chain variable region CDR1 comprising an amino acid sequence selected from the group consisting of SEQ ID NOs: 11, 19, 27, 35, and 43; (b) a heavy chain variable region CDR2 comprising an amino acid sequence selected from the group consisting of SEQ ID NOs: 12, 20, 28, 36, and 44; (c) a heavy chain variable region CDR3 comprising an amino acid sequence selected from the group consisting of SEQ ID NOs: 13, 21, 29, 37, and 45; (d) a light chain variable region CDR1 comprising an amino acid sequence selected from the group consisting of SEQ ID NOs: 14, 22, 30, 38, and 46; (e) a light chain variable region CDR2 comprising an amino acid sequence selected from the group consisting of SEQ ID NOs: 15, 23, 31, 39 and 47; and (f) a light chain variable region CDR3 comprising an amino acid sequence selected from the group consisting of SEQ ID NOs: 16, 24, 32, 40 and 48.

The substitution of rabbit or mouse CDRs into a human variable domain framework is most likely to result in retention of their correct spatial orientation if the human variable domain framework adopts the same or similar conformation to the parental variable framework from which the CDRs originated. This is achieved by obtaining the human variable domains from human antibodies whose framework sequences exhibit a high degree of sequence identity with the parental variable framework domains from which the CDRs were derived. The heavy and light chain variable framework regions can be derived from the same or different human antibody sequences. The human antibody sequences can be the sequences of naturally occurring human antibodies, be derived from human germline immunoglobulin sequences, or can be consensus sequences of several human antibody and/or germline sequences.

Suitable human antibody sequences are identified by computer comparisons of the amino acid sequences of the rabbit or mouse variable regions with the sequences of known human antibodies. The comparison is performed separately for heavy and light chains but the principles are similar for each.

In one example, the amino acid sequence of anti-renalase mAb is used to query a human antibody database compiled from public antibody sequence databases. The heavy chain variable region can be used to find the human variable region with the highest sequence identity. The variable region of the light chain can, similarly, be used to find the human variable region with the highest sequence identity. A DNA construct in which the regions coding for the CDRs of one of the heavy chain variable regions from the parental mAbs donor are transferred into the selected human heavy chain variable sequence, replacing the CDRs of the human variable region is prepared for each parental variable region.

The unnatural juxtaposition of parental CDR regions with human variable framework region can result in unnatural conformational restraints, which, unless corrected by substitution of certain amino acid residues, lead to loss of binding affinity. As noted supra, the humanized antibodies of the invention comprise variable framework region(s) substantially from a human immunoglobulin and CDRs substantially from a parental (e.g., rabbit, or mouse) immunoglobulin. Having identified the CDRs of parental antibodies and appropriate human acceptor immunoglobulin sequences, the next step is to determine which, if any, residues from these components should be substituted to optimize the properties of the resulting humanized antibody. In general, substitution of human amino acid residues with parental should be minimized, because introduction of parental residues increases the risk of the antibody eliciting an immune response in humans. Amino acids are selected for substitution based on their possible influence on CDR conformation and/or binding to the target binding partner molecule. Investigation of such possible influences can be done by modeling, examination of the characteristics of the amino acids at particular locations, or empirical observation of the effects of substitution or mutagenesis of particular amino acids. With regard to the empirical method, it has been found to be particularly convenient to create a library of variant sequences that can be screened for the desired activity, binding affinity or specificity. One format for creation of such a library of variants is a phage display vector. Alternatively, variants can be generated using other methods for variation of a nucleic acid sequence encoding the targeted residues within the variable domain.

Another method of determining whether further substitutions are required, and the selection of amino acid residues for substitution, can be accomplished using computer modeling. Computer hardware and software for producing three-dimensional images of immunoglobulin molecules are widely available. In general, molecular models are produced starting from solved structures for immunoglobulin chains or domains thereof. The chains to be modeled are compared for amino acid sequence similarity with chains or domains of solved three dimensional structures, and the chains or domains showing the greatest sequence similarity is/are selected as starting points for construction of the molecular model. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

Usually the CDR regions in humanized antibodies are substantially identical, and more usually, identical to the corresponding CDR regions in the parental antibody from which they were derived. Although not usually desirable, it is sometimes possible to make one or more conservative amino acid substitutions of CDR residues without appreciably affecting the binding affinity of the resulting humanized immunoglobulin. Occasionally, substitutions of CDR regions can enhance binding affinity.

Other than for the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin.

Because of the degeneracy of the code, a variety of nucleic acid sequences will encode each immunoglobulin amino acid sequence. The desired nucleic acid sequences can be produced by solid-phase DNA synthesis or by PCR mutagenesis of an earlier prepared variant of the desired polynucleotide. All nucleic acids encoding the antibodies described in this application are expressly included in the invention.

The variable segments of humanized antibodies produced as described supra are typically linked to at least a portion of a human immunoglobulin constant region. The antibody will contain both light chain and heavy chain constant regions. The heavy chain constant region usually includes CH1, hinge, CH2, CH3, and, sometimes, CH4 domains.

The humanized antibodies may comprise any type of constant domains from any class of antibody, including IgM, IgG, IgD, IgA and IgE, and any subclass (isotype), including IgG1, IgG2, IgG3 and IgG4. When it is desired that the humanized antibody exhibit cytotoxic activity, the constant domain is usually a complement-fixing constant domain and the class is typically IgG1. When such cytotoxic activity is not desirable, the constant domain may be of the IgG2 class. The humanized antibody may comprise sequences from more than one class or isotype.

Nucleic acids encoding humanized light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Such control sequences include a signal sequence, a promoter, an enhancer, and a transcription termination sequence (see Queen et al., Proc. Natl. Acad. Sci. USA 86, 10029 (1989); WO 90/07861; Co et al., J. Immunol. 148, 1149 (1992), which are incorporated herein by reference in their entirety for all purposes).

Methods of Using the Renalase Binding Molecules

Given the properties of the renalase binding molecules (e.g., antibodies, etc.) of the present invention, the renalase binding molecules are suitable as diagnostic, therapeutic and prophylactic agents for diagnosing, treating or preventing renalase-associated conditions in humans and animals.

In general, usage comprises administering a therapeutically or prophylactically effective amount of one or more monoclonal antibodies or binding fragments of the present invention to a susceptible subject or one exhibiting a condition in which renalase activity is known to have pathological sequelae, such as tumor growth and metastasis. Any active form of the renalase binding molecule can be administered, including antibody Fab and F(ab')2 fragments.

Preferably, the renalase binding molecule used is compatible with the recipient species such that the immune response to the renalase binding molecule does not result in an unacceptably short circulating half-life or induce an immune response to the renalase binding molecule in the subject. Preferably, the renalase binding molecule administered exhibits some secondary functions such as binding to Fc receptors of the subject and activation of ADCC mechanisms.

Treatment of individuals may comprise the administration of a therapeutically effective amount of the renalase binding molecules of the present invention. The renalase binding molecules can be provided in a kit as described below. The renalase binding molecules can be used or administered as a mixture, for example in equal amounts, or individually, provided in sequence, or administered all at once. In providing a patient with renalase binding molecule, the dosage of administered agent will vary depending upon such factors as the patient's age, weight, height, sex, general medical condition, previous medical history, etc.

In general, if administering a systemic dose of a renalase binding molecule, it is desirable to provide the recipient with a dosage of a renalase binding molecule which is in the range of from about 1 ng/kg-100 ng/kg, 100 ng/kg-500 ng/kg, 500 ng/kg-1 µg/kg, 1 µg/kg-100 µg/kg, 100 µg/kg-500 µg/kg, 500 µg/kg-1 mg/kg, 1 mg/kg-50 mg/kg, 50 mg/kg-100 mg/kg, 100 mg/kg-500 mg/kg (body weight of recipient), although a lower or higher dosage may be administered. Dosages as low as about 1.0 mg/kg may be expected to show some efficacy. Preferably, about 5 mg/kg is an acceptable dosage, although dosage levels up to about 50 mg/kg are also preferred especially for therapeutic use. Alternatively, administration of a specific amount of the renalase binding molecule may be given which is not based upon the weight of the patient such as an amount in the range of 1 µg-100 µg, 1 mg-100 mg, or 1 g-100 g. For example, site specific administration may be to body compartment or cavity such as intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, vaginal, rectal, buccal, sublingual, intranasal, ophthalmic, or transdermal means.

The renalase binding molecule composition can be prepared for use for parenteral (subcutaneous, intramuscular or intravenous) or any other administration particularly in the form of liquid solutions or suspensions; for use in vaginal or rectal administration particularly in semisolid forms such as, but not limited to, creams and suppositories; for buccal, or sublingual administration such as, but not limited to, in the form of tablets or capsules; or intranasally such as, but not limited to, the form of powders, nasal drops or aerosols or certain agents; or ophthalmically such as, but not limited to, eye drops; or for the treatment of dental disease; or transdermally such as not limited to a gel, ointment, lotion, suspension or patch delivery system with chemical enhancers such as dimethyl sulfoxide to either modify the skin structure or to increase the drug concentration in the transdermal patch, or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402).

In a similar approach, another therapeutic use of the renalase binding molecule of the present invention is the active immunization of a patient using an anti-idiotypic antibody raised against one of the present monoclonal antibodies. Immunization with an anti-idiotype which mimics the structure of the epitope could elicit an active anti-renalase response (Linthicum, D. S, and Farid, N. R., Anti-Idiotypes, Receptors, and Molecular Mimicry (1988), pp 1-5 and 285-300).

The renalase binding molecules of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle. Additional pharmaceutical methods may be employed to control the duration of action. Controlled release preparations may be achieved through the use of polymers to complex or absorb the compounds. Another possible method to control the duration of action by controlled release preparations is to incorporate the compounds of the present invention into particles of a polymeric material such as polyesters, polyamino acids, hydrogels, poly(lacticacid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions.

The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention also provides kits which are useful for carrying out the present invention. The present kits comprise a first container containing or packaged in association with the above-described antibodies. The kit may also comprise another container containing or packaged in association solutions necessary or convenient for carrying out the invention. The containers can be made of glass, plastic or foil and can be a vial, bottle, pouch, tube, bag, etc. The kit may also contain written information, such as procedures for carrying out the present invention or analytical information, such as the amount of reagent contained in the first container means. The container may be in another container apparatus, e.g. a box or a bag, along with the written information.

Yet another aspect of the present invention is a kit for detecting renalase in a biological sample. The kit includes a container holding one or more renalase binding molecules which binds an epitope of renalase and instructions for using the renalase binding molecule for the purpose of binding to renalase to form complex and detecting the formation of the complex such that the presence or absence of the complex correlates with presence or absence of renalase in the sample. Examples of containers include multiwell plates which allow simultaneous detection of renalase in multiple samples.

Combination Therapy

The renalase binding molecule compositions of the invention can be used in combination with another therapeutic treatment or agent to treat the disease or disorder. For example, the renalase binding molecule of the invention may be administered alone, or in combination with one or more therapeutically effective agents or treatments. The other therapeutically effective agent may be conjugated to the renalase binding molecule of the invention, incorporated into the same composition as the renalase binding molecule of the invention, or may be administered as a separate composition. The other therapeutically agent or treatment may be administered prior to, during and/or after the administration of the antibody of the invention or related compound.

In certain embodiments, the renalase binding molecule of the invention is co-administered with one or more other therapeutic agents or treatments. In other embodiments, the renalase binding molecule of the invention is administered independently from the administration of one or more other therapeutic agents or treatments. For example, the renalase binding molecule of the invention is administered first, followed by the administration of one or more other therapeutic agents or treatments. Alternatively, one or more other therapeutic agents are administered first, followed by the administration of a renalase binding molecule of the invention. As another example, a treatment (e.g., a surgery, radiation, etc.) is carried out first, followed by the administration of the renalase binding molecule of the invention.

Other therapeutically effective agents/treatments include surgery, anti-neoplastics (including chemotherapeutic agents and radiation), anti-angiogenesis agents, antibodies to other targets, small molecules, photodynamic therapy, immunotherapy, immunity enhancing therapy, cytotoxic agents, cytokines, chemokines, growth inhibitory agents, anti-hormonal agents, kinase inhibitors, cardioprotectants, immunostimulatory agents, immunosuppressive agents, and agents that promote proliferation of hematological cells.

In one embodiment, the "another therapeutic agent," as used herein, are second, distinct therapeutic agents or anti-cancer agents, i.e., therapeutic agents or anti-cancer agents "other than" the renalase binding molecule of the invention. Any secondary therapeutic agent may be used in the combination therapies of the present invention. Also, secondary therapeutic agents or "second anti-cancer agents" may be selected with a view to achieving additive, greater than additive and potentially synergistic effects, according to the following guidance.

To practice combined anti-tumor therapy, one would administer to an animal or patient a renalase binding molecule of the invention in combination with another, i.e., a second, distinct anti-cancer agent in a manner effective to result in their combined anti-tumor actions within the animal or patient. The agents would therefore be provided in amounts effective and for periods of time effective to result in their combined, or concurrent, presence within the tumor or tumor vasculature and their combined actions in the tumor environment. To achieve this goal, the renalase binding molecule of the invention and the second, distinct anti-cancer agents may be administered to the animal substantially simultaneously, either in a single composition, or as two distinct compositions using different administration routes.

Alternatively, the renalase binding molecule of the invention may precede, or follow, the second, distinct anti-cancer agent by, e.g., intervals ranging from minutes to weeks. In certain embodiments where the renalase binding molecule of the invention and the second, distinct anti-cancer agents are applied separately to the animal, one would ensure that a significant period of time did not expire between the time of each delivery, such that each agent would still be able to exert an advantageously combined effect on the tumor. In such instances, it is contemplated that one would contact the tumor with both agents within about 5 minutes to about one week of each other and, more preferably, within about 12-72 hours of each other, with a delay time of only about 12-48 hours being most preferred.

The secondary therapeutic agents for separately timed combination therapies may be selected based upon certain criteria, including those discussed elsewhere herein. However, a preference for selecting one or more second, distinct anti-cancer agents for prior or subsequent administration does not preclude their use in substantially simultaneous administration if desired. Second, distinct anti-cancer agents selected for administration "prior to" the primary therapeutic agents of the present invention, and designed to achieve increased and potentially synergistic effects.

Second, distinct anti-cancer agents selected for administration "subsequent to" the primary therapeutic agents of the present invention, and designed to achieve increased and potentially synergistic effects, include agents that benefit from the effects of the primary therapeutic agent. Accordingly, effective second, distinct anti-cancer agents for subsequent administration include anti-angiogenic agents, which inhibit metastasis; agents targeting necrotic tumor cells, such as antibodies specific for intracellular binding partner molecules that become accessible from malignant cells in vivo (U.S. Pat. Nos. 5,019,368, 4,861,581 and 5,882,626, each specifically incorporated herein by reference); chemotherapeutic agents; and anti-tumor cell immunoconjugates, which attack any tumor cells.

The renalase binding molecule of the invention can also be administered in combination with a cancer immunotherapy. The cancer immunotherapy can be one designed to elicit a humoral immune response against the subject's cancer cells, or a cell-mediated immune response against the subject's cancer cells, or a combination of a humoral response and a cell-mediated response against the subject's cancer cells. Non-limiting examples of cancer immunotherapy useful in combination with the renalase binding molecules of the invention include a cancer vaccine, a DNA cancer vaccine, adoptive cellular therapy, adoptive immunotherapy, CAR T-cell therapy, antibodies, immunity enhancing compounds, cytokines, interleukins (e.g., IL-2, etc.), interferons (IFN-α, etc.), and checkpoint inhibitors (e.g., PD-1 inhibitor, CTLA-4 inhibitor, etc.).

In some situations, it may be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, 7 or 8) lapse between the respective administrations. This would be advantageous in circumstances where one treatment was intended to substantially destroy the tumor, such as the primary therapeutic agent of the present invention, and another treatment was intended to prevent micrometastasis or tumor re-growth, such as the administration of an anti-angiogenic agent. Anti-angiogenics should be administered at a careful time after surgery, however, to allow effective wound healing. Anti-angiogenic agents may then be administered for the lifetime of the patient.

It is also envisioned that more than one administration of either the renalase binding molecule of the invention or the second, distinct anti-cancer agent will be utilized. The renalase binding molecule of the invention and the second, distinct anti-cancer agent may be administered interchangeably, on alternate days or weeks; or a sequence of one agent treatment may be given, followed by a sequence of the other treatment. In any event, to achieve tumor regression using a combined therapy, all that is required is to deliver both agents in a combined amount effective to exert an anti-tumor effect, irrespective of the times for administration.

Chemotherapeutic drugs can be used in combination with the renalase inhibitors of the invention. Chemotherapeutic drugs can kill proliferating tumor cells, enhancing the necrotic areas created by the overall treatment.

One aspect of the invention provides a method of treating or preventing cancer using a renalase inhibitor of the invention. The skilled artisan will understand that treating or preventing cancer in a patient includes, by way of non-limiting examples, killing and destroying a cancer cell, as well as reducing the proliferation of or cell division rate of a cancer cell. The skilled artisan will also understand that a cancer cell can be, by way of non-limiting examples, a primary cancer cell, a cancer stem cell, a metastatic cancer cell. The following are non-limiting examples of cancers that can be treated by the disclosed methods and compositions: Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytotna/Malignant Glioma; Craniopharyngioma; Ependymoblastoma; Ependymoma; Medulloblastoma; Medulloepithelioma; Pineal Parenchymal Tumors of intermediate Differentiation; Supratentorial Primitive Neuroectodermal Tumors and Pineoblastoma;

Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenstrom; Malignant Fibrous Histiocytoma of Bone and Osteosarcoma; Medulloblastoma; Melanoma; Melanoma, intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis; Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Paraganglioma; Pineal Parenchymal Tumors of Intermediate Differentiation; Pineoblastoma and Supratentorial Primitive Neuroectodermal Tumors; Pituitary Tumor; Plasma Celt Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenstrom Macroglobulinemia; and Wilms Tumor.

In one embodiment, the invention provides a method to treat cancer comprising treating the subject prior to, concurrently with, or subsequently to the administration of the renalase binding molecule of the invention, with a complementary therapy for the cancer, such as surgery, chemotherapy, chemotherapeutic agent, radiation therapy, or hormonal therapy or a combination thereof.

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cisplatinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

The renalase binding molecule of the invention can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the disclosed compounds include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; albumin-bound paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine;

edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; imilimumab; mirtazapine; BrUOG 278; BrUOG 292; RAD0001; CT-011; folfirinox; tipifarnib; R115777; LDE225; calcitriol; AZD6244; AMG 655; AMG 479; BKM120; mFOLFOX6; NC-6004; cetuximab; IM-C225; LGX818; MEK162; BBI608; MEDI4736; vemurafenib; ipilimumab; ivolumab; nivolumab; panobinostat; leflunomide; CEP-32496; alemtuzumab; bevacizumab; ofatumumab; panitumumab; pembrolizumab; rituximab; trastuzumab; STAT3 inhibitors (e.g., STA-21, LLL-3, LLL12, XZH-5, S31-201, SF-1066, SF-1087, STX-0119, cryptotanshinone, curcumin, diferuloylmethane, FLLL11, FLLL12, FLLL32, FLLL62, C3, C30, C188, C188-9, LYS, OPB-31121, pyrimethamine, OPB-51602, AZD9150, etc.); hypoxia inducing factor 1 (HIF-1) inhibitors (e.g., LW6, digoxin, laurenditerpenol, PX-478, RX-0047, vitexin, KC7F2, YC-1, etc.) and zinostatin stimalamer. In one embodiment, the anti-cancer drug is 5-fluorouracil, taxol, or leucovorin.

Methods of Diagnosis

In some embodiments, a change (e.g., an increase) in the level of renalase, or a renalase fragment, in a subject's cell, tissue, or bodily fluid, compared with a comparator is used in the methods of the invention as marker for the diagnosis of a disease or disorder, assessing the severity of a disease or disorder, and for monitoring the effect or effectiveness of a treatment of a disease or disorder. In various embodiments, the disease or disorder is acute renal failure (i.e., acute tubular necrosis, or ATN, an ischemic condition in the kidney), a cardiovascular disease or disorder (e.g., hypertension, pulmonary hypertension, systolic hypertension, diabetic hypertension, asymptomatic left ventricular dysfunction, chronic congestive heart failure, myocardial infarction, cardiac rhythm disturbance, atherosclerosis, etc.), cancer, heart disease or disorder, a kidney disease or disorder, a gastrointestinal disease or disorder, a liver disease or disorder, a lung disease or disorder, a pancreas disease or disorder (e.g., pancreatitis), mental disease or disorder (e.g., depression, anxiety, etc.), or a neurological disease or disorder.

In one embodiment, the invention is a method of diagnosing a disease or disorder of a subject by assessing the level of renalase, or a renalase fragment, in a biological sample of the subject. In one embodiment, the biological sample of the subject is a cell, tissue, or bodily fluid. Non-limiting examples of bodily fluids in which the level of renalase, or a renalase fragment, can be assessed include, but are not limited to, blood, serum, plasma and urine. In various embodiments, the level of renalase, or a renalase fragment, in the biological sample of the subject is compared with the renalase, or the renalase fragment, level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of In various embodiments, the disease or disorder is acute renal failure (i.e., acute tubular necrosis, or ATN, an ischemic condition in the kidney), a cardiovascular disease or disorder (e.g., hypertension, pulmonary hypertension, systolic hypertension, diabetic hypertension, asymptomatic left ventricular dysfunction, chronic congestive heart failure, myocardial infarction, cardiac rhythm disturbance, atherosclerosis, etc.), cancer, heart disease or disorder, a kidney disease or disorder, a gastrointestinal disease or disorder, a liver disease or disorder, a lung disease or disorder, a pancreas disease or disorder (e.g., pancreatitis), mental disease or disorder (e.g., depression, anxiety, etc.), or a neurological disease or disorder. In some embodiments, the method of diagnosing includes a further step of treating the patient for the diagnosed disease or disorder.

In another embodiment, the invention is a method of assessing the severity of a disease or disorder of a subject by assessing the level of renalase, or a renalase fragment, in a biological sample of the subject. In one embodiment, the biological sample of the subject is a cell, tissue, or bodily fluid. Non-limiting examples of bodily fluids in which the level of renalase, or a renalase fragment, can be assessed include, but are not limited to, blood, serum, plasma and urine. In various embodiments, the level of renalase, or a renalase fragment, in the biological sample of the subject is compared with the renalase, or a renalase fragment, level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of. In various embodiments, the disease or disorder is acute renal failure (i.e., acute tubular necrosis, or ATN, an ischemic condition in the kidney), a cardiovascular disease or disorder (e.g., hypertension, pulmonary hypertension, systolic hypertension, diabetic hypertension, asymptomatic left ventricular dysfunction, chronic congestive heart failure, myocardial infarction, cardiac rhythm disturbance, atherosclerosis, etc.), cancer, heart disease or disorder, a kidney disease or disorder, a gastrointestinal disease or disorder, a liver disease or disorder, a lung disease or disorder, a pancreas disease or disorder (e.g., pancreatitis), mental disease or disorder (e.g., depression, anxiety, etc.), or a neurological disease or disorder. In some embodiments, the method of assessing the severity includes a further step of treating the patient for the disease or disorder.

In another embodiment, the invention is a method of monitoring the effect of a treatment of a disease or disorder of a subject by assessing the level of renalase, or a renalase fragment, in a biological sample of the subject. In one embodiment, the biological sample of the subject is a cell, tissue, or bodily fluid. Non-limiting examples of bodily fluids in which the level of renalase, or a renalase fragment, can be assessed include, but are not limited to, blood, serum, plasma and urine. In various embodiments, the level of renalase, or a renalase fragment, in the biological sample of the subject is compared with the renalase, or a renalase fragment, level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of. In various embodiments, the disease or disorder is acute renal failure (i.e., acute tubular necrosis, or ATN, an ischemic condition in the kidney), a cardiovascular disease or disorder (e.g., hypertension, pulmonary hypertension, systolic hypertension, diabetic hypertension, asymptomatic left ventricular dysfunction, chronic congestive heart failure, myocardial infarction, cardiac rhythm disturbance, atherosclerosis, etc.), cancer, heart disease or disorder, a kidney disease or disorder, a gastrointestinal disease or disorder, a liver disease or disorder, a lung disease or disorder, a pancreas disease or disorder (e.g., pancreatitis), mental disease or disorder (e.g., depression, anxiety, etc.), or a neurological disease or disorder. In some embodiments, the method of monitoring the effect of a treatment includes a further step of treating the patient for the disease or disorder.

In various embodiments, the subject is a human subject, and may be of any race, sex and age. Representative subjects include those who are suspected of having experienced a disease or disorder, those who have been diagnosed as having experienced a disease or disorder, those who have been diagnosed as having a disease or disorder, and those who are at risk of developing a disease or disorder.

Information obtained from the methods of the invention described herein can be used alone, or in combination with other information (e.g., disease status, disease history, vital signs, blood chemistry, etc.) from the subject or from the biological sample obtained from the subject.

In the diagnostic methods of the invention, a biological sample obtained from a subject is assessed for the level of renalase, or a renalase fragment, contained therein. In one embodiment, the biological sample is a sample containing at least a fragment of a renalase polypeptide useful in the methods described herein.

In other various embodiments of the methods of the invention, the level of renalase is determined to be increased when the level of renalase, or a renalase fragment, is increased by at least 10%, by at least 20%, by at least 30%, by at least 40%, by at least 50%, by at least 60%, by at least 70%, by at least 80%, by at least 90%, by at least 100%, by at least 200%, by at least 300%, by at least 400%, by at least 500%, by at least 600%, by at least 700%, by at least 800%, by at least 900%, or by at least 1000%, when compared to with a comparator control. In various embodiments, an increased level of renalase, or a renalase fragment, is indicative of a disease or disorder. In various embodiments, the disease or disorder is acute renal failure (i.e., acute tubular necrosis, or ATN, an ischemic condition in the kidney), cardiovascular disease, pancreatitis, hepatitis, inflammatory disorders of the kidney, and cancer.

In the methods of the invention, a biological sample from a subject is assessed for the level of renalase, or a renalase fragment, in the biological sample obtained from the patient.

The level of renalase, or a renalase fragment, in the biological sample can be determined by assessing the amount of renalase polypeptide, or a fragment, in the biological sample, the amount of renalase mRNA, or a fragment, in the biological sample, the amount of renalase activity (e.g., enzymatic activity, substrate binding activity, receptor binding activity, etc.) in the biological sample, or a combination thereof. In some embodiments, the level of renalase in the biological sample is determined in an assay using at least one of the renalase binding molecules of the invention described elsewhere herein.

In various embodiments of the methods of the invention, methods of measuring renalase levels in a biological sample obtained from a patient include, but are not limited to, an immunochromatography assay, an immunodot assay, a Luminex assay, an ELISA assay, an ELISPOT assay, a protein microarray assay, a Western blot assay, a mass spectrophotometry assay, a radioimmunoassay (MA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, FACS, an enzyme-substrate binding assay, an enzymatic assay, an enzymatic assay employing a detectable molecule, such as a chromophore, fluorophore, or radioactive substrate, a substrate binding assay employing such a substrate, a substrate displacement assay employing such a substrate, and a protein chip assay (see also, 2007, Van Emon, Immunoassay and Other Bioanalytical Techniques, CRC Press; 2005, Wild, Immunoassay Handbook, Gulf Professional Publishing; 1996, Diamandis and Christopoulos, Immunoassay, Academic Press; 2005, Joos, Microarrays in Clinical Diagnosis, Humana Press; 2005, Hamdan and Righetti, Proteomics Today, John Wiley and Sons; 2007). In some embodiments, the level of renalase in the biological sample is measure with an assay that uses at least one of the renalase binding molecules of the invention that are described elsewhere herein.

Kits

The invention also includes a kit comprising a renalase binding molecule (e.g., antibody, etc.), or combinations thereof, of the invention and an instructional material which describes, for instance, administering the renalase binding molecule, or a combination thereof, to an individual as a therapeutic treatment or a non-treatment use as described elsewhere herein. In an embodiment, this kit further comprises a (preferably sterile) pharmaceutically acceptable carrier suitable for dissolving or suspending the therapeutic composition, comprising a renalase binding molecule, or combinations thereof, of the invention, for instance, prior to administering the renalase binding molecule of the invention to an individual. Optionally, the kit comprises an applicator for administering the renalase binding molecule.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLE 1: Novel Compositions and Methods for Treating Cancer

The results described herein provide data supporting the utility of novel compositions and methods for treating cancer.

The materials and methods employed in these experiments are now described.

Synthesis of Anti-Renalase Monoclonal Antibodies in Rabbit

Protein Antigen Preparation: Renalase-1 cDNA was subcloned into the pET27 expression vector (Novagen) which was then used to transform the BL21 DE3 strain of bacteria (Novagen). Renalase protein was isolated from bacterial inclusion bodies by a standard procedure. Briefly, bacterial inclusion bodies were isolated and solubilized in a combination of Chaotropic salt and reducing agent. The protein was refolded by dilution of the solubilization buffer. After a final dialysis of the solubilized and refolded protein into Phosphate Buffered Saline (PBS), the protein was used as an antigen to immunize rabbits.

Peptide Antigen Preparation: The peptides for immunization were designed to cover several areas of the renalase-1 or 2 polypeptides and to include an N or C-terminal cysteine residue to be used in subsequent conjugations. Peptides were produced using standard peptide synthesis procedures and were conjugated via the cysteine residue to either bovine serum albumin (BSA) for screening purposes or to the adjuvant keyhole limpet hemocyanin (KLH) for animal immunization.

Immunization and Antibody Selection: Using standard procedures, each of the KLH-conjugated peptide antigens and the whole protein antigen were used to immunize 6 rabbits using a multi-dose injection protocol. Pre and post-immunization test bleeds from each of the rabbits were tested for anti-renalase titer using a standard ELISA protocol with either the BSA-peptide conjugate or the refolded whole protein as coated antigen (see protocol below). Rabbits with antiserum that had the highest titer for anti-renalase and the desired detection characteristics for endogenous renalase in Western blot analysis were selected for further analysis. The selected animals were either used in terminal bleeds for the production of anti-renalase polyclonal antibodies or the selected rabbit spleens were harvested for lymphocytes. After standard cell fusion, hybridoma pools from each animal were screened using the conditioned cell culture media in the same peptide and whole protein ELISA format described above. Hybridomas with the highest anti-renalase titer and the preferred endogenous renalase binding characteristics were selected and subcloned. The cloned hybridomas were subsequently expanded and monoclonal antibody was purified from the conditioned cell supernatant.

Hybridoma Culture and Expansion: Hybridoma cells were cultured in Hybridoma-SFM serum-free medium (Gibco/Invitrogen) supplemented with 55 µM 2-mercaptoethanol. For antibody purification, 107 hybridoma cells suspended in 15 mL culture medium were applied to the cell compartment of a CELLine 1000 bioreactor flask (Wilson Wolf) and the upper compartment was filled with 1 L culture medium. After 7 days of continuous culture, the cell compartment contents (containing cells and secreted antibody) were removed and cells were pelleted by centrifugation at 1000 g for 5 minutes. The supernatant was recovered, centrifuged at 10,000 g for 15 minutes and filtered (0.2 μM) to remove cellular debris prior to antibody purification.

Antibody Purification: For the anti-renalase monoclonal antibodies, precleared, conditioned hybridoma supernatant was pumped over a pre-equilibrated protein A affinity column (GE life sciences) at constant pressure. The column was washed with 20 column volumes PBS pH 7.4. Antibody was eluted from the column in 0.1M glycine pH 2.5 and was immediately neutralized using Tris buffer. The pure antibody was dialyzed against excess PBS pH 7.4, filter sterilized and stored at either—80° C. or 4° C. in aliquots. For the anti-renalase polyclonal antibodies raised against either a peptide—conjugate or whole renalase protein immunogen, terminal rabbit bleed sera was initially passed over a protein A affinity column. The total purified IgG pool from this protein A column was dialyzed against PBS pH 7.4. The anti-renalase antibodies were further purified by passing the pool over Actigel ALD columns (Sterogene) conjugated with either the relevant peptide antigen or the whole renalase protein (Actigel-antigen conjugation was completed protocol according to manufacturer's instructions). The columns were washed with PBS and bound IgG was eluted with 0.1 M glycine pH 2.5. Purified IgG was neutralized using Tris buffer and dialyzed against PBS.

General ELISA Screening Assay: 100 ng/well of recombinant renalase protein or renalase peptide-BSA conjugate was bound to a 96 well microtiter plate by overnight incubation at 4° C. The plate was blocked with a solution of 5% milk in phosphate-buffered saline containing 0.05% Tween-20 (PBST) for one hour at 33° C. The renalase antibody bleeds were diluted in PBS and 50 μL was added to each well. After one hour incubation at 33° C., the plate was rinsed three times with PB ST. 50 μL anti-rabbit-horseradish peroxidase (HRP) conjugated antibody (Dako, diluted to 0.25 μg/mL in PBST) was added to each well and the plate was incubated at 33° C. for 45 minutes. The plate was washed three times with PBST and once with PBS. 100 μL of 3, 3', 5, 5'-tetramethylbenzidine (TMB) substrate was added to each well and the plate was incubated for approximately 5 minutes at room temperature. To stop the reaction, 100 μL 2 N $H_2SO_4$ was added to each well. The plate was read at 450 nm in a spectrophotometer.

General Sandwich ELISA Assay: Typically, 400 ng/well of capture antibody in phosphate-buffered saline (PBS) was bound to a 96 well microtiter plate by overnight incubation at 4° C. The plate was blocked with a solution of 8% non-fat dried milk (NFDM) in PBS for one hour at 33° C. The samples, containing renalase, were diluted in PBS containing Tween-20 to 0.05% (PBST), and 50 μL was added to each well. After one hour incubation at 33° C., the plate was rinsed three times with PBST. The biotinylated antibody probe was diluted to 4 μg/mL in PBST, and 50 μL was added to each well. After incubation for 1 hour at 33° C., the plate was washed 3 times with PBST. For detection, 50 μL of horseradish peroxidase-conjugated (HRP) Neutravidin (NA-HRP) diluted to 0.4 μg/mL, was added to each well and the plate was incubated at room temperature for 45 minutes. After incubation, the plate was washed three times with PBST and once with PBS. The HRP substrate 3, 3', 5, 5'-tetramethylbenzidine (TMB) was added to 100 μL per well, and plate was incubated for approximately 5 minutes at room temperature. To stop the reaction, 100 μL 2 N $H_2SO_4$ was added to each well. The plate was read at 450 nm in a spectrophotometer.

Western Blotting Procedure: Protein samples were resolved on 4-20% Tris-Glycine gradient gels (Invitrogen). Proteins were transferred from the gel to polyvinyldifluoride (PVDF) membranes using an XCell II blot module (Invitrogen). PVDF membranes were blocked with a solution of 5% non-fat powdered milk in phosphate-buffered saline containing 0.1% Tween-20 (PBST) for one hour at room temperature. The blocking buffer was then removed and the membrane was incubated with the detection antibody, diluted in 20 mL 5% milk/PB ST. After incubation at room temperature for one hour, the membrane was washed three times for 10 minutes each with PBST. 20 mL anti-rabbit IgG horseradish peroxidase (HRP) conjugate (Dako, diluted to 0.25 μg/mL in 5% milk/PBST) was applied to the membrane and incubated for a further one hour at room temperature. The membrane was washed three times for 10 minutes each with PBST. Excess PBST was drained from the membrane and sufficient enhanced chemiluminescence (ECL) plus reagent (GE Lifesciences) to cover the surface of the membrane was applied, and incubated for one minute. Excess ECL plus reagent was then drained and the membrane was wrapped in plastic film. Protein bands were visualized by exposing the membrane to Hyperfilm-ECL (GE Lifesciences), which was processed using an automatic film developer (Konica).

Peptide-Antigen Specificity ELISA: Bovine serum albumin (BSA)-conjugated renalase peptide antigen, diluted to 100 ng/well in PBS, was bound to a 96 well microtiter plate by overnight incubation at 4° C. The plate was blocked with a solution of 8% NFDM in PBS for one hour at 33° C. The peptide antigen was probed with a dilution series of the antibody raised against it, or with an antibody raised against a different antigen. The starting concentration of antibody was typically 5 μg/mL, with two-fold dilution steps prepared in PBS containing Tween-20 to 0.05% (PBST). After one hour incubation at 33° C., the plate was rinsed three times with PBST. Antibody binding was assayed by adding HRP-conjugated anti-rabbit IgG at 50 ng/mL, 50 μL per well. The plate was incubated at room temperature for 40 minutes. After incubation, the plate was washed three times with PBST and once with PBS. The HRP substrate 3, 3', 5, 5'-tetramethylbenzidine (TMB) was added to 100 μL per well, and plate was incubated for approximately 5 minutes at room temperature. To stop the reaction, 100 μL 2 N $H_1SO_4$ was added to each well. The plate was read at 450 nm in a spectrophotometer.

Specificity of Epitope Binding: Bacterially-expressed renalase isoforms, diluted to 100 ng/well in PBS, were bound to a 96 well microtiter plate by overnight incubation at 4° C. The plate was blocked with a solution of 8% NFDM in PBS for one hour at 33° C. The renalase protein was probed with a dilution series of an unconjugated antibody, typically starting at 1 μg/mL, mixed with a different biotinylated antibody. The concentration of the biotinylated antibody was held constant at 125 ng/well. Both antibodies were mixed together in PBST and applied as one addition of 50 μL per well. After one hour incubation at 33° C., the plate was rinsed three times with PBST. Binding of the biotinylated antibody to renalase was assayed by adding HRP-conjugated Neutravidin (HRP-NA) at 0.4 ng/mL, 50 μL per well. The plate was incubated at room temperature for 40 minutes. After incubation, the plate was washed three times with PBST and once with PBS. The HRP substrate 3, 3', 5, 5'-tetramethylbenzidine (TMB) was added to 100 μL per well, and plate was incubated for approximately 5 minutes at room temperature. To stop the reaction, 100 μL 2 N H2SO4 was added to each well. The plate was read at 450 nm in a spectrophotometer.

Biacore Measurements of Antibody Affinity: Binding studies were performed using a Biacore T100 essentially as described (Guo X et al., 2016, Scientific Reports, 6:22996). Assays were completed at 25° C. using 25 mM Tris pH 8, 150 mM NaCl, 1 mM EDTA, 10% glycerol, 0.005% Tween-20 and 0.1 mg/mL BSA as the running buffer. The biotinylated antibodies were captured on individual streptavidin sensor chip flow cells and purified, recombinant renalase-1 was injected over the surface of the chips.

Synthesis and Characterization of Humanized Anti-Renalase Monoclonal Antibodies

Humanization strategy and protocols: Complementary determining regions (CDRs) from M28 and M42 were grafted onto the 4D5 (Herceptin) framework in the Fab antibody fragment format within a phagemid using standard methods (Nelson B, 2012, Methods in molecular biology, 899:27-41). Oligonucleotides used for this CDR grafting, including resulting amino acid composition, are listed in Table 1. In addition, HC-A71 (numbering according to Chothia (Chothia C et al., 1987, Journal of molecular biology, 196(4):901-17)) was changed to K71 or R71 for M28 and M42 respectively to accommodate parental M28 and M42 CDR-H2. Oligonucleotide-directed mutagenesis was used to construct affinity maturation libraries M28 and M42 variants. Individual M28 CDR-L3, -H1, -H2, and -H3 and M42 CDR-L1, -H1, -H2, and -H3 were targeted for diversification as independent libraries. Applicable CDRs were first replaced with STOP codons using oligonucleotides listed in Table 1 to create STOP templates for affinity maturation libraries. These STOP templates were then used for creation of affinity maturation libraries (4 for M28 and 4 for M42) using oligonucleotides listed in Table 1 that diversified with a "soft randomization" strategy whereby the nucleotide ratio at degenerate positions was adjusted to 70% of the parental nucleotide and 10% of each of the other nucleotides using standard protocols (Nelson B, 2012, Methods in molecular biology, 899:27-41).

Selection of higher affinity variants that were cross-reactive to human and mouse renalase and direct phage ELISAs were performed as described (Nelson B, 2012, Methods in molecular biology, 899:27-41; Reshetnyak AV et al., 2013, Proc of Nat Acad of Sci of the USA, 110(44): 17832-7). Briefly, library phage pools were cycled through 3-5 rounds of binding selections using alternating rounds of human renalase (hRNLS) or mouse renalase (mRNLS) coated on 96-well Maxisorp plates (Nunc). After 3-5 rounds of selections, specific binding of individual clones was evaluated by phage ELISA as described (Reshetnyak AV et al., 2013, Proc of Nat Acad of Sci of the USA, 110(44): 17832-7). Clones that exhibited at least 10-fold greater signals for binding hRNLS and mRNLS compared with streptavidin (New England Biolabs) were subjected to DNA sequencing to decode the sequences of the phage-displayed Fabs.

Three cross-reactive M28 variants were isolated, two with changes to multiple CDRs indicating recombination during library construction or antibody selections. Variant CDRs were combined systematically using standard methods to derive 23 unique variants with changes ranging from a single variant CDR to 4 variant CDRs. All 23 variants were rank ordered using in-solution competitive ELISAs (Reshetnyak AV et al., 2013, Proc of Nat Acad of Sci of the USA, 110(44):17832-7). Six variants, M28-K2, M28-K5, M28-K9, M28-13, M28-14, and M28-19, were chosen for reformatting to mouse IgG1 (chimera with human Fv) for multipoint ELISA, and cell-based testing, surface plasmon resonance, and in vivo testing.

Eight cross-reactive M42 variants were isolated, each with changes to single CDRs. Multipoint ELISAs were used to rank order between two CDR-H2 and two CDR-H3 variants. One variant for each CDR-H2 and CDR-H3 were chosen and CDRs were combined for a total of 11 variants. These 11 variants were subjected to in-solution competitive ELISAs to rank order. 3 variants, M42-K31, M42-K34, and M42-35, were chosen for reformatting to mouse IgG1 (chimera with human Fv).

IgG1 conversion, expression and purification: Light chain Fv fragments from variants were PCR amplified to include 5' EcoRI and 3' BstAPI sites used for cloning into the pFUSE2ss-CLIg-mk vector (InvivoGen) for conversion to mouse IgG kappa light chain expression (human-mouse chimera). Light chain Fv fragments from variants were PCR amplified to include 5' EcoRI and 3' BsiWI sites used for cloning into the pFUSE2ss-CLIg-hk vector (InvivoGen) for conversion to human IgG kappa light chain expression. Heavy chain Fv fragments were PCR amplified to include 5' EcoRI and 3' NheI sites used for cloning into the pFUSEss-CHIg-mG1 (InvivoGen) for conversion to mouse IgG1 heavy chain expression (human-mouse chimera) or pFUSEss-CHIg-hG4 (InvivoGen) for conversion to human IgG4 heavy chain expression. Heavy and light chain vectors were co-transfected into Expi293F cells (ThermoFisher) according to manufacturer's instructions. Cell cultures were incubated for 5 days before purification from supernatant using protein A sepharose beads (GE Healthcare).

The results of the experiments are now described.

Renalase Antigen Selection, Immunization and Antibody Production

Renalase is a FAD-containing protein that has been implicated in the control and maintenance of blood pressure (Xu, J. et al., 2005, J Clin Invest, 115(5):1275-80). The lack of high-affinity, high-specificity anti-renalase antibodies has hindered the research and development of both renalase biology and potential renalase-associated therapeutics. To date several polyclonal research-reagent antibodies have been developed, but these are low affinity and fail to robustly detect endogenous renalase in either tissue or bodily fluid samples. Thus, the development of a set of renalase antibodies with specificity for the different isoforms of renalase and further, different peptide sequences within the intact protein will allow for definitive detection and characterization of the renalase gene product. Further the selection of only high affinity antibodies will allow for the detection of potentially low levels of renalase and thus may lead to the development of a protein-based diagnostic for renalase levels.

In order to produce a range of antibodies with high affinity and specificity for renalase, two methods were employed. In the first method, polyclonal antibodies were raised using the full-length renalase-1 protein as an immunogen. Renalase-1 cDNA was subcloned into the pET27 expression vector (Novagen) which was then used to transform the BL21 DE3 strain of bacteria (Novagen). Renalase protein was isolated from bacterial inclusion bodies by a standard procedure. Briefly, bacterial inclusion bodies were isolated and solublized in a combination of chaotropic salt and reducing agent. The protein was refolded by dilution of the solublization buffer followed by a final dialysis into Phosphate Buffered Saline (PBS).

The sequence of the full-length renalase protein used as immunogen can be seen in FIG. 2. This protein was used as an antigen to immunize 6 rabbits. The antisera from these animals was screened for renalase binding specificity by ELISA assay where the antigen was the same, refolded renalase protein. The antisera was also selected based on the criteria of ability to detect endogenous renalase in human tissue lysates by western blot. Terminal bleed antisera with the highest anti-renalase titer and greatest specificity for endogenous renalase was selected for antibody purification. Total IgG was purified from the antisera using protein G affinity chromatography and the specific, anti-renalase antibodies were further purified on a column conjugated with the recombinant renalase protein. As can be seen in later examples, the antibodies raised in this way bind to renalase and further are shown to bind to multiple epitopes on renalase.

In the second approach for raising anti-renalase antibodies, peptides were used as immunogens. The peptides generated ranged from 9 to 21 amino acids and corresponded to regions of the renalase-1 and renalase-2 proteins. All of the peptides had an N or C-terminal cysteine residue. The sequence of the peptides can be seen in FIG. 1 and where these peptides correspond to the renalase-1 or 2 sequences is demonstrated in the sequence alignment of FIG. 3. As can be seen the renalase-1 specific peptides are labeled 1A-F and the renalase-2 specific peptide is labeled 3A5. Each peptide was conjugated to the adjuvant KLH via the cysteine and used to immunize 6 rabbits. The antisera of each animal was screened for anti-renalase antibody titer by ELISA assay using both the relevant peptide (BSA-conjugate) or full length renalase-1 or 2. The antisera were also tested for their ability to detect endogenous renalase in tissue lysates by western blot. Using these screening criteria the animals producing antibodies with the preferred characteristics were selected. In some examples and for some peptides, several animals produced antibodies with the required specificity. In these cases one animal had a final antisera bleed for polyclonal antibody production and one or in some examples two other animals were used to harvest spleen lymphocytes. In other examples a single animal had a terminal bleed and a splenectomy. Polyclonal antibodies raised against all of the peptides were generated by purification of total IgG from terminal bleeds by protein G chromatography followed by further purification on peptide affinity chromatography. Further and using standard procedures, lymphocytes from the spleens of selected animals were fused to myeloma cells for hybridoma generation. The hybridoma supernatants were screened for binding to both the peptides against which they were raised and secondarily screened against whole renalase protein. Selected hybridomas were sub-cloned and expanded for antibody purification. The monoclonal antibodies were purified from conditioned hybridoma culture supernatant by protein A affinity chromatography. The peptides for which monoclonal antibodies were generated can be seen in FIG. 1.

The Nucleotide and Amino Acid Sequence of Anti-renalase Antibodies

The monoclonal antibodies 1D-28-4, 1D-37-10, 1F-26-1, 1F-42-7 and 3A-5-2 were selected for their renalase binding specificity and high affinity (see later sections). Using standard polymerase chain reaction procedures and degenerate primer sets, the cDNA of the antibody heavy and light chain variable regions for these antibodies were amplified from the subcloned hybridomas. The variable region nucleotide and amino acid sequences are shown in FIG. 4 through FIG. 13. In this way the composition of antibodies with preferred characteristics is exemplified.

Antibodies Show Specificity for Renalase in Both ELISA and Western Blot

Figure 14:
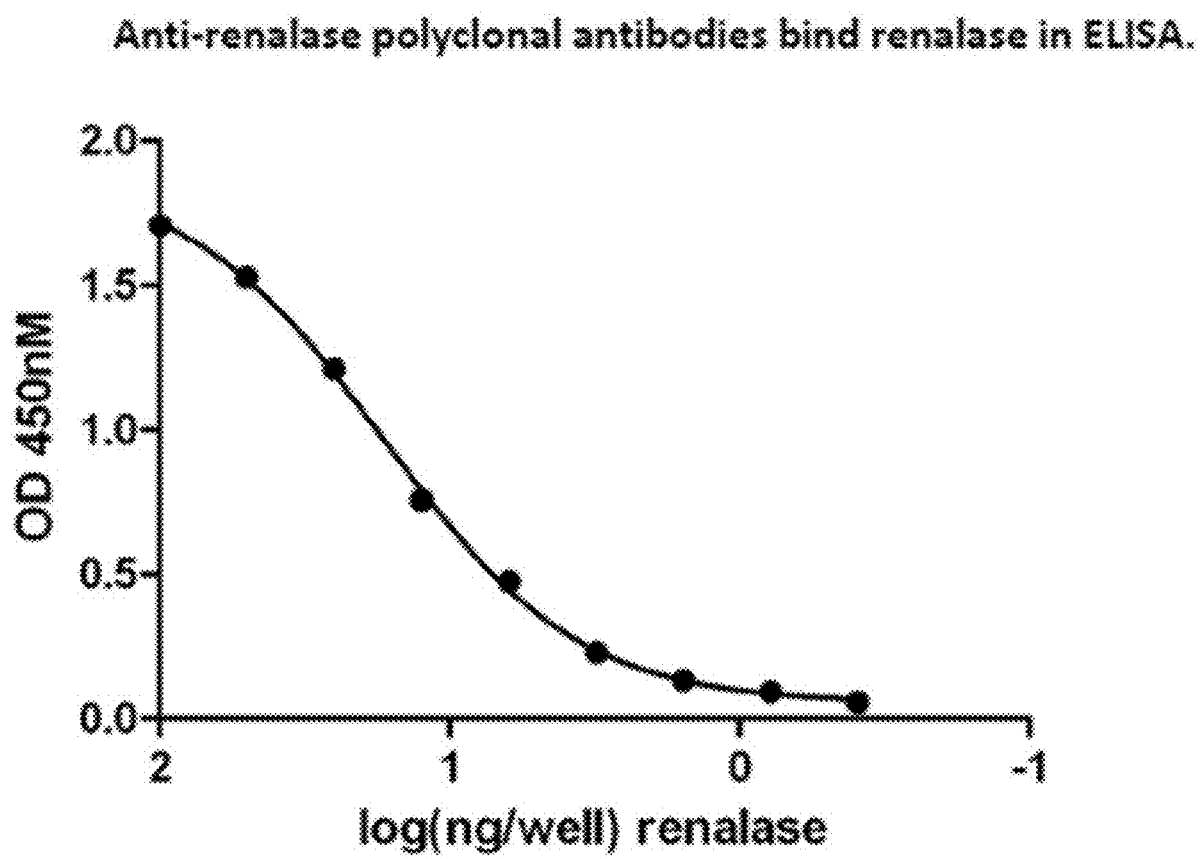
FIG. 14 depicts that anti-renalase polyclonal antibody raised against full-length renalase protein specifically binds bound renalase protein in an ELISA assay.

As can be seen in FIG. 14, anti-renalase polyclonal antibody raised against full-length renalase protein specifically binds bound renalase protein in an ELISA assay. Bacterially-expressed renalase-1, diluted to 100 ng/well in PBS, was bound to a 96 well microtiter plate by overnight incubation at 4° C. After blocking with NFDM, the renalase protein was probed with a dilution series of polyclonal antibody E2930, starting at a concentration of 1 µg/mL. Antibody binding was assayed by adding HRP-conjugated anti-rabbit IgG. The plate was read at 450 nm in a spectrophotometer after reaction of HRP with the substrate TMB.

Figure 15:
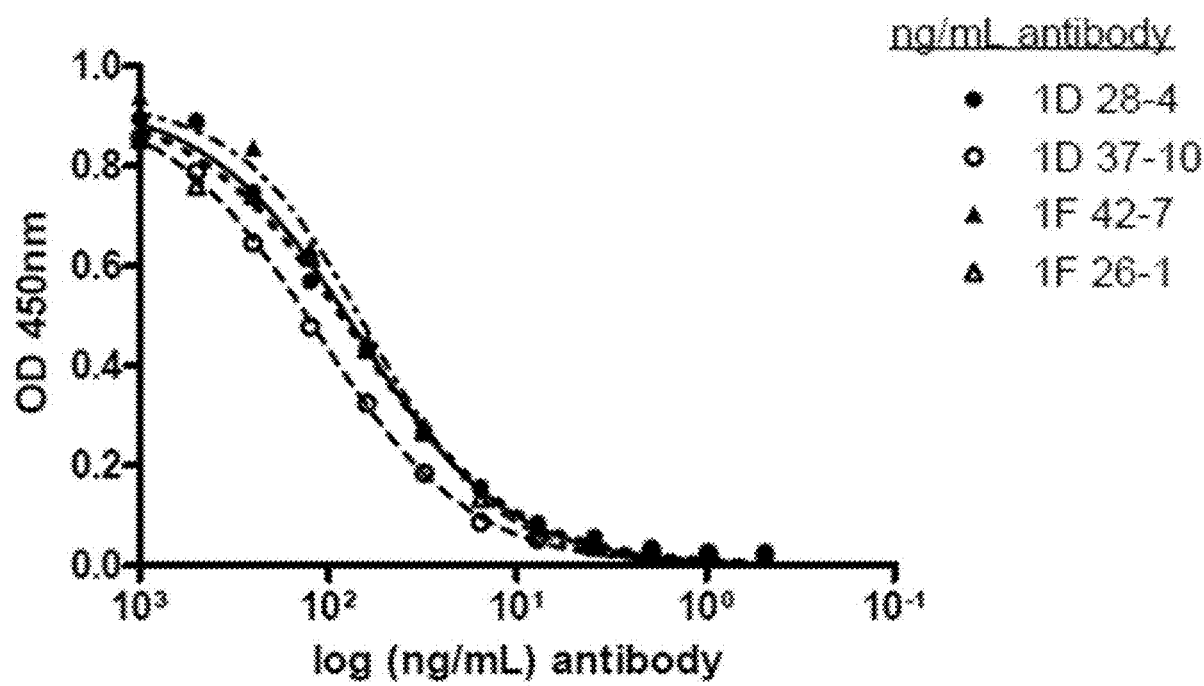
FIG. 15 depicts that the monoclonal antibodies 1D 28-4 and 1D 37-10, which were raised against the 1D peptide, bound to renalase-1 in a concentration dependent manner. The 1D peptide is present in both renalase-1 and renalase-2. The monoclonal antibodies IF 42-7 and IF 26-1, were raised against the IF peptide, which is present only in renalase-1. The IF mAbs bound to renalase-1 in a concentration-dependent manner.

In the second example, all polyclonal antibodies and selected monoclonal antibody clones bound to the peptides antigens to which they were raised. For example and as can be seen in FIG. 15 the monoclonal antibodies 1D 28-4 and 1D 37-10, which were raised against the 1D peptide, bound to renalase-1 in a concentration dependent manner. The 1D peptide is present in both renalase-1 and renalase-2. The monoclonal antibodies 1F 42-7 and 1F 26-1, were raised against the 1F peptide, which is present only in renalase-1. The 1F mAbs bound to renalase-1 in a concentration-dependent manner.

Figure 16:
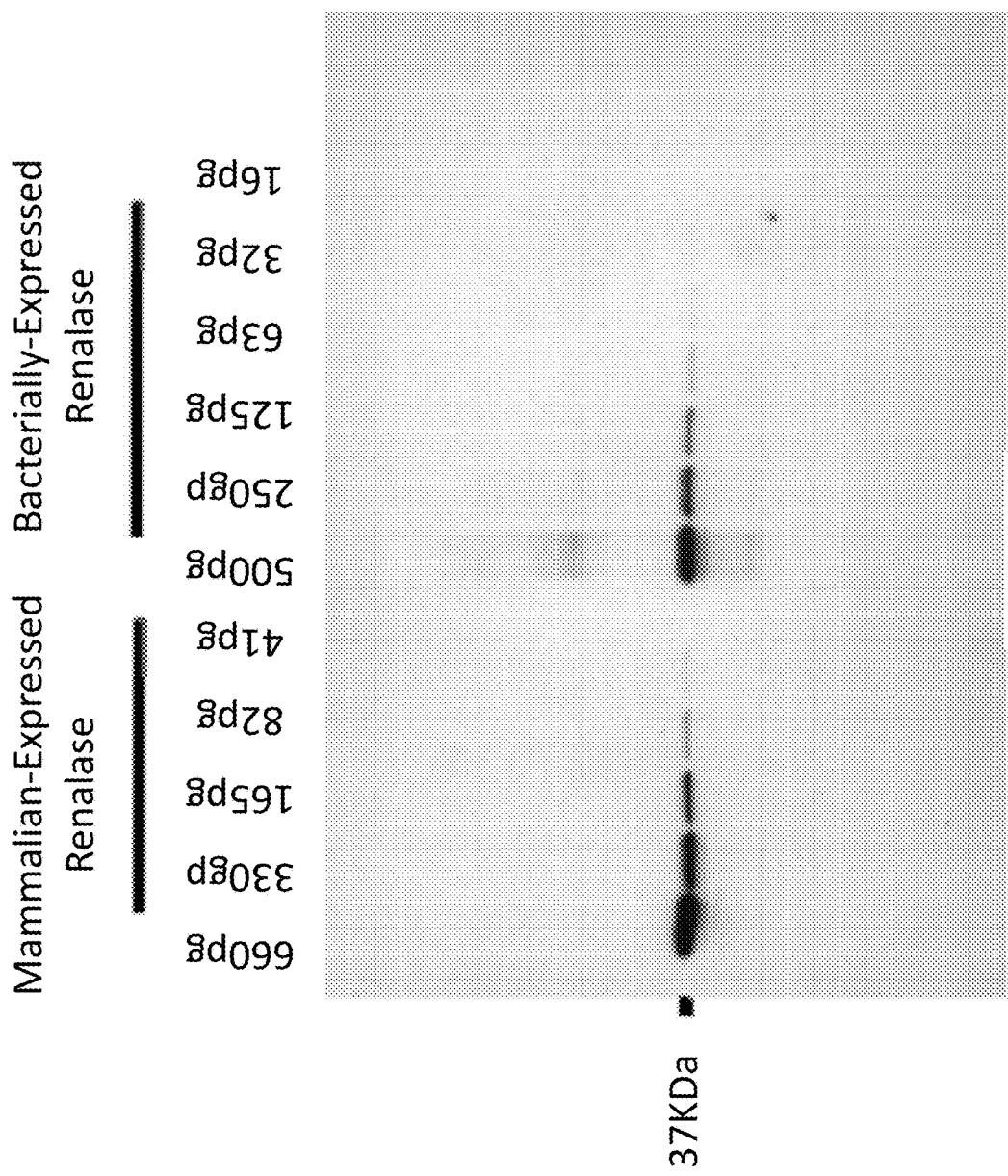
FIG. 16 depicts that to establish whether the antibodies could be used to detect renalase by Western blotting, a dilution series of recombinant renalase protein, of bacterial or mammalian origin, was run on SDS-PAGE and Western blotting was performed using the Ren1D 28-4 antibody. The recombinant protein, of either origin, was clearly identified by this method.

In a further example, to establish whether the antibodies could be used to detect renalase by Western blotting, a dilution series of recombinant renalase protein, of bacterial or mammalian origin, was run on SDS-PAGE and Western blotting was performed using the Ren1D 28-4 antibody. The recombinant protein, of either origin, was clearly identified by this method as can be seen in FIG. 16. In this way, anti-renalase antibodies specific for the full length renalase protein (SEQ ID NOs. 8 or 50 or 92 or 94) or the peptide antigens described in SEQ ID NOs. 1-7 were generated.

Antibodies are Specific for Either Renalase-1 or Renalase-2

In this example, monoclonal antibodies raised against either renalase-1 or renalase-2 specific peptides showed absolute specificity for the relevant full-length renalase isoform. Antibodies 1D-28-4 and 1D-37-10 were raised against the 1D peptide and therefore should bind to both renalase-1 and renalase-2. Antibodies 1F-42-7 and 1F-26-1 were raised against the 1F peptide (see FIG. 3 for alignment) and therefore should only be specific for renalase-1. Antibody 3A5-2 was raised against peptide 3A and therefore should be specific for renalase-2.

Bacterially-expressed renalase-1 and 2 isoforms, were diluted to 100 ng/well in PBS and bound to a 96 well microtiter plate. The plate was blocked with a solution of 8% NFDM in PBS for one hour at 33° C. The renalase proteins were probed with a dilution series of the antibodies 1D-28-4, 1D-37-10, 1F-42-7, 1F-26-1 and 3A5-2. The starting concentration of antibody was typically 1 µg/mL, with two-fold dilution steps prepared in PBS containing Tween-20 to 0.05% PBST. After one hour incubation at 33° C., the plate was rinsed three times with PBST. Antibody binding was assayed by adding HRP-conjugated anti-rabbit IgG at 50 ng/mL, 50 µL per well. The plate was incubated at room temperature for 40 minutes. After incubation, the plate was washed three times with PBST and once with PBS. The HRP substrate 3, 3', 5, 5'-tetramethylbenzidine (TMB) was added to 100 µL per well, and plate was incubated for approximately 5 minutes at room temperature. To stop the reaction, 100 µL 2 N $H_2SO_4$ was added to each well. The plate was read at 450 nm in a spectrophotometer.

Antibodies 1D-28-4, 1D-37-10, 1F-42-7 and 1F-26-1 bound renalase-1 protein in a concentration-dependent manner by ELISA assay (FIG. 15). However, when the same antibodies were used to detect recombinant renalase-2 on an ELISA plate assay, only 1D-28-4 and 1D-37-10 showed robust, concentration-dependent binding (FIG. 17). Antibody 3A5-2 was seen to bind to renalase-2 isoform in ELISA assay (FIG. 17). Thus it can be seen that antibodies raised to peptides corresponding to one or other renalase isoform show specificity for the relevant full-length proteins.

Epitope-Specific Anti-Renalase Antibodies

Figure 18:
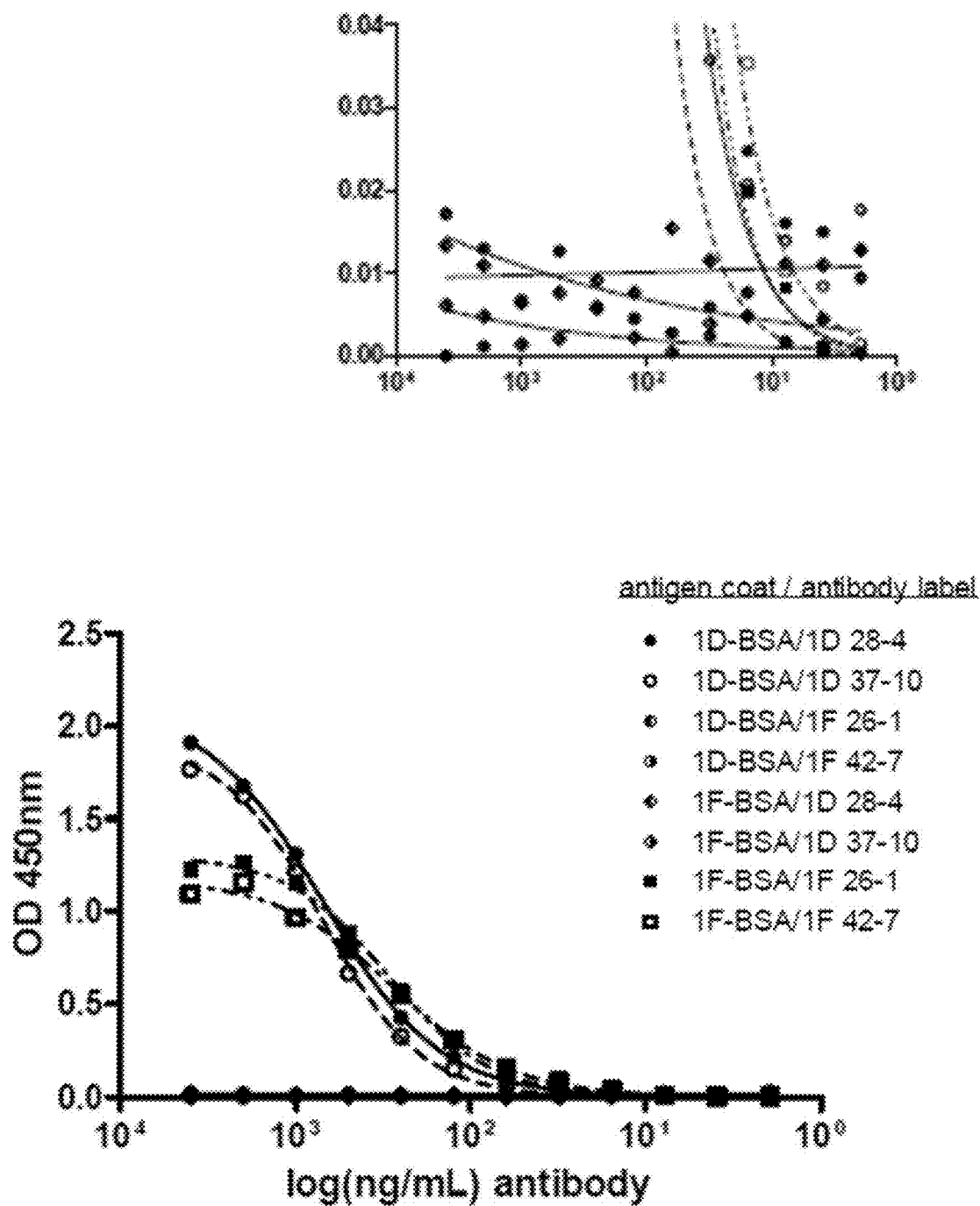
FIG. 18 depicts that the monoclonal antibodies 1D 28-4 and 1D 37-10, raised against the 1D epitope, bound to the 1D-BSA protein in a concentration dependent manner (solid circle for 1D 28-4, clear circle for 1D 37-10).

Renalase peptides used for immunization were synthesized, then conjugated to bovine serum albumin (BSA). The conjugated peptides were diluted to 100 ng/well in PBS, and bound to a 96 well microtiter plate by overnight incubation at 4° C. After blocking with NFDM, the BSA-conjugated peptides were probed with a dilution series of antibody. Binding of antibody was assayed by adding HRP-conjugated anti-rabbit IgG. The plate was read at 450 nm in a spectrophotometer after reaction of HRP with the substrate TMB. The monoclonal antibodies 1D 28-4 and 1D 37-10, raised against the 1D epitope, bound to the 1D-BSA protein in a concentration dependent manner (FIG. 18 solid circle for 1D 28-4, clear circle for 1D 37-10). However, these monoclonals demonstrated very poor binding to the 1F antigen (semi-filled diamonds for 1D 28-4, and 1D 37-10, inset). The monoclonal antibodies 1F 42-7 and 1F 26-1, raised against the 1F epitope, bound to the 1F-BSA protein in a concentration dependent manner (solid square for 1F 26-1, clear square for 1F 42-7 binding). However, the 1F mAbs demonstrated very poor binding to the 1D peptide (semi-filled circle for 1F 26-1, and 1F 42-7, inset). In a further example the same epitope-specificity was seen for antibody 3A5-2 on peptide 3A and antibody 1C-22-1 on peptide 1C. In yet a further example all of the purified polyclonal antibodies raised against peptides 1A, 1B, 1C, 1D, 1E, 1F and 3A bound specifically to the relevant BSA-peptide fusion.

Therefore, multiple examples of antibodies raised against peptide epitopes within the renalase protein showed absolute epitope specificity. The amino acid composition of both the epitopes and the monoclonal antibodies that bind them are seen and described herein.

Anti-Renalase Antibody Conjugations

The renalase-specific antibodies can be conjugated to any number of entities which would aid in the antibodies use as a detection reagent for renalase or a renalase-directed therapeutic. These conjugations can be completed without interfering with the relative epitope specificity or affinity of the antibodies. Examples of conjugates include, but are not limited to radioactive ions, colored, metallic or fluorescent labels, tags or toxins. In the present example, the anti-renalase antibodies were conjugated to the vitamin Biotin. Biotin is a small, naturally occurring vitamin that binds with extremely high affinity to proteins avidin, strepavidin and variants thereof. Conjugation is completed via an N-hydroxysuccinimide (NHS) ester linkage of the Biotin to primary amino groups on the antibodies. Excess, unconjugated biotin can be removed by dialysis.

Figure 19:
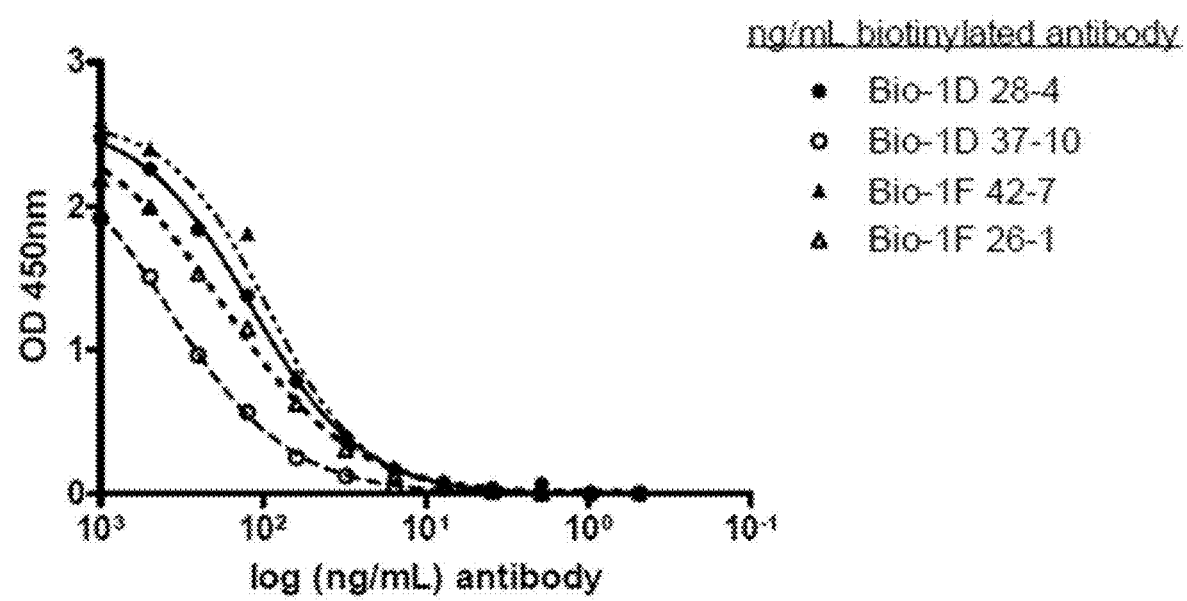
FIG. 19 depicts that the biotinylated monoclonal antibodies 1D 28-4 (solid circle), 1D 37-10 (clear circle), IF 42-7 (solid triangle), and IF 26-1 (clear triangle), bound to renalase-1 in a concentration dependent manner.

In a further example, anti-renalase antibodies conjugated in this way were seen to maintain their ability to bind to renalase protein in an ELISA assay. Bacterially-expressed renalase-1, diluted to 100 ng/well in PBS, was bound to a 96 well microtiter plate by overnight incubation at 4° C. After blocking with NFDM, the renalase protein was probed with a dilution series of biotinylated antibody, starting at a concentration of 1 µg/mL. Presence of bound biotinylated antibody was assayed by adding HRP-conjugated NeutrAvidin. The plate was read at 450 nm in a spectrophotometer after reaction of HRP with the substrate TMB. The biotinylated monoclonal antibodies 1D 28-4 (FIG. 19 solid circle), 1D 37-10 (clear circle), IF 42-7 (solid triangle), and IF 26-1 (clear triangle), bound to renalase-1 in a concentration dependent manner.

Multiple Antibodies Can Compete for Binding to the Same Epitope on Renalase

In this example, various combinations of both monoclonal and polyclonal anti-renalase antibodies were shown to compete with each other for binding to renalase. This demonstrates overlapping epitopes of multiple antibodies. In a further example a polyclonal antibody was seen to compete two different monoclonal antibodies demonstrating the multiple epitope specificities of this polyclonal. Bacterially-expressed renalase-1, diluted to 100ng/well in PBS, was bound to a 96 well microtiter plate by overnight incubation at 4° C. After blocking, the protein was probed with a dilution series of an unconjugated antibody, typically starting at 1 µg/mL, mixed with a different biotinylated antibody. The concentration of the biotinylated antibody was held constant at 125 ng/well. Both antibodies were mixed together in PBST and applied to the pre-blocked renalase plate as one addition of 50 µL per well. After one hour incubation at 33° C., binding of the biotinylated antibody to renalase was assayed by adding HRP-conjugated Neutravidin (HRP-NA) at 0.4 ng/mL, 50 µL per well. The HRP substrate TMB was added for visualization of bound biotinylated antibody. The plate was then read at 450 nm in a spectrophotometer.

Figure 20A:
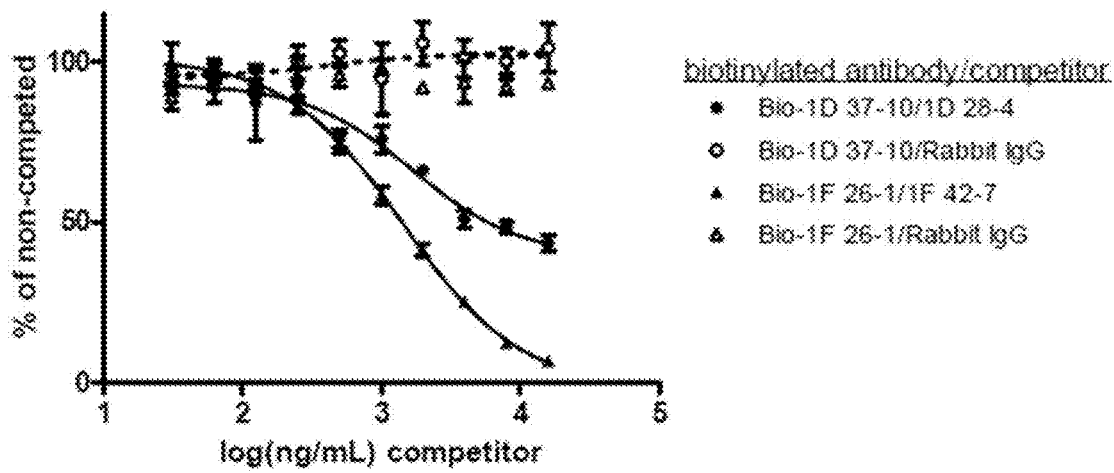
FIG. 20A and FIG. 20B, depicts that overlapping epitopes can be detected by competition ELISA.

The specificity of anti-renalase antibodies was shown by the decrease in signal when a biotinylated antibody is incubated with unconjugated antibodies which share the same epitope. One example is shown in FIG. 20A by the monoclonal antibodies raised to the 1D peptide. Biotinylated 1D 37-10 was competed by unconjugated 1D 28-4 (solid circle, FIG. 20A). Analogously, the antibodies raised against the IF peptide also competed with one another: biotinylated IF 26-1 was competed by unconjugated IF 42-7 (solid triangle, FIG. 20A). The signal from the biotinylated monoclonal antibodies did not decrease when it was incubated with an unconjugated antibody from an unimmunized rabbit (clear circle and triangle, FIG. 20A).

Figure 20B:
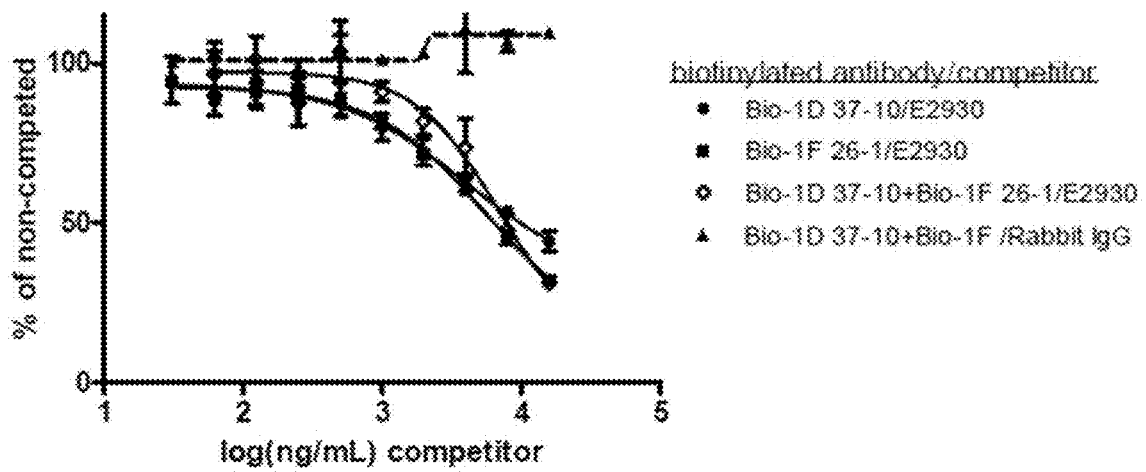

In a further example, and as can be seen in FIG. 20B, the polyclonal antibody E2930, raised against full-length renalase-1, was shown to compete with each of the biotinylated monoclonal antibodies 1D 37-10, 1F 26-1, as well a mixture of the two biotinylated mAbs (solid circle, solid square, and clear diamond, FIG. 20B). Again, a mixture of the two biotinylated antibodies was not competed by unconjugated antibody from an unimmunized rabbit (solid triangle, FIG. 20B). The competition seen with the polyclonal antibody E2930 against the two biotinylated monoclonal antibodies suggests that this polyclonal antibody binds to multiple epitopes on the renalase polypeptide.

Antibodies Bind to Renalase with High Affinity and Different Binding Kinetics

Figure 21:
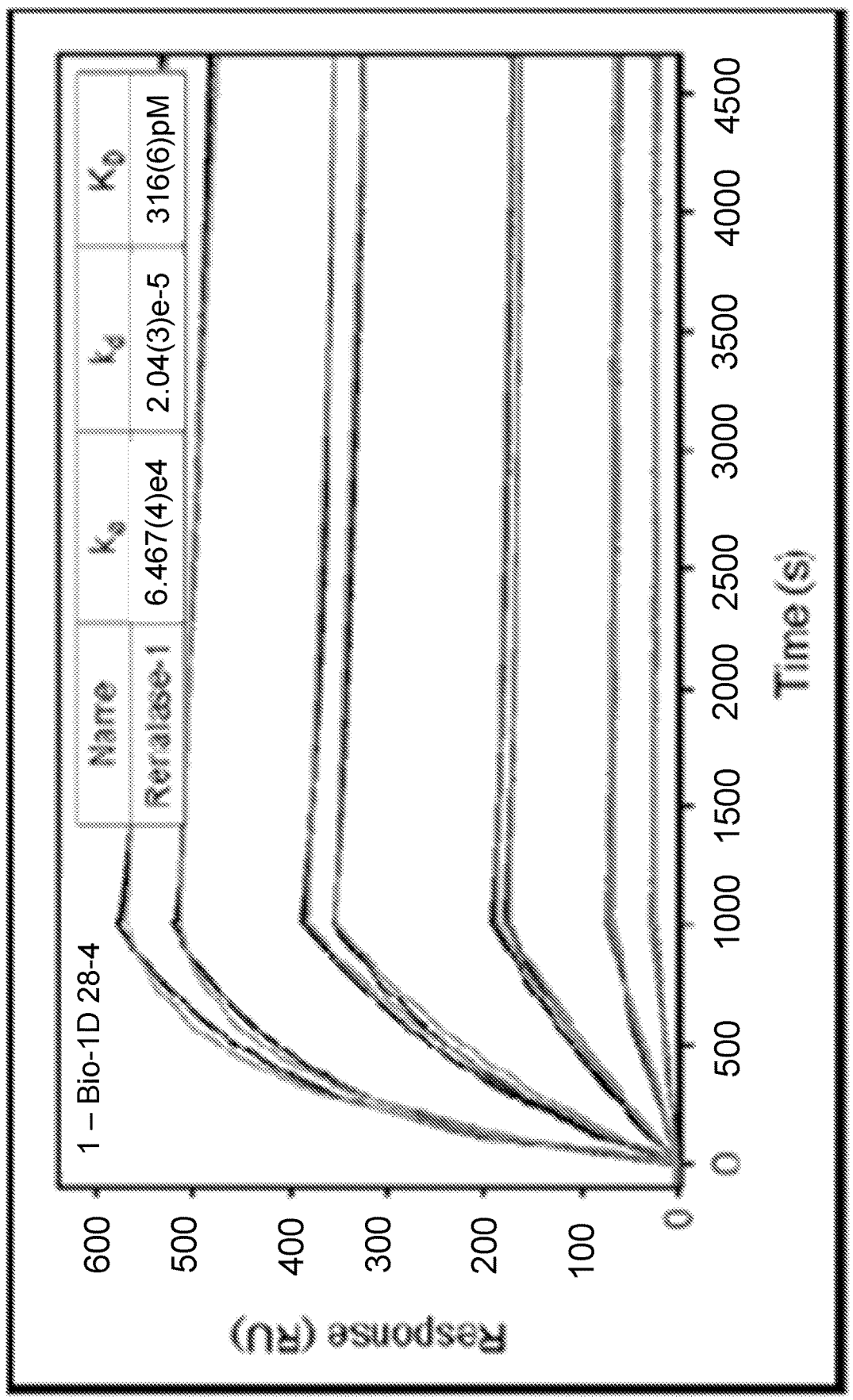
FIG. 21 depicts that the antibodies 1D-28-4, 1F-42-7, 1D-37-10 and 1F-26-1 all bound renalase with high affinity—values ranging from 2.67 nM to 0.316 nM $K_D$. A wide range of association and dissociation rates were seen between the antibodies demonstrating different attributes of the different antibody compositions.
Figure 21:
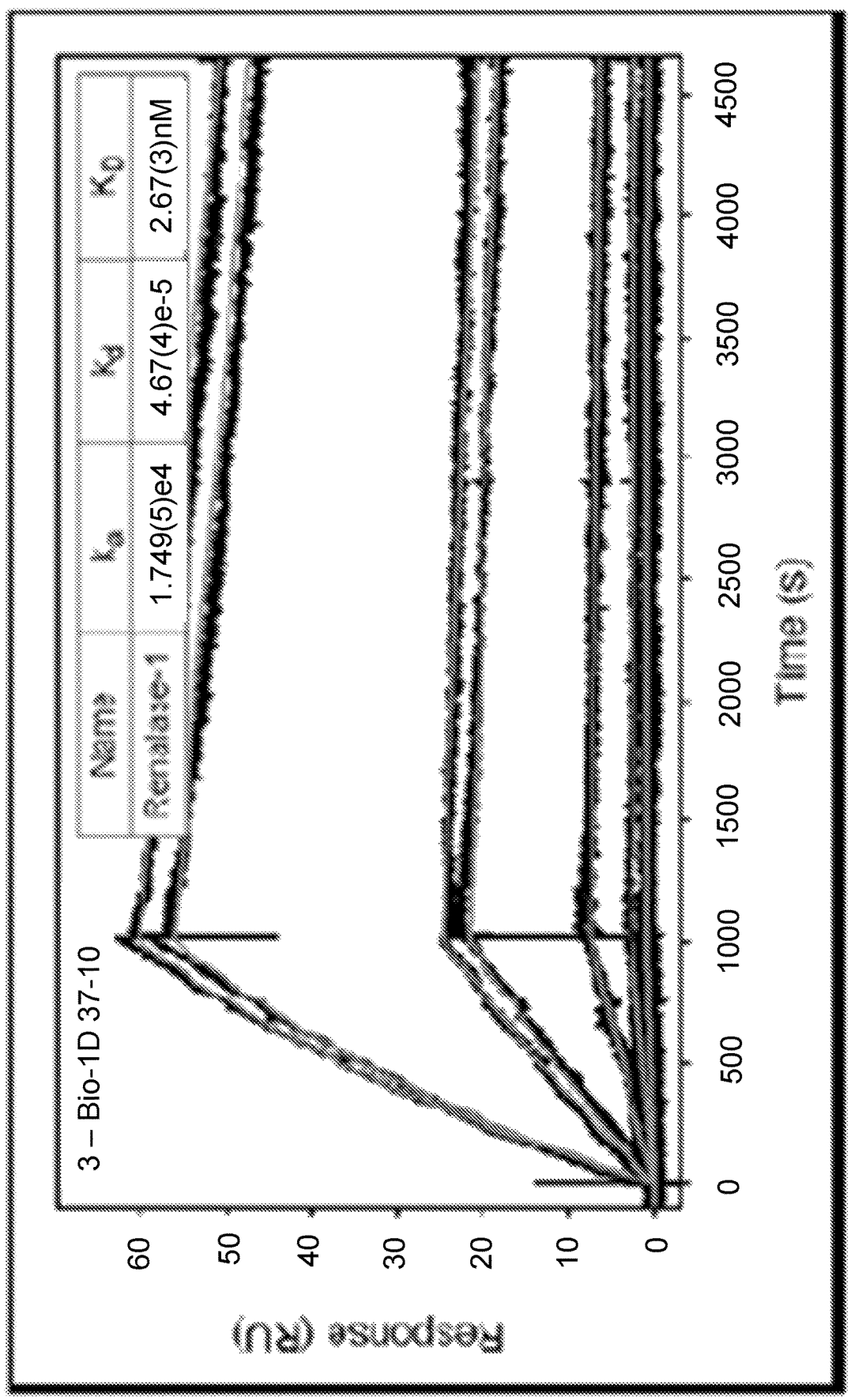
Figure 21:
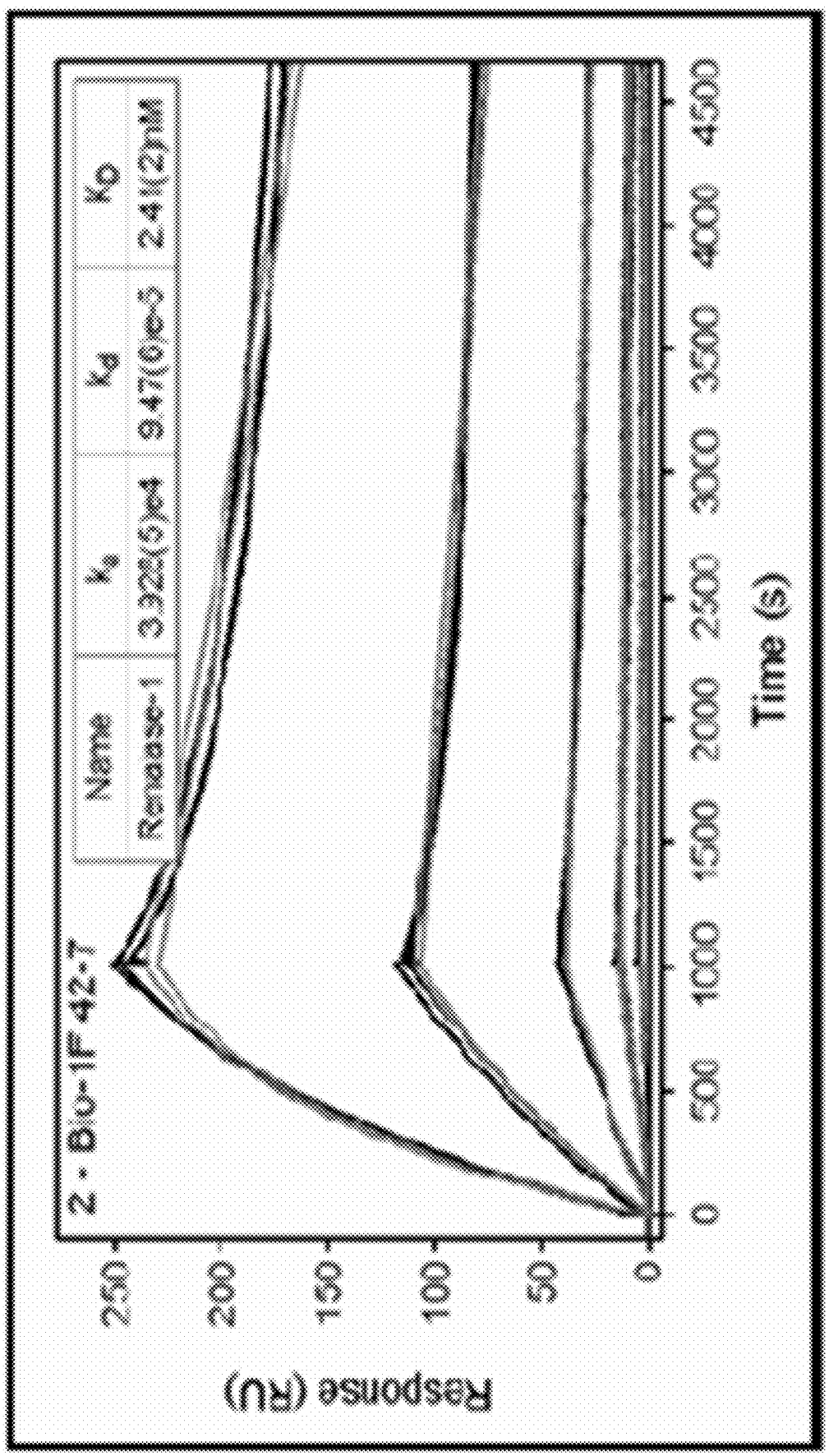
Figure 21:
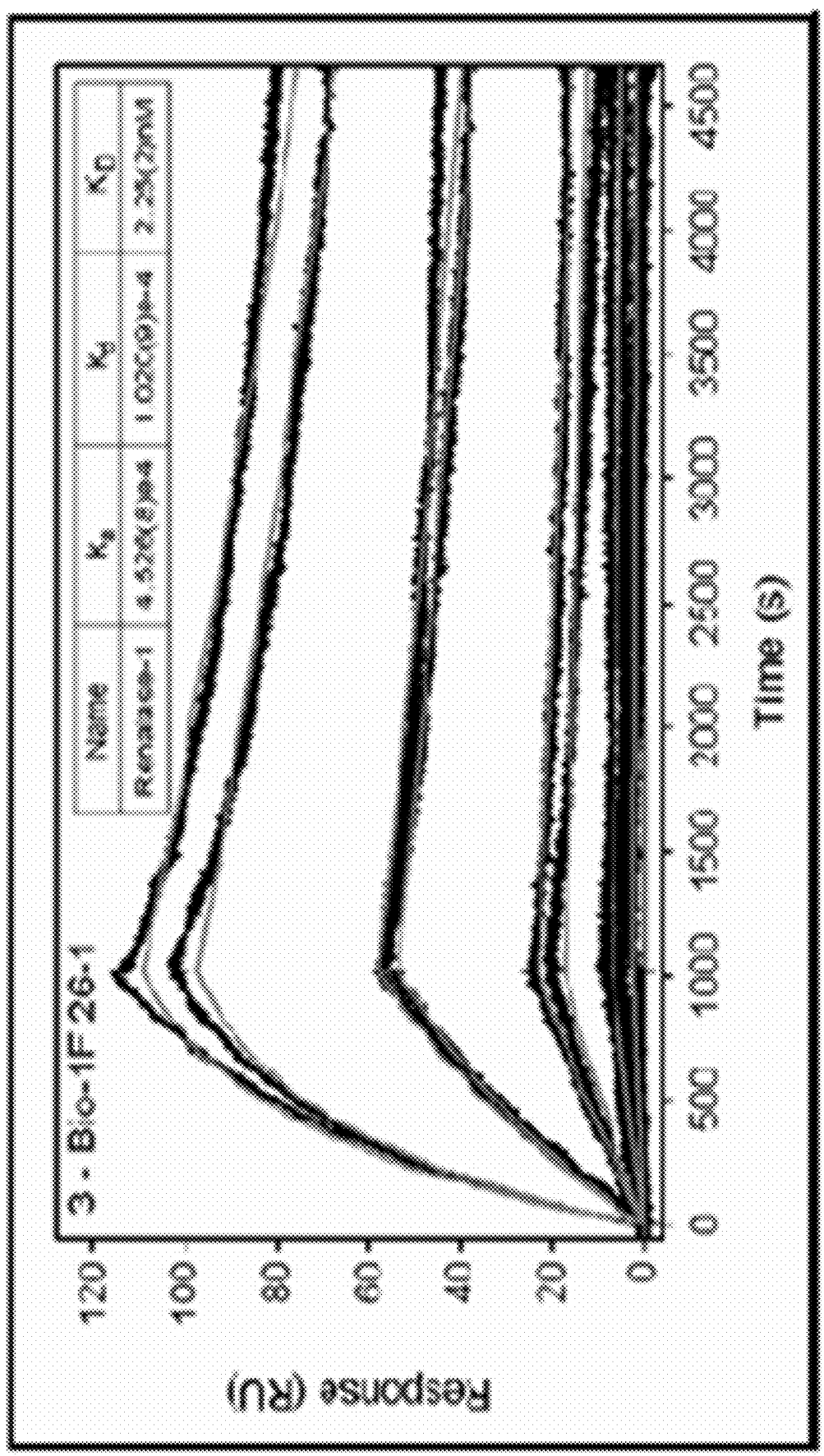

If an antibody is to be used for the detection of an endogenous protein it must display high affinity for the target. To date no binding kinetics have been described for anti-renalase antibodies. In the present example, multiple anti-renalase antibodies were demonstrated to have low or sub-nanomolar affinities for full-length renalase in a solution binding assay. Purified anti-renalase antibodies were biotinylated and bound to a Streptavidin CMS sensor chip for a Biacore T100 instrument. Pure recombinant renalase-1 was injected over the surface of the chip. Binding studies were performed at 25° C. using 25 mM Tris pH 8, 150 mM NaCl, 1 mM EDTA, 10% glycerol, 0.005% Tween-20 and 0.1 mg/mL BSA as the running buffer. The binding kinetics of the renalase to the immobilized antibodies can be measured in this way. As can be seen FIG. 21 and summarized in FIG. 22, the antibodies 1D-28-4, 1F-42-7, 1D-37-10 and 1F-26-1 all bound renalase with high affinity—values ranging from 2.67 nM to 0.316 nM KD. A wide range of association and dissociation rates were seen between the antibodies demonstrating different attributes of the different antibody compositions.

Anti-RNLS Therapy with Monoclonal Antibody m28-RNLS Markedly Inhibits Melanoma Tumor Growth in a Xenograft Mouse Model (Hollander L et al., 2016, Cancer Research, 76(13):3884-94)

Figure 23:
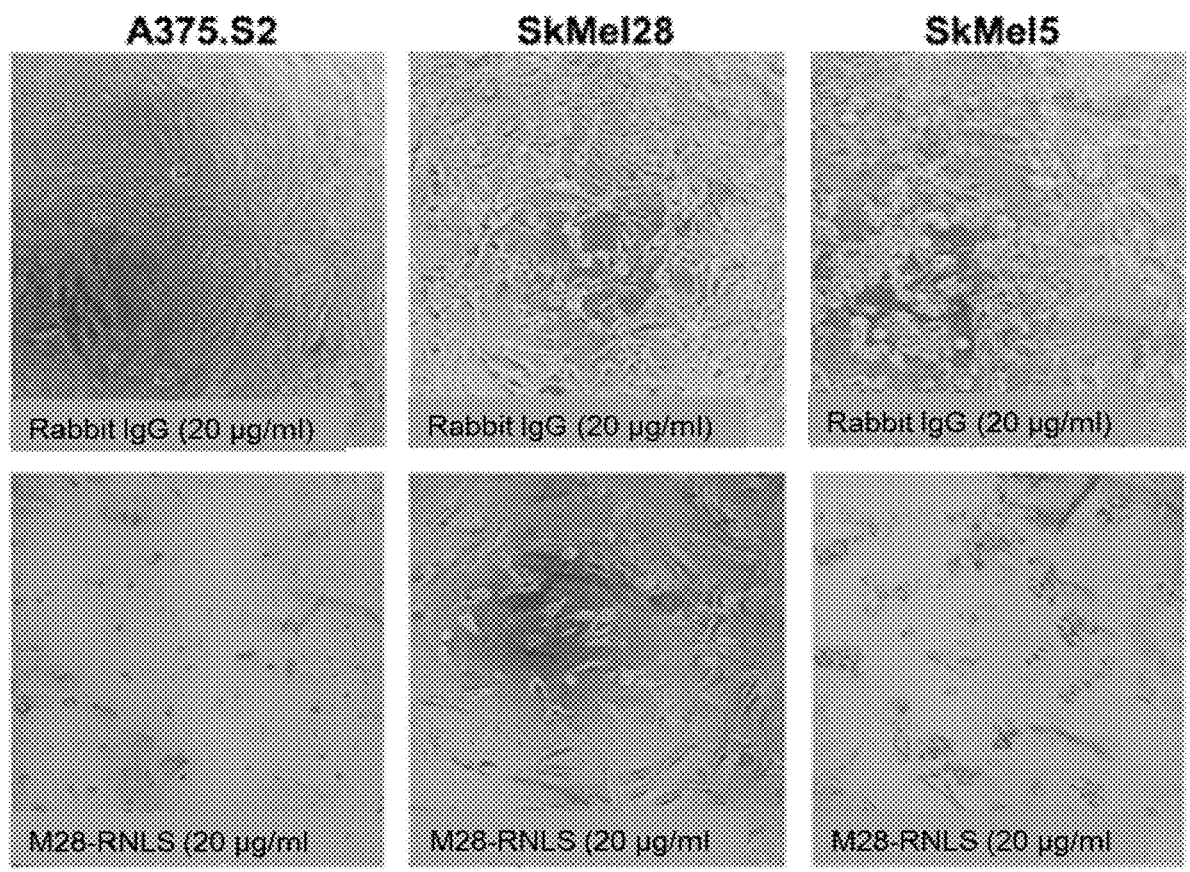
FIG. 23 depicts that two monoclonal antibodies generated against RNLS, [clones #28-4 (m28-RNLS), 37-10 (m37-RNLS)] decreased the viability of all (total of 5) melanoma cell lines tested, and representative examples are shown.

Two monoclonal antibodies generated against RNLS, [clones #28-4 (m28-RNLS), 37-10 (m37-RNLS)] decreased the viability of all (total of 5) melanoma cell lines tested, and representative examples are shown in FIG. 23. m28-RNLS demonstrated increasing levels of cytotoxicity in correlation with increasing treatment concentrations (p<0.05, FIG. 24).

Figure 25:
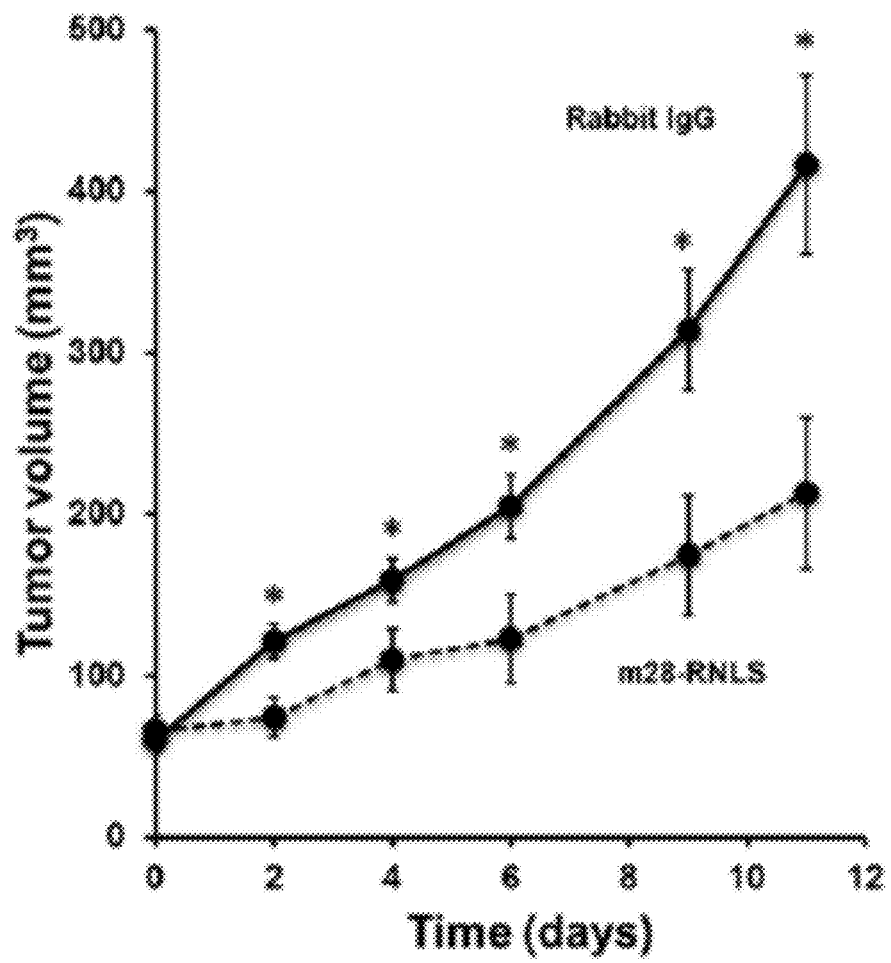
FIG. 25 depicts tumor volume as a function of time between control (rabbit IgG) and anti-renalase (m28-RNLS) treatment groups. For in vivo studies, A375.S2 (human melanoma) cells were injected subcutaneously into athymic nude mice to generate tumors. Once the tumors reached a volume of ~50 mm$^3$, the animals were then treated with either control rabbit IgG or a RNLS neutralizing monoclonal antibody, m28-RNLS. As overall animal health and activity was maintained throughout the study, the antibody treatment did not appear to be toxic. Tumor size was measured every other day, and treatment with m28-RNLS decreased tumor volume at all points tested ($p<0.05$).
Figure 26:
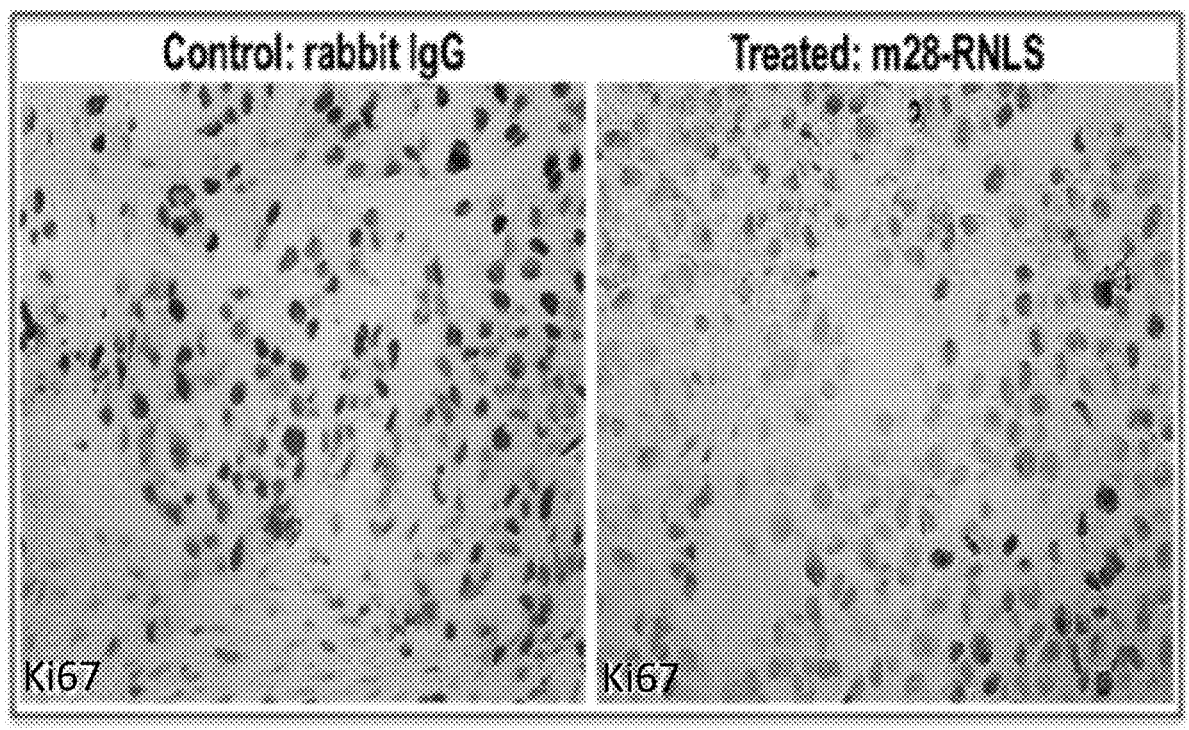
FIG. 26 depicts that IHC staining of sections from the xenografted tumors with the cellular proliferation marker Ki67 revealed a significant decrease in cellular proliferation within the tumors treated with the anti-RNLS antibody versus to those treated with rabbit IgG: of 35.1±2.3 positive cells/high power field in the control group vs. 13.4±3.0 in the RNLS Ab treated group, n=14, p=0.0004.
Figure 27:
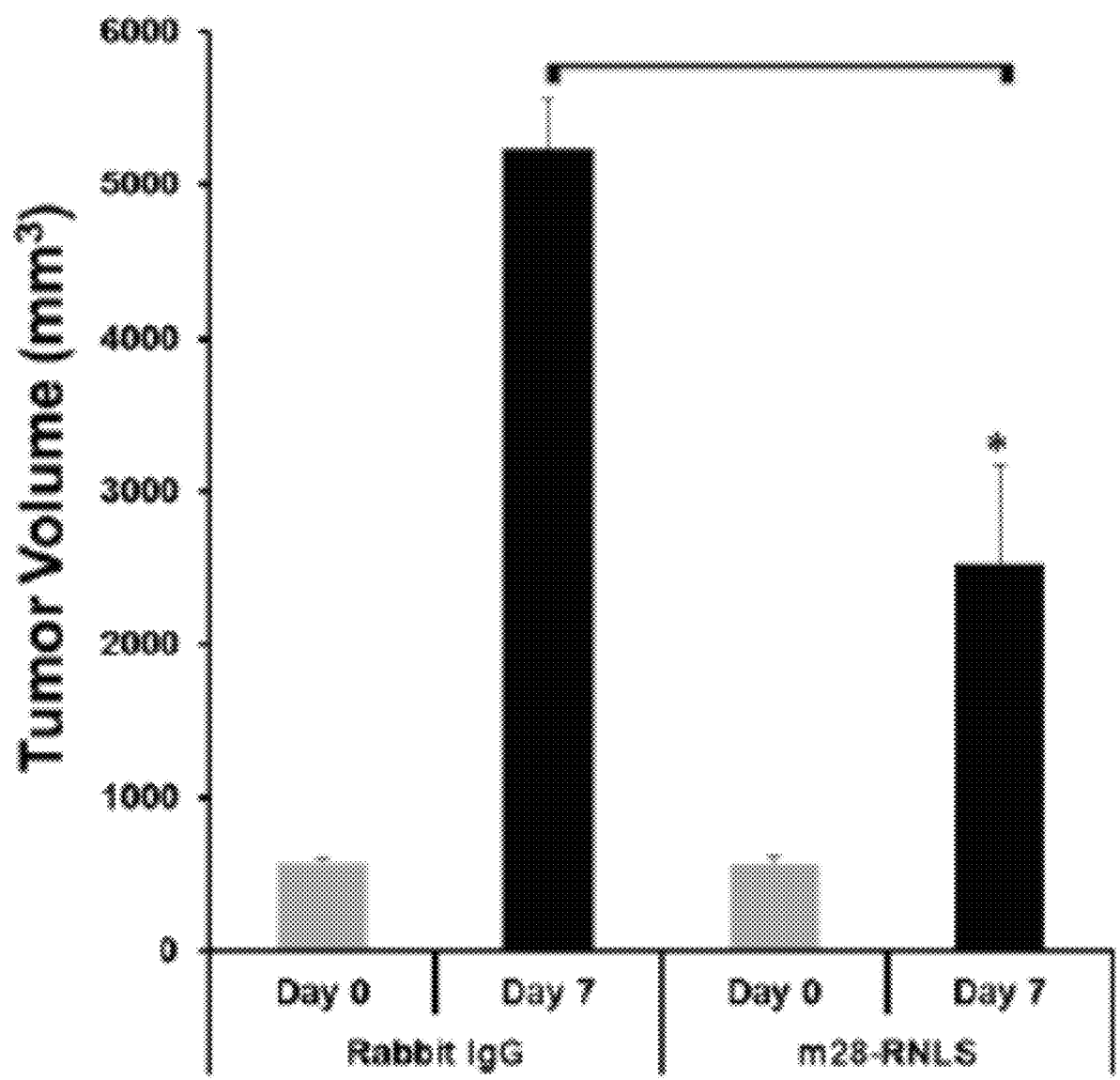
FIG. 27 depicts that m28-RNLS administration caused a significant reduction in tumor volume compared to rabbit IgG.

For in vivo studies, A375.S2 (human melanoma) cells were injected subcutaneously into athymic nude mice to generate tumors. Once the tumors reached a volume of ~50 mm$^3$, the animals were then treated with either control rabbit IgG or a RNLS neutralizing monoclonal antibody, m28-RNLS. As overall animal health and activity was maintained throughout the study, the antibody treatment did not appear to be toxic. Tumor size was measured every other day, and treatment with m28-RNLS decreased tumor volume at all points tested (p<0.05, FIG. 25). The animals were sacrificed at day 11 due to overall tumor size and ulceration in some animals. IHC staining of sections from the xenografted tumors with the cellular proliferation marker Ki67 revealed a significant decrease in cellular proliferation within the tumors treated with the anti-RNLS antibody versus to those treated with rabbit IgG: of 35.1±2.3 positive cells/high power field in the control group vs. 13.4±3.0 in the RNLS Ab treated group, n=14, p=0.0004 (FIG. 26). To test the efficacy of anti-RNLS therapy in immunocompetent, B16f10 cells (mouse melanoma line) were subcutaneously into C57BL/6 mice. Once the tumors reached a volume of ~500 mm$^3$, the animals were treated with either control rabbit IgG or a RNLS neutralizing monoclonal antibody, m28-RNLS and sacrificed at day 7 due to the very large tumor burden of the control group. As depicted in FIG. 27, m28-RNLS administration caused a significant reduction in tumor volume compared to rabbit IgG.

Anti-RNLS Therapy with Monoclonal Antibody m28-RNLS Markedly Inhibits Pancreatic Adenocarcinoma Tumor Growth in a Xenograft Mouse Model (Guo X et al., 2016, Scientific Reports, 6:22996)

Figure 28:
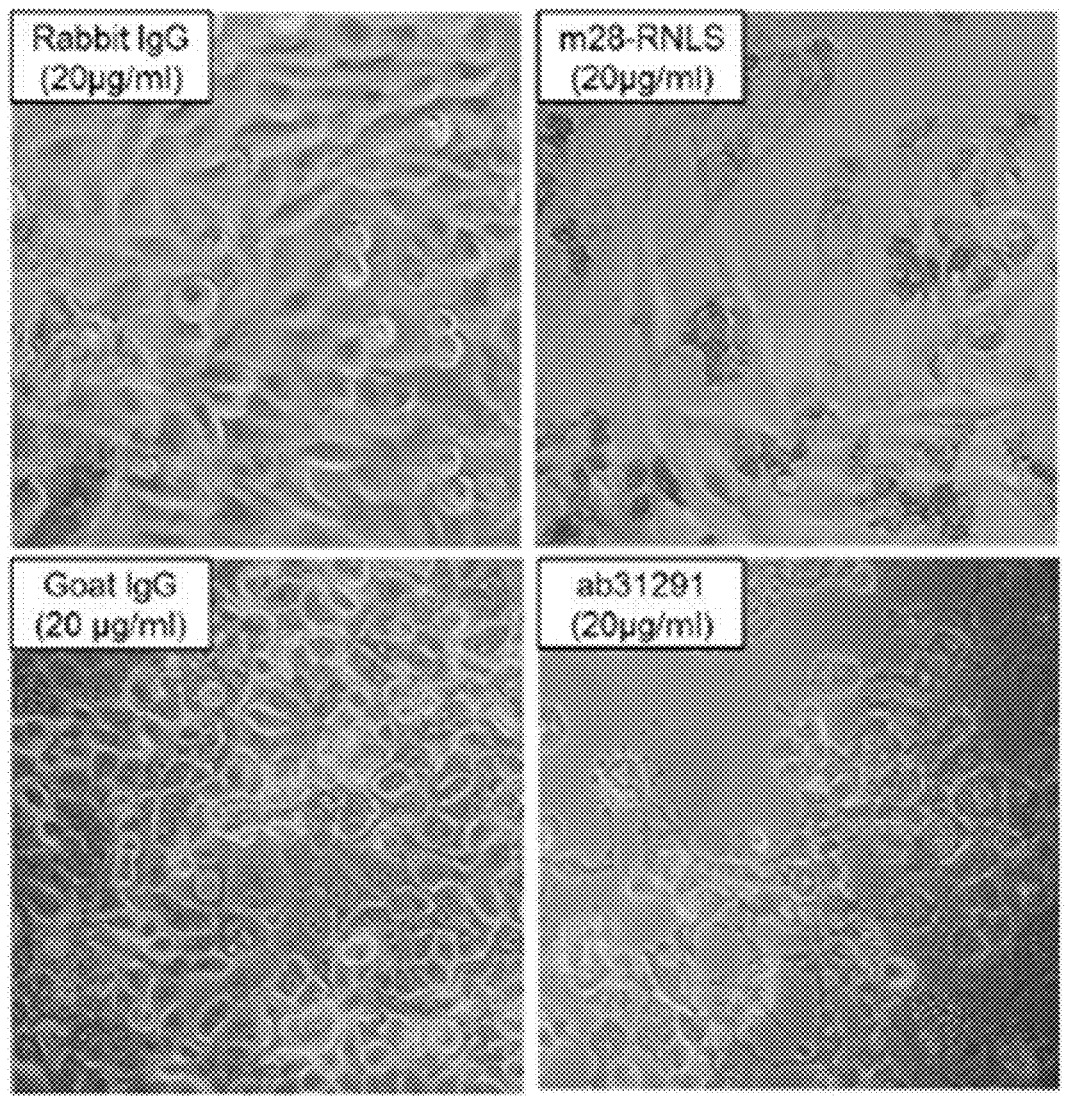
FIG. 28 depicts that the inhibitory effects of m28-RNLS, m37-RNLS, and of a commercially available polyclonal (against a partial sequence of RP-220) on human pancreatic adenocarcinoma cells growth.
Figure 29:
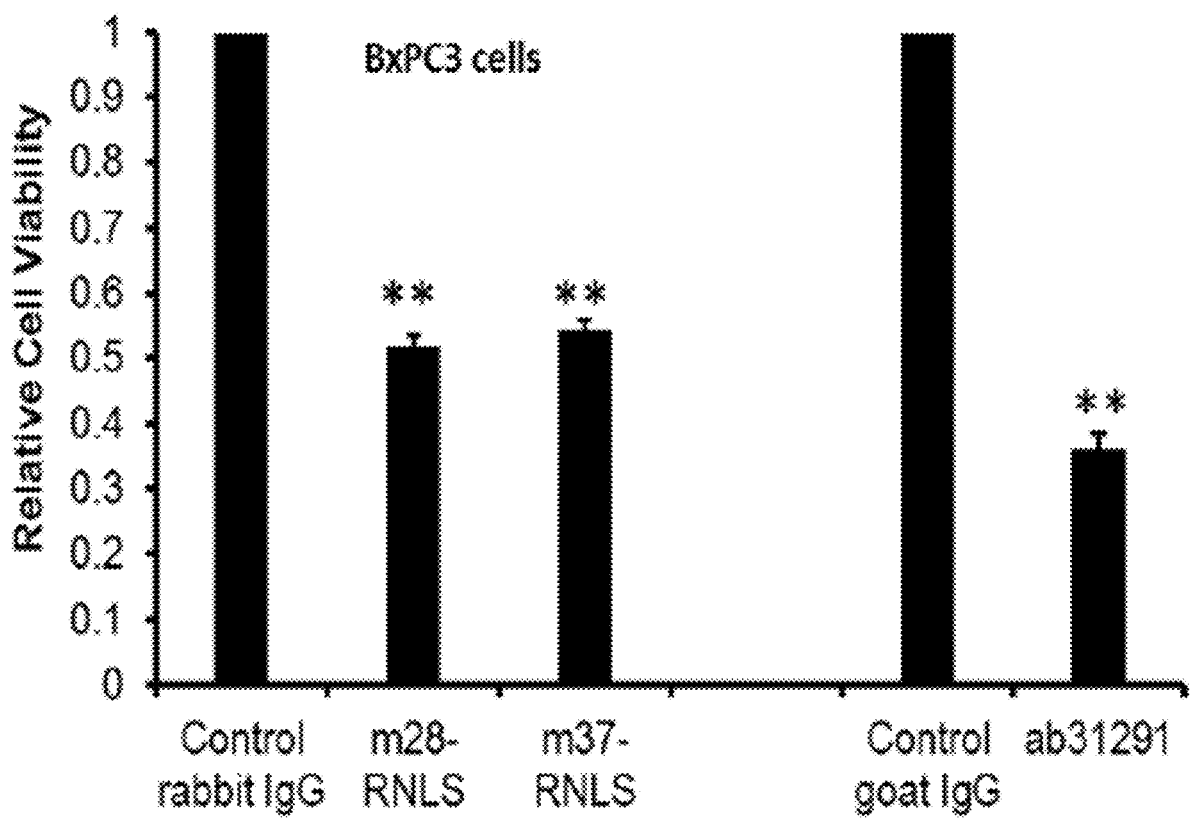
FIG. 29 depicts that the inhibitory effects of m28-RNLS, m37-RNLS, and of a commercially available polyclonal (against a partial sequence of RP-220) on human pancreatic adenocarcinoma cells growth.
Figure 30:
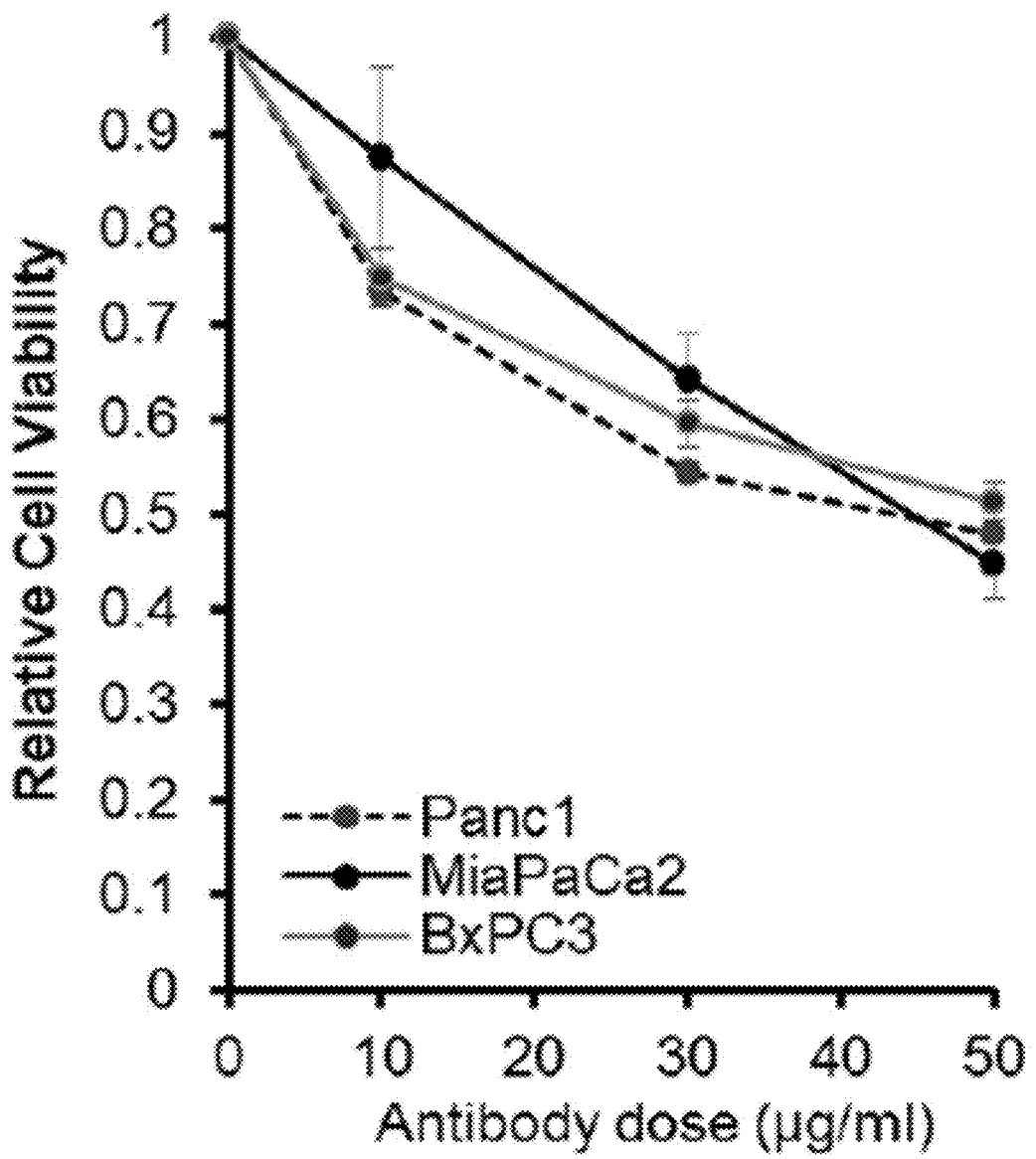
FIG. 30 depicts that the inhibitory effects of m28-RNLS, m37-RNLS, and of a commercially available polyclonal (against a partial sequence of RP-220) on human pancreatic adenocarcinoma cells growth.

From a panel of monoclonal antibodies in rabbit against RP-220, two clones, m28-RNLS, and m37-RNLS, were selected based on their high binding affinity (KD of 0.316 and 2.67 nM respectively). The inhibitory effects of m28-RNLS, m37-RNLS, and of a commercially available polyclonal (against a partial sequence of RP-220) on human pancreatic adenocarcinoma cells growth are shown by the representative examples depicted in FIG. 28, FIG. 29, and FIG. 30.

Figure 31:
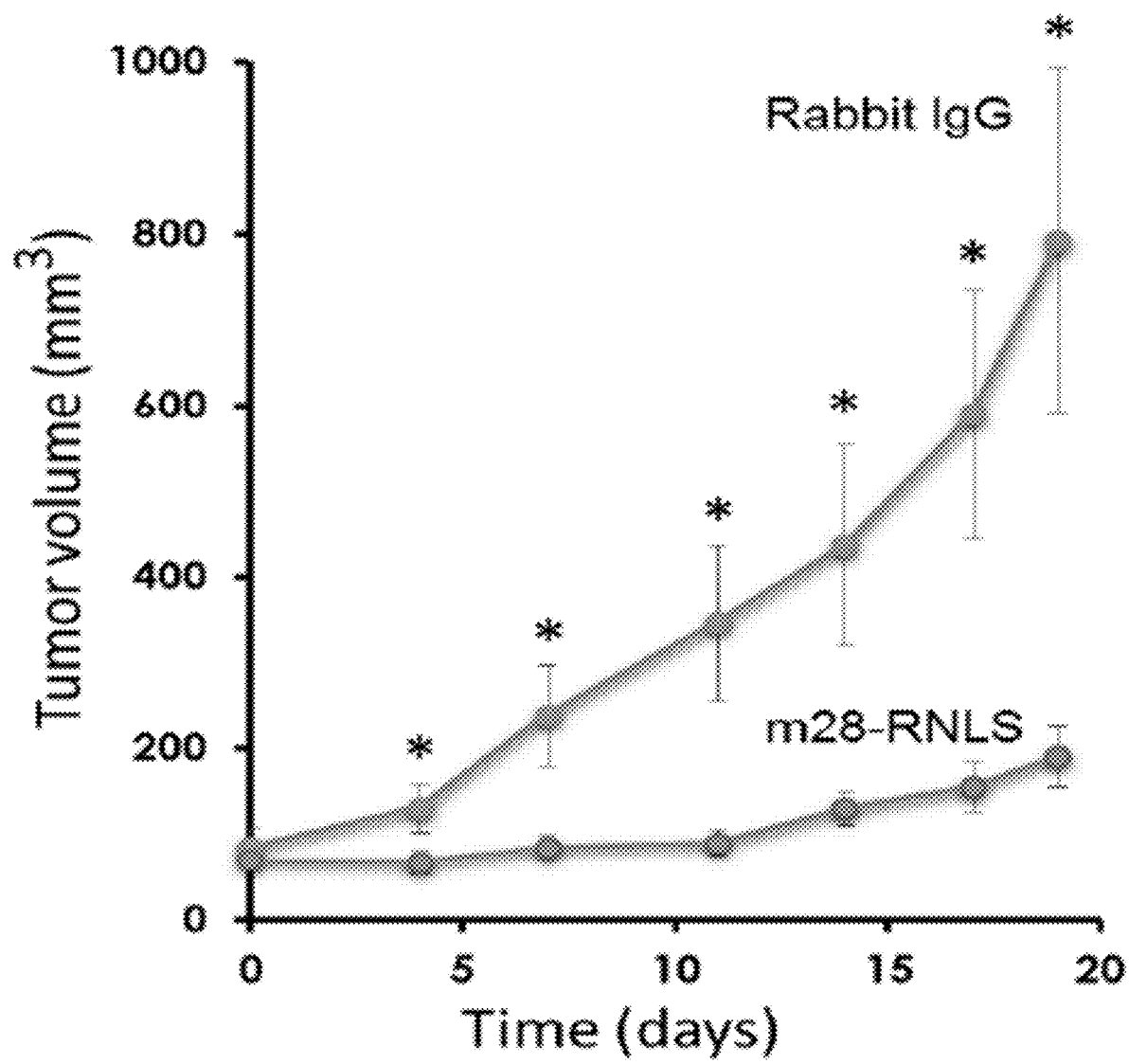
FIG. 31 depicts that compared to rabbit IgG, m28-RNLS treatment caused a significant decrease in tumor volume.

To evaluate the therapeutic potential of inhibitory antibodies, BxPC3 cells were subcutaneously injected into athymic nude mice, which were treated with either control rabbit IgG or m28-RNLS, and tumor volume was measured for up to 3 weeks. As shown in FIG. 31, compared to rabbit IgG, m28-RNLS treatment caused a significant decrease in tumor volume.

Anti-RNLS Therapy with m28-RNLS Humanized Variant Inhibits Tumor Growth

Melanoma (human: SK-MEL-28, mouse: YUMM1.7) and pancreatic adenocarcinoma (human: BxPC3) cells were seeded in 6-well culture plates at a density of 5×10$^4$ cells/well. Cellular proliferation and viability rates were determined using the Trypan blue assay. The cells were washed twice with PBS, trypsinized, and stained with 0.5% trypan blue dye. Using the Bio-Rad TC10 automated cell counter (Hercules, CA, USA), the total number of cells, total number of live cells, and the percentage of live cells in each sample was assessed. The recorded numbers were used to determine the proliferation and viability rates.

Figure 32:
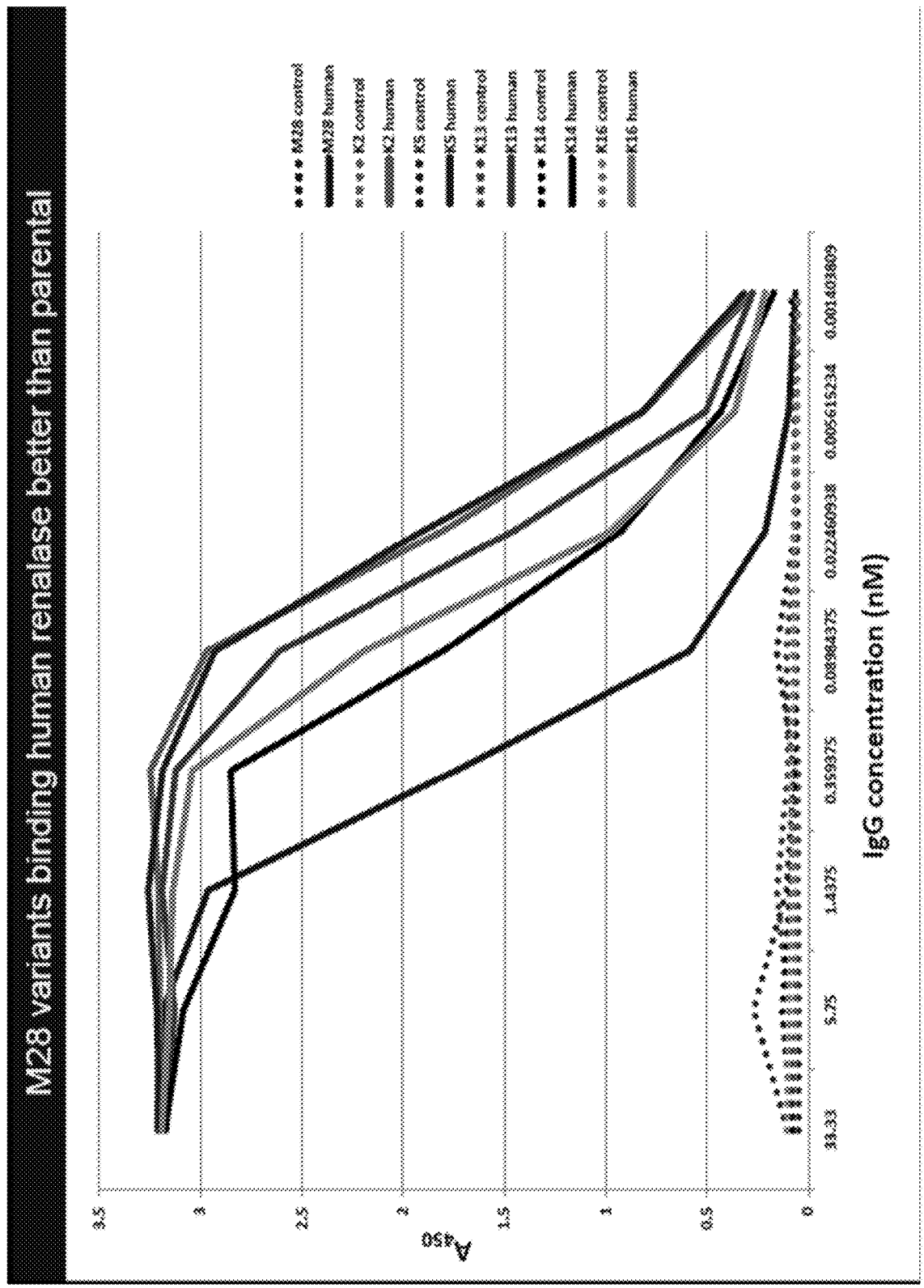
FIG. 32 depicts that five humanized m28 variants (m28-K2, m2-K5, m28-K13, m28-K14 and m28-K16, Table 2) showed increased binding to both human and mouse RNLS.
Figure 33:
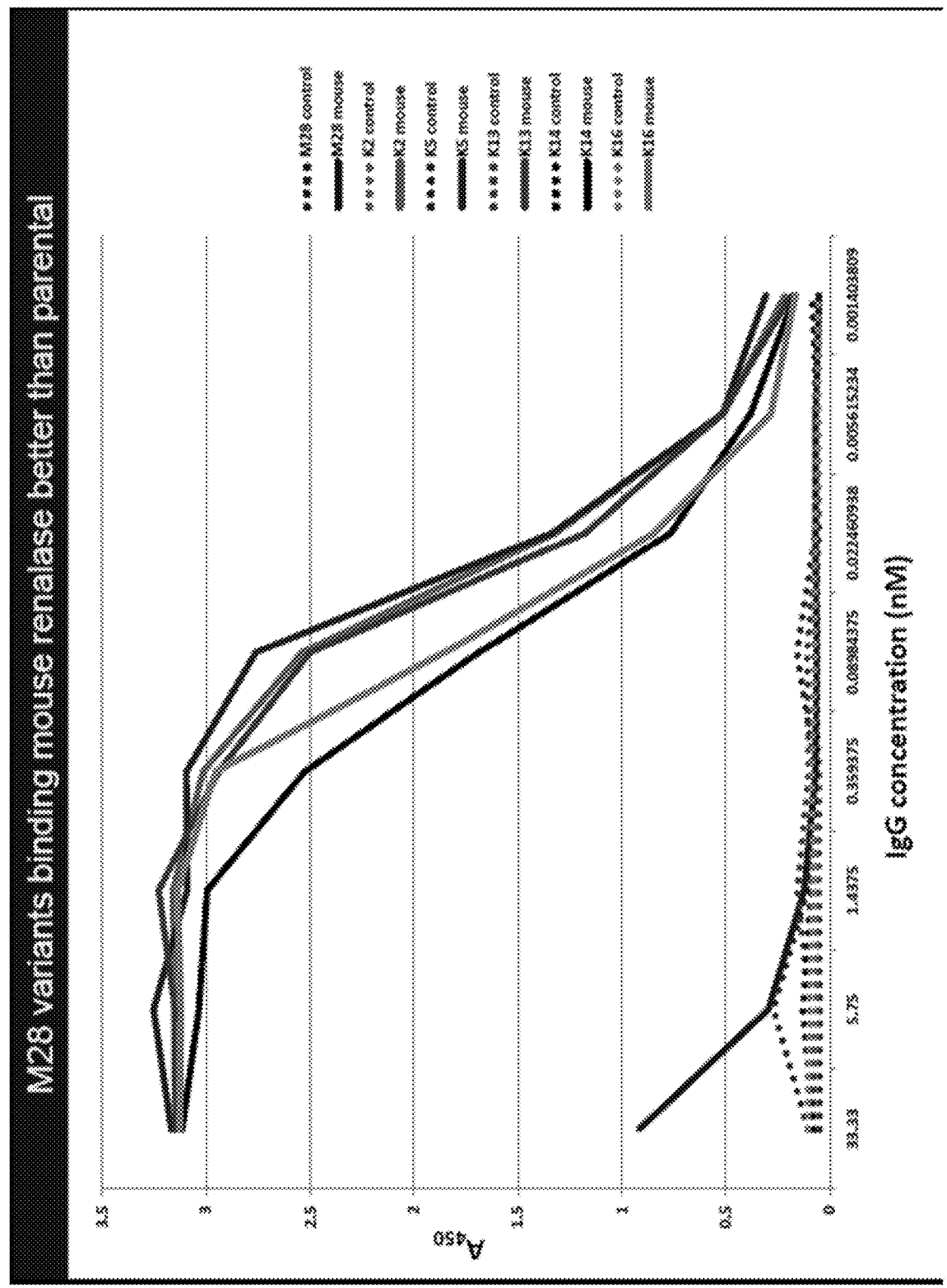
FIG. 33 depicts that five humanized m28 variants (m28-K2, m2-K5, m28-K13, m28-K14 and m28-K16, Table 2) showed increased binding to both human and mouse RNLS.
Figure 34:
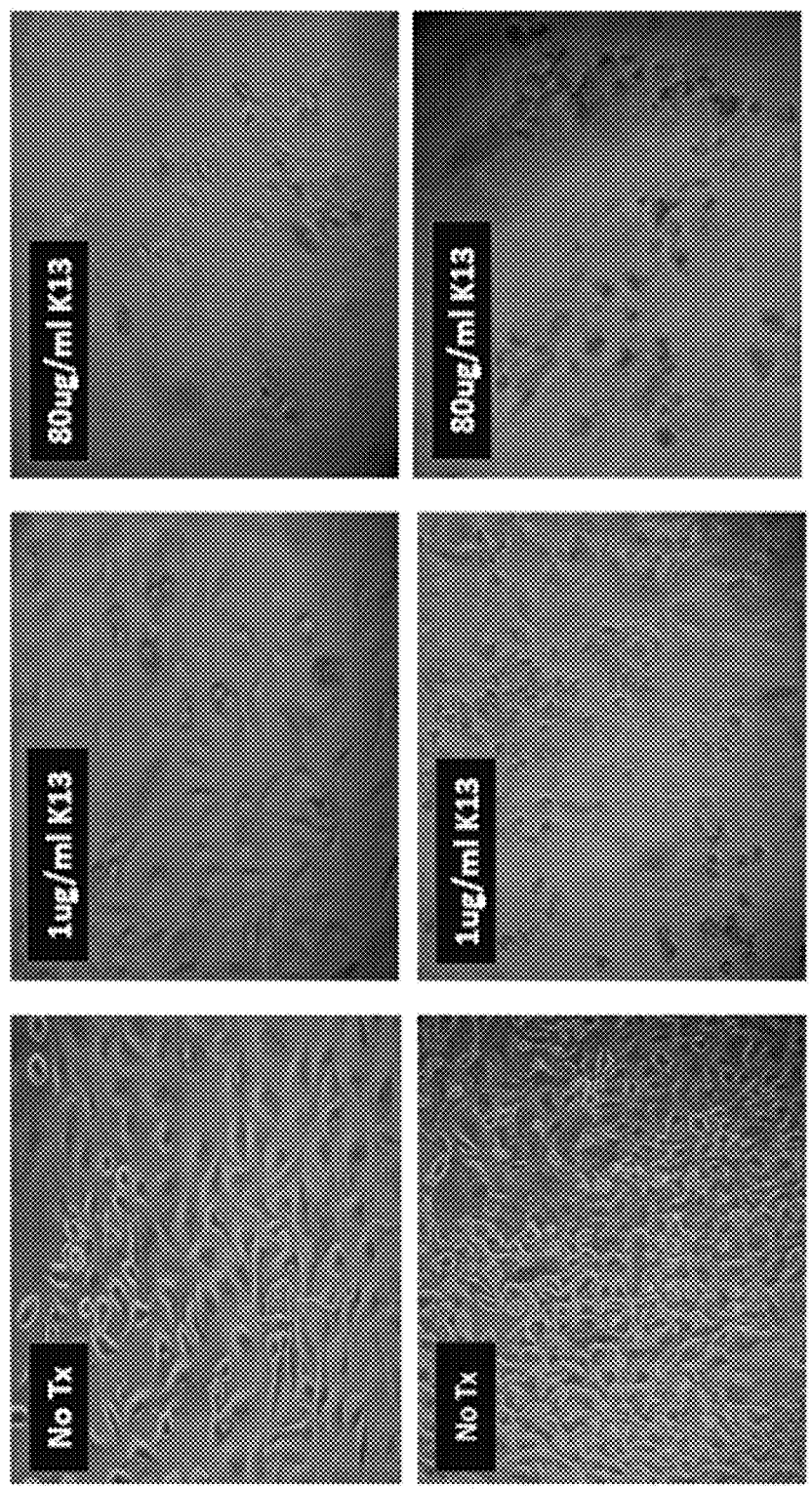
FIG. 34 depicts that five humanized m28 variants (m28-K2, m2-K5, m28-K13, m28-K14 and m28-K16, Table 2) also decreased the viability of human cell lines of melanoma (SK-MEL-28) and pancreatic adenocarcinoma (BxPC3), (representative examples shown), indicating potential therapeutic utility of m28 variants in human cancer.
Figure 35:
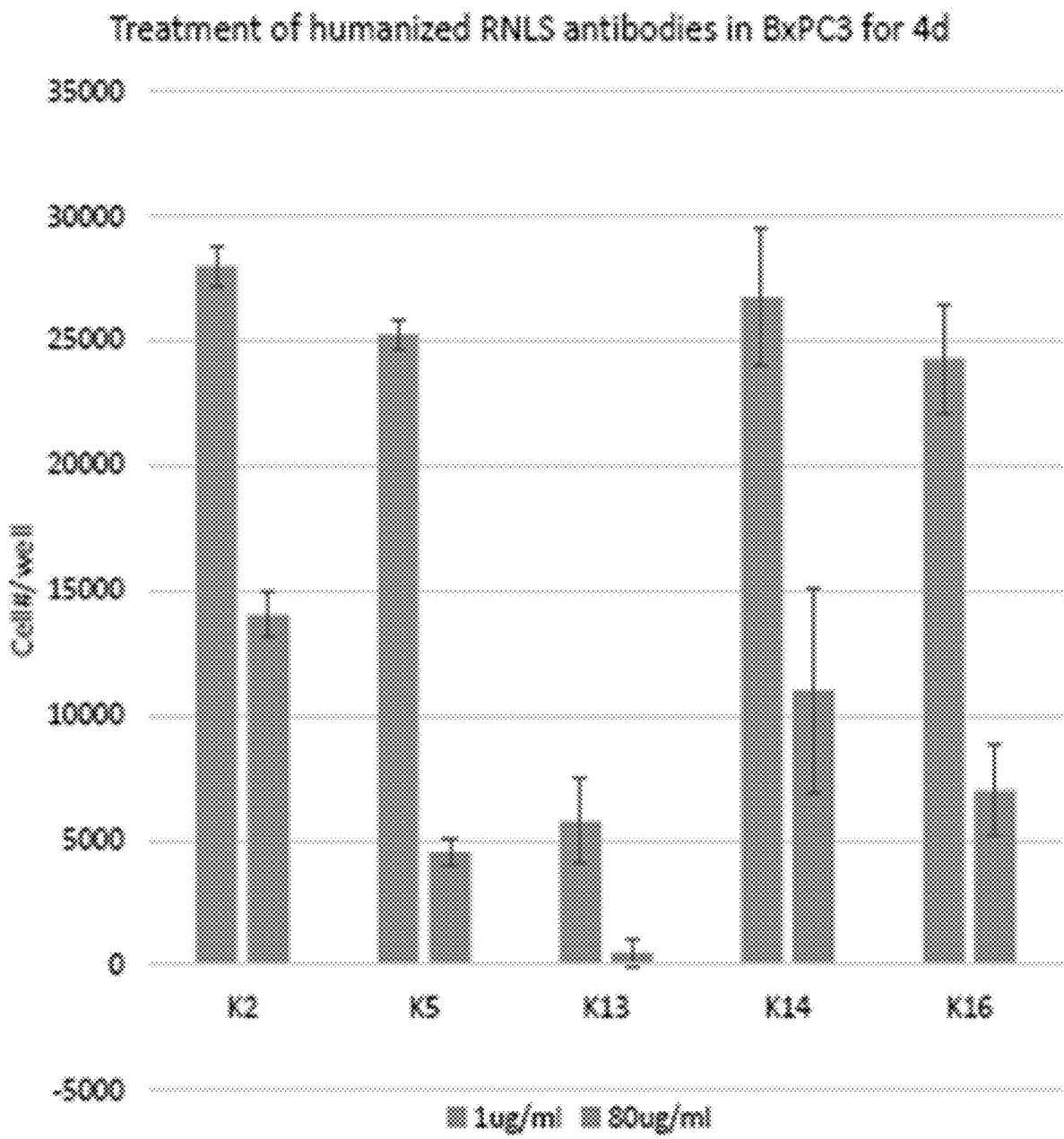
FIG. 35 depicts that five humanized m28 variants (m28-K2, m2-K5, m28-K13, m28-K14 and m28-K16, Table 2) also decreased the viability of human cell lines of melanoma (SK-MEL-28) and pancreatic adenocarcinoma (BxPC3), (representative examples shown), indicating potential therapeutic utility of m28 variants in human cancer.

Five humanized m28 variants (m28-K2, m2-K5, m28-K13, m28-K14 and m28-K16, Table 2) showed increased binding to both human and mouse RNLS (FIG. 32 and FIG. 33). These m28 variants also decreased the viability of human cell lines of melanoma (SK-MEL-28) and pancreatic adenocarcinoma (BxPC3), (representative examples shown in FIG. 34, and FIG. 35), indicating potential therapeutic utility of m28 variants in human cancer.

Example 2: Sequences

TABLE 1

Oligonucleotides used for humanization and affinity maturation of M28 and M42

| Oligo-nucleotide name | Nucleotide sequence | Amino acid sequence |
|---|---|---|
| BN452 M28L1 | TGCCGTGCCAGTCAGA GCGTGTATGACAACAA CAACGTAGCCTGGTAT CAA (SEQ ID NO: 96) | CRASQSVYDNNNVAW YQ (SEQ ID NO: 97) |

TABLE 1-continued

Oligonucleotides used for humanization and affinity maturation of M28 and M42

| Oligo-nucleotide name | Nucleotide sequence | Amino acid sequence |
|---|---|---|
| BN453 M42L1 | TGCCGTGCCAGTCAGA CCGTGTATAACAACAA CTACGTAGCCTGGTAT CAA (SEQ ID NO: 98) | CRASQTVYNNNYVAW YQ (SEQ ID NO: 99) |
| BN454 M28 L2 | AAGCTTCTGATTTACG GCGCCAGCACCCTCTA CTCTGGAGTC (SEQ ID NO: 100) | KLLIYGASTLYSGV (SEQ ID NO: 101) |
| BN455 M42 L2 | AAGCTTCTGATTTACG AAACCAGCAAACTCTA CTCTGGAGTC (SEQ ID NO: 102) | KLLIYETSKLYSGV (SEQ ID NO: 103) |
| BN456 M28L3 | GCAACTTATTACTGTC TGGGCGAATTCAGCTG CAGCAGCGCTGACTGC TTCGCCTTCGGACAGG GTACC (SEQ ID NO: 104) | ATYYCLGEFSCSSADCF AFGQGT (SEQ ID NO: 105) |
| BN457 M42 L3 | GCAACTTATTACTGTC AGGGCGGCTACAGCG GCGTGGACTTCATGGC TTTCGGACAGGGTACC (SEQ ID NO: 106) | ATYYCQGGYSGVDFM AFGQGT (SEQ ID NO: 107) |
| BN458 M28H1 | GCTTCTGGCTTCAACC TGAGCAGCTTCGCCGT TCACTGGGTGCGTCAG (SEQ ID NO: 108) | ASGFNLSSFAVHWVRQ (SEQ ID NO: 109) |
| BN459 M42H1 | GCTTCTGGCTTCAACC TGACCACCTACGGCGT TCACTGGGTGCGTCAG (SEQ ID NO: 110) | ASGFNLTTYGVHWVRQ (SEQ ID NO: 111) |
| BN460 M28 H2 | CTGGAATGGGTTGCAA TCATCAGCAGCGTTGG CATCACCCGCTATGCC GATAGCGTC (SEQ ID NO: 112) | LEWVAIISSVGITRYAD SV (SEQ ID NO: 113) |
| BN461 M42 H2 | CTGGAATGGGTTGCAC TGATCGGCGATCGCGG CACCACCTATTATGCC GATAGCGTC (SEQ ID NO: 114) | LEWVALIGDRGTTYYA DSV (SEQ ID NO: 115) |
| BN462 M28 H3 | TATTATTGTGCTCGCT ATGGCTATAGCGGCGA CGTGAACCGCCTGGAC CTGTGGGGTCAAGGA ACC (SEQ ID NO: 116) | YYCARYGYSGDVNRL DLWGQGT (SEQ ID NO: 117) |
| BN463 M42 H3 | TATTATTGTGCTCGCG GCAGCGGCTATGGCGC TCGCATCTGGGGTCAA GGAACC (SEQ ID NO: 118) | YYCARGSGYGARIWGQ GT (SEQ ID NO: 119) |
| BN464 M28 HC71 | CGTTTCACTATAAGCA AAGACACATCCAAAA AC (SEQ ID NO: 120) | RFTISKDTSKN (SEQ ID NO: 121) |
| BN465 M42 HC71 | CGTTTCACTATAAGCC GCGACACATCCAAAA AC (SEQ ID NO: 122) | RFTISRDTSKN (SEQ ID NO: 123) |
| BN498 M28 L3 STOP | GCAACTTATTACTGTT AATGATAATTCGGACA GGGTACC (SEQ ID NO: 124) | ATYYC *** FGQGT * denotes STOP (SEQ ID NO: 125) |
| BN484 M28 H1 STOP | GCTTCTGGCTTCAATT AATGATAACACTGGGT GCGTCAG (SEQ ID NO: 126) | ASGFN *** HWVRQ * denotes STOP (SEQ ID NO: 127) |
| BN467 M28 and M42 H2 STOP | CTGGAATGGGTTGCAT GATAATGATATGCCGA TAGCGTC (SEQ ID NO: 128) | LEWVA *** YADSV * denotes STOP (SEQ ID NO: 129) |
| BN485 M28 and M42 H3 STOP | TATTATTGTGCTCGCT AATGATAATGGGGTCA AGGAACC (SEQ ID NO: 130) | YYCAR *** WGQGT * denotes STOP (SEQ ID NO: 131) |
| BN469 M42 L1 STOP | TGCCGTGCCAGTCAGT GATAATGAGTAGCCTG GTATCAA (SEQ ID NO: 132) | CRASQ *** VAWYQ * denotes STOP (SEQ ID NO: 133) |
| BN466 M42 H1 STOP | GCTTCTGGCTTCAACT GATAATGACACTGGGT GCGTCAG (SEQ ID NO: 134) | ASGFN *** HWVRQ * denotes STOP (SEQ ID NO: 135) |
| BN492 M28 L3 randomization | GCAACTTATTACTGTC TGGGCGAATTCAGCTG CAGCAGCGCTGACTGC TTCGCCTTCGGACAGG GTACC Nucleotides in underline are degenerate; parental = 70%, others = 10% each (SEQ ID NO: 136) | ATYYCLGEFSCSSADCF AFGQGT Residues in underline are randomized (SEQ ID NO: 137) |
| BN488 M28H1 randomization | GCTTCTGGCTTCAACC TGAGCAGCTTCGCCGT TCACTGGGTGCGTCAG Nucleotides in underline are degenerate; parental = 70%, others = 10% each (SEQ ID NO: 138) | ASGFNLSSFAVHWVRQ Residues in underline are randomized (SEQ ID NO: 139) |
| BN489 M28 H2 randomization | CTGGAATGGGTTGCAA TCATCAGCAGCGTTGG CATCACCCGCTATGCC GATAGCGTC Nucleotides in underline are degenerate; parental = 70%, others = 10% each (SEQ ID NO: 140) | LEWVAIISSVGITRYAD SV Residues in underline are randomized (SEQ ID NO: 141) |

TABLE 1-continued

Oligonucleotides used for humanization and affinity maturation of M28 and M42

| Oligonucleotide name | Nucleotide sequence | Amino acid sequence |
|---|---|---|
| BN490 M28 H3 randomization | TATTATTGTGCTCGCT ATGGCTATAGCGGCGA CGTGAACCGCCTGGAC CTGTGGGGTCAAGGA ACC Nucleotides in underline are degenerate; parental = 70%, others = 10% each (SEQ ID NO: 142) | YYCARYGYSGDVNRL DLWGQGT Residues in underline are randomized (SEQ ID NO: 143) |
| BN496 M42L1 randomization | TGCCGTGCCAGTCAGA CCGTGTATAACAAC AACTACGTAGCCTGG TATCAA Nucleotides in underline are degenerate; parental = 70%, others = 10% each (SEQ ID NO: 144) | CRASQTVYNNNYVAW YQ Residues in underline are randomized (SEQ ID NO: 145) |
| BN493 M42H1 randomization | GCTTCTGGCTTCAACC TGACCACCTACGGCGT TCACTGGGTGCGTCAG Nucleotides in underline are degenerate; parental = 70%, others = 10% each (SEQ ID NO: 146) | ASGFNLTTYGVHWVRQ Residues in underline are randomized (SEQ ID NO: 147) |
| BN494 M42 H2 randomization | CTGGAATGGGTTGCAC TGATCGGCGATCGCGG CACCACCTATTATGCC GATAGCGTC Nucleotides in underline are degenerate; parental = 70%, others = 10% each (SEQ ID NO: 148) | LEWVALIGDRGTTYYA DSV Residues in underline are randomized (SEQ ID NO: 149) |
| BN495 M42 H3 randomization | TATTATTGTGCTCGCG GCAGCGGCTATGGCGC TCGCATCTGGGGTCAA GGAACC Nucleotides in underline are degenerate; parental = 70%, others = 10% each (SEQ ID NO: 150) | YYCARGSGYGARIWGQ GT Residues in are underline Randomized (SEQ ID NO: 151) |

TABLE 2

M28/M42 and variant CDRs

| | CDR-L1 | L2 | L3 | H1 | H2 | H3 |
|---|---|---|---|---|---|---|
| M28 parental | SVYDNN N (SEQ ID NO: 152) | GAST (SEQ ID NO: 153) | LGEFSC SSADCF A (SEQ ID NO: 154) | LSSFAV (SEQ ID NO: 155) | IISSVGIT R (SEQ ID NO: 156) | YGYSGD VNRLDL (SEQ ID NO: 157) |
| M28-K2 | SVYDNN N (SEQ ID NO: 158) | GAST (SEQ ID NO: 159) | LGEGPC SVTDCLI (SEQ ID NO: 160) | LSSFAV (SEQ ID NO: 161) | LIGVRG SLY (SEQ ID NO: 162) | HWYSG GVVRLD A (SEQ ID NO: 163) |
| M28-K5 | SVYDNN N (SEQ ID NO: 164) | GAST (SEQ ID NO: 165) | LGEGPC SVTDCLI (SEQ ID NO: 166) | LSSFAV (SEQ ID NO: 167) | LISGRGT RF (SEQ ID NO 168) | HWYSG GVVRLD A (SEQ ID NO: 169) |
| M28-K9 | SVYDNN N (SEQ ID NO: 170) | GAST (SEQ ID NO: 171) | LGEGPC SVTDCLI (SEQ ID NO: 172) | LSSFAV (SEQ ID NO: 173) | IISSVGIT R (SEQ ID NO: 174) | HWYSG GVVRLD A (SEQ ID NO: 175) |
| M28-K13 | SVYDNN N (SEQ ID NO: 176) | GAST (SEQ ID NO: 177) | LGEFSC SSADCF A (SEQ ID NO: 178) | LSSFAV (SEQ ID NO: 179) | LIGVRG SLY (SEQ ID NO: 180) | HWYSG GVVRLD A (SEQ ID NO 181) |

TABLE 2-continued

M28/M42 and variant CDRs

| | CDR-L1 | L2 | L3 | H1 | H2 | H3 |
|---|---|---|---|---|---|---|
| M28-K14 | SVYDNNN (SEQ ID NO: 182) | GAST (SEQ ID NO: 183) | LGEGPCSVTDCLI (SEQ ID NO: 184) | LSSFAV (SEQ ID NO: 185) | LISGRGTRF (SEQ ID NO: 186) | YGYSGDVNRLDL (SEQ ID NO: 187) |
| M28-K16 | SVYDNNN (SEQ ID NO: 188) | GAST (SEQ ID NO: 189) | LGEFSCSSADCFA (SEQ ID NO: 190) | LSSFAV (SEQ ID NO: 191) | LISGRGTRF (SEQ ID NO: 192) | HWYSGGVVRLDA (SEQ ID NO: 193) |
| M42 parental | TVYNNNY (SEQ ID NO: 194) | ETSK (SEQ ID NO: 195) | QGGYSGVDFMA (SEQ ID NO: 196) | LTTYGV (SEQ ID NO: 197) | LIGDRGTTY (SEQ ID NO: 198) | GSGYGARI (SEQ ID NO: 199) |
| M42-K31 | SVYRNNY (SEQ ID NO: 200) | ETSK (SEQ ID NO: 201) | QGGYSGVDFMA (SEQ ID NO: 202) | MSSERR (SEQ ID NO: 203) | LIRDRGWNY (SEQ ID NO: 204) | GICYCARS (SEQ ID NO: 205) |
| M42-K34 | SVYRNNY (SEQ ID NO: 206) | ETSK (SEQ ID NO: 207) | QGGYSGVDFMA (SEQ ID NO: 208) | LTTYGV (SEQ ID NO: 209) | LIRDRGWNY (SEQ ID NO: 210) | GICYCARS (SEQ ID NO: 211) |
| M42-K35 | TVYNNNY (SEQ ID NO: 212) | ETSK (SEQ ID NO: 213) | QGGYSGVDFMA (SEQ ID NO: 214) | MSSERR (SEQ ID NO: 215) | LIRDRGWNY (SEQ ID NO: 216) | GICYCARS (SEQ ID NO: 217) |

M28-humanized Fv sequence Heavy chain nucleotide

SEQ ID NO: 218

GAGGTTCAGCTGGTGGAGTCTGGCGGTGGCCTGGT

GCAGCCAGGGGGCTCACTCCGTTTGTCCTGTGCAG

CTTCTGGCTTCAATCTGAGCAGCTTCGCCGTTCAC

TGGGTGCGTCAGGCCCCCGGGTAAGGGGCCTGGAATG

GGTTGCAATCATCAGCAGCGTTGGCATCACCCGCT

ATGCCGATAGCGTCAAGGGCCGTTTCACTATAAGC

AAAGACACATCCAAAAACACAGCCTACCTACAAAT

GAACAGCTTAAGAGCTGAGGACACTGCCGTCTATT

ATTGTGCTCGCTATGGCTATAGCGGCGACGTGAAC

CGCCTGGACCTGTGGGGTCAAGGAACCCTGGTCAC

CGTCTCCTCG

M28-humanized Fv sequence Heavy chain Amino acid (M28 CDR and HC71 grafts underlined)

SEQ ID NO: 219

EVQLVESGGGLVQPGGSLRLSCAASGFN<u>LSSFAVH</u>

WVRQAPGKGLEWVA<u>IISSVGITRYADSVKGRFTIS</u>

<u>K</u>DTSKNTAYLQMNSLRAEDTAVYYCARY<u>G</u>

<u>YSGDVNRLDL</u>WGQGTLVTVSS

M28-humanized Fv sequence Light chain nucleotide

SEQ ID NO: 220

GATATCCAGATGACCCAGTCCCCGAGCTCCCTGTC

CGCCTCTGTGGGCGATAGGGTCACCATCACCTGCC

GTGCCAGTCAGAGCGTATATGACAACAACAACGTA

GCCTGGTATCAACAGAAACCAGGAAAAGCTCCGAA

GCTTCTGATTTACGGCGCCAGCACCCTCTACTCTG

GAGTCCCTTCTCGCTTCTCTGGTAGCCGTTCCGGG

ACGGATTTCACTCTGACCATCAGCAGTCTGCAGCC

GGAAGACTTCGCAACTTATTACTGTCTGGGCGAAT

TCAGCTGCAGCAGCGCTGACTGCTTCGCCTTCGGA

CAGGGTACCAAGGTGGAGATCAAACGA

M28-humanized Fv sequence Light chain Amino acid (M28 CDR and HC71 grafts underlined)

SEQ ID NO: 221

DIQMTQSPSSLSASVGDRVTITCRASQ<u>SVYDNNNV</u>

<u>A</u>WYQQKPGKAPKLLIY<u>GASTLYSGVPSRFGSRSG</u>

TDFTLTISSLQPEDFATYYC<u>LGEFSCSSADCFA</u>FG

QGTKVEIKR

M42 humanized Fv sequence Heavy
chain nucleotide
SEQ ID NO: 222
GAGGTTCAGCTGGTGGAGTCTGGCGGTGGCCTGGT

GCAGCCAGGGGGCTCACTCCGTTTGTCCTGTGCAG

CTTCTGGCTTCAACCTGACCACCTACGGCGTTCAC

TGGGTGCGTCAGGCCCCGGGTAAGGGCCTGGAATG

GGTTGCACTGATCGGCGATCGCGGCACCACCTATT

ATGCCGATAGCGTCAAGGGCCGTTTCACTATAAGC

CGCGACACATCCAAAAACACAGCCTACCTACAAAT

GAACAGCTTAAGAGCTGAGGACACTGCCGTCTATT

ATTGTGCTCGCGGCAGCGGCTATGGCGCTCGCATC

TGGGGTCAAGGAACCCTGGTCACCGTCTCCTCG

M42 humanized Fv sequence Heavy
chain Amino acid (M42 CDR and
HC71 grafts underlined)
SEQ ID NO: 223
EVQLVESGGGLVQPGGSLRLSCAASGFNLTTYGVH

WVRQAPGKGLEWVALIGDRGTTYYADSVKGRFTIS

RDTSKNTAYLQMNSLRAEDTAVYYCARGSGYGARI

WGQGTLVTVSS

M42 humanized Fv sequence Light
chain nucleotide
SEQ ID NO: 224
GATATCCAGATGACCCAGTCCCCGAGCTCCCTGTC

CGCCTCTGTGGGCGATAGGGTCACCATCACCTGCC

GTGCCAGTCAGACCGTGTATAACAACAACTACGTA

GCCTGGTATCAACAGAAACCAGGAAAAGCTCCGAA

GCTTCTGATTTACGAAACCAGCAAACTCTACTCTG

GAGTCCCTTCTCGCTTCTCTGGTAGCCGTTCCGGG

ACGGATTTCACTCTGACCATCAGCAGTCTGCAGCC

GGAAGACTTCGCAACTTATTACTGTCAGGGCGGCT

ACAGCGGCGTGGACTTCATGGCTTTCGGACAGGGT

ACCAAGGTGGAGATCAAACGA

M42 humanized FIT sequence Light
chain Amino acid (M42 CDR and
HC71 grafts underlined)
SEQ ID NO: 225
DIQMTQSPSSLSASVGDRVTITCRASQTVYNNNYV

AWYQQKPGKAPKLLIYETSKLYSGVPSRFSGSRSG

TDFTLTISSLQPEDFATYYCQGGYSGVDFMAFGQG

TKVEIKR

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising an antibody or binding portion thereof that specifically binds to renalase, wherein the antibody or binding portion thereof comprises: a) a heavy chain (HC) CDR1 comprising the amino acid sequence of SEQ ID NO: 191, b) a HC CDR2 comprising the amino acid sequence of SEQ ID NO: 192, c) a HC CDR3 comprising the amino acid sequence of SEQ ID NO: 193, d) a light chain (LC) CDR1 comprising the amino acid sequence of SEQ ID NO: 188, e) a LC CDR2 comprising the amino acid sequence of SEQ ID NO: 189, and f) a LC CDR3 comprising the amino acid sequence of SEQ ID NO: 190.

2. The composition of claim 1, wherein the antibody or binding portion thereof specifically binds to renalase with an affinity of at least $10^{-6}$ M.

3. The composition of claim 1, wherein the antibody or binding portion thereof specifically binds a peptide comprising an amino acid sequence selected from the group consisting of SEQ ID NO: 1-8.

4. The composition of claim 1, wherein the renalase is human renalase.

5. The composition of claim 1, wherein the antibody or binding portion thereof is selected from the group consisting of a monoclonal antibody, a polyclonal antibody, a single chain antibody, an immunoconjugate, a defucosylated antibody, a bispecific antibody, a humanized antibody, a chimeric antibody, and a fully human antibody.

6. The composition of claim 5, wherein the immunoconjugate comprises a therapeutic agent or a detection moiety.

7. An isolated nucleic acid molecule comprising a sequence encoding the antibody or binding portion thereof of claim 1 that specifically binds to renalase.

8. An expression vector comprising the nucleic acid molecule of claim 7.

9. A cell comprising the nucleic acid molecule of claim 7.

10. A method of treating a renalase expressing cancer in a subject in need thereof, the method comprising administering to the subject the composition of claim 1, wherein the cancer is pancreatic cancer or melanoma.

11. The method of claim 10, further comprising the step of administering to the subject at least one additional agent.

* * * * *